US010526289B2

(12) United States Patent
Silverman et al.

(10) Patent No.: US 10,526,289 B2
(45) Date of Patent: *Jan. 7, 2020

(54) SUBSTITUTED PYRAZOLONE COMPOUNDS FOR USE IN TREATMENT OF AMYOTROPHIC LATERAL SCLEROSIS

(71) Applicant: Northwestern University, Evanston, IL (US)

(72) Inventors: Richard B. Silverman, Winnetka, IL (US); Yinan Zhang, Lexington, KY (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,131

(22) Filed: Aug. 22, 2017

(65) Prior Publication Data
US 2017/0349552 A1 Dec. 7, 2017

Related U.S. Application Data

(63) Continuation of application No. 14/867,624, filed on Sep. 28, 2015, now Pat. No. 9,809,556, which is a continuation of application No. 14/103,728, filed on Dec. 11, 2013, now Pat. No. 9,145,424, and a continuation-in-part of application No. 13/129,854, filed as application No. PCT/US2009/006237 on Nov. 20, 2009, now Pat. No. 10,167,263.

(60) Provisional application No. 61/735,867, filed on Dec. 11, 2012, provisional application No. 61/116,571, filed on Nov. 20, 2008.

(51) Int. Cl.
| | |
|---|---|
| *C07D 231/20* | (2006.01) |
| *C07D 231/18* | (2006.01) |
| *C07D 498/04* | (2006.01) |
| *C07D 403/06* | (2006.01) |
| *C07D 401/06* | (2006.01) |
| *C07D 471/04* | (2006.01) |

(52) U.S. Cl.
CPC ......... *C07D 231/18* (2013.01); *C07D 231/20* (2013.01); *C07D 401/06* (2013.01); *C07D 403/06* (2013.01); *C07D 471/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 2,334,495 | A | 11/1943 | Kendall et al. |
| 2,459,226 | A | 1/1949 | Kendall et al. |
| 2,927,928 | A | 3/1960 | Heinz |
| 2007/0049574 | A1 | 3/2007 | Amrein et al. |

FOREIGN PATENT DOCUMENTS

| | | | |
|---|---|---|---|
| EP | 1693369 | | 8/2006 |
| EP | 1714960 | | 10/2006 |
| EP | 1063227 | | 10/2007 |
| WO | 9801427 | | 1/1998 |
| WO | 0109121 | | 2/2001 |
| WO | 2006071730 | | 7/2006 |
| WO | 2008052441 | | 5/2008 |
| WO | WO2010059241 | * | 5/2010 |

OTHER PUBLICATIONS

Adenot et al., "Blood-brain barrier permeation models: discriminating between potential CNS and non-CNS drugs including P-glycoprotein substrates," J. Chem. Inf. Com put. Sci. 2004, 44(1 ), 239-48.
Auluck et al., "Chaperone suppression of alpha-synuclein toxicity in a *Drosophila* model for Parkinson's disease," Science 2002, 295(5556), 865-8.
Bailey et al., "Molecular chaperones enhance the degradation of expanded polyglutamine repeat androgen receptor in a cellular model of spinal and bulbar muscular atrophy," Hum. Mol. Genet. 2002, 11 (5), 515-23.
Carmichael et al., "Bacterial and yeast chaperone reduce both aggregate formation and cell death in mammalian cell models of Huntington's disease," Proc. Nat I. Acad. Sci. USA 2000, 97(17), 9701-5.
Chai et al., "Live-cell imagining reveals divergent intracellular dynamics of polyglutamine disease proteins and supports a sequestration model of pathogenesis," Proc. Natl. Acad. Sci. USA 2002, 99(14), 9310-5.
Communication pursuant to Article 94(3) EPC for European Application No. 09827890.6 dated Apr. 5, 2016, 7 pages.
Cummings et al., "Chaperone suppression of aggregation and altered subcellular proteasome localization imply protein misfolding in SCA 1," Nat. Genet. 1998, 19(2), 148-54.
Davies et al., "Formation of neuronal intranuclear inclusions underlies the neurological dysfunction in mice transgenic for the HD mutation," Cell 1997, 90(3), 537-48.
Diet al., "High throughput artificial membrane permeability assay for blood-brain barrier," Eur. J. Med. Chem. 2003, 38(3), 223-32.
DiFiglia et al., "Aggregation of huntingtin in neuronal intranuclear inclusions and dystrophic neurites in brain," Science 1997, 277 (5334 ), 1990-3.
Di, L. et ai.,"Profiling drug-like properties in discovery research," Curr. Opin. Chem. Bioi. 2003, 7(3), 402-8.
El-Telbani et al., "Meldrum's acid in heterocyclic synthesis: azoles incorporating a 2,4-dichlorophenoxy moiety with anticipated molluscicidal activity", Monatsh. Chem., 139, 2008, 685-689.
European Search Report for EP09827890.6, 5 Pages (dated Feb. 13, 2013).
Gavrilenko et al., "Synthesis and Properties of 3-Amino-3-pyrazolin-5-ones", J. Org. Chem., 40,(19), 1975, 2720-2724.

(Continued)

*Primary Examiner* — Bong-Sook Baek
(74) *Attorney, Agent, or Firm* — Quarles & Brady LLP; M. Scott McBride

(57) ABSTRACT

The present invention relates to the identification of compounds and pharmaceutical compositions thereof for treating subjects with amyotrophic lateral sclerosis (ALS) and other neurodegenerative diseases. The invention also provides methods of preparing the provided compounds.

22 Claims, 38 Drawing Sheets

(56) References Cited

OTHER PUBLICATIONS

Gething, M.J., "The difference with prokaryotes," Nature 1997, 388(6640), 329-331.

Gidalevitz et al., "Progressive disruption of cellular protein folding in models of polyglutamine diseases," Science 2006, 311 (5766), 1471-4.

Hartl, F.U., "Molecular chaperones in cellular protein folding," Nature 1996, 381 (6583), 571-9.

Hatab, A.S.A et al., "Synthesis of New 4-Substituted-3-alkoxy-2-butenoic Acid Esters and Pyrazole-3-one Derivatives", Jordan Journal of Chemistry, 3(3):211-221 (2008).

Hitzel et al., "An increased throughput method for the determination of partition coefficients," Pharm. Res. 2000, 17(11 ), 1389-95.

Horwich et al., "Deadly conformations—protein misfolding in prion disease," Cell1997, 89(4), 499-510.

International Search Report and Written Opinion for PCT/US09/06237 dated Jul. 22, 2010.

Ishihama et al., "A rapid method for pKa determination of drugs using pressure-assisted capillary electrophoresis with photodiode array detection in drug discovery," J. Pharm. Sci. 2002, 91 (4), 933-42.

Ito, et al., "Synthesis of Pyrazolone Derivatives. XX. On the Cyclization of 4-Bromo-3-(2-formamidophenyl) 14 thiomethyl-2-methyl-1-phenyl-3-pyrazolin-5 one," Journal of the Pharmaceutical Society of Japan, 1973, 93(2): 207-213.

Ikeda et al., "Expanded polyglutamine in the Machado-Joseph disease protein induces cell death in vitro and in vivo," Nat Genet. 1996, 13(2), 196-202.

Jana et al., "Altered proteasomal function due to the expression of polyglutamine-expanded truncated N-terminal 17 huntingtin induces apoptosis by caspase activation through mitochondral cytochrome c release," Hum. Mol. Genet. 2001, 10(10), 1049-59.

Johnson et al., "TDP-43 is intrinsically aggregation-prone, and amyotrophic lateral sclerosis linked mutations accelerate aggregation and increase toxicity," J. Bioi. Chem. 2009, 284(30), 20329-20339.

Jung et al., "Efficient Synthesis of 4-Ethoxycarbonyl Pyrazolin-5-One Derivatives", Synth. Comm., 32(24), 2002, 3767-3777.

Kabashi et al., "TARDBP mutations in individuals with sporadic and familial amyotrophic lateral sclerosis," Nature Genetics 2008, 40(5), 572-574.

Kassel, D.B., "Applications of high-throughput ADME in drug discovery," Curr. Opin. Chem. Bioi. 2004, 8(3), 339-45.

Kazantsev et al., "Insoluble detergent-resistant aggregates form between pathological and nonpathological lengths of polyglutamine in mammalian cells," Proc. Natl. Acad. Sci. USA 1999, A96(20), 11404-9.

Kazemi-Esfarjani et al., "Genetic suppression of polyglutamine toxicity in Drosophila," Science 2000, 287(5459), 1837-40.

Kazemi-Esfarjani et al., "Suppression of polyglutamine toxicity by a Drosophila homolog of myeloid leukemia factor 1," Hum. Mol. Genet. 2002, 11(21), 2657-72.

Kerns et al., "Multivariate pharmaceutical profiling for drug discovery," Curr. Top. Med. Chem. 2002, 2(1), 87-98.

Kieran et al., "Treatment with arimoclomol, a coinducer of heat shock proteins, delays disease progression in ALS mice," Nat. Med. 2004, 10(4), 402-5.

Kim et al., "Polyglutamine protein aggregates are dynamic," Nat. Cell Bioi. 2002, 4(10), 826-31.

Koo et al., "Amyloid diseases: abnormal protein aggregation in neurodegeneration," Proc. Natl. Acad. Sci. USA. 1999, 96( 18), 9989-90.

Kopito et al., "Conformational disease," Nat. Cell Bio. 2000, 2(11 ), E207-9.

Kwong et al., "TDP-43 proteinopathy: the neuropathology underlying major forms of sporadic and familial frontotemporal lobar degeneration and motor neuron disease," Acta Neuropath. 2007, 114, 63-70.

Lankau et al. (Pharmazie 54 (9): 705-706, 1999).

Lansbury et al., "A century-old debate on protein aggregation and neurodegeneration enters the clinic," Nature 2006, 443(7113), 774-9.

Mackenzie et al., "Pathological TDP-43 distinguishes sporadic amyotrophic lateral sclerosis from amyotrophic lateral sclerosis with SOD1 mutations," Ann. Neurol. 2007, 61 (5), 427-434.

Matsumoto et al., "Huntingtin and mutant SOD1 form aggregate structures with distinct molecular properties in human cells," J. Bioi. Chem. 2005, 281 (7), 4477-4485.

Morimoto et al., "Stress-inducible responses and heat shock proteins: new pharmacologic targets for cytoprotection," Nat. Biotechnol. 1998, 16(9), 833-8.

Morimoto, R.I., "Dynamic remodeling of transcription complexes by molecular chaperones," Cell 2002, 110(3), 281-4.

Neumann et al., "Ubiquitinated TDP-43 in frontotemporal lobar degeneration and amyotrophic lateral sclerosis," Science 2006, 314, 130-133.

Nollen et al., "Chaperoning signaling pathways: molecular chaperones as stress-sensing 'heat shock' proteins," J. Cell Sci. 2002, 115(14), 2809-16.

Nucifora et al., "Interference by huntingtin and atrophin-1 with cbp-mediated transcription leading to cellular toxicity," Science 2001, 291 (5512), 2423-8.

Orr, H.T. "Beyond the Qs in the polyglutamine diseases," Genes Dev. 2001, 15(8), 925-32.

Pan et al., "Constructing optimum blood brain barrier QSAR models using a combination of 40-molecular similarity measures and cluster analysis," J. Chem. Inf. Comput. Sci. 2004, 44(6), 2083-98.

Pasinelli et ai.,"Molecular Biology of amyotrophic lateral sclerosis: insights from genetics," Nat. Rev. Neurosci. 2006, 7(9), 710-23.

Parsell et al., "Protein disaggregation mediated by heat-shock protein Hsp1 04," Nature 1994, 372(6505), 4 75-8.

Perez et al., "Recruitment and the role of nuclear localization in polyglutamine-mediated aggregation," J. Cell Bioi. 1998,143(6),1457-70.

Perutz, M.F., "Glutamine repeats and neurodegenerative diseases," Brain Res. Bull. 1999, 50(5-6), 467.

Rose et al., "Modeling blood-brain barrier partitioning using the electrotopological state," J. Chem. Inf. Comput. Sci. 2002, 42(3), 651-66.

Ross,C.A., "Intranuclear neuronal inclusions: a common pathogenic mechanism for glutamine-repeat neurodegenerative diseases" Neuron 1997,19(6),1147-50.

Ross, C.A., "Polyglutamine pathogenesis: emergence of unifying mechanisms for Huntington's disease and related disorders," Neuron 2002, 35(5), 819-22.

Rubinsztein, D.C., "The roles of intracellular protein-degradation pathways in neurodegeneration," Nature 2006, 443(7113), 780-6.

Sakahira et al., "Molecular chaperones as modulators of polyglutamine protein aggregation and toxicity," Proc. Natl. Acad. Sci. USA 2002, 99, 6412-8.

Schroder et al., "DnaK, DnaJ and GrpE form a cellular chaperone machinery capable of repairing heat-induced protein damage," EMBO J. 1993, 12(11),4137-44.

Sreedharan et al., "TDP-43 mutations in familial and sporadic amyotrophic lateral sclerosis," Science 2008, 319, 1668-1672.

Stenoien et al., "Polyglutamine-expanded androgen receptors form aggregates that sequester heat shock proteins, 32 proteasome components and SRC-1, and are suppressed by the HDJ-2 chaperone," Hum. Mol. Genet. 1999, 8(5), 731-41.

Suhr et al., "Identities of sequestered proteins in aggregates from cells with induced polyglutamine expression," J. Cell Biol. 2001, 153(2), 283-94.

Takeuchi et al., "Hsp70 and Hsp40 improve neurite outgrowth and suppress intra cytoplasmic aggregate formation in cultured neuronal cells expressing mutant SOD1 ," Brain Res. 2002, 949(1-2), 11-22.

Taylor et al., "Toxic proteins in neurodegenerative disease," Science 2002, 296(5575), 1991-5.

Traynor et al., "Neuroprotective agents for clinical trials in ALS: a systematic assessment," Neurology. 2006, 67(1 ), 20-7.

(56) References Cited

OTHER PUBLICATIONS

Warrick et al., "Suppression of polyglutamine-mediated neurodegeneration in *Drosophila* by the molecular chaperone HSP70," Nat. Genet. 1999, 23(4), 425-8.
Wegorzewska et al., "TDP-43 mutant transgenic mice develop features of ALS and frontotemporal lobar degeneration," Proc. Natl. Acad. Sci. USA 2009, 106(44), 18809-18814.
Westerheide et al., "Heat shock response modulators as therapeutic tools for diseases of protein conformation," J. Bioi. Chem. 2005, 280(39), 33097-100.
Wils et al., "TDP-43 transgenic mice develop spastic paralysis and neuronal inclusions characteristic of ALS and frontotemporal lobar degeneration," Pro c. Nat I. Acad. Sci. USA 2010, 1 07(8) ,3858-3863.
Yokoseki et al., "TDP-43 mutation in familial amyotrophic lateral sclerosis," Ann. Neural. 2008, 63, 538-542.
Wikipedia entry on Pyrazolone, dated May 11, 2018.

\* cited by examiner

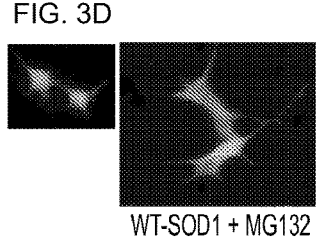
FIG. 3D
WT-SOD1 + MG132
FIG. 3A
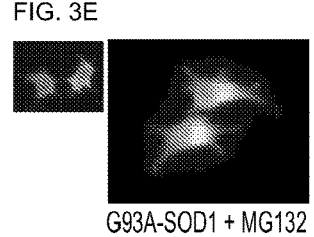
FIG. 3E
G93A-SOD1 + MG132
FIG. 3B
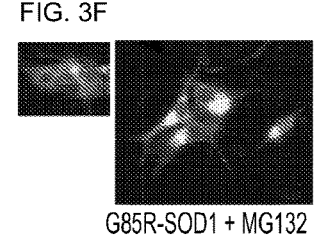
FIG. 3F
G85R-SOD1 + MG132
FIG. 3C

G93A-SOD1

200 nM MG132

G93A-SOD1

200 nM MG132 + 1µM RADICICOL

G85R-SOD1

200 nM MG132

G85R-SOD1

200 nM MG132 + 1µM RADICICOL

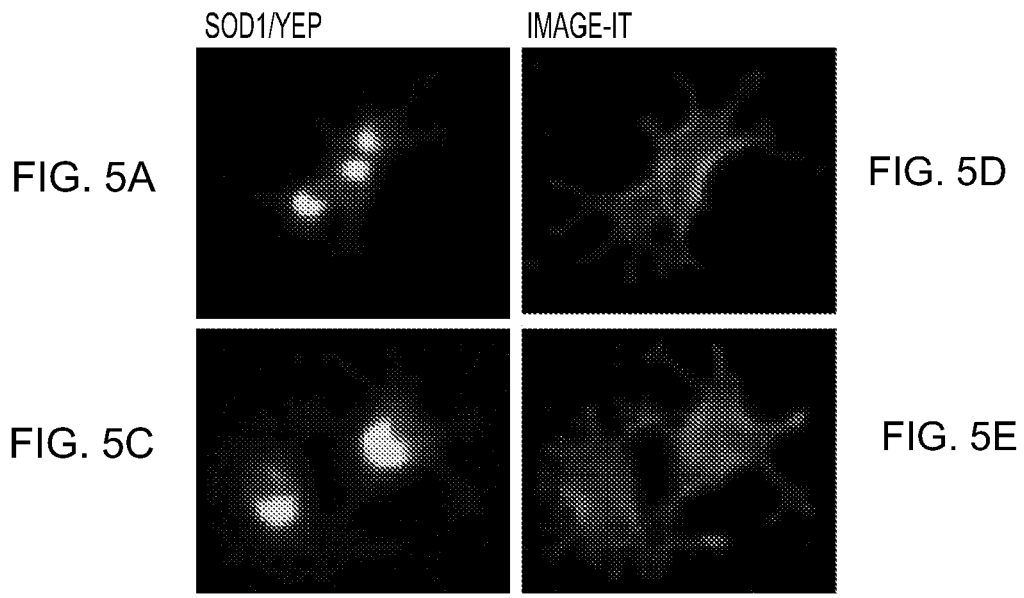
FIG. 5A
FIG. 5C
FIG. 5D
FIG. 5E
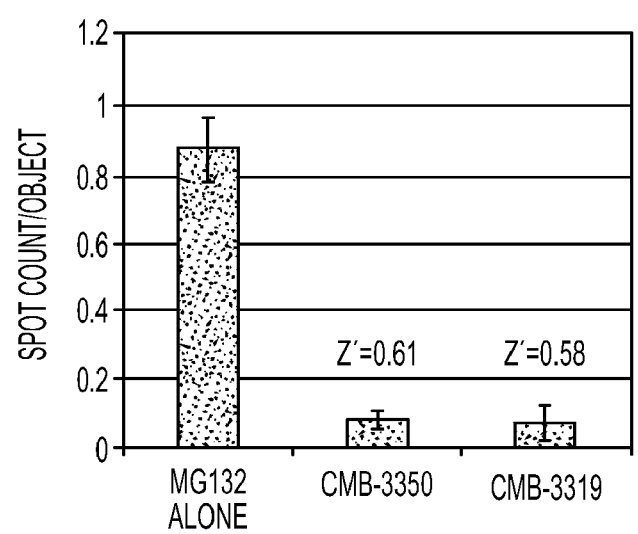
FIG. 5B

| SERIES[1] | MARKUSH STRUCTURE | NO. OF COMPOUNDS TESTED | MW RANGE | POSITION SUBSTITUTIONS | NO. ACTIVES /INACTIVES[2] | NO. TOXIC IN SERIES[3] | EFFECT ON AGGREGATION[4] |
|---|---|---|---|---|---|---|---|
| ASP | | 20 | 174 – 280 | R1 = AROMATIC OR HETEROCYCLE, ALKYL OR H<br>R2 = AROMATIC OR HETEROCYCLE, AMINE OR H<br>R3 = H | 16 / 4 | 0 | STRONG (9)<br>MODERATE (1)<br>INACTIVE (10) |
| ASP | | 15 | 208 – 407 | R1 = AROMATIC OR HETEROCYCLE, ALKYL OR H<br>R2 = AROMATIC OR HETEROCYCLE SULFANYL<br>R3 = H | 12 / 3 | 0 | STRONG (6)<br>MODERATE (3)<br>WEAK (1)<br>INACTIVE (6) |
| ASP | | 6 | 160 – 260 | R1 = AROMATIC OR HETEROCYCLE, ALKYL OR H<br>R2 = AROMATIC OR HETEROCYCLE, SULFANYL<br>R3 = H | 6 / 0 | 0 | STRONG (3)<br>INACTIVE (3) |
| ASP | | 6 | 266 – 364 | R1 = H<br>R2 = AROMATIC OR HETEROCYCLE SULFANYL<br>R3 = DIMETHYLAMINE | 4 / 2 | 1 | STRONG (3)<br>INACTIVE (1) |
| ASP | | 49 | 400 – 700 | R1 = AROMATIC OR HETEROCYCLE, ALKYL OR H<br>R2 = AROMATIC OR HETEROCYCLE SULFANYL<br>R3 = HYDRAZINE, AMINE, AROMATIC, HETEROCYCLE | 11 / 38 | 1 | STRONG (8)<br>INACTIVE (15) |
| ASP | | 12 | 400 – 500 | R1 = HYDRAZINE, AROMATIC, ALKYL OR H<br>R2 = AROMATIC OR HETEROCYCLE SULFANYL<br>R3 = HYDRAZINE | 0 / 12 | 1 | NT |

FIG. 24

| SERIES[1] | MARKUSH STRUCTURE | COMPOUND ID | R1 | R2 | R3 | PROTECTION[2] ED50 ± SD (μM) | TOXICITY[3] IC50 (μM) | PROTECTIVE EFFICACY[4] MAX % VIABILITY @ CONC (μM) | AGGREGATION[5] EFFECT |
|---|---|---|---|---|---|---|---|---|---|
| ASP | (pyrazolone core with R1-N, R2, R3, =O) | CMB-003319 | H | 2,4-dichlorophenyl-S-CH2CH2- | H | 0.374 ± 0.005 (n=4) | >100 (n=2) | 108 @ 64 | STRONG |
|  |  | CMB-003350 | H | 2,4-dichlorophenyl-S-CH2CH2- | -CH=N(CH3)2 | 0.6 ± 0.1 (n=4) | >100 (n=2) | 130 @ 14 | MODERATE |
|  |  | CMB-050231 | phenyl | 4-chlorophenyl-S-CH2CH2- | 4-tBu-styryl | 1.3 ± 0.1 (n=2) | >100 (n=2) | 98 @ 20 | STRONG |

FIG. 25

Figure 36, continued
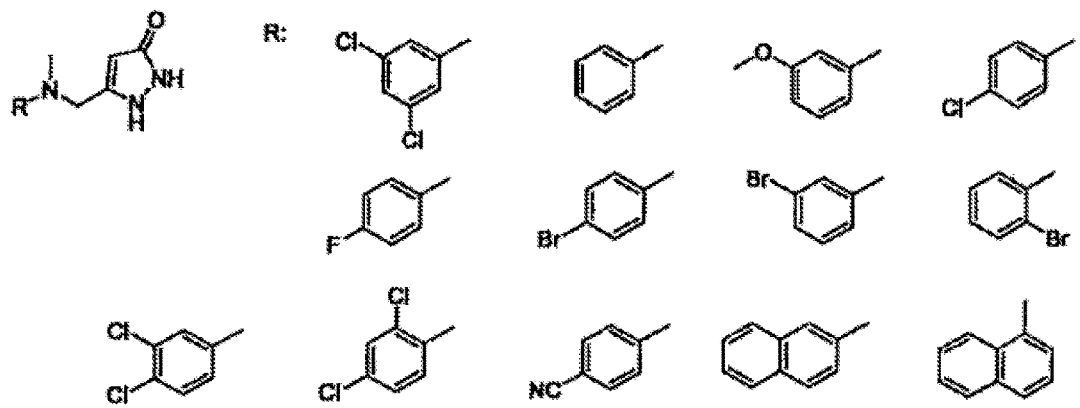
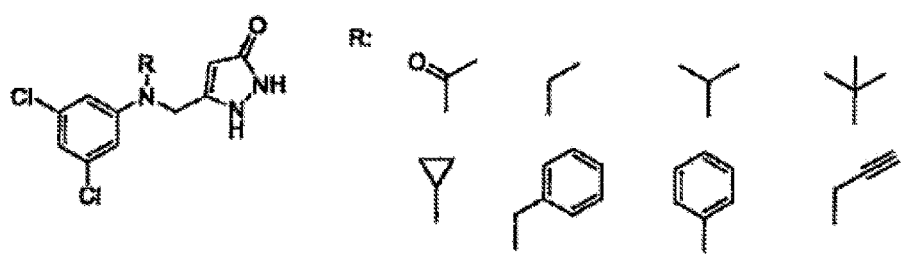
And compounds corresponding to substructure II:
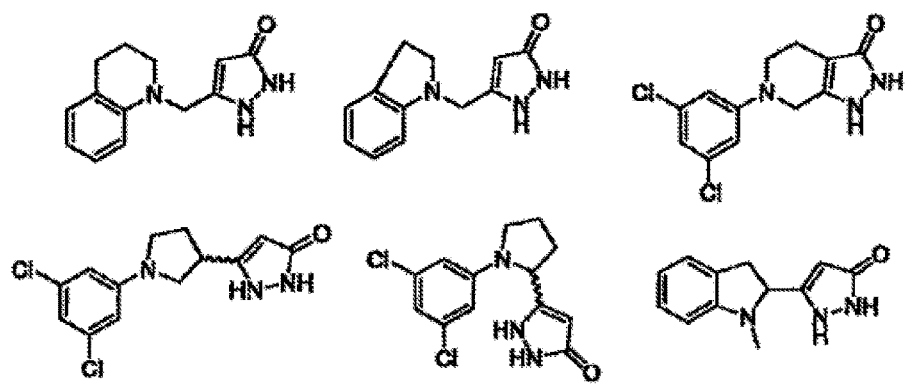

Figure 36, continued
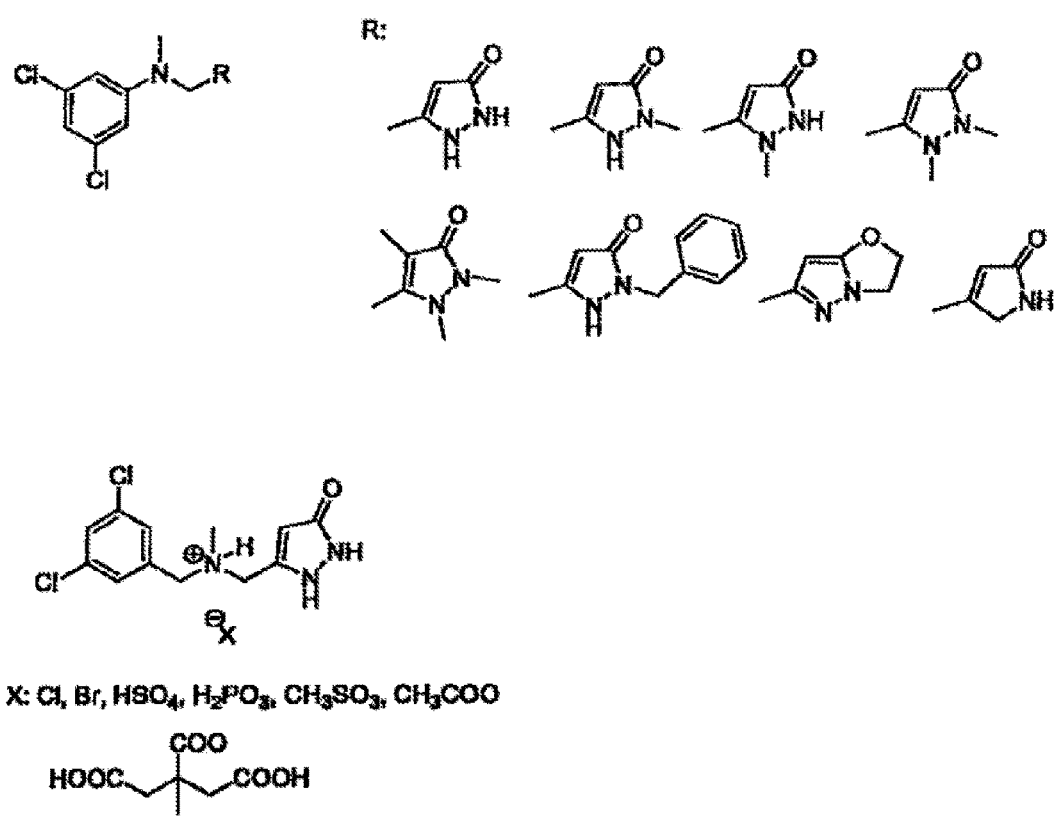

SUBSTITUTED PYRAZOLONE COMPOUNDS FOR USE IN TREATMENT OF AMYOTROPHIC LATERAL SCLEROSIS

CROSS-REFERENCE TO RELATED APPLICATIONS

This application is a continuation of and claims priority to and the benefit of application Ser. No. 14/867,624, filed Sep. 28, 2015, which is a continuation of and claims priority to and the benefit of application Ser. No. 14/103,728 filed Dec. 11, 2013 and issued as U.S. Pat. No. 9,145,424 on Sep. 29, 2015, which claimed priority to U.S. provisional application No. 61/735,867 filed Dec. 11, 2012, and is a continuation-in-part of and claims priority to application Ser. No. 13/129,854, filed May 18, 2011 which is a United States National Phase Application under 35 U.S.C. § 371 of International PCT Application No. PCT/US09/06237, filed Nov. 20, 2009, which claimed priority to U.S. provisional application Ser. No. 61/116,571, filed Nov. 20, 2008—each of which is hereby incorporated herein by reference in its entirety.

GOVERNMENT SUPPORT

This invention was made with government support under R43 NS057849 awarded by the National Institutes of Health and W81XWH-10-1-0356 awarded by the U.S. Army Medical Research and Materiel Command. The government has certain rights in the invention.

BACKGROUND OF THE INVENTION

Amyotrophic lateral sclerosis (ALS) is a fatal neurodegenerative disorder caused by motor neuron death (Rowland et al, *N. Engl. J. Med.*, 2001, 334, 1688-1700) and characterized in part by the presence of abnormal aggregates of insoluble protein in selectively vulnerable populations of neurons and glia. ALS, an orphan disease, is estimated to afflict about 87,000 people worldwide, but its prevalence would be much higher were it not for the fact that ALS patients survive for only 3 to 5 years on average after diagnosis. Approximately 10% of ALS cases are familial, with the rest of the cases being sporadic (Rowland et al., *N. Engl. J. Med.*, 2001, 334, 1688-1700). Approximately 20% of the cases of familial ALS are caused by inherited mutations in the protein Cu/Zn superoxide dismutase (SOD1) (Rosen et al, *Nature,* 1993, 362, 59-62). Rodent models in mutant SOD are often used as a disease model because of its phenotypic and pathologic resemblance to sporadic and familial human ALS (Dal Canto et al., *Brain Res.,* 1995, 676, 25-40; Wong, et al., *Neuron,* 1995, 14, 1105-1116; Bruijn et al., *Science,* 1998, 281, 1851-1854; Bruijn et al., *Neuron,* 1997, 18, 327-338; Wang et al., *Hum. Mol. Genet.,* 2003, 12, 2753-2764; Wang et al., *Neurobiol. Dis.,* 2002, 10, 128-138; Jonsson, et al., *Brain,* 2004, 127, 73-88).

The causes of sporadic ALS remain unknown, and the clinical courses are variable, suggesting that multiple factors are involved. Different hypotheses have been proposed, such as glutamate-mediated excitotoxicity, impaired mitochondrial function, oxidative stress, and aberrant protein aggregation (Dib et al., *Drugs,* 2003, 63, 289-310; Strong et al., *Pharmacology & Therapeutics,* 2003, 98, 379-414; Kunst et al., *Am. J. Hum. Genet.,* 2004, 75, 933-947; Bruijn, et al., *Annu. Rev. Neurosci,* 2004, 27, 723-749; Dibernardo et al., *Biochimica et Biophysica Acta,* 2006, 1762, 1139-1149). Riluzole, which decreases glutamate excitotoxicity, is the only FDA approved ALS drug (Jimonet et al., *J. Med. Chem.,* 1999, 42, 2828-2843.). However, it can only extend median survival life for 2 to 3 months, suggesting mechanisms other than glutamate-mediated excitotoxicity should be considered during ALS drug development (Miller et al., *ALS and Other Motor Neuron Disorders,* 2003, 4, 191-206; Taylor et al., *Neurology,* 2006, 67, 20-27).

Imbalances in protein homeostasis, which can be caused by cell stress or expression of certain mutant proteins, can result in the appearance of alternative conformational states that are able to self-associate to form protein aggregates and inclusion bodies. In familial as well as sporadic forms of ALS and mutant SOD1 transgenic models, aberrant protein aggregation has been reported as a common feature (Brnijin et al., *Science,* 1998, 281, 1851-1854; Leigh et al., Cytoskeletalpathology in Motor Neuron Diseases, in: Rowland, L. P. (Editor), *Amyotrophic Lateral Sclerosis and Other Motor Neuron Disease*, Raven Press, New York, 1991, pp. 3-pp. 23; Mather et al., *Neurosci. Lett.,* 1993, 160, 13-16; Pasinelli et al., *Neuron,* 2004, 43, 19-30; Watanabe, et al., *Neruobiol. Dis.,* 2001, 8, 933-941). The ubiquity of this feature in various forms of ALS suggests that perhaps drugs that inhibit aberrant protein aggretation may provide new and improved treatment options. Thus, there is an urgent need to identify and develop drugs for the treatment of ALS.

SUMMARY OF THE INVENTION

The present invention encompasses the recognition that there exists a need new compounds and methods for treating patients with amyotrophic lateral sclerosis (ALS) or other neurodegenerative diseases characterized by the presence of aberrant protein aggregates.

The present invention relates to the identification of provided compounds and pharmaceutical compositions thereof to treat neurodegenerative diseases. Among other things, the present invention provides methods of treating amyotrophic lateral sclerosis (ALS) with provided compounds. Without wishing to be bound by any particular theory, provided compounds may be useful in the treatment of ALS or other neurodegenerative diseases where abnormal protein aggregation has been implicated, as they may prevent the aggregation of protein in a cell or limit the toxicity of such aggregates.

In one aspect, the invention provides compounds of the formula:

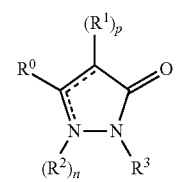

I or a pharmaceutically acceptable salt thereof, or a tautomer thereof, wherein $R^0$, $R^1$, $R^2$, $R^3$, n, and p are as defined herein. In some embodiments, such compounds, or pharmaceutically acceptable salts thereof, or tautomers thereof, are used in the treatment of neurodegenerative diseases.

In another aspect, the invention provides methods for treating a subject with amyotrophic lateral sclerosis (ALS) or other neurodegenerative disease (e.g., Alzheimer's Disease, prion disease, or Huntington's Disease) by administering a therapeutically effective amount of an inventive compound, or a pharmaceutical composition thereof. In certain embodiments, the compound is of one of the classes described herein or is a species described herein. In another aspect, the invention provides methods for treating a subject with ALS or other neurodegenerative disease by administering both an inventive compound or pharmaceutical composition thereof, and a second therapeutic agent or pharmaceutical composition thereof. The two compounds and/or compositions may be administered as a combination composition comprising both compounds. Alternatively, the two compounds may be administered separately (e.g., as two different compositions) either simultaneously or sequentially.

The present invention also provides methods of identifying compounds that protect against the cytotoxic effects of abnormal protein aggregation. Additionally, the present invention provides methods of identifying compounds that prevent, inhibit, or reverse protein aggregation. In some embodiments, the inventive assay involves the use of PC12 cells expressing the protein SOD1. In certain embodiments, SOD1 is labeled with a detectable moiety (e.g., a fluorescent moiety). Assays may be high-throughput assays.

In another aspect, the present invention provides methods of inhibiting or reversing abnormal protein aggregation (e.g., SOD1 protein aggregates). Inhibiting or reversing abnormal protein aggregation may occur in vivo (e.g., in a subject as described herein) or in vitro (e.g., in a cell). In yet another aspect, the invention provides methods of protecting cells from the cytotoxic effects of aggregated protein (e.g., SOD1) using an inventive compound. Protection of cells may occur in vivo or in vitro. In some embodiments, protection occurs in vitro and the cells are PC12 cells. In another aspect, the invention provides methods of modulating proteasome activity in vivo or in vitro using a provided compound. In some embodiments, protection occurs in vitro, and the cells used are PC12 cells or HeLa cells. In certain embodiments, the cells are mammalian cells. In certain embodiments, the cells are in an organism (e.g., a mammal).

The present invention contemplates provided compounds for use in medicine.

All publications and patent documents cited in this application are incorporated herein by reference in their entirety.

Definitions

Aliphatic: The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkyl: As used herein, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Alkylene: The term "alkylene" refers to a bivalent alkyl group. An "alkylene chain" is a polymethylene group, i.e., —(CH$_2$)$_n$—, wherein n is a positive integer, preferably from 1 to 20, 1 to 12, 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Alkenyl. As used herein, the term "alkenyl" refers to unsaturated aliphatic groups analogous in possible substitution to the alkyls described above, but that contain at least one double bond.

Alkenylene: As used herein, the term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Alkynyl: As used herein, the term "alkynyl" refers to unsaturated aliphatic groups analogous in possible substitution to the alkyls described above, but that contain at least one triple bond.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl" used alone or as part of a larger moiety as in "aralkyl," "aralkoxy," or "aryloxyalkyl," refers to monocyclic and bicyclic ring systems having a total of five to fourteen ring members, wherein at least one ring in the system is aromatic and wherein each ring in the system contains three to seven ring members. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Arylalkyl: As used herein, the term "arylalkyl" refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Effective amount: As used herein, an "effective amount" is an amount that achieves, or is expected to achieve, a desired result, and can be administered in one dose or in multiple doses. Compositions may be considered to contain an effective amount if they include a dose that is effective in the context of a dosing regimen, even if the composition as a single dose is not expected to be effective.

Heteroaryl: The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein one or more ring in the system is aromatic, one or more ring in the system contains one or more heteroatoms, and wherein each ring in the system contains 3 to 7 ring members. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^1$ (as in N-substituted pyrrolidinyl)).

Heterocycle: As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Intraperitoneal: The phrases "intraperitoneal administration" and "administered intraperitoneally" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Lower alkyl: The term "lower alkyl" refers to a $C_{1-4}$ straight or branched alkyl group. Exemplary lower alkyl groups are methyl, ethyl, propyl, isopropyl, butyl, isobutyl, and tert-butyl.

Lower haloalkyl: The term "lower haloalkyl" refers to a $C_{1-6}$ straight or branched alkyl group that is substituted with one or more halogen atoms.

Optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise indicated, suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-4}$Ph which may be substituted with R°; —CH=CHPh, which may be substituted with R°; —(CH$_2$)$_{0-4}$O(CH$_2$)$_{0-4}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°: —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph. —O(CH$_2$)$_{0-1}$Ph. —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Unless otherwise indicated, suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$^{0-2}$NR$^\bullet_2$, —NO$_2$, —SiR$^\bullet_3$, —OSiR$^\bullet_3$, —C(O)SR$^\bullet$. —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Unless otherwise indicated, suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Unless otherwise indicated, suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Unless otherwise indicated, suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Unless otherwise indicated, suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Unless otherwise indicated, suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Patient: As used herein, the term "patient," "subject," or "test subject" refers to any organism to which a provided compound is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition (e.g., a neurodegenerative disease, a disease, disorder or condition associated with protein aggregation, ALS, etc.).

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Prodrug: A general, a "prodrug," as that term is used herein and as is understood in the art, is an entity that, when administered to an organism, is metabolized in the body to deliver a therapeutic agent of interest. Various forms of "prodrugs" are known in the art. For examples of such prodrug derivatives, see:

a) *Design of Prodrugs*, edited by H. Bundgaard, (Elsevier, 1985) and *Methods in Enzymology*, 42:309-396, edited by K. Widder, et al. (Academic Press, 1985);
b) A Textbook of Drug Design and Development, edited by Krogsgaard-Larsen;
c) Bundgaard, Chapter 5 "Design and Application of Prodrugs," by H. Bundgaard, p. 113-191 (1991);
d) Bundgaard, *Advanced Drug Delivery Reviews*, 8:1-38 (1992);
e) Bundgaard, et al., *Journal of Pharmaceutical Sciences*, 77:285 (1988); and
f) Kakeya, et al., *Chem. Pharm. Bull.*, 32:692 (1984).

The methods and structures described herein relating to the provided compounds also apply to pharmaceutically acceptable salts thereof.

Protecting group: The term "protecting group," as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isborynl carbamate, isobutyl carbamate, isonicotinyl carbamate, p-(p'-methoxyphenylazo)benzyl carbamate, 1-methyl cyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, pr-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitmophenoxyacetamide, acetoacetamide, (N'-dithiobenzyloxycarbonylamino)acetamide, 3-(p-hydroxyphenyl)propanamide, 3-(n-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one. N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5 substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone. N-methylamine, N'-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenyl fluorenylamine (PhF), N-2,7-dichloro-9-fluorenylmethyleneamine, N-ferrocenylmethylamino (Fcm), N-2-picolylamino N'-oxide, N-1,1-dimethylthiomethylenecamine, N-benzylidencamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative. N-diphenylborinic acid derivative, N-[phenyl(pentacarbonylchromium- or tungsten)carbonyl]amine, N-copper chelate, N-zinc chelate, W-nitroamine, N-nitrosoamine, amine NV-oxide, diphenylphosphinamidc (Dpp), dimethylthiophosphinamide (Mpt), diphenyithiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Unless otherwise indicated, suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, tri-isopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Unless otherwise indicated, suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4'''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, i-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t- butoxydisiloxane-1,3-diylidene derivative (TBDS), cyclic carbonates, cyclic boronates, ethyl boronate, and phenyl boronate.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contains a non-amino-acid moiety (e.g., a glycan, etc.). In some embodiments, a protein includes more than one polypeptide chain, for example linked by one or more disulfide bonds or associated by other means. In some embodiments, proteins contain L-amino acids, D-amino acids, or both, in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Provided compound: The term "provided compound," as used herein, refers to a compound of formula I:

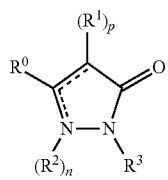

or a pharmaceutically acceptable salt thereof, wherein:
p is 1-2;
⁓⁓⁓ designates a single or double bond, wherein one ⁓⁓⁓ is a single bond and one ⁓⁓⁓ is a double bond;
each $R^1$ is independently —R, —OR, —SR, —S(O)R, —SO$_2$R, —OSO$_2$R, —N(R)$_2$, —CN, —NO$_2$—NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur; or
two $R^1$ groups are taken together to form

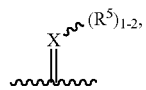

wherein:
X is N or C;
each $R^5$ is independently —R, —OR, —SR, —S(O)R, —SO$_2$R, —OSO$_2$R, —N(R)$_2$, —CN, —NO$_2$—NRC(O)R, —NRC(O)((CO)R, —NRC(O)N(R)$_2$.

—NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or a 3-8 membered saturated, partially unsaturated, or aryl monocyclic ring having 0-4 heteroatoms independently selected from nitrogen, oxygen, or sulfur, or an 8-10 membered saturated, partially unsaturated, or aryl bicyclic ring having 0-4 heteroatoms independently selected from nitrogen, oxygen, or sulfur, wherein $R^5$ is optionally substituted with 1-5 R groups;

each R is independently hydrogen, halogen, optionally substituted $C_{1-20}$ aliphatic, optionally substituted $C_{1-20}$ heteroaliphatic, optionally substituted phenyl, optionally substituted arylalkyl, or two R on the same nitrogen are taken together to form a 5-6 membered saturated, partially saturated, or aryl ring having 1-3 heteroatoms independently selected from nitrogen, oxygen, and sulfur, or two R on the same carbon or on adjacent carbons are optionally taken together to form a 3-6 membered saturated cycloalkyl or fused monocyclic ring containing 0-2 heteroatoms independently selected from nitrogen, oxygen, and sulfur;

n is 0-1;

each $R^2$ and $R^3$ are independently —R, —OR, —SR, —S(O)R, —SO$_2$R, —OSO$_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur;

$R^o$ is R, —OR, —SR, —S(O)R, —SO$_2$R, —OSO$_2$R, N(R)$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or

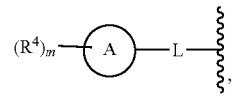

wherein:
L is a valence bond or a bivalent saturated or partially unsaturated $C_{1-10}$ hydrocarbon chain, wherein 1-4 methylene units of L are optionally and independently replaced by —O—, —S—, —C(O)—, —OC(O)—, —C(O)O—, —OC(O)O—, —S(O)—, —S(O)$_2$—, —OSO$_2$O—, —N(R)C(O)—, —C(O)NR—, —N(R)C(O)O—, —OC(O)NR—, —N(R)C(O)NR—, —N($R^6$)—, or -Cy-, and wherein L is optionally substituted with 1-4 R groups; wherein:
each -Cy- is independently a bivalent optionally substituted saturated, partially unsaturated, or aromatic monocyclic or bicyclic ring selected from a 6-10 membered arylene, a 5-10 membered heteroarylene having 1-4 heteroatoms independently selected from oxygen, nitrogen, or sulfur, a 3-8 membered carbocyclylene, or a 3-10 membered heterocyclylene having 1-4 heteroatoms independently selected from oxygen, nitrogen, or sulfur;

$R^6$ is —R, —OR, —SR, —S(O)R, —SO$_2$R, —OSO$_2$R, —C(O)R, —C(O)OR, —OC(O)R, —OC(O)OR, —C(O)N(R)$_2$. —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur;

Ring A is a 3-8 membered saturated, partially unsaturated, or aryl monocyclic ring optionally containing 0-4 heteroatoms independently selected from nitrogen, oxygen, or sulfur, or an 8-10 membered saturated, partially unsaturated, or aryl bicyclic ring optionally containing 0-4 heteroatoms independently selected from nitrogen, oxygen, or sulfur, and wherein Ring A is optionally substituted with m occurrences of $R^4$;

m is 0-5; and each $R^4$ is independently —R, —OR, —SR, —CN, —S(O)R. —SO$_2$R, —OSO$_2$R, —N(R)$_2$, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or a 3-8 membered saturated, partially unsaturated, or aryl monocyclic ring optionally containing 0-4 heteroatoms independently selected from nitrogen, oxygen, or sulfur.

In some embodiments, the term "provided compound" may encompass prodrugs and/or esters of compounds of formula I. As discussed herein, provided compounds may be provided in salt form. In particular, in some embodiments, a provided compound is provided as a pharmaceutically acceptable salt of a compound of formula I.

Provided compounds may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. That is, in some embodiments, the present invention provides isolated single isomers. In some embodiments, the present invention provides mixtures of two or more isomers. In certain embodiments, the present invention relates to a provided compound represented by any of the structures outlined herein, wherein the compound is provided as a single stereoisomer.

The terms acid or base addition salt also comprise the hydrates and the solvent addition forms which the compounds are able to form. Examples of such forms are, e.g., hydrates, alcoholates and the like.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

Stereochemically isomeric forms: The phrase "stereochemically isomeric forms," as used herein, refers to different compounds made up of the same atoms bonded by the same sequence of bonds but having different three-dimensional structures which are not interchangeable. In some embodiments of the invention, chemical compositions may be provided as pure preparations of individual stereochemically isomeric forms of a compound; in some embodiments, chemical compositions may be provided that are or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. Unless otherwise indicated, the present invention encompasses all stereochemically isomeric forms of relevant compounds, whether in pure form or in admixture with one another. If a particular enantiomer of a compound of the present invention is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present invention. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the invention, chemical compositions may be provided that are or include pure preparations of a single tautomeric form of a compound. In some embodiments of the invention, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the invention, chemical compositions may contain all tautomeric forms of a compound. In some embodiments of the invention, chemical compositions may contain less than all tautomeric forms of a compound. In some embodiments of the invention, chemical compositions may contain one or more tautomeric forms of a compound in amounts that vary over time as a result of interconversion. Unless otherwise indicated, the present invention encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount. In some embodiments, a composition may be considered to include a therapeutically effective amount of a provided compound when it includes an amount that is effective when administered as part of a dosing regimen even if a single dose (i.e., only the amount in the composition) alone is not expected to be effective.

Treat: As used herein, the term "treat," "treatment," or "treating" refers to any method used to partially or completely alleviate, ameliorate, relieve, inhibit, delay onset of, reduce severity of, and/or reduce incidence of one or more symptoms or features of a disease, disorder, and/or condition; in some embodiments, treatment prevents one or more symptoms of features of the disease, disorder, or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Unsaturated: The term "unsaturated," as used herein, means that a moiety has one or more units of unsaturation.

For purposes of this invention, the chemical elements are identified in accordance with the Periodic Table of the Elements, CAS version, *Handbook of Chemistry and Physics*, 67th Ed., 1986-87, inside cover.

The methods and structures described herein relating to compounds and compositions of the invention also apply to the pharmaceutically acceptable acid or base addition salts and all stereoisomeric forms of these compounds and compositions.

BRIEF DESCRIPTION OF THE DRAWING

FIGS. 3A-F. Mutant but not wild type SOD 1 aggregates in cells treated with the proteasome inhibitor MG132. Fluorescence micrographs of PC12 cells expressing YFP tagged wild type (WT), G93A mutant (G93A), and G85R mutant (G85R) SOD1 proteins (3A-C). The micrographs show the effects of treating cells with 200 nM MG132 for 24 hours (untreated cells are shown in insets on left, 3D-F, respectively). The wild type SOD1 expressing cells are unaffected while cells expressing mutant SOD 1 show large perinuclear aggregates.

FIGS. 5A-E. Automated detection of mutant SOD 1 aggregates. Left: compound microscope fluorescence micrographs of the same G85R SOD 1 cells using GFP filter set to image the SOD1-YFP aggregates (5A) and the TRITC filter set to image iT-WGA plasma membrane (5C). Right: Aggregate detection from the Cellomics Arrayscan 3.5 using spot detector software to image cells with Image-iT in channel 1 (5D) and SOD1-YFP aggregates in channel 2 (5E). Data are expressed (5B) as spot count (aggregates) per object (cell).

FIG. 24. Active arylsulfanyl pyrazolones

FIG. 25. Preliminary SAR of selected arylsulfanylpyrazolones.

FIG. 28. Kaplan-Meier survival curve for dose response using CMB-087229 in G93A SOD1 ALS mice. A 13.4% extension in survival at the highest dose (20 mg/kg) with significance at p<0.05 was observed.

FIG. 29. A schematic illustration of sub-structures of various AAP analogues, as can be considered in conjunction with certain embodiments of this invention.

FIG. 30. Comparison of ether (1) and secondary amine (2)-linked compounds of the prior art with a tertiary amine-linked compound of the present invention.

FIG. 31. AAP analogues with different substituents in the aromatic moiety, in accordance with certain non-limiting embodiments of this invention.

FIG. 32. AAP analogues with different N-substituents, in accordance with certain non-limiting embodiments of this invention.

FIG. 33. AAP analogues with different linkers, in accordance with certain non-limiting embodiments of this invention.

FIG. 34. AAP analogues with different pyrazolone substitutions, in accordance with certain non-limiting embodiments of this invention.

FIG. 35. Compound tautomerism, and a schematic illustration of HMBC, and NOE spectral results observed for compounds 3, 30, and 31.

FIG. 36. Various other AAP compounds, in accordance with certain non limiting embodiments of this invention.

DETAILED DESCRIPTION OF CERTAIN EMBODIMENTS OF THE INVENTION

Figure 1A:
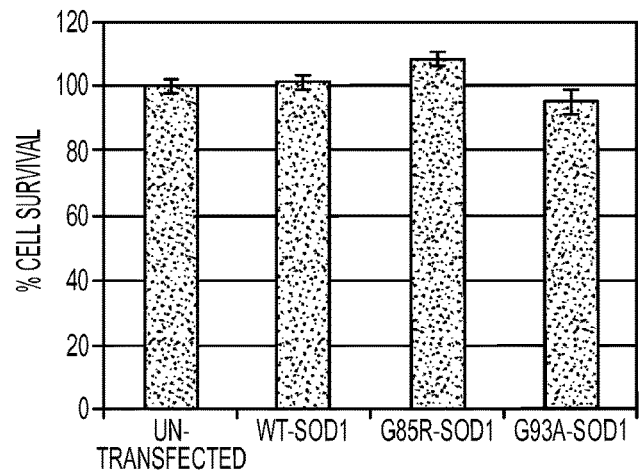
FIGS. 1A-C. Proteasome inhibition is selectively toxic to PC12 cells expressing mutant G93A SOD 1. Cell survival was determined using the viability stain calcein-AM. At 24 hours, treatment with 100 nM MG132 shows no toxicity against any of the cell lines although large numbers of aggregates are seen in the G85R SOD1 cell lines (1A). Treatment with 100 nM MG 132 is selectively toxic to the G93A SOD1 cell line after 48 hours (1B). Washing of the cells at 24 hours to remove the compound does not reverse toxicity to the G93A SOD 1 cell line suggesting that an irreversible toxic event, potentially related the aggregation of G93A SOD1, has been triggered prior to wash out (1C).

Imbalances in protein homeostasis are often associated with protein misfolding and/or protein conformational changes that lead to protein aggregation and formation of protein inclusion bodies. Many neurodegenerative diseases, including the polyglutamine (polyQ)-repeat diseases, Alzheimer's disease, Parkinson's disease, prion diseases, and ALS, are characterized by the appearance of damaged and aggregated proteins, including huntingtin, polyQ proteins, amyloid A prion (PrP and Sup35) fibrils, and mutant SOD1 (Taylor et al., Science 2002, 296(5575), 1991-1995; Ross, C. A., Neuron. 1997, 19(6), 1147-1150; Perutz, M. F., Brain Res. Bull. 1999, 50(5-6), 467; and Kopito et al., Nat. Cell Bio. 2000, 2(11), E207-E209). The fact that such diverse proteins form aggregates in patients with distinct neurological diseases suggests that a common molecular etiology may contribute to the neuropathology in these diseases and that, perhaps, protein misfolding and the subsequent appearance of protein aggregates are early events that play a role in neuronal toxicity in multiple human neurological diseases (Orr H. T., Genes. Dev. 2001, 15(8), 925-932; Ikeda et al., Nat. Genet 1996, 13(2), 196-202; DiFiglia et al., Science 1997, 277(5334), 1990-1993; Davies et al., Cell 1997, 90(3), 537-548; and Koo et al., Proc. Natl. Acad. Sci. USA. 1999, 96(18), 9989-9990).

One model for the molecular basis of these neurodegenerative diseases is that insoluble protein aggregates associate and interfere with the activity of other critical soluble cellular proteins, and that loss of function of these diverse proteins has serious negative consequences on cellular function. Affected proteins could include ubiquitin, components of the proteasome, components of the cytoskeleton, transcription factors (TBP (i.e., TATA binding protein), EYA (i.e., Eyes Absent protein), CBP (i.e., CREB binding protein), and molecular chaperones Hsc-70, Hsp-70, Hdj-1, and Hdj-2 (Davies et al., *Cell* 1997, 90(3), 537-548; Ross, C. A., *Neuron.* 2002, 35(5), 819-822; Cummings et al., *Nat. Genet.* 1998, 19(2) 148-154; Perez et al., *J. Cell Biol.* 1998, 143(6), 1457-1470; Kazantsev et al., *Proc. Natl. Acad. Sci. USA.* 1999, 96(20), 11404-11409; Jana et al., *Hum. Mol. Genet.* 2001, 10(10), 1049-1059; Nucifora et al., *Science* 2001, 291(5512) 2423-2428; and Suhr et al., *J. Cell Biol.* 2001, 153(2), 283-294). Recent studies showed that TBP and CBP are irreversibly sequestered in polyQ/huntington aggregates, while the chaperone Hsp70 is transiently associated with the surface (Chai et al., *Proc. Natl. Acad. Sci. USA.* 2002, 99(14), 9310-9315; Kim et al., *Nat. Cell. Biol.* 2002, 4(10), 826-31). Sequestration of CBP into polyglutamine aggregates is linked directly with loss of cellular function in neuronal cells, and overexpression of CBP suppressed polyQ toxicity (Nucifora et al., *Science* 2001, 291(5512) 2423-2428). Furthermore, expression of polyglutamine proteins in *C. elegans* causes other metastable proteins to lose function. Thus, a single aggregation-prone protein may be able to destabilize protein homeostasis in otherwise normal cells (Gidalevitz et al., *Science* 2006, 311(5766) 1471-1474). These studies indicate that the sequestration of essential soluble cellular proteins in insoluble protein aggregates could play a significant role in the neuropathology and neurotoxicity in ALS and related diseases.

It is also possible that the cellular mechanism(s) that remove misfolded or damaged proteins (Morimoto, R. I., *Cell* 2002, 110(3), 281-284; Horwich et al., *Cell* 1997, 89(4), 499-510; and Nollen et al., *J. Cell. Sci.* 2002, 115(Pt 14) 2809-2816) are overwhelmed in neurodegenerative diseases due to the presence of abundant protein aggregates. The activity of molecular chaperones is one of the most important mechanisms to prevent and/or rescue protein misfolding and aggregation. Molecular chaperones are a large and diverse protein family which includes Hsp104, Hsp90, Hsp70, dnaJ (Hsp40), immunophilins (Cyp40, FKBP), Hsp60 (chapemnins), the small heat shock proteins, and components of the steroid aporeceptor complex (p23, Hip, Hop, Bag1) (Gething, M. J., *Nature* 1997, 388(6640) 329-331; Bakau, B., Amsterdam: Harwood Academic Publishers. 1999, 690). They ensure proper protein folding by preventing hydrophobic surfaces from interacting with each other, by enhancing protein refolding, and, when necessary, by stimulating protein degradation to remove misfolded proteins that tend to aggregate (Horwich et al., *Cell* 1997, 89(4), 499-510; Bakau, B., Amsterdam: Harwood Academic Publishers. 1999, 690; Schroder et al., *Embo. J.* 1993, 12(11), 4137-4144; Parsell et al., *Nature* 1994, 372(6505), 475-478; Hartl, F. U., *Nature* 1996, 381(6583) 571-579; and Morimoto et al., *Nat. Biotechnol.* 1998, 16(9), 833-838). Accordingly, overexpression of molecular chaperones can suppress the toxicity of mutant huntingtin, α-synuclein, and SOD1 (Sakahira et al., *Proc. Natl. Acad. Sci. USA.* 2002, 99 Suppl 4, 6412-6418: Stenoien et al., *Hum. Mol. Genet.* 1999, 8(5), 731-741; Warrick et al., *Nat. Genet.* 1999, 23(4), 425-428; Carmichael et al., *Proc. Natl. Acad. Sci. USA.* 2000, 97(17), 9701-9705; Takeuchi et al., *Brain Res.* 2002, 949(1-2), 11-22; Auluck et al., *Science* 2002, 295 (5556), 865-868; and Bailey et al., *Hum. Mol. Genet.* 2002, 11(5), 515-523). Recently, non-chaperone proteins were identified that also suppress toxicity associated with protein aggregation (Kazemi-Esfarjani et al., *Science* 2000, 287(5459) 1837-1840; and Kazemi-Esfarjani et al., *Hum. Mol. Genet.* 2002, 11(21), 2657-2672).

The chaperone system is a highly appealing therapeutic target, because multiple small molecular weight modulators of chaperone activity have already been identified, two of which are active in a mouse model of ALS (Westerheide et al., *J. Biol. Chem.* 2005, 280(39), 33097-33100; Kieran et al., *Nat. Med.* 2004, 10(4), 402-405; and Traynor et al., *Neurology* 2006, 67(1), 20-27). Accordingly, recent analyses identified protein folding/misfolding and protein aggregation as a relevant therapeutic target for neurodegenerative diseases (Pasinelli et al., *Nat. Rev. Neurosci.* 2006, 7(9), 710-723; Lansbury et al., *Nature* 2006, 443(7113), 774-9; Rubinsztein et al., *Nature* 2006, 443(7113), 780-786).

Provided Compounds

The present invention provides compounds and methods for treating patients with amyotrophic lateral sclerosis (ALS) or other neurodegenerative diseases characterized by the presence of aberrant protein aggregates. Without wishing to be bound by any particular theory or mechanism of action, compounds and methods of the invention are useful in inhibiting or reversing abnormal protein aggregation or reducing the toxicity of protein aggregation (e.g., SOD1). In certain embodiments, provided compounds are useful in modulating proteosome function. The invention provides methods for treating a subject with ALS or other neurodegenerative disease including the step of administering to the subject a therapeutically effective amount of an inventive compound or a pharmaceutical composition thereof. In certain embodiments, the subject is a mammal.

In one aspect, the present invention provides compounds of the formula:

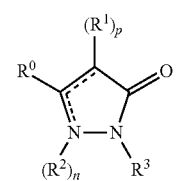
I or a pharmaceutically acceptable salt thereof, wherein:
p is 1-2;
⸺ designates a single or double bond, wherein one ⸺ is a single bond and one ⸺ is a double bond;
each $R^1$ is independently —R, —OR, —SR, —S(O)R, —$SO_2$R, —$OSO_2$R, —N(R)$_2$, —CN, —$NO_2$—NRC(O)R, —NRC(O)(CO)R, —NRC(O)N(R)$_2$, —NRC(O)OR, —N(R)S(O)R, —N(R)$SO_2$R, —N(R)$SO_2$OR, —C(O)R, —C(O)OR, —OC(O)R, —OC(O)OR, —C(O)N(R)$_2$, —OC(O)N(R)$_2$, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur, or
two $R^1$ groups are taken together to form

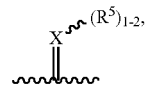

wherein:
X is N or C;
each $R^5$ is independently —R, —OR, —SR, —S(O)R, —$SO_2$R, —$OSO_2$R, —N(R)$_2$, —CN, —$NO_2$—NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or a 3-8 membered saturated, partially unsaturated, or aryl monocyclic ring having 0-4 heteroatoms independently selected from nitrogen, oxygen, or sulfur, or an 8-10 membered saturated, partially unsaturated, or aryl bicyclic ring having 0-4 heteroatoms independently selected from nitrogen, oxygen, or sulfur, wherein R$^5$ is optionally substituted with 1-5 R groups;

each R is independently hydrogen, halogen, optionally substituted C$_{1-20}$ aliphatic, optionally substituted C$_{1-20}$ heteroaliphatic, optionally substituted phenyl, or optionally substituted arylalkyl, or two R on the same nitrogen are taken together to form a 5-6 membered saturated, partially saturated, or aryl ring having 1-3 heteroatoms independently selected from nitrogen, oxygen, and sulfur, or two R on the same carbon or on adjacent carbons are optionally taken together to form a 3-6 membered saturated cycloalkyl or fused monocyclic ring containing 0-2 heteroatoms independently selected from nitrogen, oxygen, and sulfur;

n is 0-1;

each R$^2$ and R$^3$ are independently —R, —OR, —SR, —S(O)R, —SO$_2$R, —OSO$_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur;

R$^0$ is R, —OR, —SR, —S(O)R, —SO$_2$R, —OSO$_2$R, N(R)$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or

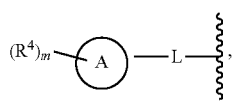

wherein:

L is a valence bond or a bivalent saturated or partially unsaturated C$_{1-10}$ hydrocarbon chain, wherein 1-4 methylene units of L are optionally and independently replaced by —O—, —S—, —C(O)—, —OC(O)—, —C(O)O—, —OC(O)O—, —S(O)—, —S(O)$_2$—, —OSO$_2$O—, —N(R)C(O)—, —C(O)NR—, —N(R)C(O)O—, —OC(O)NR—, —N(R)C(O)NR—, —N(R$^6$)—, or -Cy-, and wherein L is optionally substituted with 1-4 R groups; wherein:

each -Cy- is independently a bivalent optionally substituted saturated, partially unsaturated, or aromatic monocyclic or bicyclic ring selected from a 6-10 membered arylene, a 5-10 membered heteroarylene having 1-4 heteroatoms independently selected from oxygen, nitrogen, or sulfur, a 3-8 membered carbocyclylene, or a 3-10 membered heterocyclylene having 1-4 heteroatoms independently selected from oxygen, nitrogen, or sulfur;

R$^6$ is —R, —OR, —SR, —S(O)R, —SO$_2$R, —OSO$_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur;

Ring A is a 3-8 membered saturated, partially unsaturated, or aryl monocyclic ring optionally containing 0-4 heteroatoms independently selected from nitrogen, oxygen, or sulfur, or an 8-10 membered saturated, partially unsaturated, or aryl bicyclic ring optionally containing 0-4 heteroatoms independently selected from nitrogen, oxygen, or sulfur, and wherein Ring A is optionally substituted with m occurrences of R$^4$; m is 0-5; and each R$^4$ is independently —R, —OR, —SR, —CN, —S(O)R, —SO$_2$R, —OSO$_2$R, —N(R)$_2$, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or a 3-8 membered saturated, partially unsaturated, or aryl monocyclic ring optionally containing 0-4 heteroatoms independently selected from nitrogen, oxygen, or sulfur.

In certain embodiments, n is 0. In certain embodiments, n is 1.

In certain embodiments, p is 1. In certain embodiments, p is 2.

As described above and herein, ⸺ designates a single or double bond. It will be understood by one of ordinary skill in the art that when one ⸺ designates a double bond between two carbons to provide a compound of formula Ia:

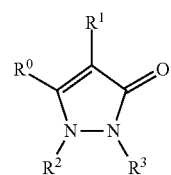

Ia then n is 1 and p is 1. Similarly, when ⸺ designates a double bond between a carbon and a ⸺ nitrogen to provide a compound of formula Ib:

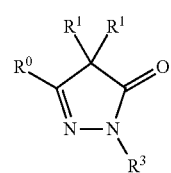

Ib then n is 0 and p is 1 or 2, depending on the tautomeric form of 1b, e.g., in compounds of formula 1b wherein at least one R$^1$ is hydrogen, provided compounds may exist in any tautomeric form available. One such exemplary pair of tautomers is as shown below:

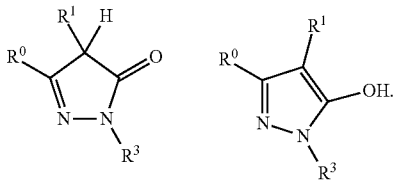

As defined generally above, each $R^1$ is independently —R, —OR, —SR, —S(O)R, —SO$_2$R, —OSO$_2$R, —N(R)$_2$, —CN, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur; or two $R^1$ groups are taken together to form

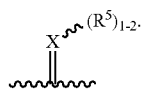

In some embodiments, each $R^1$ is independently —R, —OR, —SR, —S(O)R, —SO$_2$R, —OSO$_2$R, N(R)$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, or —OC(O)N(R)$_2$.

In some embodiments, at least one $R^1$ is optionally substituted 3-8 membered saturated monocyclic ring having 0-4 heteroatoms independently selected from nitrogen, oxygen, or sulfur. In some embodiments, at least one $R^1$ is an optionally substituted 3-6 membered saturated monocyclic ring having 0-2 heteroatoms independently selected from nitrogen, oxygen, or sulfur. In some embodiments, at least one $R^1$ is an optionally substituted 5-6 membered saturated monocyclic ring having 0-2 heteroatoms independently selected from nitrogen, oxygen, or sulfur.

In some embodiments, at least one $R^1$ is an optionally substituted 3-8 membered partially unsaturated monocyclic ring having 0-4 heteroatoms independently selected from nitrogen, oxygen, or sulfur. In some embodiments, at least one $R^1$ is an optionally substituted 3-6 membered partially unsaturated monocyclic ring having 0-2 heteroatoms independently selected from nitrogen, oxygen, or sulfur. In some embodiments, at least one $R^1$ is an optionally substituted 5-6 membered partially unsaturated monocyclic ring having 0-2 heteroatoms independently selected from nitrogen, oxygen, or sulfur.

In some embodiments, at least one $R^1$ is an optionally substituted 5-6 membered aryl ring having 0-4 heteroatoms independently selected from nitrogen, oxygen, or sulfur. In some embodiments, at least one $R^1$ is an optionally substituted 5-6 membered aryl ring having 0-2 heteroatoms independently selected from nitrogen, oxygen, or sulfur. In some embodiments, at least one $R^1$ is an optionally substituted 5 membered aryl ring having 1-3 heteroatoms independently selected from nitrogen, oxygen, or sulfur. In some embodiments, at least one $R^1$ is an optionally substituted 6 membered aryl ring having 1-3 nitrogens. In some embodiments, at least one $R^1$ is an optionally substituted phenyl. In certain embodiments, at least one $R^1$ is unsubstituted phenyl.

In some embodiments, at least one $R^1$ is an optionally substituted 8-10 membered saturated bicyclic ring having 0-4 heteroatoms independently selected from nitrogen, oxygen, or sulfur. In some embodiments, at least one $R^1$ is an optionally substituted 8-10 membered saturated bicyclic ring having 0-2 heteroatoms independently selected from nitrogen, oxygen, or sulfur. In some embodiments, at least one $R^1$ is an optionally substituted 8-10 membered saturated bicyclic carbocycle.

In some embodiments, at least one $R^1$ is an optionally substituted 8-10 membered partially unsaturated bicyclic ring having 0-4 heteroatoms independently selected from nitrogen, oxygen, or sulfur. In some embodiments, at least one $R^1$ is an optionally substituted 8-10 membered partially unsaturated bicyclic ring having 0-2 heteroatoms independently selected from nitrogen, oxygen, or sulfur. In some embodiments, at least one $R^1$ is an optionally substituted 8-10 membered partially unsaturated carbocycle.

In some embodiments, at least one $R^1$ is an optionally substituted 9-10 membered aryl ring having 0-4 heteroatoms independently selected from nitrogen, oxygen, or sulfur. In some embodiments, at least one $R^1$ is an optionally substituted 9-10 membered aryl ring having 0-2 heteroatoms independently selected from nitrogen, oxygen, or sulfur. In some embodiments, at least one $R^1$ is an optionally substituted 9 membered aryl ring having 1-3 heteroatoms independently selected from nitrogen, oxygen, or sulfur. In some embodiments, at least one $R^1$ is an optionally substituted 10 membered aryl ring having 1-3 heteroatoms independently selected from nitrogen, oxygen, or sulfur. In some embodiments, at least one $R^1$ is optionally substituted naphthyl.

In some embodiments, two $R^1$ are taken together to form

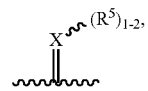

wherein X is N or C. In certain embodiments wherein X is N, one $R^5$ group is present. In certain embodiments wherein X is C, either one or two $R^5$ groups may be present. In certain embodiments, two $R^1$ are taken together to form any one of the following formulae:

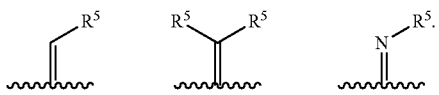

In some embodiments, each $R^5$ is independently —R, —OR, —SR, —S(O)R, —SO$_2$R, —OSO$_2$R, —N(R)$_2$, —CN, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$. In some embodiments, at least one $R^5$ is a 3-8 membered saturated, partially unsaturated, or aryl monocyclic ring having 0-4 heteroatoms independently selected from nitrogen, oxygen, or sulfur, or an 8-10 membered saturated, partially unsaturated, or aryl bicyclic ring having 0-4 heteroatoms independently selected from nitrogen, oxygen, or sulfur, wherein $R^5$ is optionally substituted with 1-5 R groups.

As defined generally above and herein, $R^2$ is independently —R, —OR, —SR, —S(O)R, —SO$_2$R, —OSO$_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur.

In some embodiments, $R^2$ is —R, —OR, —SR, —N(R)$_2$, or a suitable amino protecting group. In certain embodiments, $R^2$ is halogen or R. In certain embodiments, $R^2$ is hydrogen, methyl, ethyl, propyl, or butyl. In certain embodiments, $R^2$ is hydrogen. In certain embodiments, $R^2$ is methyl.

In some embodiments, $R^2$ is an optionally substituted 3-8 membered saturated monocyclic ring having 0-4 heteroatoms independently selected from nitrogen, oxygen, or sulfur. In some embodiments, $R^2$ is an optionally substituted 3-6 membered saturated monocyclic ring having 0-2 heteroatoms independently selected from nitrogen, oxygen, or sulfur. In some embodiments, $R^2$ is an optionally substituted 5-6 membered saturated monocyclic ring having 0-2 heteroatoms independently selected from nitrogen, oxygen, or sulfur.

In some embodiments, $R^2$ is an optionally substituted 3-8 membered partially unsaturated monocyclic ring having 0-4 heteroatoms independently selected from nitrogen, oxygen, or sulfur. In some embodiments, $R^2$ is an optionally substituted 3-6 membered partially unsaturated monocyclic ring having 0-2 heteroatoms independently selected from nitrogen, oxygen, or sulfur. In some embodiments, $R^2$ is an optionally substituted 5-6 membered partially unsaturated monocyclic ring having 0-2 heteroatoms independently selected from nitrogen, oxygen, or sulfur.

In some embodiments, $R^2$ is an optionally substituted 5-6 membered aryl ring having 0-4 heteroatoms independently selected from nitrogen, oxygen, or sulfur. In some embodiments, $R^2$ is an optionally substituted 5-6 membered aryl ring having 0-2 heteroatoms independently selected from nitrogen, oxygen, or sulfur. In some embodiments, $R^2$ is an optionally substituted 5 membered aryl ring having 1-3 heteroatoms independently selected from nitrogen, oxygen, or sulfur. In some embodiments, $R^2$ is an optionally substituted 6 membered aryl ring having 1-3 nitrogens. In some embodiments, $R^1$ is an optionally substituted phenyl. In certain embodiments, $R^2$ is unsubstituted phenyl.

In some embodiments, $R^2$ is an optionally substituted 8-10 membered saturated bicyclic ring having 0-4 heteroatoms independently selected from nitrogen, oxygen, or sulfur. In some embodiments, $R^2$ is an optionally substituted 8-10 membered saturated bicyclic ring having 0-2 heteroatoms independently selected from nitrogen, oxygen, or sulfur. In some embodiments, $R^2$ is an optionally substituted 8-10 membered saturated bicyclic carbocycle.

In some embodiments, $R^2$ is an optionally substituted 8-10 membered partially unsaturated bicyclic ring having 0-4 heteroatoms independently selected from nitrogen, oxygen, or sulfur. In some embodiments, $R^1$ is an optionally substituted 8-10 membered partially unsaturated bicyclic ring having 0-2 heteroatoms independently selected from nitrogen, oxygen, or sulfur. In some embodiments, $R^2$ is an optionally substituted 8-10 membered partially unsaturated carbocycle.

In some embodiments, $R^2$ is an optionally substituted 9-10 membered aryl ring having 0-4 heteroatoms independently selected from nitrogen, oxygen, or sulfur. In some embodiments, $R^2$ is an optionally substituted 9-10 membered aryl ring having 0-2 heteroatoms independently selected from nitrogen, oxygen, or sulfur. In some embodiments, $R^2$ is an optionally substituted 9 membered aryl ring having 1-3 heteroatoms independently selected from nitrogen, oxygen, or sulfur. In some embodiments, $R^2$ is an optionally substituted 10 membered aryl ring having 1-3 heteroatoms independently selected from nitrogen, oxygen, or sulfur. In some embodiments, $R^2$ is optionally substituted naphthyl.

Exemplary optionally substituted $R^2$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl.

As defined generally above and herein, $R^3$ is independently —R, —OR, —SR, —S(O)R, —SO$_2$R, —OSO$_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur.

In some embodiments, $R^3$ is —R, —OR, —SR, —N(R)$_2$, or a suitable amino protecting group. In certain embodiments, $R^3$ is halogen or R. In certain embodiments, $R^3$ is hydrogen, methyl, ethyl, propyl, or butyl. In certain embodiments, $R^3$ is hydrogen. In certain embodiments, $R^3$ is methyl.

In some embodiments, $R^3$ is an optionally substituted 3-8 membered saturated monocyclic ring having 0-4 heteroatoms independently selected from nitrogen, oxygen, or sulfur. In some embodiments, $R^3$ is an optionally substituted 3-6 membered saturated monocyclic ring having 0-2 heteroatoms independently selected from nitrogen, oxygen, or sulfur. In some embodiments, $R^3$ is an optionally substituted 5-6 membered saturated monocyclic ring having 0-2 heteroatoms independently selected from nitrogen, oxygen, or sulfur.

In some embodiments, $R^3$ is an optionally substituted 3-8 membered partially unsaturated monocyclic ring having 0-4 heteroatoms independently selected from nitrogen, oxygen, or sulfur. In some embodiments, $R^3$ is an optionally substituted 3-6 membered partially unsaturated monocyclic ring having 0-2 heteroatoms independently selected from nitrogen, oxygen, or sulfur. In some embodiments, $R^3$ is an optionally substituted 5-6 membered partially unsaturated monocyclic ring having 0-2 heteroatoms independently selected from nitrogen, oxygen, or sulfur.

In some embodiments, $R^3$ is an optionally substituted 5-6 membered aryl ring having 0-4 heteroatoms independently selected from nitrogen, oxygen, or sulfur. In some embodiments, $R^3$ is an optionally substituted 5-6 membered aryl ring having 0-2 heteroatoms independently selected from nitrogen, oxygen, or sulfur. In some embodiments, $R^3$ is an optionally substituted 5 membered aryl ring having 1-3 heteroatoms independently selected from nitrogen, oxygen, or sulfur. In some embodiments, $R^3$ is an optionally substituted 6 membered aryl ring having 1-3 nitrogens. In some embodiments, $R^3$ is an optionally substituted phenyl. In certain embodiments, $R^3$ is unsubstituted phenyl.

In some embodiments, $R^3$ is an optionally substituted 8-10 membered saturated bicyclic ring having 0-4 heteroatoms independently selected from nitrogen, oxygen, or sulfur. In some embodiments, $R^3$ is an optionally substituted 8-10 membered saturated bicyclic ring having 0-2 heteroatoms independently selected from nitrogen, oxygen, or sulfur. In some embodiments, $R^3$ is an optionally substituted 8-10 membered saturated bicyclic carbocycle.

In some embodiments, $R^3$ is an optionally substituted 8-10 membered partially unsaturated bicyclic ring having 0-4 heteroatoms independently selected from nitrogen, oxygen, or sulfur. In some embodiments, $R^3$ is an optionally substituted 8-10 membered partially unsaturated bicyclic ring having 0-2 heteroatoms independently selected from nitrogen, oxygen, or sulfur. In some embodiments, $R^3$ is an optionally substituted 8-10 membered partially unsaturated carbocycle.

In some embodiments, $R^3$ is an optionally substituted 9-10 membered aryl ring having 0-4 heteroatoms independently selected from nitrogen, oxygen, or sulfur. In some embodiments, $R^3$ is an optionally substituted 9-10 membered aryl ring having 0-2 heteroatoms independently selected from nitrogen, oxygen, or sulfur. In some embodiments, $R^3$ is an optionally substituted 9 membered aryl ring having 1-3 heteroatoms independently selected from nitrogen, oxygen, or sulfur. In some embodiments, $R^3$ is an optionally substituted 10 membered aryl ring having 1-3 heteroatoms independently selected from nitrogen, oxygen, or sulfur. In some embodiments, $R^3$ is optionally substituted naphthyl.

Exemplary optionally substituted $R^3$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl.

In certain embodiments, $R^3$ is of any one of the following formulae:

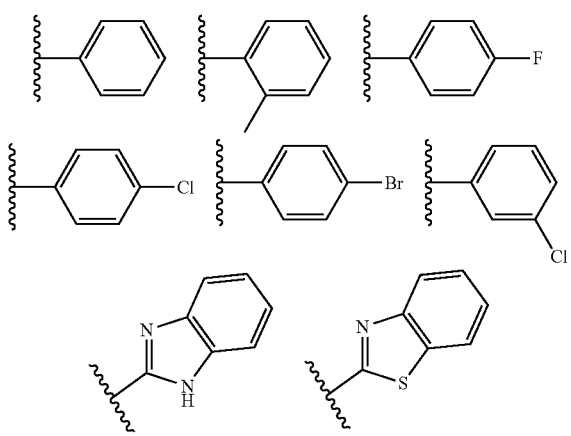

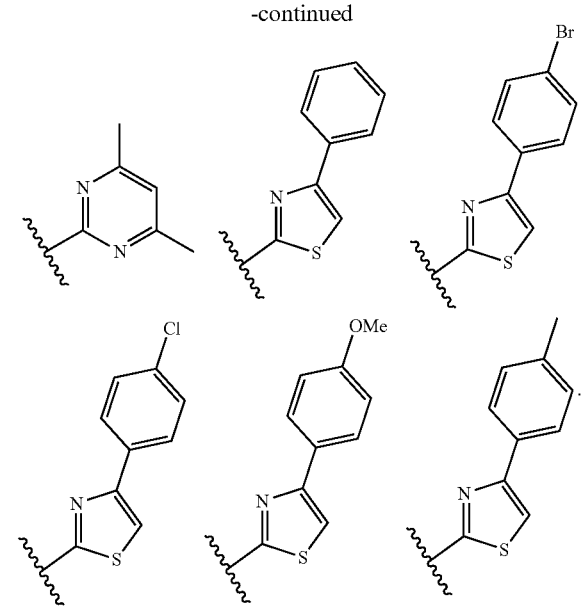

As described generally above and herein. $R^0$ is —R —OR, —SR. —S(O)R, —SO$_2$R, —OSO$_2$R, —N(R)$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, —OC(O)N(R)$_2$, or

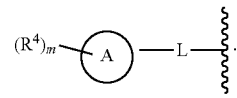

In some embodiments, $R^0$ is R, wherein R is hydrogen, optionally substituted $C_{1-6}$ aliphatic, optionally substituted $C_{1-6}$ heteroaliphatic, or optionally substituted phenyl. In certain embodiments, $R^0$ is methyl, ethyl, propyl, or butyl.

In some embodiments, $R^0$ is

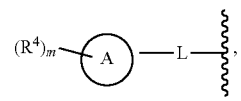

wherein $R^4$, m, and Ring A are as defined above and L is a valence bond. In some embodiments, $R^0$ is

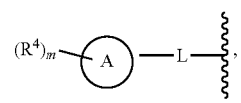

wherein $R^4$, m, and Ring A are as defined above and L is not a valence bond.

As defined generally above, L is a valence bond or a bivalent saturated or partially unsaturated $C_{1-10}$ hydrocarbon chain, wherein 1-4 methylene units of L are optionally and independently replaced by —O—, —S—, —C(O)—, —OC(O)—, —C(O)O—, —OC(O)O—, —S(O)—, —S(O)$_2$—, —OSO$_2$O—, —N(R)C(O)—, —C(O)NR—, —N(R)C(O)

O—, —OC(O)NR—, —N(R)C(O)NR—, —N($R^6$)—, or -Cy-, and wherein L is optionally substituted with 1-4 R groups; wherein:
  each -Cy- is independently a bivalent optionally substituted saturated, partially unsaturated, or aromatic monocyclic or bicyclic ring selected from a 6-10 membered arylene, a 5-10 membered heteroarylene having 1-4 heteroatoms independently selected from oxygen, nitrogen, or sulfur, a 3-8 membered carbocyclylene, or a 3-10 membered heterocyclylene having 1-4 heteroatoms independently selected from oxygen, nitrogen, or sulfur;
  $R^6$ is —R, —OR, —SR, —S(O)R, —$SO_2$R, —$OSO_2$R, —C(O)R, —C(O)OR, —OC(O)R, —OC(O)OR, —C(O)N(R)$_2$, —OC(O)N(R)$_2$, a suitable amino protecting group, or an optionally substituted 3-8 membered saturated, partially unsaturated, or aryl monocyclic ring having 0-4 heteroatoms independently selected from nitrogen, oxygen, or sulfur, or an optionally substituted 8-10 membered saturated, partially unsaturated, or aryl bicyclic ring having 0-4 heteroatoms independently selected from nitrogen, oxygen, or sulfur.

In some embodiments, L a bivalent saturated or partially unsaturated $C_{1-10}$ hydrocarbon chain, wherein 1-4 methylene units of L are optionally and independently replaced by —O—, —N($R^6$)—, —S—, —C(O)—, —OC(O)—, —C(O)O—, —OC(O)O—, —S(O)—, —S(O)$_2$—, —$OSO_2$O—, —N(R)C(O)—, —C(O)NR—, —N(R)C(O)O—, —OC(O)NR—, —N(R)C(O)NR—, and wherein L is optionally substituted with 1-4 R groups. In some embodiments, L a bivalent saturated or partially unsaturated $C_{2-7}$ hydrocarbon chain, wherein 1-3 methylene units of L are optionally and independently replaced by —N($R^6$)—, —N(R)C(O)—, —C(O)N(R)—, —O—, —C(O)—, —OC(O)—, —C(O)O—, —S—, —S(O)— or —$SO_2$—, and wherein L is optionally substituted with 1-4 R groups. In some embodiments, L is a bivalent saturated $C_{2-7}$ hydrocarbon chain, wherein one or more methylene units of L is replaced by —N($R^6$)—, —N(R)C(O)—, —C(O)N(R)—. In some embodiments, L is a bivalent saturated $C_{2-7}$ hydrocarbon chain, wherein one or more methylene units of L is replaced by —O—, —C(O)—, —OC(O)—, or —C(O)O—. In some embodiments, L is a bivalent saturated $C_{2-7}$ hydrocarbon chain, wherein one or more methylene units of L is replaced by —S—, —S(O)— or —$SO_2$—.

In certain embodiments, L is of any of the following formulae:

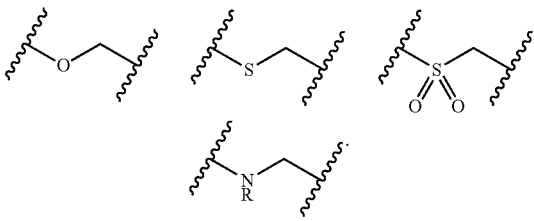

In certain embodiments, L is of any of the following formulae:

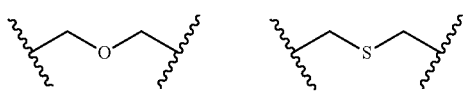

In certain embodiments, L is of any of the following formulae:

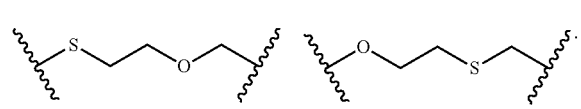 [SMILES: *COCCS* ; *CSCCO*]

In some embodiments, L is a bivalent saturated $C_{1-10}$ hydrocarbon chain, wherein one or more methylene unit is independently replaced by -Cy-, and wherein one or more -Cy- is independently a bivalent optionally substituted saturated monocyclic ring. In some embodiments, one or more -Cy- is independently a bivalent optionally substituted partially unsaturated monocyclic ring. In some embodiments, one or more -Cy- is independently a bivalent optionally substituted aromatic monocyclic ring. In certain embodiments, -Cy- is optionally substituted phenylene.

In some embodiments, one or more -Cy- is independently a bivalent optionally substituted saturated bicyclic ring. In some embodiments, one or more -Cy- is independently a bivalent optionally substituted partially unsaturated bicyclic ring. In some embodiments, one or more -Cy- is independently a bivalent optionally substituted aromatic bicyclic ring. In certain embodiments, -Cy- is optionally substituted naphthylene.

In some embodiments, one or more -Cy- is independently an optionally substituted 6-10 membered arylene. In some embodiments, one or more -Cy- is independently an optionally substituted a 5-10 membered heteroarylene having 1-4 heteroatoms independently selected from oxygen, nitrogen, or sulfur. In some embodiments, one or more -Cy- is independently an optionally substituted a 5-6 membered heteroarylene having 1-4 heteroatoms independently selected from oxygen, nitrogen, or sulfur. In some embodiments, one or more -Cy- is independently an optionally substituted 5 membered heteroarylene having 1-4 heteroatoms independently selected from oxygen, nitrogen, or sulfur. In some embodiments, one or more Cy- is independently an optionally substituted 6 membered heteroarylene having 1-4 heteroatoms independently selected from oxygen, nitrogen, or sulfur.

Exemplary optionally substituted -Cy- heteroarylene groups include thienylene, furanylene, pyrrolylene, imidazolylene, pyrazolylene, triazolylene, tetrazolylene, oxazolylene, isoxazolylene, oxadiazolylene, thiazolylene, isothiazolylene, thiadiazolylene, pyridylene, pyridazinylene, pyrimidinylene, pyrazinylene, indolizinylene, purinylene, naphthyridinylene, pteridinylene, indolylene, isoindolylene, benzothienylene, benzofuranylene, dibenzofuranylene, indazolylene, benzimidazolylene, benzthiazolylene, quinolylene, isoquinolylene, cinnolinylene, phthalazinylene, quinazolinylene, quinoxalinylene, 4H-quinolizinylene, carbazolylene, acridinylene, phenazinylene, phenothiazinylene, phenoxazinylene, tetrahydroquinolinylene, tetrahydroisoquinolinylene, pyrido[2,3-b]-1,4-oxazin-3(4H)-onylene, and chromanylene.

In certain embodiments, -Cy- is selected from the group consisting of tetrahydropyranylene, tetrahydrofuranylene, morpholinylene, thiomorpholinylene, piperidinylene, piperazinylene, pyrrolidinylene, tetrahydrothiophenylene, and tetrahydrothiopyranylene, wherein each ring is optionally substituted.

In some embodiments, one or more -Cy- is independently an optionally substituted 3-8 membered carbocyclylene. In some embodiments, one or more -Cy- is independently an optionally substituted 3-6 membered carbocyclylene. In some embodiments, one or more -Cy- is independently an optionally substituted cyclopropylene, cyclopentylene, or cyclohexylene.

In some embodiments, one or more -Cy- is independently an optionally substituted 3-10 membered heterocyclylene having 1-4 heteroatoms independently selected from oxygen, nitrogen, or sulfur. In some embodiments, one or more -Cy- is independently an optionally substituted 5-7 membered heterocyclylene having 1-3 heteroatoms independently selected from oxygen, nitrogen, or sulfur. In some embodiments, one or more -Cy- is independently an optionally substituted 3 membered heterocyclylene having 1 heteroatom independently selected from oxygen, nitrogen, or sulfur. In some embodiments, one or more -Cy- is independently an optionally substituted 5 membered heterocyclylene having 1-2 heteroatoms independently selected from oxygen, nitrogen, or sulfur. In some embodiments, one or more -Cy- is independently an optionally substituted 6 membered heterocyclylene having 1-3 heteroatoms independently selected from oxygen, nitrogen, or sulfur.

Exemplary -Cy- saturated 3-8 membered optionally substituted heterocyclenes include oxiranylene, oxetanylene, tetrahydrofuranylene, tetrahydropyranylene, oxepaneylene, aziridineylene, azetidineylene, pyrrolidinylene, piperidinylene, azepanylene, thiiranylene, thietanylene, tetrahydrothiophenylene, tetrahydrothiopyranylene, thiepanylene, dioxolanylene, oxathiolanylene, oxazolidinylene, imidazolidinylene, thiazolidinylene, dithiolanylene, dioxanylene, morpholinylene, oxathianylene, piperazinylene, thiomorpholinylene, dithianylene, dioxepanylene, oxazepanylene, oxathiepanylene, dithiepanylene, diazepanylene, dihydrofuranonylene, tetrahydropyranonylene, oxepanonylene, pyrolidinonylene, piperidinonylene, azepanonylene, dihydrothiophenonylene, tetrahydrothiopyranonylene, thiepanonylene, oxazolidinonylene, oxazinanonylene, oxazepanonylene, dioxolanonylene, dioxanonylene, dioxepanonylene, oxathiolinonylene, oxathianonylene, oxathiepanonylene, thiazolidinonylene, thiazinanonylene, thiazepanonylene, imidazolidinonylene, tetrahydropyrimidinonylene, diazepanonylene, imidazolidinedionylene, oxazolidinedionylene, thiazolidinedionylene, dioxolanedionylene, oxathiolanedionylene, piperazinedionylene, morpholinedionylene, and thiomorpholinedionylene.

In some embodiments, $R^6$ is —R, —OR, —SR, —S(O)R, —SO$_2$R, —OSO$_2$R, —C(O)R, —C(O)OR, —OC(O)R, —OC(O)OR, —C(O)N(R)$_2$, or —OC(O)N(R)$_2$. In some embodiments, $R^1$ is a suitable amino protecting group. In certain embodiments. $R^6$ is —SO$_2$R. In some embodiments, $R^6$ is R. In some embodiments, $R^6$ is optionally substituted arylalkyl.

In some embodiments, $R^6$ is an optionally substituted 3-8 membered saturated monocyclic ring having 0-4 heteroatoms independently selected from nitrogen, oxygen, or sulfur. In some embodiments, $R^6$ is an optionally substituted 3-6 membered saturated monocyclic ring having 0-2 heteroatoms independently selected from nitrogen, oxygen, or sulfur. In some embodiments, $R^6$ is an optionally substituted 5-6 membered saturated monocyclic ring having 0-2 heteroatoms independently selected from nitrogen, oxygen, or sulfur.

In some embodiments, $R^6$ is an optionally substituted 3-8 membered partially unsaturated monocyclic ring having 0-4 heteroatoms independently selected from nitrogen, oxygen, or sulfur. In some embodiments, $R^6$ is an optionally substituted 3-6 membered partially unsaturated monocyclic ring having 0-2 heteroatoms independently selected from nitrogen, oxygen, or sulfur. In some embodiments, $R^6$ is an optionally substituted 5-6 membered partially unsaturated monocyclic ring having 0-2 heteroatoms independently selected from nitrogen, oxygen, or sulfur.

In some embodiments, $R^6$ is an optionally substituted 5-6 membered aryl ring having 0-4 heteroatoms independently selected from nitrogen, oxygen, or sulfur. In some embodiments, $R^6$ is an optionally substituted 5-6 membered aryl ring having 0-2 heteroatoms independently selected from nitrogen, oxygen, or sulfur. In some embodiments, $R^6$ is an optionally substituted 5 membered aryl ring having 1-3 heteroatoms independently selected from nitrogen, oxygen, or sulfur. In some embodiments, $R^6$ is an optionally substituted 6 membered aryl ring having 1-3 nitrogens. In some embodiments, $R^6$ is an optionally substituted phenyl. In certain embodiments, $R^6$ is unsubstituted phenyl.

In some embodiments, $R^6$ is an optionally substituted 8-10 membered saturated bicyclic ring having 0-4 heteroatoms independently selected from nitrogen, oxygen, or sulfur. In some embodiments, $R^6$ is an optionally substituted 8-10 membered saturated bicyclic ring having 0-2 heteroatoms independently selected from nitrogen, oxygen, or sulfur. In some embodiments, $R^6$ is an optionally substituted 8-10 membered saturated bicyclic carbocycle.

In some embodiments, $R^6$ is an optionally substituted 8-10 membered partially unsaturated bicyclic ring having 0-4 heteroatoms independently selected from nitrogen, oxygen, or sulfur. In some embodiments, $R^6$ is an optionally substituted 8-10 membered partially unsaturated bicyclic ring having 0-2 heteroatoms independently selected from nitrogen, oxygen, or sulfur. In some embodiments. $R^6$ is an optionally substituted 8-10 membered partially unsaturated carbocycle.

In some embodiments, $R^6$ is an optionally substituted 9-10 membered aryl ring having 0-4 heteroatoms independently selected from nitrogen, oxygen, or sulfur. In some embodiments, $R^6$ is an optionally substituted 9-10 membered aryl ring having 0-2 heteroatoms independently selected from nitrogen, oxygen, or sulfur. In some embodiments, $R^6$ is an optionally substituted 9 membered aryl ring having 1-3 heteroatoms independently selected from nitrogen, oxygen, or sulfur. In some embodiments, $R^6$ is an optionally substituted 10 membered aryl ring having 1-3 heteroatoms independently selected from nitrogen, oxygen, or sulfur. In some embodiments, $R^6$ is optionally substituted naphthyl.

Exemplary optionally substituted $R^6$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl.

In certain embodiments, L is a bivalent saturated $C_{2-7}$ hydrocarbon chain wherein two methylene units are replaced by —N($R^6$)—, —N(R)C(O)—, —C(O)N(R)—, —O—, —C(O)—, —OC(O)—, —C(O)O—, —S—, —S(O)— or —SO$_2$—. In certain embodiments, L is a bivalent saturated C$_{2-7}$ hydrocarbon chain wherein two methylene units are replaced by —O—, —S—, —S(O)—, or —SO$_2$—. In certain embodiments, L is a bivalent saturated C$_2$ hydrocarbon chain wherein at least one methylene unit is replaced by —N(R$^6$)—, —N(R)C(O)—, —C(O)N(R)—, —O—, —C(O)—, —OC(O)—, —C(O)O—, —S—, —S(O)— or —SO$_2$—. In certain embodiments, L is a bivalent saturated C$_2$ hydrocarbon chain wherein at least one methylene unit is replaced by —N(R$^6$)—, —O—, —S—, —S(O)—, or —SO$_2$—.

In certain embodiments, L is of any of the following formulae:

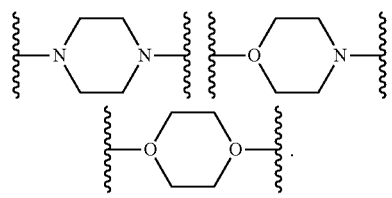

As described generally above and herein, Ring A is a 3-8 membered saturated, partially unsaturated, or aryl monocyclic ring optionally containing 0-4 heteroatoms independently selected from nitrogen, oxygen, or sulfur, or an 8-10 membered saturated, partially unsaturated, or aryl bicyclic ring optionally containing 0-4 heteroatoms independently selected from nitrogen, oxygen, or sulfur, and wherein Ring A is optionally substituted with m occurrences of R$^4$, wherein m is 0-5. In some embodiments, m is 0, 1, 2, or 3.

In certain embodiments, Ring A is phenyl substituted with 1-5 R$^4$ groups. In certain embodiments, Ring A is unsubstituted phenyl.

In certain embodiments, Ring A is naphthyl substituted with 1-5 R$^4$ groups. In certain embodiments, Ring A is unsubstituted naphthyl.

In some embodiments, Ring A is a 5-6 membered monocyclic saturated, partially unsaturated or aromatic heterocyclic ring having 1-4 heteroatoms independently selected from nitrogen, oxygen, or sulfur, and optionally substituted with 1-5 R$^4$ groups. In some embodiments, Ring A is a 5 membered monocyclic heteroaryl ring having 1-3 heteroatoms independently selected from nitrogen, oxygen, or sulfur, and optionally substituted with 1-2 R$^4$ groups. In other embodiments, Ring A is a 6 membered monocyclic heteroaryl ring having 1-2 nitrogens independently selected from nitrogen, oxygen, or sulfur, and optionally substituted with 1-2 R$^4$ groups.

In certain embodiments, Ring A is an 8-10 membered bicyclic ring having 0-4 heteroatoms independently selected from nitrogen, oxygen, or sulfur, and optionally substituted with 1-5 R$^4$ groups. In some embodiments, Ring A is an 8 membered bicyclic ring having 1-3 heteroatoms independently selected from nitrogen, oxygen, or sulfur, and optionally substituted with 1-3 R$^4$ groups. In some embodiments, Ring A is a 9 membered bicyclic ring having 1-3 heteroatoms independently selected from nitrogen, oxygen, or sulfur, and optionally substituted with 1-3 R$^4$ groups. In some embodiments, Ring A is a 10 membered bicyclic ring having 1-3 heteroatoms independently selected from nitrogen, oxygen, or sulfur, and optionally substituted with 1-3 R$^4$ groups.

In some embodiments, Ring A is an 8-10 membered bicyclic ring comprised of 0-2 aromatic rings and optionally substituted with 1-5 R$^4$ groups.

Exemplary Ring A heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl, wherein Ring A is optionally substituted with 1-5 R$^4$ groups.

As described generally above and herein, each R$^4$ is independently —R, —OR, —SR, —S(O)R. —SO$_2$R, —OSO$_2$R, —N(R)$_2$, —CN, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$. —OC(O)N(R)$_2$, or a 3-8 membered saturated, partially unsaturated, or aryl monocyclic ring optionally containing 0-4 heteroatoms independently selected from nitrogen, oxygen, or sulfur.

In some embodiments, at least one R$^1$ is independently —OR, —SR, —S(O)R, —SO$_2$R, —OSO$_2$R, N(R)$_2$, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, or —OC(O)N(R)$_2$. In certain embodiments, m is 1 and R$^4$ is —OR. In certain embodiments, m is 1 and R$^4$ is —OMe. In certain embodiments, m is 1 and R$^4$ is —NO$_2$. In certain embodiments, m is 1 and R$^4$ is —NR$_2$. In certain embodiments, m is 1 and R$^4$ is —NMe$_2$.

In some embodiments, at least one R$^4$ is independently a 3-8 membered saturated, partially unsaturated, or aryl monocyclic ring optionally containing 0-4 heteroatoms independently selected from nitrogen, oxygen, or sulfur.

In some embodiments, at least one R$^4$ is independently a 3-6 membered saturated monocyclic ring optionally containing 0-1 heteroatoms independently selected from nitrogen, oxygen, or sulfur. In some embodiments, at least one R$^4$ is independently a 3 membered saturated monocyclic ring optionally containing 0-1 heteroatoms independently selected from nitrogen, oxygen, or sulfur. In certain embodiments, at least one R$^4$ is cyclopropyl. In certain embodiments, two R$^4$ are cyclopropyl.

In certain embodiments, at least one R$^4$ is optionally substituted phenyl. In certain embodiments, at least one R$^4$ is unsubstituted phenyl. In some embodiments, at least one R$^4$ is independently a 5-6 membered aryl monocyclic ring containing 1-4 heteroatoms independently selected from nitrogen, oxygen, or sulfur.

In certain embodiments, R$^4$ is of any of the following formulae:

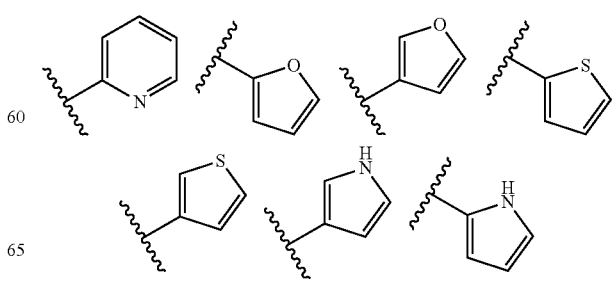

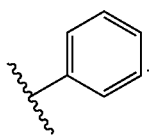

In some embodiments, each $R^4$ is R, wherein R is hydrogen, halogen, or optionally substituted $C_{1-20}$ aliphatic. In certain embodiments, each $R^4$ is independently $C_{1-6}$ aliphatic. In certain embodiments, each $R^4$ is independently selected from the group consisting of methyl, ethyl, propyl, or butyl. In certain embodiments, m is 1 and $R^4$ is methyl, ethyl, propyl, or butyl. In certain embodiments, m is 1 and $R^4$ is $C_{14}$ aliphatic. In some embodiments, m is 2 and each $R^4$ is methyl. In some embodiments, m is 2 and each $R^4$ is $-CF_3$.

In certain embodiments, each $R^4$ is independently selected from the group consisting of fluorine, chlorine, bromine, and iodine. In certain embodiments, m is 1 and $R^4$ is fluorine. In certain embodiments, m is 1 and $R^4$ is chlorine. In certain embodiments, m is 1 and $R^4$ is bromine. In certain embodiments, m is 2 and each $R^4$ is fluorine. In certain embodiments, m is 2 and each $R^4$ is chlorine. In certain embodiments, m is 2 and each $R^4$ is bromine. In certain embodiments, m is 2, wherein one $R^4$ is fluorine and one $R^4$ is chlorine. In certain embodiments, m is 3 and each $R^4$ is independently methyl or chlorine.

In certain embodiments, Ring A is of any one of the formulae:

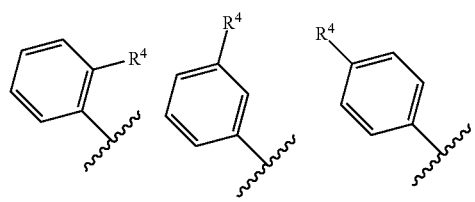

wherein $R^4$ is as defined above and herein.

In certain embodiments, Ring A is of any one of the formulae:

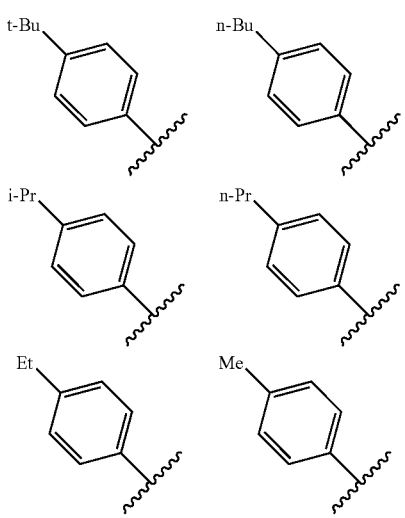

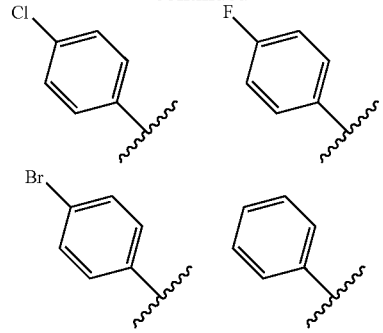

In certain embodiments, Ring A is of either one of the formulae:

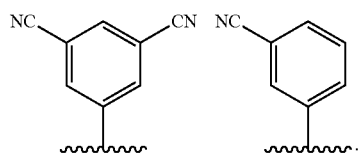

In certain embodiments, Ring A is of the formula:

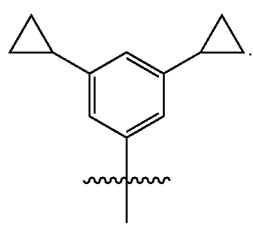 [SMILES: *c1cc(C2CC2)cc(C2CC2)c1]

In certain embodiments, Ring A is of any one of the formulae:

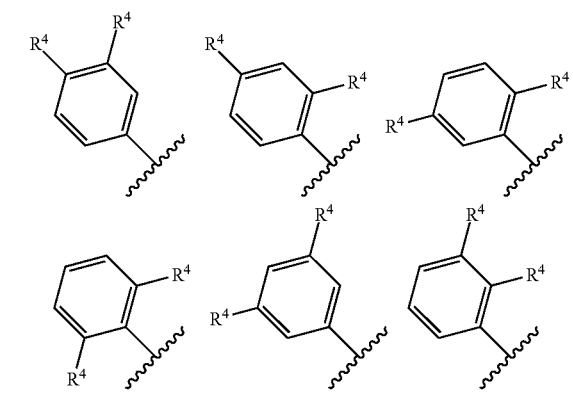

wherein $R^4$ is as defined above and herein.

In certain embodiments, Ring A is of the formula:

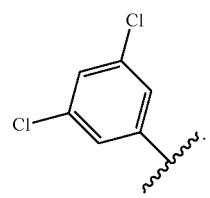 [SMILES: *c1cc(Cl)cc(Cl)c1]

In certain embodiments, Ring A is of any one of the formulae:
wherein $R^4$ is as defined above and herein.

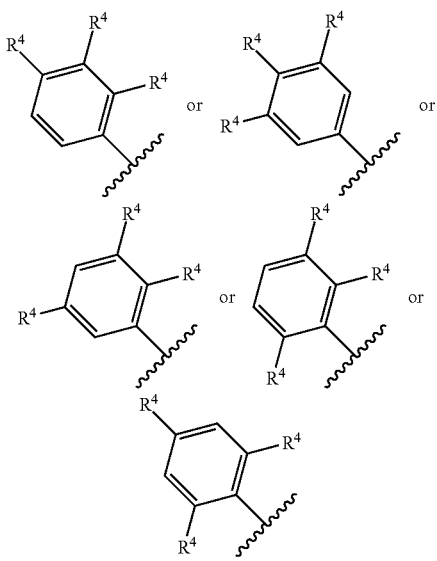

In certain embodiments, Ring A is of either of the formulae:

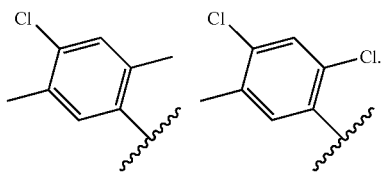

In certain embodiments, Ring A is of any one of the formulae:

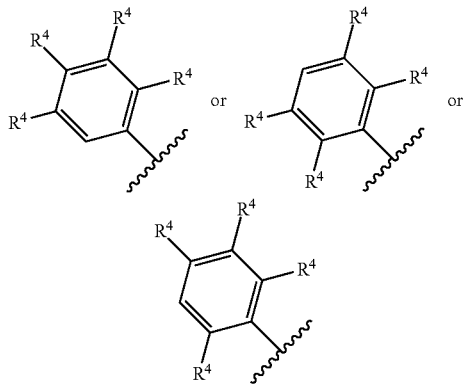

wherein $R^4$ is as defined above and herein.

In certain embodiments, Ring A of the formula:

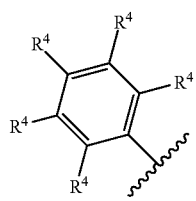

wherein $R^4$ is as defined above and herein.

In some embodiments, a provided compound is of either of the formulae:

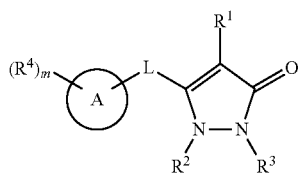

1a(i)

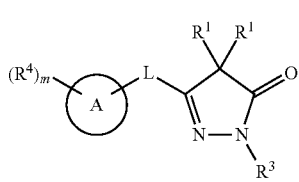

1b(i)

wherein $R^1$, $R^2$, $R^3$, $R^4$, L, m, and Ring A are as defined and described above and herein.

In some embodiments, a provided compound is of either of the formulae:

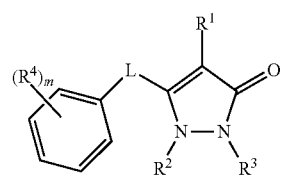

1a(i-a)

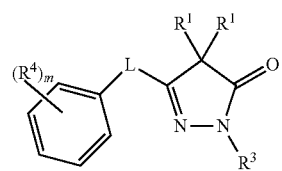

1b(i-a)

wherein $R^1$, $R^2$, $R^1$, $R^4$, L and m are as defined and described above and herein. In certain embodiments, wherein compounds are of formula 1a(i-a) or 1b(i-a), m is 1, 2, or 3. In certain embodiments, wherein compounds are of formula 1a(i-a) or 1b(i-a), m is 1 and $R^4$ is meta to L. In certain embodiments, wherein compounds are of formula 1a(i-a) or 1b(i-a), m is 2 and each $R^4$ is meta to L.

In certain embodiments, wherein compounds are of formula 1a(i-a) or 1b(i-a), L is not a bivalent saturated $C_2$ hydrocarbon chain wherein one methylene unit is replaced with —S(O)—. In certain embodiments, wherein compounds are of formula 1a(i-a) or 1b(i-a), L is a bivalent saturated $C_2$ hydrocarbon chain wherein one methylene unit is replaced with —S—, —O—, or —SO$_2$—.

In certain embodiments, wherein compounds are of formula 1a(i-a) or 1b(i-a), at least one of $R^1$, $R^2$, or $R^3$ is hydrogen. In certain embodiments, wherein compounds are of formula 1a(i-a) or 1b(i-a), at least two of $R^1$, $R^2$, and/or $R^3$ are hydrogen. In certain embodiments, wherein compounds are of formula 1a(i-a) or 1b(i-a), $R^1$, $R^2$, and $R^3$ are all hydrogen.

In certain embodiments, a provided compound is of the formula:

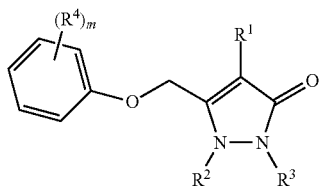

wherein $R^1$, $R^2$, $R^3$, $R^4$, and m are as defined and described above and herein.

In some embodiments, a provided compound is of any one of the formulae:

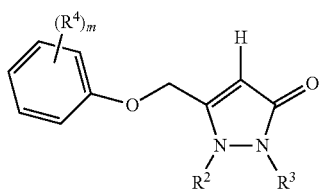

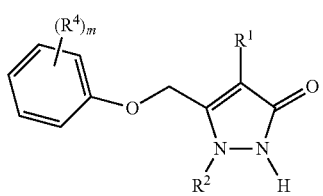

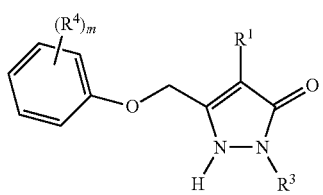

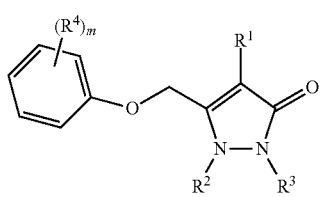

wherein $R^1$, $R^2$, $R^3$, $R^4$, and m are as defined and described above and herein.

In certain embodiments, a provided compound is of the formula:

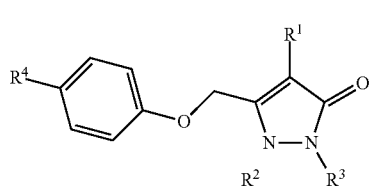

wherein $R^1$, $R^2$, $R^3$, and $R^4$ are as defined and described above and herein.

In some embodiments, a provided compound is of any one of the formulae:

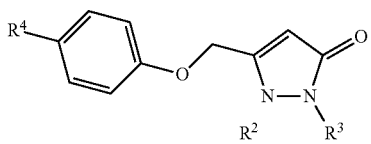

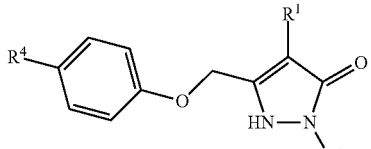

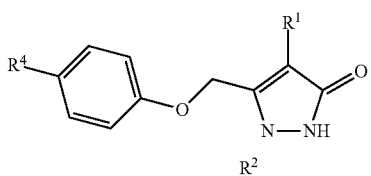

wherein $R^1$, $R^2$, $R^3$, and $R^4$ are as defined and described above and herein.

In some embodiments, a provided compound is of any one of the formulae:

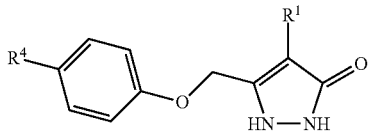

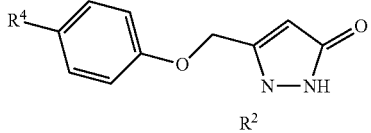

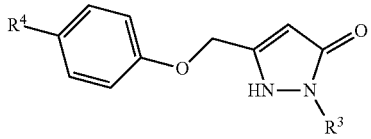

wherein $R^1$, $R^2$, $R^3$, and $R^4$ are as defined and described above and herein.

In some embodiments, a provided compound is of any one of the formulae:

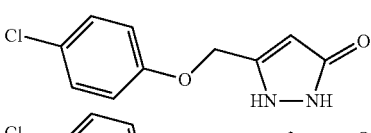

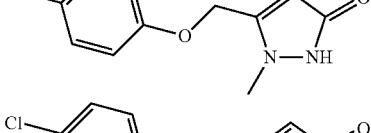

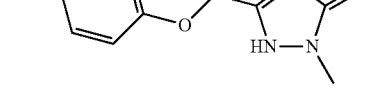

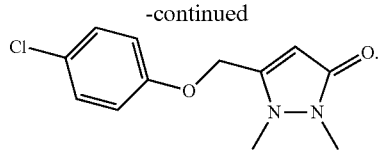
In some embodiments, a provided compound is of any one of the formulae:
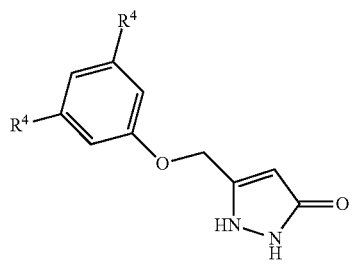
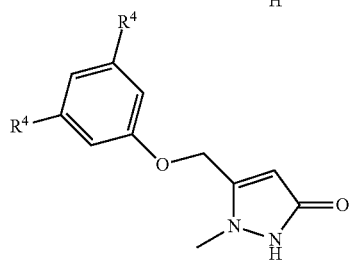
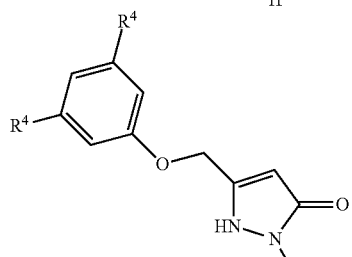
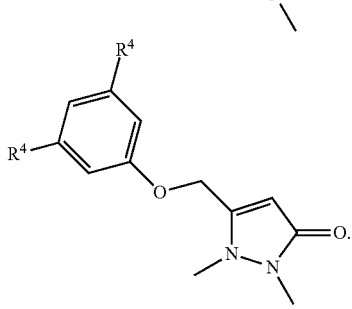
In some embodiments, a provided compound is of any one of the formulae:
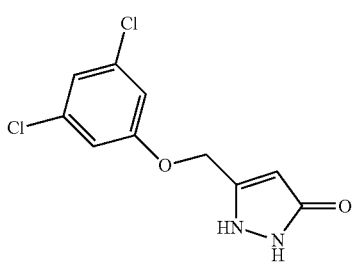
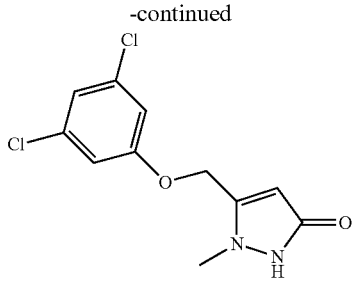
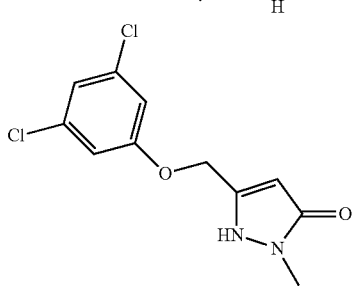
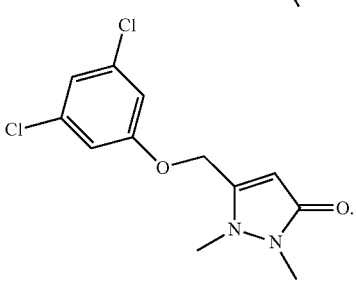
In some embodiments, a provided compound is of any one of the formulae:
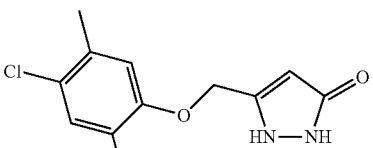
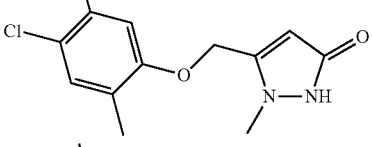
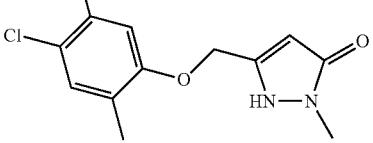
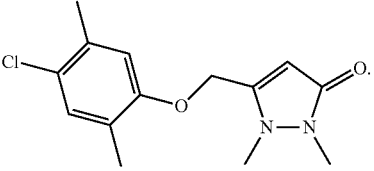
In some embodiments, a provided compound is of any one of the formulae:

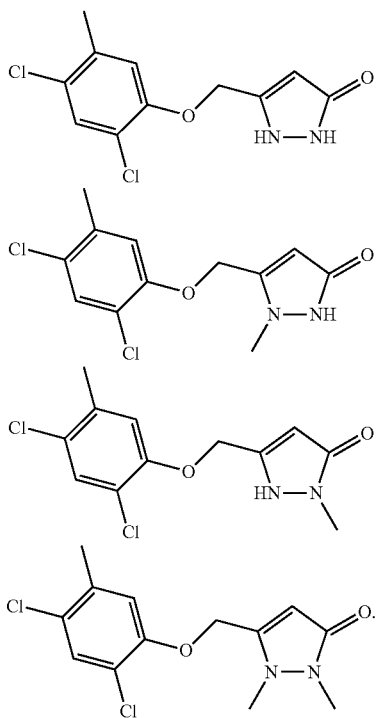

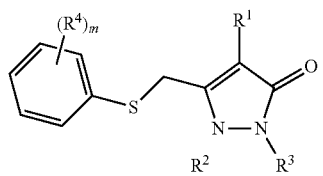

In certain embodiments, a provided compound is of the formula:

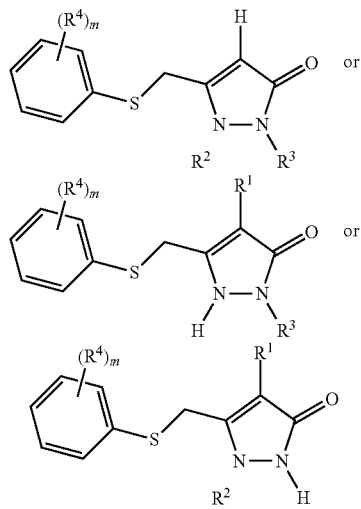

wherein $R^1$, $R^2$, $R^3$, $R^4$, and m are as defined and described above and herein.

In some embodiments, a provided compound is of any one of the formulae:

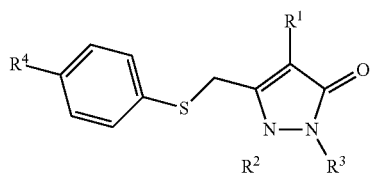

wherein $R^1$, $R^2$, $R^3$, and $R^4$ are as defined and described above and herein.

In some embodiments, a provided compound is of any one of the formulae:

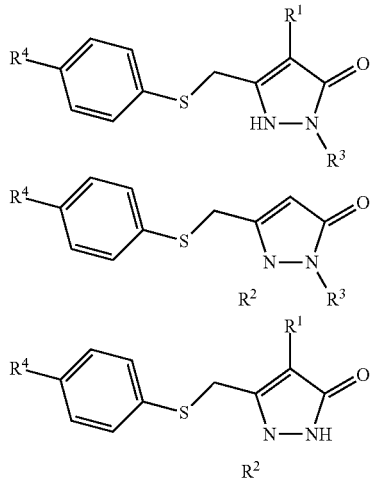

wherein $R^1$, $R^2$, $R^3$, and $R^4$ are as defined and described above and herein.

In some embodiments, a provided compound is of any one of the formulae:

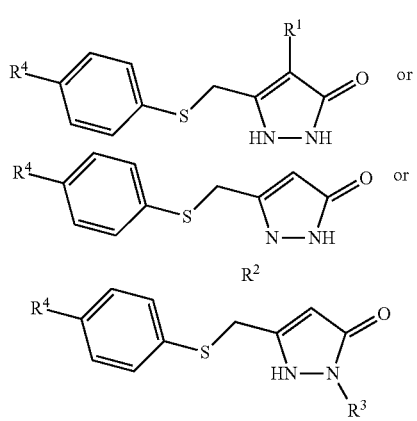

wherein $R^1$, $R^2$, $R^3$, and $R^4$ are as defined and described above and herein.

In some embodiments, a provided compound is of any one of the formulae:

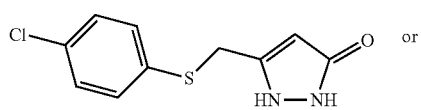 or
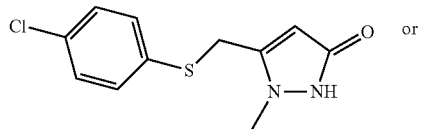 or
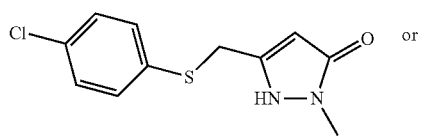 or
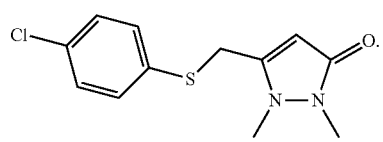.
In some embodiments, a provided compound is of any one of the formulae:
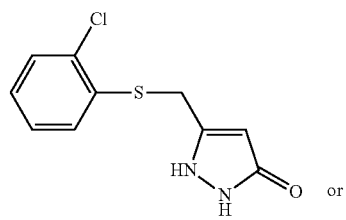 or
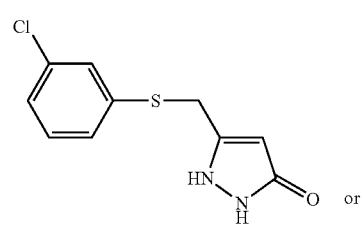 or
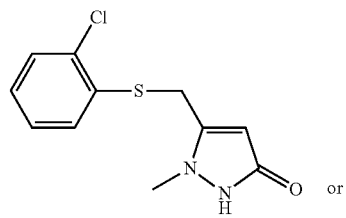 or
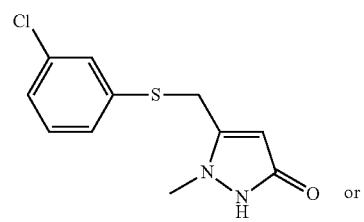 or
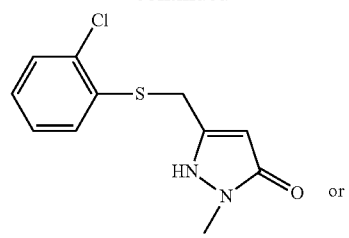 or
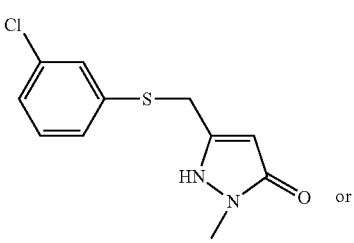 or
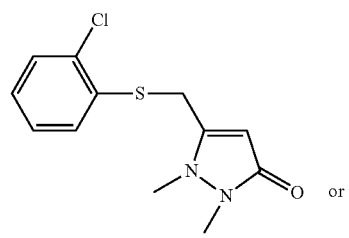 or
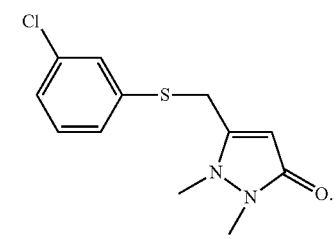.
In some embodiments, a provided compound is of any one of the formulae:
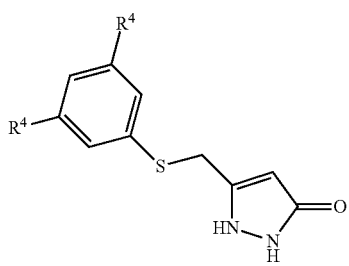
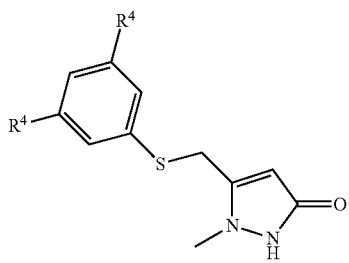

-continued
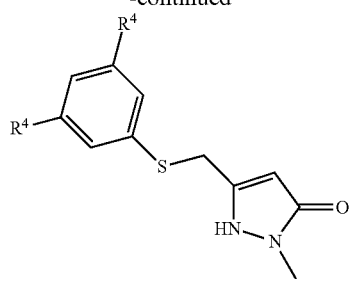
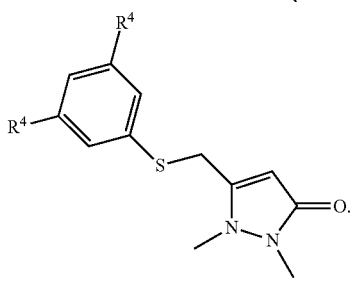
In some embodiments, a provided compound is of any one of the formulae:
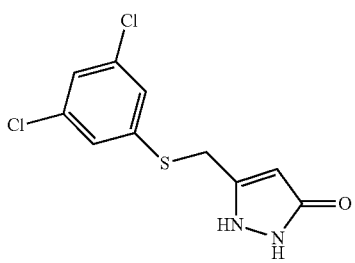
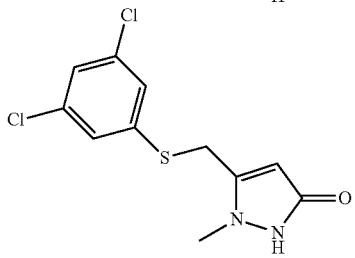
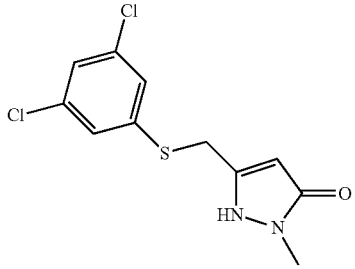
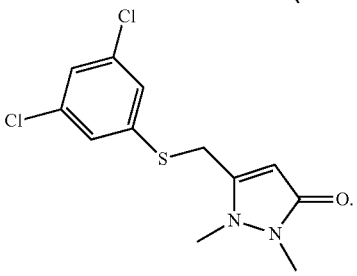
In some embodiments, a provided compound is of any one of the formulae:
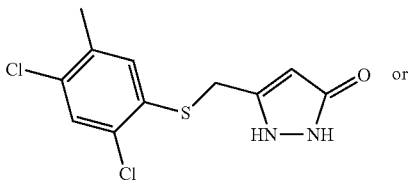 or
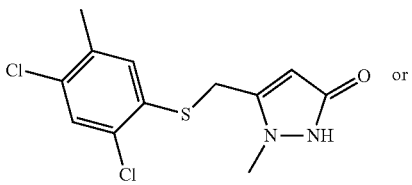 or
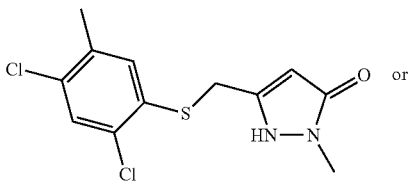 or
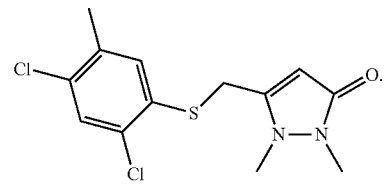
In some embodiments, a provided compound is of any one of the formulae:
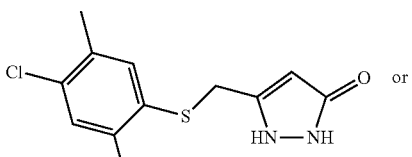 or
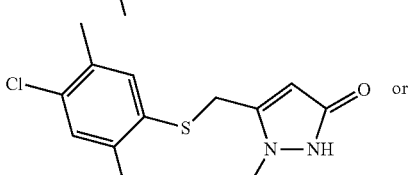 or
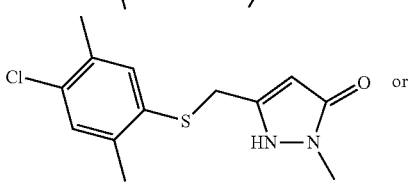 or
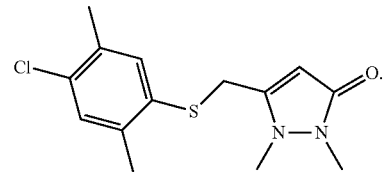
In some embodiments, a provided compound is of any one of the formulae:

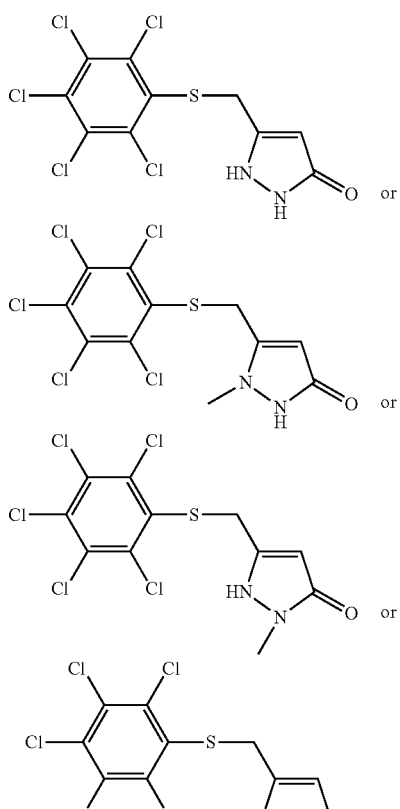

In some embodiments, a provided compound is of the formula:

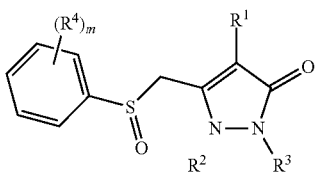

wherein $R^1$, $R^2$, $R^3$, $R^4$, and m are as defined and described above and herein.

In some embodiments, a provided compound is of any one of the formulae:

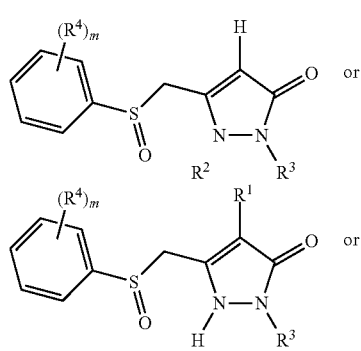

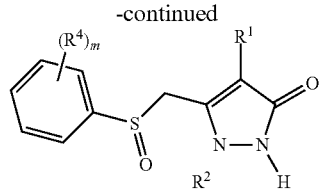

wherein $R^1$, $R^2$, $R^3$, $R^4$, and m are as defined and described above and herein.

In some embodiments, a provided compound is of the formula:

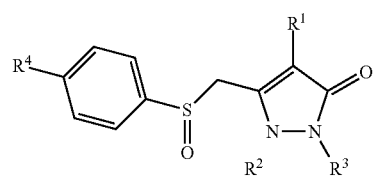

wherein $R^1$, $R^2$, $R^3$, and $R^4$ are as defined and described above and herein.

In some embodiments, a provided compound is of any one of the formulae:

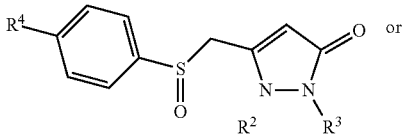

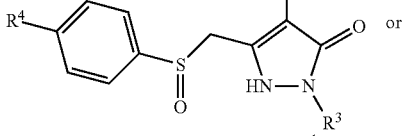

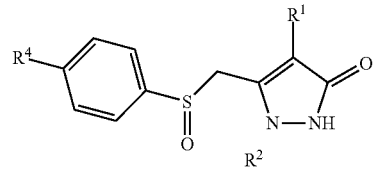

wherein $R^1$, $R^2$, $R^3$, and $R^4$ are as defined and described above and herein.

In some embodiments, a provided compound is of any one of the formulae:

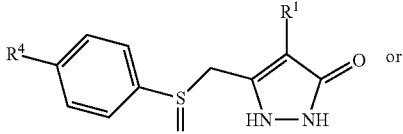

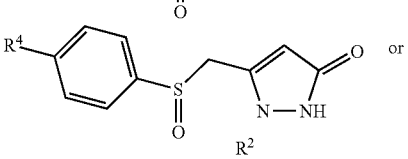

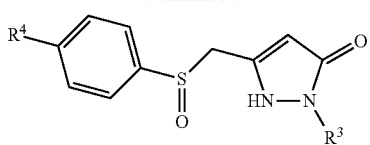

wherein R¹, R², R³, and R⁴ are as defined and described above and herein.

In some embodiments, a provided compound is of any one of the formulae:

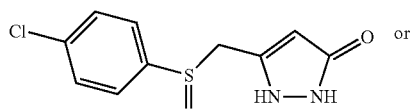

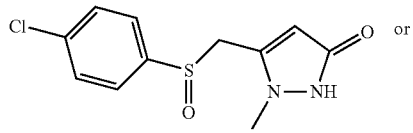

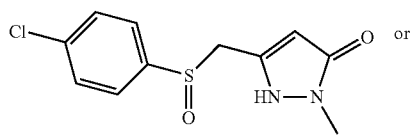

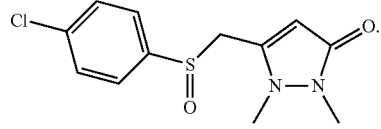

In some embodiments, a provided compound is of any one of the formulae:

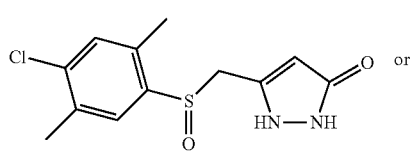

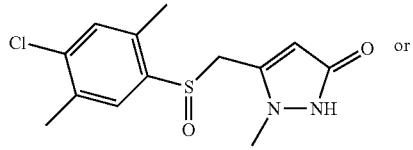

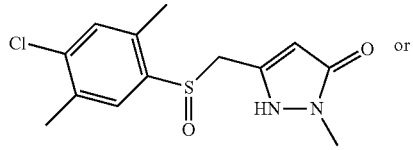

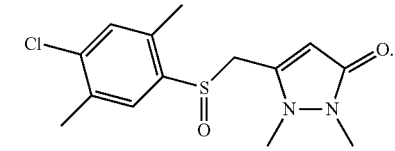

In some embodiments, a provided compound is of the formula:

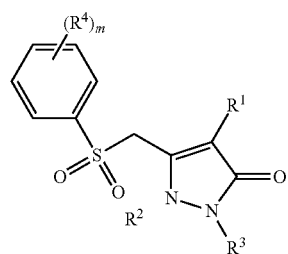

wherein $R^1$, $R^2$, $R^3$, $R^4$, and m are as defined and described above and herein. In certain embodiments, $R_4$ is halogen or $C_1$-$C_6$ alkyl.

In some embodiments, a provided compound is of any one of the formulae:

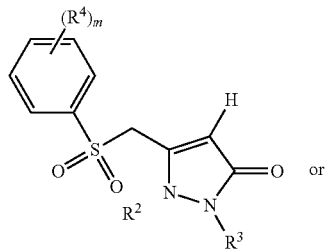

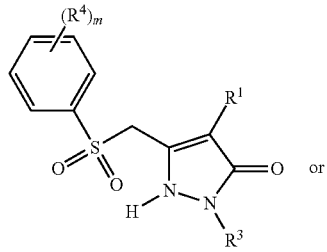

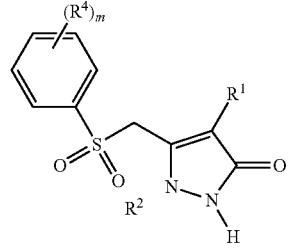

wherein $R^1$, $R^2$, $R^1$, $R^4$, and m are as defined and described above and herein.

In some embodiments, a provided compound is of the formula:

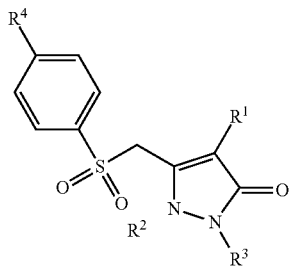

wherein $R^1$, $R^2$, $R^3$, and $R^4$ are as defined and described above and herein.

In some embodiments, a provided compound is of any one of the formulae:

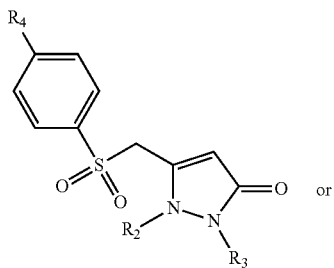

or

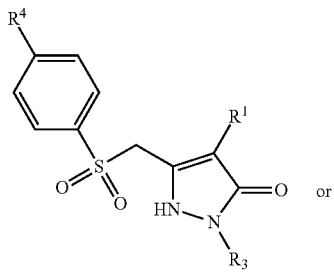

or

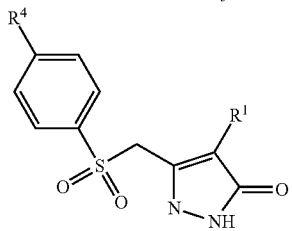

wherein $R^1$, $R^2$, $R^3$, and $R^4$ are as defined and described above and herein.

In some embodiments, a provided compound is of any one of the formulae:

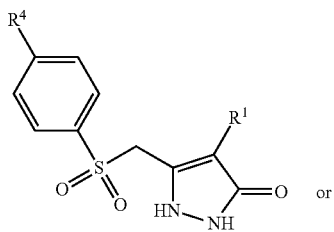

or

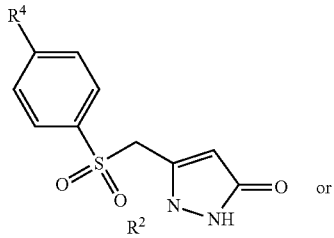

or

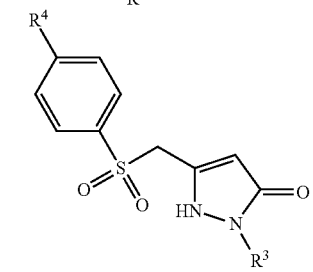

wherein $R^1$, $R^2$, $R^3$, and $R^4$ are as defined and described above and herein.

In some embodiments, a provided compound is of any one of the formulae:

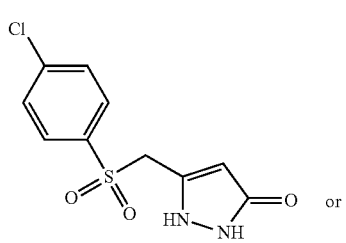

or

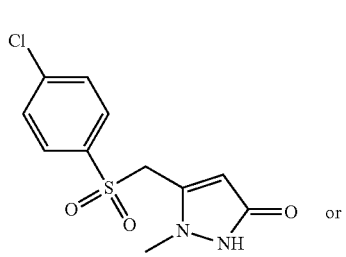

or

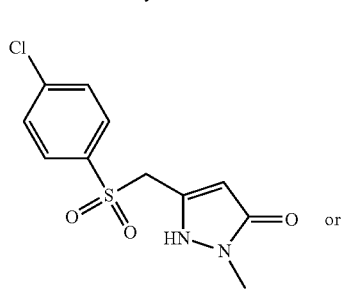

or

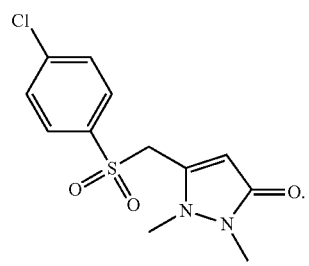

In some embodiments, a provided compound is of any one of the formulae:

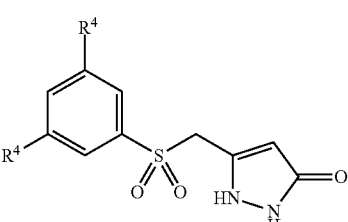

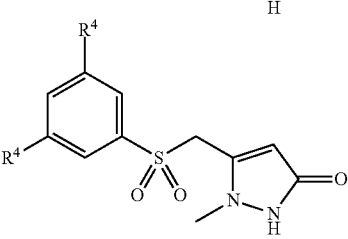

-continued

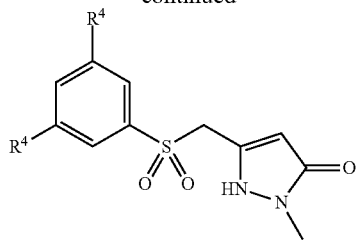

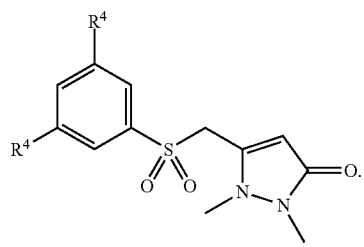

In some embodiments, a provided compound is of any one of the formulae:

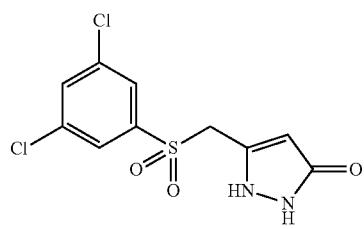

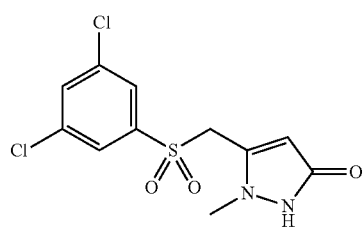

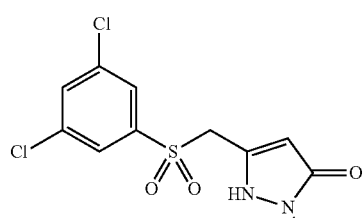

In some embodiments, a provided compound is of the formula:

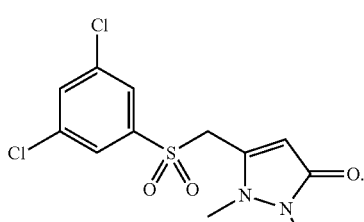

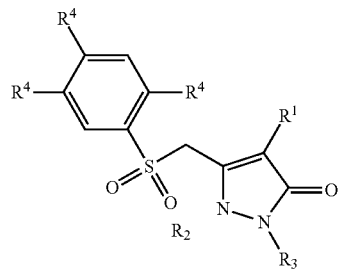

wherein $R^1$, $R^2$, $R^3$, and $R^4$ are as defined and described above and herein.

In some embodiments, a provided compound is of any one of the formulae:

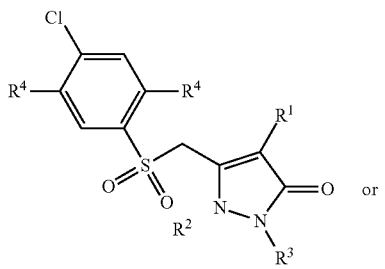 or

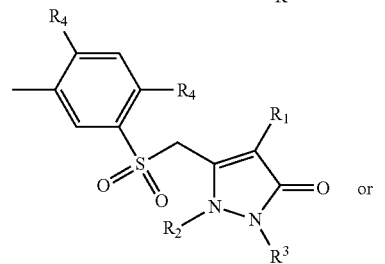 or

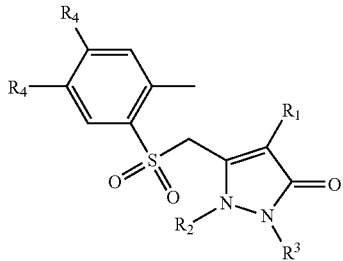

wherein $R^1$, $R^2$, $R^3$, and $R^4$ are as defined and described above and herein.

In some embodiments, a provided compound is of any one of the formulae:

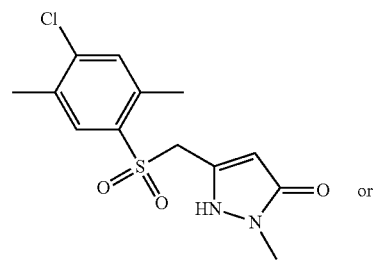 or

-continued

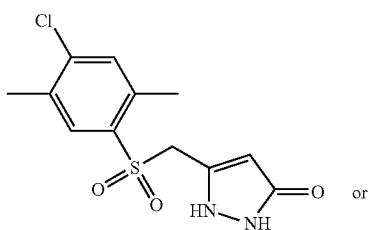

or

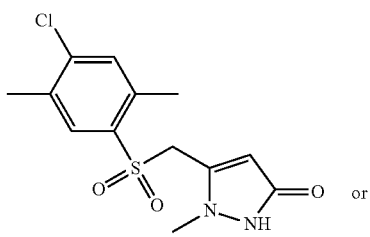

or

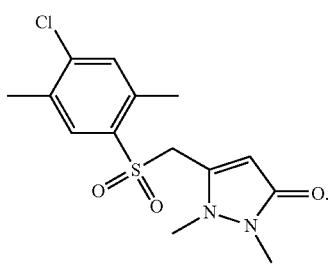

In certain embodiments, a provided compound is the formula:

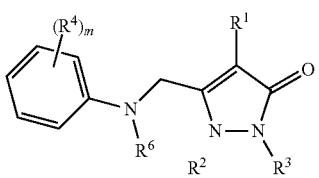

wherein $R^1$, $R^2$, $R^3$, $R^4$, $R^6$ and m are as defined and described above and herein.

In certain embodiments, a provided compound is the formula:

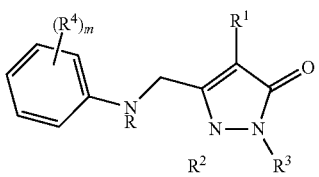

wherein R, $R^1$, $R^2$, $R^3$, $R^4$, and m are as defined and described above and herein.

In certain embodiments, a provided compound is the formula:

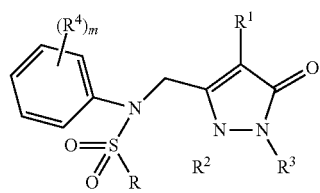

wherein R, $R^1$, $R^2$, $R^3$, $R^4$, and m are as defined and described above and herein.

In certain embodiments, a provided compound is the formula:

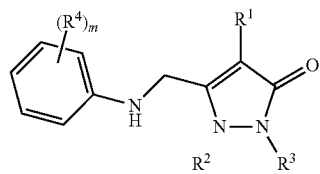

wherein $R^1$, $R^2$, $R^3$, $R^4$, and m are as defined and described above and herein.

In some embodiments, a provided compound is of any one of the formulae:

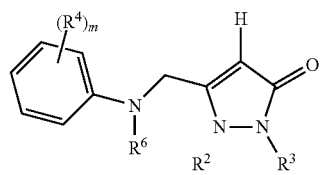

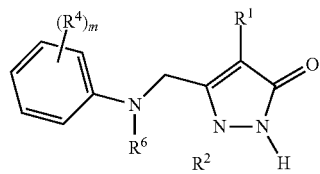

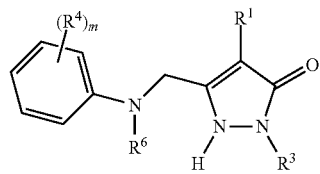

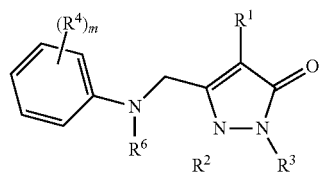

wherein $R^1$, $R^2$, $R^3$, $R^4$, $R^6$ and m are as defined and described above and herein.

In some embodiments, a provided compound is of any one of the formulae:

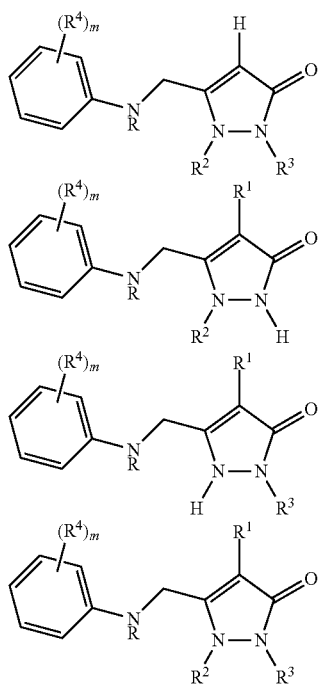

wherein R, R¹, R², R³, R⁴, and m are as defined and described above and herein.

In some embodiments, a provided compound is of any one of the formulae:

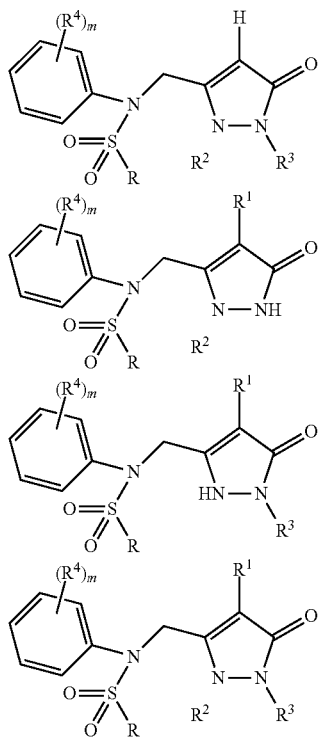

wherein R, R¹, R², R³, R⁴, and m are as defined and described above and herein.

In some embodiments, a provided compound is of any one of the formulae:

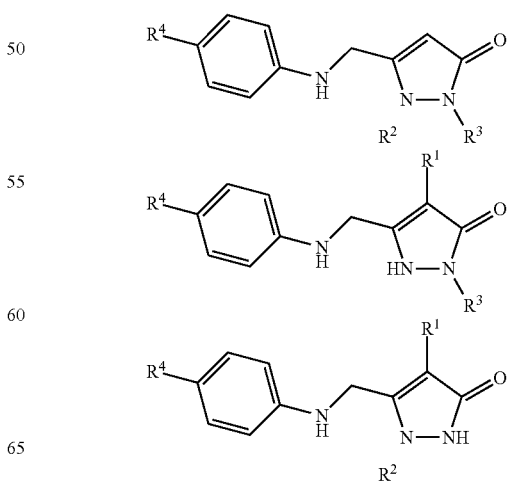

wherein R¹, R², R³, R⁴, and m are as defined and described above and herein.

In certain embodiments, a provided compound is of the formula:

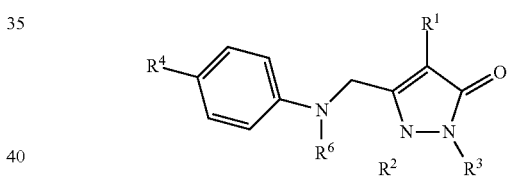

wherein R¹, R², R³, R⁴ and R⁶ are as defined and described above and herein.

In some embodiments, a provided compound is of any one of the formulae:

wherein $R^1$, $R^2$, $R^3$, and $R^4$ are as defined and described above and herein.

In some embodiments, a provided compound is of any one of the formulae:

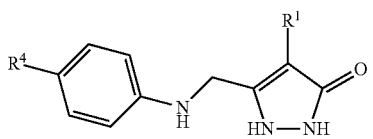

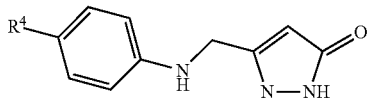

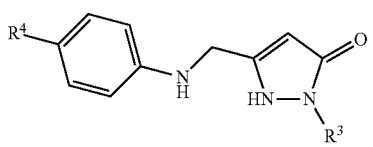

wherein $R^1$, $R^2$, $R^3$, and $R^4$ are as defined and described above and herein.

In some embodiments, a provided compound is of any one of the formulae:

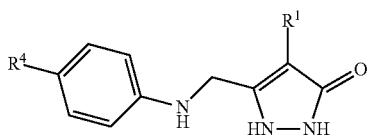

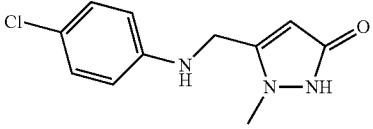

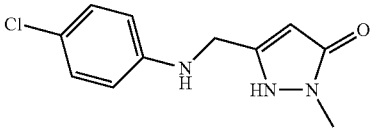

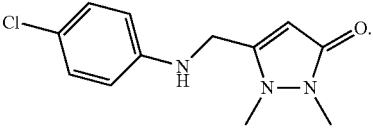

In some embodiments, a provided compound is of any one of the formulae:

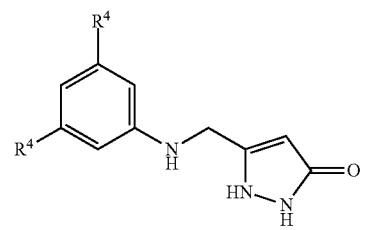

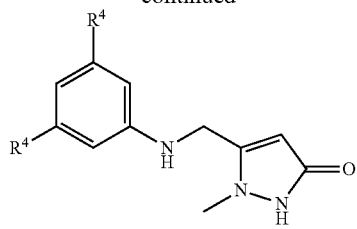

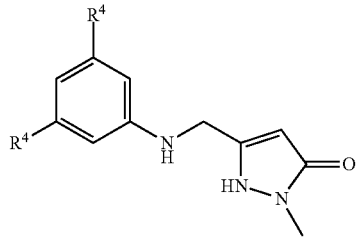

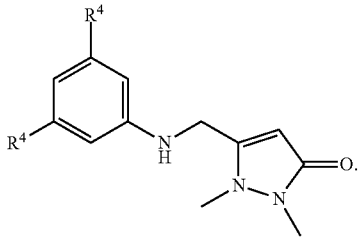

In some embodiments, a provided compound is of any one of the formulae:

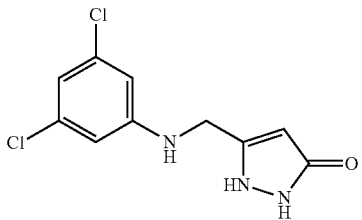

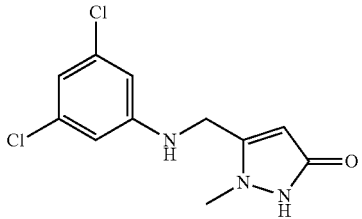

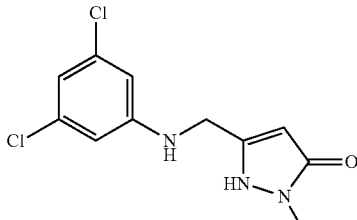

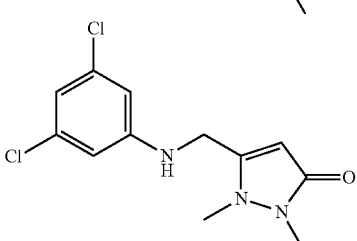

In some embodiments, a provided compound is of any one of the formulae:

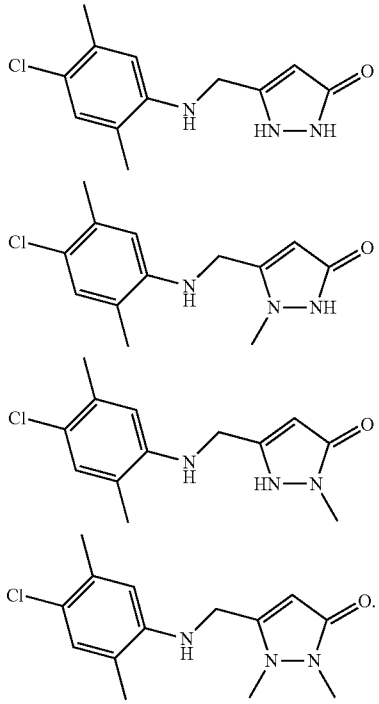

In some embodiments, a provided compound is of any one of the formulae:

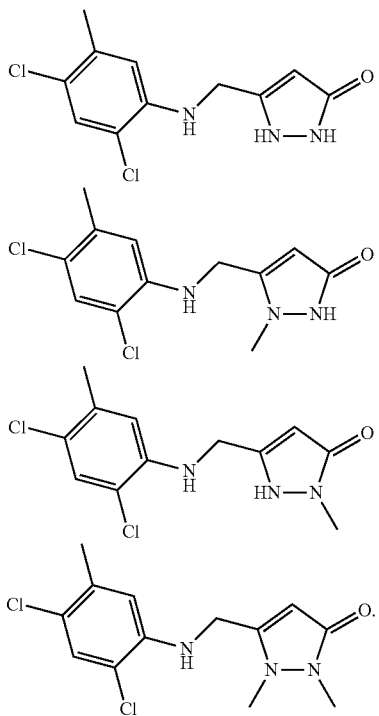

In some embodiments, a provided compound is of either of the formulae:

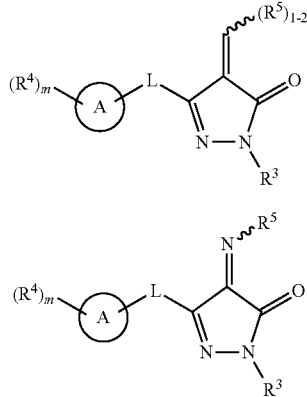

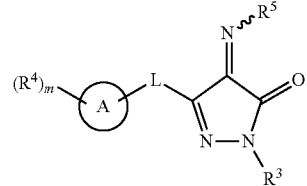

wherein $R^3$, $R^4$, $R^5$, m, L, and Ring A are as defined and described above and herein.

In certain embodiments, a provided compound is of formula 1b(i-b) or 1 b(i-c) above, wherein each $R^5$ is independently —R. In certain embodiments, a provided compound is of formula 1b(i-b) or 1b(i-c) above, wherein each $R^5$ is independently —OR, —SR, —S(O)R, —SO$_2$R, —OSO$_2$R, —N(R)$_2$, —CN, —NO$_2$, —NRC(O)R, —NRC(O)(CO)R, —NRC(O)N(R)$_2$, —NRC(O)OR, —N(R)S(O)R, —N(R)SO$_2$R, —N(R)SO$_2$OR, —C(O)R, —C(O)OR, —OC(O)R, —OC(O)OR, —C(O)N(R)$_2$, or —OC(O)N(R)$_2$. In certain embodiments, $R^5$ is —NMe$_2$.

In certain embodiments, a provided compound is of formula 1b(i-b) or 1b(i-c) above, wherein at least one $R_5$ is a 3-8 membered saturated, partially unsaturated, or aryl monocyclic ring having 0-4 heteroatoms independently selected from nitrogen, oxygen, or sulfur, wherein $R^5$ is optionally substituted with 1-5 R groups. In certain embodiments, at least one $R_5$ is a 5-6 membered aryl monocyclic ring having 0-4 heteroatoms independently selected from nitrogen, oxygen, or sulfur, wherein $R^5$ is optionally substituted with 1-5 R groups. In certain embodiments, at least one $R^5$ is phenyl optionally substituted with 1-5 R groups.

In certain embodiments, a provided compound is of formula 1b(i-b) or 1b(i-c) above, wherein at least one $R^5$ is a 5-6 membered heteroaryl monocyclic ring having 1-4 heteroatoms independently selected from nitrogen, oxygen, or sulfur, and wherein $R^5$ is optionally substituted with 1-5 R groups.

In certain embodiments, a provided compound is of formula 1b(i-b) or 1b(i-c) above, wherein $R^5$ is an 8-10 membered saturated, partially unsaturated, or aryl bicyclic ring having 1-4 heteroatoms independently selected from nitrogen, oxygen, or sulfur, wherein $R^5$ is optionally substituted with 1-5 R groups.

Exemplary $R^5$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1, 4-oxazin-3(4H)-one, or chromanyl, wherein $R^5$ is optionally substituted with 1-5 R groups.

In certain embodiments, a provided compound is of formula 1b(i-b) or 1b(i-c) above, wherein $R^5$ is of the formula:

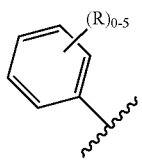

wherein R is as defined and described above and herein.

In certain embodiments, a provided compound is of formula 1b(i-b) or 1b(i-c) above, wherein $R^5$ is of any of the formulae:

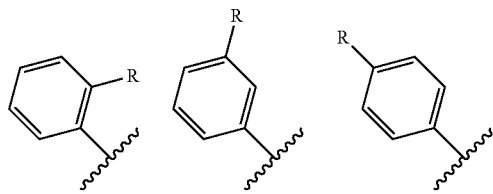

wherein R is as defined and described above and herein.

In certain embodiments, a provided compound is of formula 1b(i-b) or 1b(i-c) above, wherein $R^5$ is of any of the formulae:

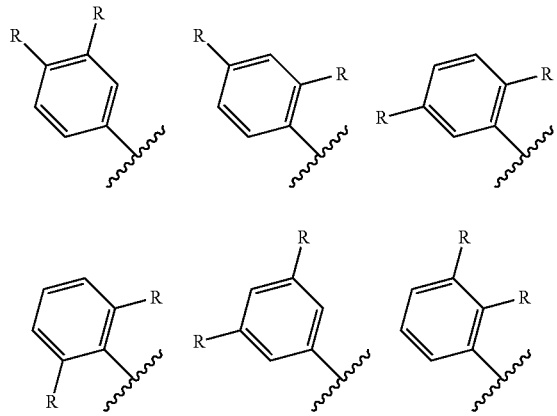

wherein R is as defined and described above and herein.

In certain embodiments, a provided compound is of formula 1b(i-b) or 1b(i-c) above, wherein $R^5$ is of any of the formulae:

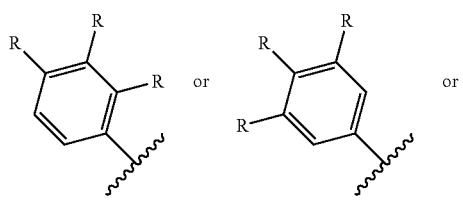

-continued

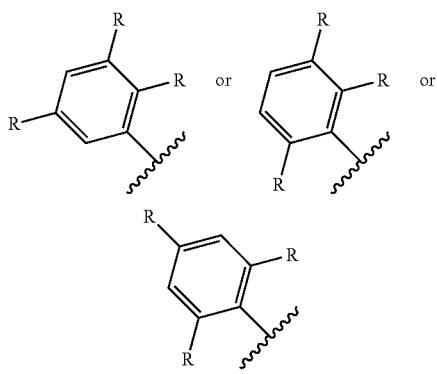

wherein R is as defined and described above and herein.

In certain embodiments, a provided compound is of formula 1b(i-b) or 1b(i-c) above, wherein $R^5$ is of any of the formulae:

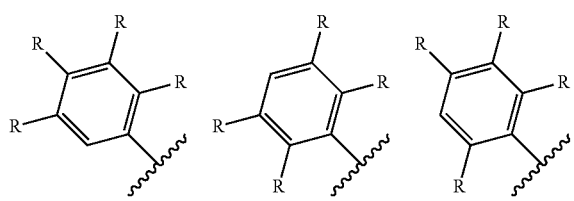

wherein R is as defined and described above and herein.

In certain embodiments, a provided compound is of formula 1b(i-b) or 1b(i-c) above, wherein $R^5$ of the formula:

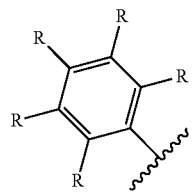

wherein R is as defined and described above and herein.

In certain embodiments, a provided compound is of formula 1b(i-b) or 1b(i-c) above, wherein $R^5$ of any of the formulae:

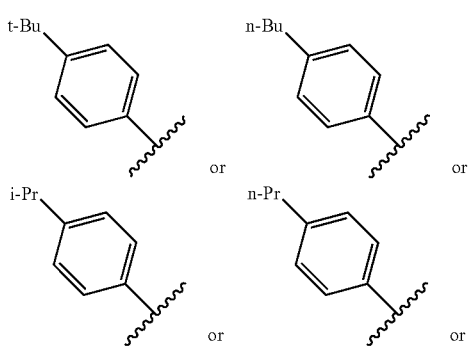

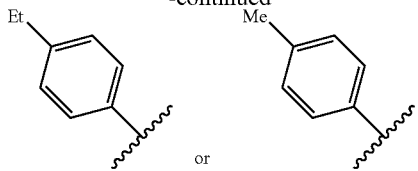

In certain embodiments, a provided compound is of the formula:

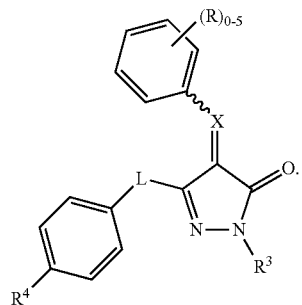

In certain embodiments, a provided compound is of formula 1b(i-b) or 1b(i-c) above, wherein $R^5$ of any of the formulae:

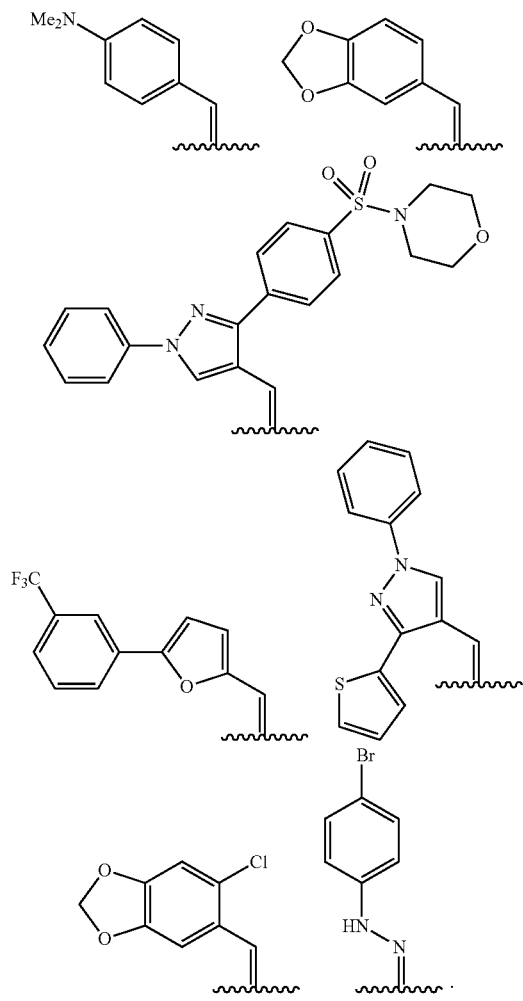

wherein R, $R^1$, $R^4$, L, and X are as defined and described above and herein.

In certain embodiments, a provided compound is of the formula:

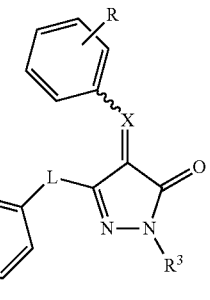

wherein R, $R^3$, $R^4$, L, and X are as defined and described above and herein.

In certain embodiments, a provided compound is of the formula:

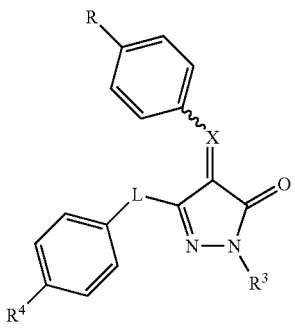

wherein R, $R^3$, $R^4$, L, and X are as defined and described above and herein.

In certain embodiments, a provided compound is of the formula:

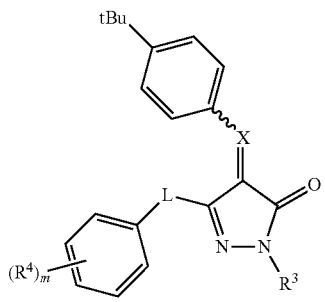

wherein R, $R^3$, $R^4$, L, X, and m are as defined and described above and herein.

In some embodiments, a provided compound is of any one of the formulae:

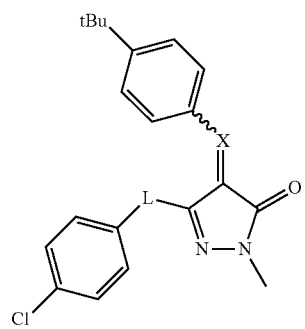

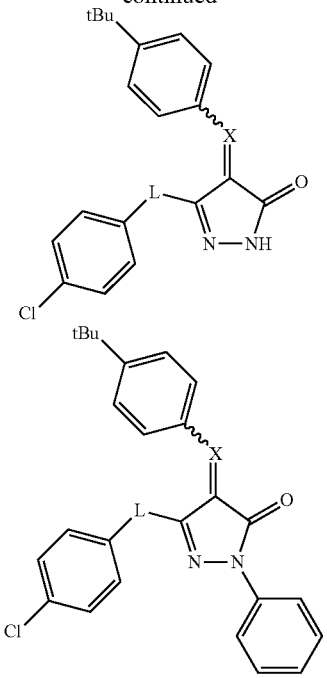

wherein L and X are as defined and described above and herein.

In some embodiments, a provided compound is of any one of the formulae:

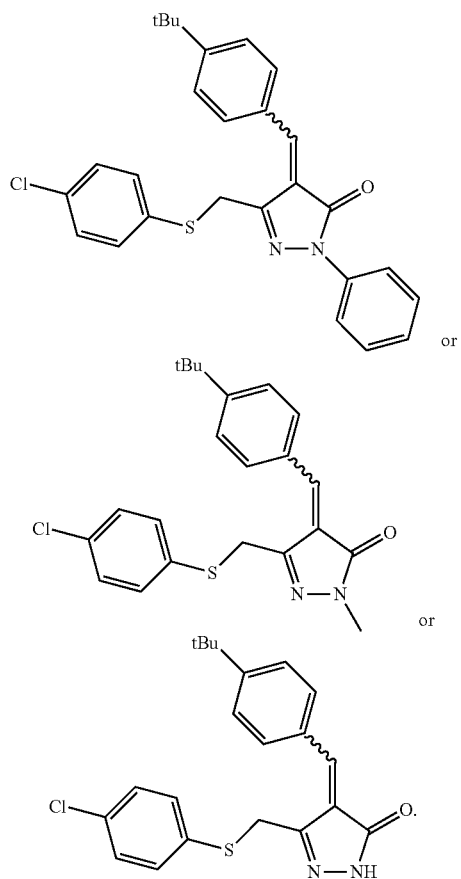

In certain embodiments, a provided compound is of the formula:

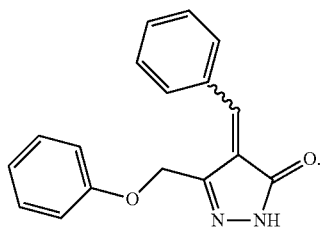 [SMILES: O=C1NN=C(COc2ccccc2)C1=Cc1ccccc1]

In certain embodiments, a provided compound is of the formula:

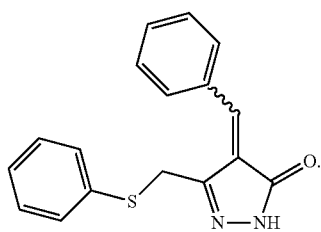 [SMILES: O=C1NN=C(CSc2ccccc2)C1=Cc1ccccc1]

In certain embodiments, a provided compound is of the formula:

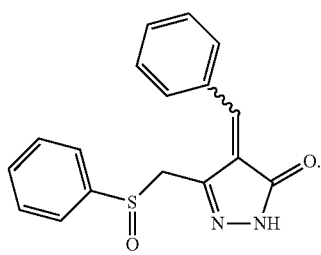 [SMILES: O=C1NN=C(CS(=O)c2ccccc2)C1=Cc1ccccc1]

In certain embodiments, a provided compound is of the formula:

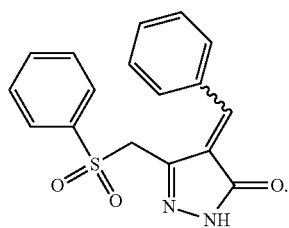 [SMILES: O=C1NN=C(CS(=O)(=O)c2ccccc2)C1=Cc1ccccc1]

In certain embodiments, a provided compound is of the formula:

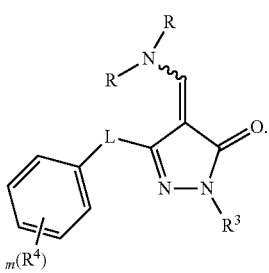

wherein R, $R^3$, $R^4$, L, and m are as defined and described above and herein.

In some embodiments, a provided compound is of any one of the formulae:

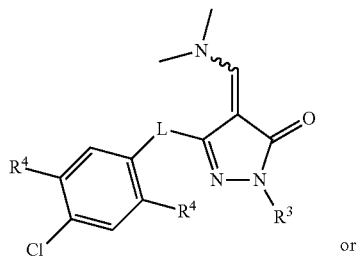

or

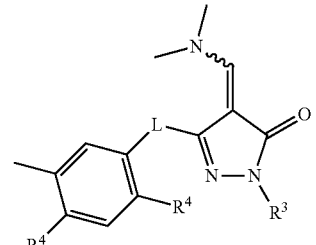

or

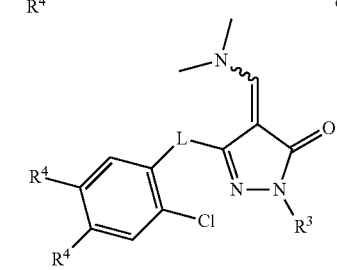

wherein R³ and R⁴ are as defined and described above and herein, and wherein L is selected from the group consisting of —CH₂O—, —CH₂S—, —CH₂S(O)—, or —CH₂SO₂—.

In some embodiments, a provided compound is of any one of the formulae:

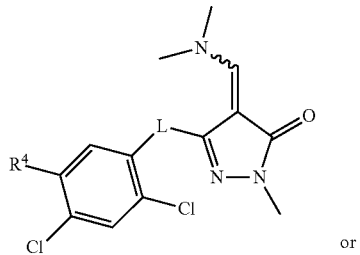

or

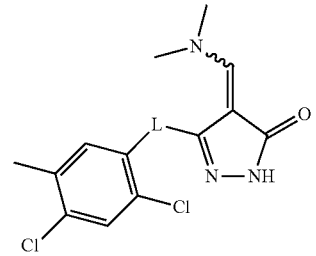

or

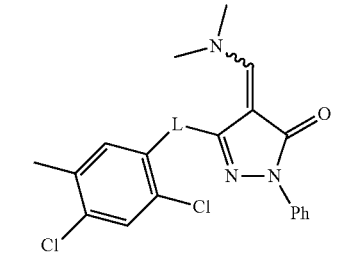

wherein L is selected from the group consisting of —CH₂O—, —CH₂S—, —CH₂S(O)—, or —CH₂SO₂—.

In certain embodiments, a provided compound is of the formula:

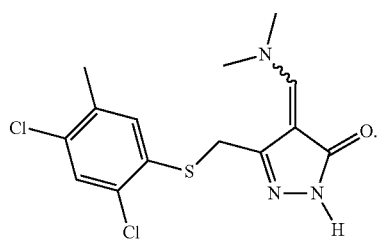 [SMILES: Cc1cc(SCC2=NNC(=O)C2=CN(C)C)c(Cl)cc1Cl]

In some embodiments, a provided compound is of the formula:

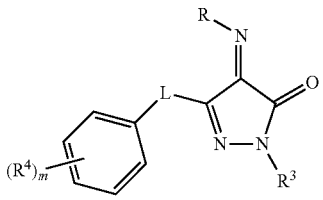

wherein R, R³, R⁴, and m are as defined and described above and herein, and wherein L is selected from the group consisting of —CH₂O—, —CH₂S—, —CH₂S(O)—, or —CH₂SO₂—.

Exemplary compounds of the present invention having an EC₅₀ of <20 µM in assays for protection of mutant SOD1-induced cytotoxicity are as shown below in Table 1:

TABLE 1

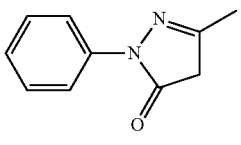 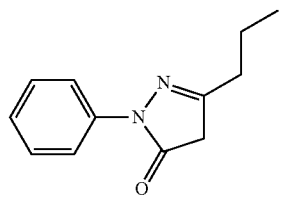

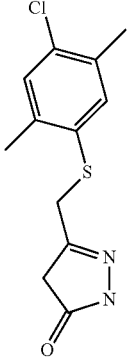 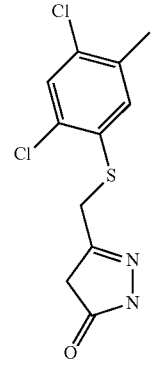 [SMILES: Cc1cc(SCC2=NNC(=O)C2)c(Cl)cc1Cl]

TABLE 1-continued
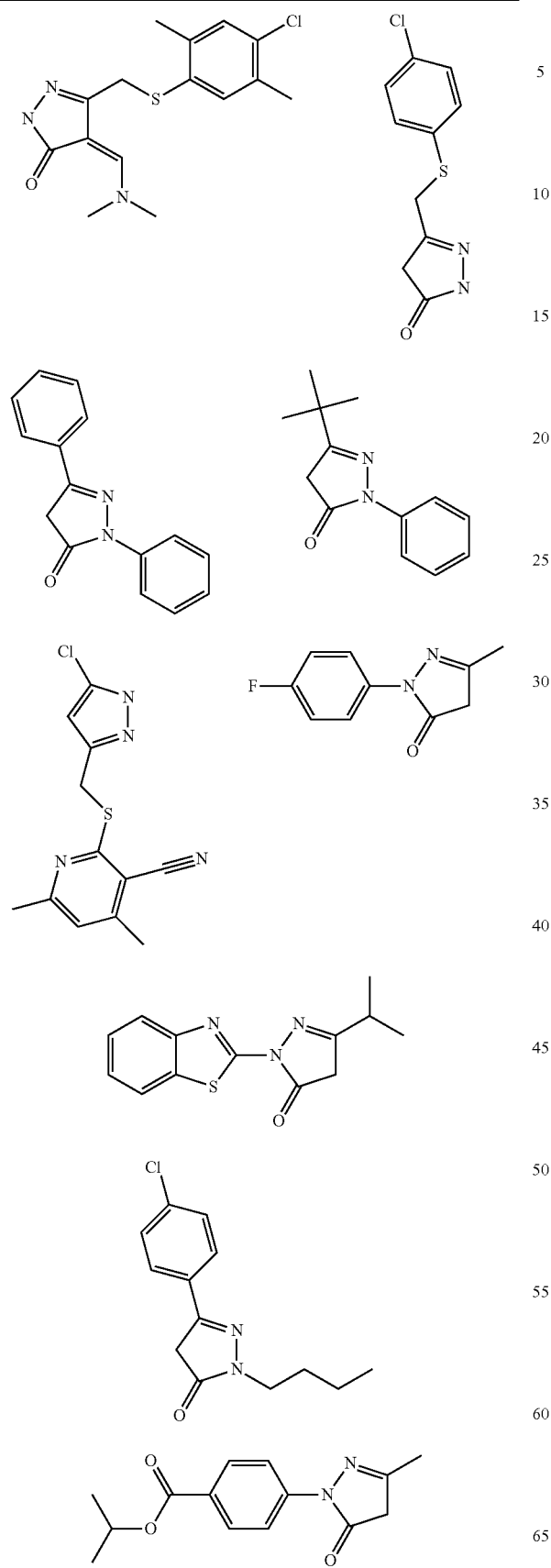
TABLE 1-continued
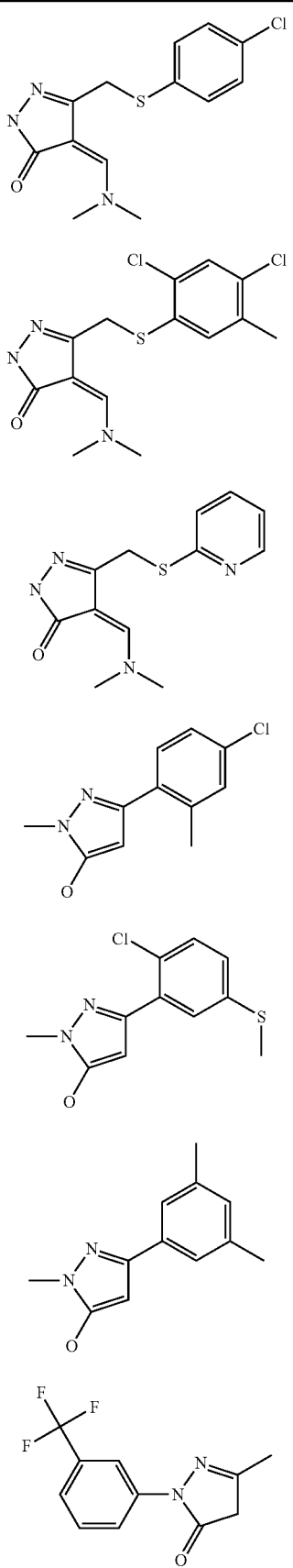

TABLE 1-continued
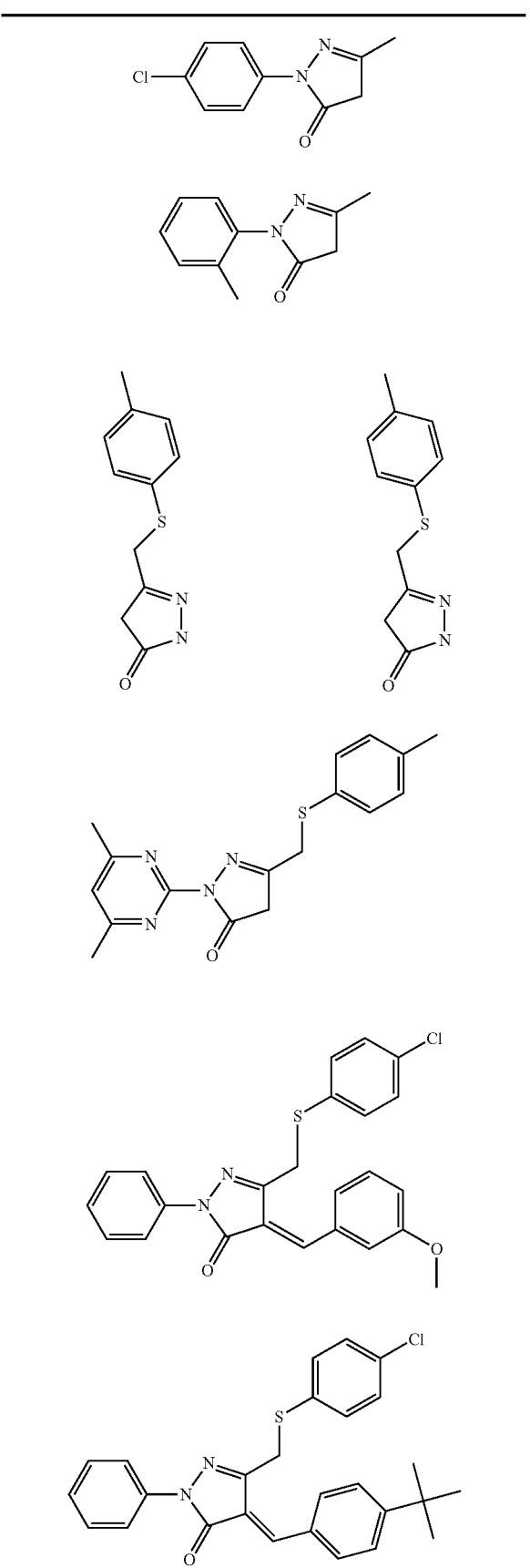
TABLE 1-continued
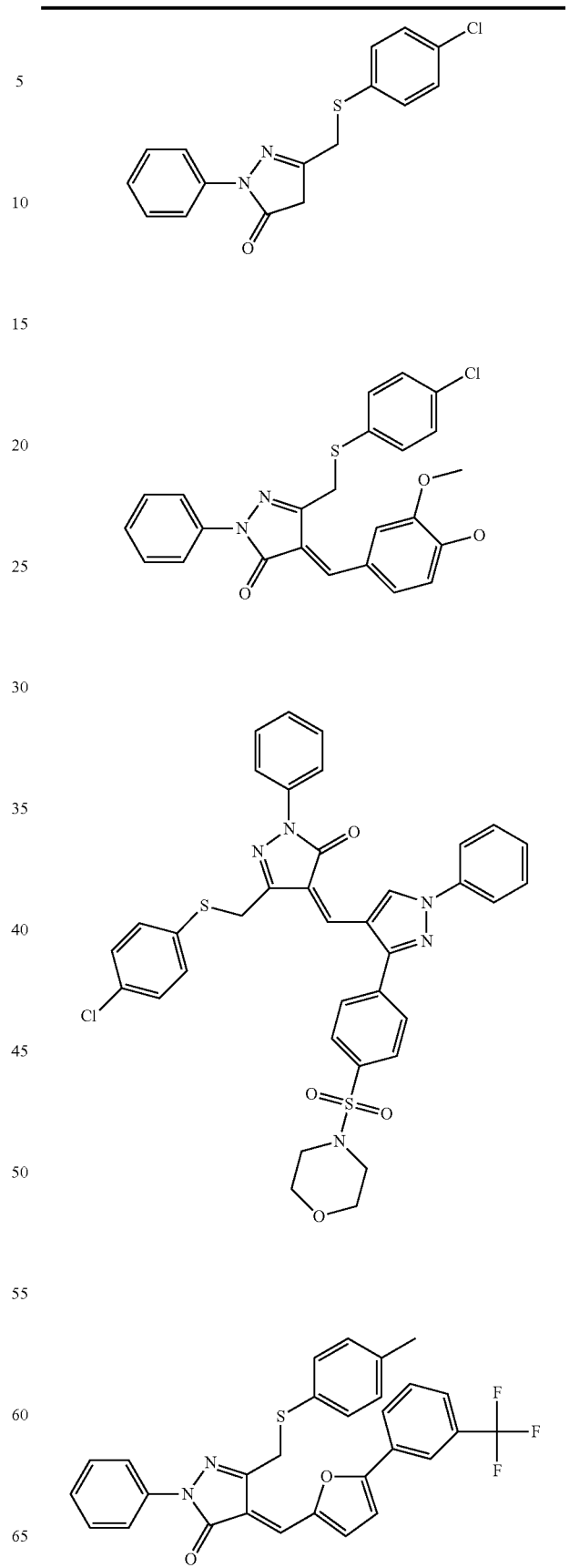

TABLE 1-continued
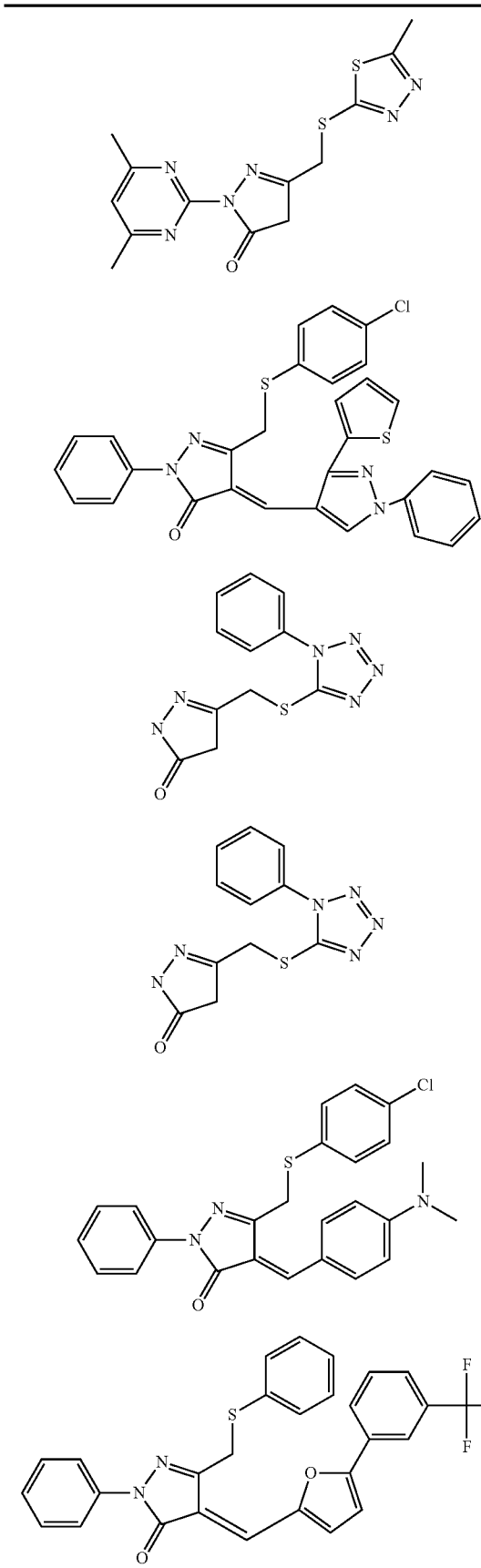
TABLE 1-continued
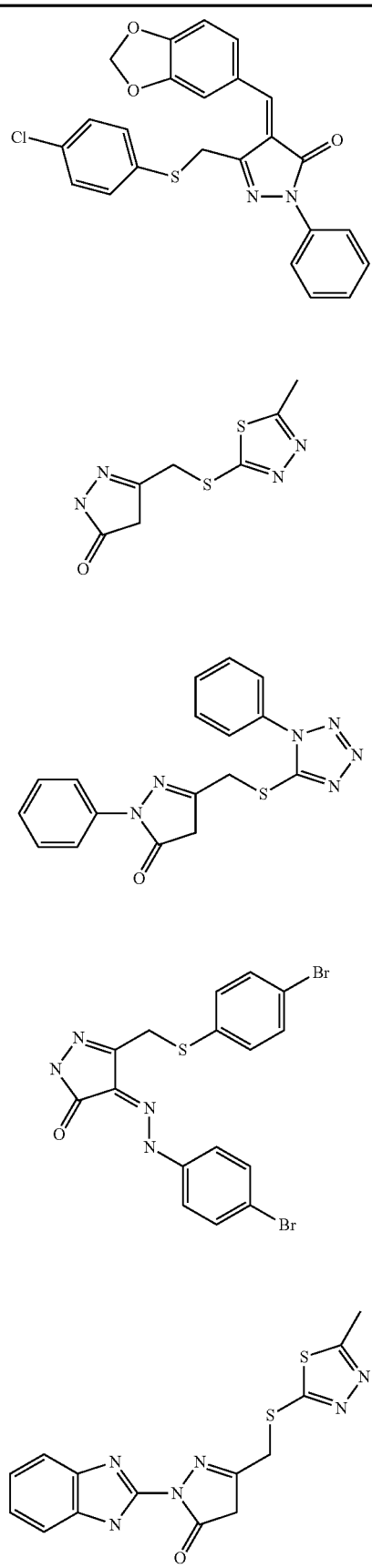

TABLE 1-continued
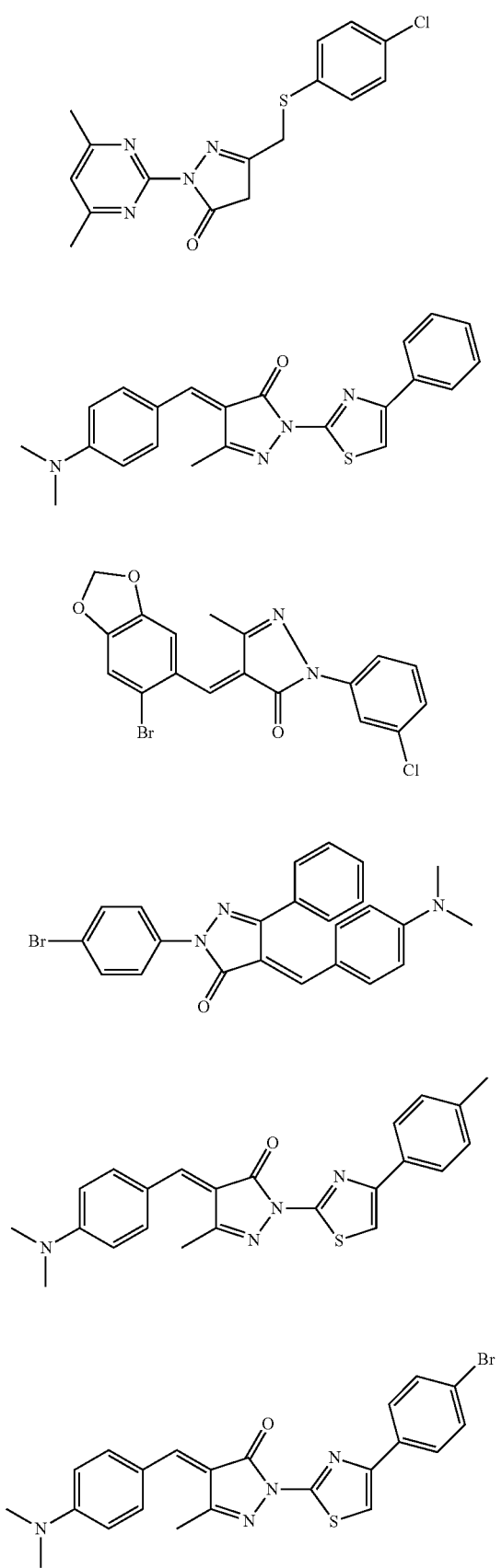
TABLE 1-continued
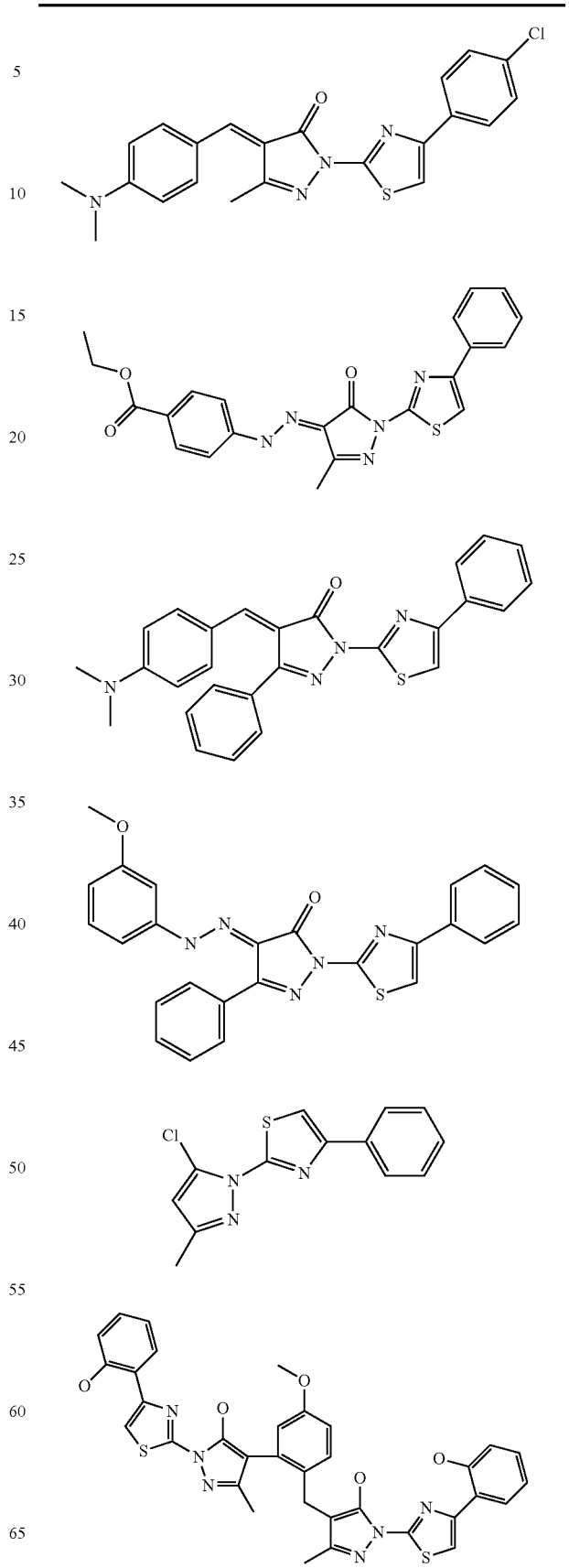

TABLE 1-continued

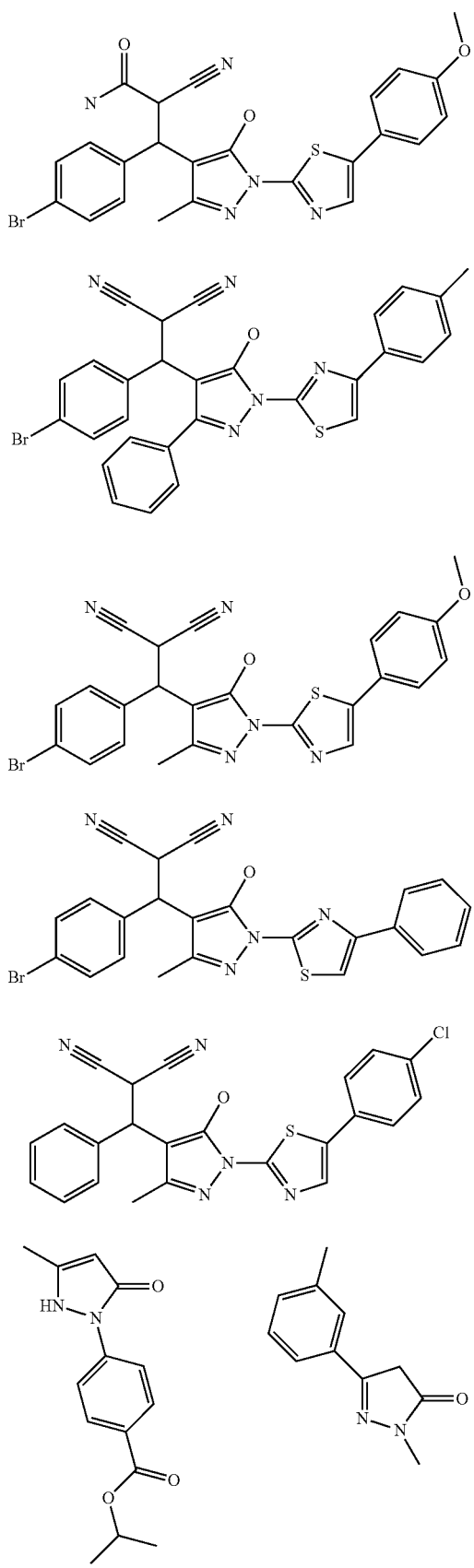

TABLE 1-continued

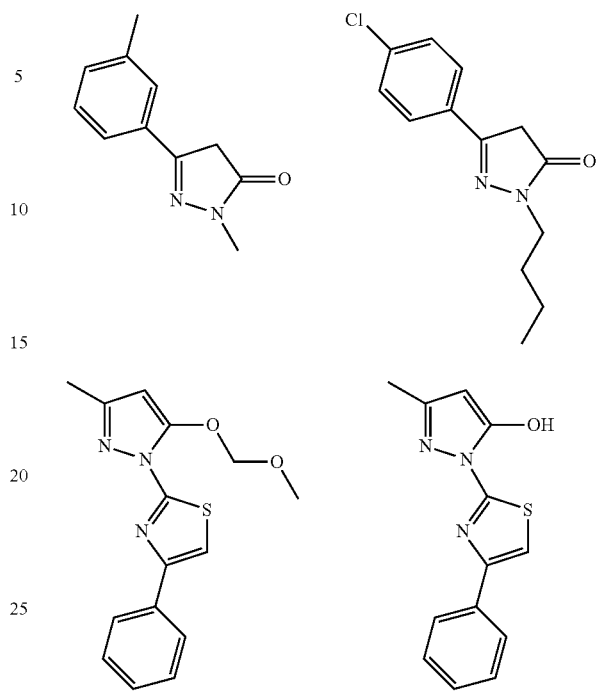

Methods of Treating Amyotrophic Lateral Sclerosis (ALS)

The present invention provides methods of treating ALS comprising administering a therapeutically effective amount of a provided compound or analog thereof, or pharmaceutical composition thereof, to a subject with ALS. The inventive pyrazolone may be administered to a subject in need thereof using any method of administration known in the medical arts. In certain embodiments, treatment may be administered orally or parenterally. In some embodiments, treatment is administered once a day. In some embodiments, the compound is administered two, three, four, or five times a day. In some embodiments, the compound is administered every other day. In some embodiments, the compound is administered every two days. In some embodiments, the compound is administered every three days. In some embodiments, the compound is administered every four days. In some embodiments, the compound is administered every five days. In some embodiments, the compound is administered every six days. In some embodiments, the compound is administered once a week. In some embodiments, the compound is administered at intervals as instructed by a physician for the duration of the life of the patient being treated. In certain embodiments, treatment is administered as many times a day as necessary to provide a therapeutically effective amount of a provided compound to treat a subject with ALS. In some embodiments, the subject with ALS is a mammal. In some embodiments, the subject with ALS is a rodent, such as a rat or mouse, for example, a mouse model of ALS. In certain embodiments, the subject with ALS is a human.

The efficacy of the inventive treatment may be evaluated and followed using any method known in the medical arts. The treatment of ALS may be evaluated, for example, by physical examination, laboratory testing, imaging studies, electrophysiological studies, etc.

Method of Inhibiting or Reversing Abnormal Protein Aggregation

The present invention provides a method of inhibiting or reversing abnormal protein aggregation comprising contacting in vitro or in vivo a compound of the instant invention with a cell in a therapeutically effective amount to inhibit or reverse abnormal protein aggregation. In certain embodiments, inhibition of abnormal protein aggregation occurs in vivo in a subject with ALS or another neurodegenerative disease characterized by aberrant protein aggregation (e.g., Huntington's disease, prion disease, or Alzheimer's disease). In some embodiments, the subject is a mammal. In some embodiments, the subject is a mouse or rat. In some embodiments, the subject is a human.

In certain embodiments, contact occurs in vitro, and the cell is derived from a mammalian cell line. In certain embodiments, contact occurs in vitro, and the cell is derived from a PC12 cell line. In certain embodiments, PC12 cells may additionally contain a detectable moiety to measure the extent of inhibition of aggregation. In certain embodiments, a detectable moiety is associated with a protein (e.g., SOD1). In certain embodiments, the detectable moiety is a fluorescent moiety (e.g., a YFP tag). In some embodiments, the detectable moiety is a phosphorescent moiety, a radiolabel, or any other detectable moiety known in the art, and may be detected using any of the methods known in the art. In some embodiments, the detectable moiety may be detected using a high content microscopy system to allow for high-throughput screening. In certain embodiments, the detectable moiety allows for the measurement of cell viability.

Assays for the Identification of Compounds that Protect Against Protein Aggregate-induced Cytotoxicity The present invention also provides assays for the identification of compounds that protect against protein aggregate-induced cytotoxicity. In certain embodiments, the assays are cell protection assays that are used to identify compounds that protect cells from the cytotoxic effects of aberrant protein aggregation. In some embodiments, the assays are protein aggregation inhibition assays that are used to identify compounds that inhibit protein aggregation in a cell or in vitro. In some embodiments, the inventive assay may screen at least 1,000, 5,000, 10,000, 20,000, 30,000, 40,000, or 50,000 compounds in parallel.

Cytotoxicity Protection Assays

Compounds which protect against protein aggregate-induced cytotoxicity can be identified using methods according to the present invention. In some embodiments, the present invention provides a method of identifying compounds that protect against protein aggregate-induced cytotoxicity comprising contacting a cell expressing SOD1 or another protein susceptible to aggregation with a test compound, incubating the cell with the test compound under suitable conditions for an amount of time sufficient to observe a protective effect against protein aggregate-induced cytotoxicity, and then measuring viability in the cells treated with the test compound. In some embodiments, the extent of protein aggregation-induced cytotoxicity is measured by determining the level of a detectable moiety (e.g., a fluorescent moiety) in the cell.

In certain embodiments, the expressed protein is a mutant SOD1 protein. In some embodiments, the expressed protein is an SOD1 protein associated with a detectable moiety. In certain embodiments, the expressed protein is a fluorescently tagged mutant SOD1 protein, and the fluorescent moiety is a YFP tag. In some embodiments, the detectable moiety is a phosphorescent moiety, epitope, or radiolabel. In some embodiments, the detectable moiety is any suitable detectable moiety known to those or ordinary skill in the art and may be detected using any method known in the art. In some embodiments, the detectable moiety is a fluorescent tag (e.g., a YFP tag) that can be detected with a high content microscopy system. In some embodiments, the high content microscopy system detects cell viability and facilitates high-throughput screening of a plurality of compounds.

Cells may be pre-treated with an agent that modulates the expression of a protein of interest (e.g., SOD1) in the assay. The agent may, for instance, induce the expression of a gene responsible for the protein of interest (e.g., doxycycline-inducible promoter). In some embodiments, cells may also be treated with an agent that modulates proteasome activity. In certain embodiments, the agent may be a proteasome inhibitor (e.g., MG 132). In some embodiments, cell viability of cells pre-treated with an agent described herein is measured using methods described above.

In certain embodiments, the time of incubation of a cell with a test compound ranges from approximately 1 minute to approximately 1 week. In some embodiments, the time of incubation ranges from approximately 5 minutes to approximately 1 week. In some embodiments, the time of incubation ranges from approximately 30 minutes to approximately 2 days. In some embodiments, the time of incubation ranges from approximately 30 minutes to approximately 1 day. In some embodiments, the time of incubation ranges from approximately 1 hour to approximately 1 day. In some embodiments, the time of incubation ranges from approximately 1 hour to approximately 18 hours. In some embodiments, the time of incubation ranges from approximately 1 hour to approximately 12 hours. In some embodiments, the time of incubation ranges from approximately 1 hour to approximately 6 hours. In some embodiments, the time of incubation ranges from approximately 1 hour to approximately 3 hours. In some embodiments, the time of incubation is approximately 6 hours. In some embodiments, the time of incubation is approximately 12 hours. In some embodiments, the time of incubation is approximately 18 hours. In some embodiments, the time of incubation is approximately 24 hours.

In certain embodiments, the temperature during incubation of a cell with a test compound ranges from approximately 20° C. to approximately 45° C. In certain embodiments, the temperature ranges from approximately 20° C. to approximately 40° C. In certain embodiments, the temperature ranges from approximately 25° C. to approximately 40 OC. In certain embodiments, the temperature ranges from approximately 30° C. to approximately 40° C. In certain embodiments, the temperature is approximately 30° C. In certain embodiments, the temperature is approximately 37° C.

Compounds that are active in the above-mentioned assay could theoretically protect against abnormal protein aggregate-induced cytotoxicity through a number of biological mechanisms. The present invention additionally provides methods to screen for compounds that protect against abnormal protein-aggregate induced cytotoxicity wherein the protein aggregation is inhibited in a non-specific manner.

Compounds which inhibit aberrant protein aggregation can be identified using methods similar to those described above in the aforementioned cytotoxicity assay. In some embodiments, the present invention provides a method of identifying compounds that inhibit aberrant protein aggregation comprising contacting a cell expressing SOD1 or other protein susceptible to aggregation with a test compound, incubating the cell with the test compound under suitable conditions, and then measuring the extent of protein aggregation in the cells treated with the test compound as compared to a control. In certain embodiments, the extent of inhibition of protein aggregation is measured by staining the protein aggregates with a detectable stain (e.g., Image-iT plasma membrane dye). In some embodiments, the detectable stain is detected using a scanning device (e.g., Cellomics Arrayscan). In certain embodiments, the protein aggregates are detected using any method of detecting protein aggregates known in the art.

Compounds identified using the above-mentioned assays may be further examined using biological assays to guide structure-activity relationship (SAR) analyses of the identified compounds. Biological assays and SAR analyses are known to those of skill in the art.

Method of Protecting Cells from the Cytotoxic Effects of Aggregated SOD1

The present invention provides a method of protecting cells against the cytotoxic effects of aggregated SOD1 protein comprising contacting in vitro or in vivo a compound of the invention with a cell in a therapeutically effective amount to protect the cell from the effects of aggregated SOD1. In certain embodiments, protection of a cell occurs in vivo in a subject with ALS. In some embodiments, the subject is a mammal. In some embodiments, the subject is a mouse or rat. In some embodiments, the subject is a human.

In other instances, protection of a cell from the cytotoxic effect of aggregated SOD1 occurs in vitro. In certain embodiments, protection occurs in vitro in a cell culture. In some embodiments, compounds of the invention are contacted with a cell line in vitro and the cell line is a mammalian cell line. In certain embodiments, the cell line is the PC12 cell line. In some embodiments, cells are associate with a detectable moiety such as those described above. In some embodiments, cells contain a protein labeled with a detectable moiety. In certain embodiments, the protein labeled with a detectable moiety is SOD1 and the detectable moiety is a fluorescent moiety. In certain embodiments, the fluorescent moiety (e.g., a YFP tag) that may be detected using a high content microscopy system to allow for high-throughput screening. In some embodiments, the detectable moiety is a phosphorescent moiety, an epitope, radiolabel, or any other detectable moiety known in the art, and may be detected using any of the methods known in the art. In certain embodiments, the detectable moiety allows for the measurement of cell viability.

Method of Measuring Changes in Ubiquitin Proteasome Activity

The present invention provides a method of measuring changes in ubiquitin proteasome activity comprising contacting in vitro or in vivo a compound of the instant invention with a cell in a therapeutically effective amount to effect a change in ubiquitin proteasome activity. In certain embodiments, modulation of proteasome activity with an inventive compound occurs in vivo in a subject with ALS. In some embodiments, the subject is a mammal. In some embodiments, the subject is a mouse or rat. In some embodiments, the subject is a human.

In certain embodiments, contact occurs in vitro by contacting a test compound with a cell, incubating the test compound with the cell using methods described above, and measuring the extent of inhibition of protein aggregation in the cell. In certain embodiments, the cell is derived from a mammalian cell line. In some embodiments, the cell is derived from a PC12 cell line or a HeLa cell line. In certain embodiments, the cells contain a detectable moiety to measure the extent to which proteasome activity is inhibited. In some embodiments, cells contain a protein labeled with a detectable moiety. In certain embodiments, the protein is SOD1 and the detectable moiety is a fluorescent moiety. In certain embodiments, the detectable moiety is a fluorescent moiety (e.g., a Ubi-YFP tag). In some embodiments, the detectable moiety is a Ubi-YFP tag, which is detectable by fluorescence microscopy. In some embodiments, the detectable moiety is a phosphorescent moiety, an epitope, a radiolabel, or any other detectable moiety known in the art, and may be detected using any of the methods known in the art. In some embodiments, the detectable moiety may be detected using a high content microscopy system to allow for high-throughput screening. In certain embodiments, the detectable moiety allows for the measurement of cell viability.

Pharmaceutical Compositions

In another aspect, the present invention provides pharmaceutically compositions, which comprise a therapeutically effective amount of one or more of a provided compound, formulated together with one or more pharmaceutically acceptable carriers (additives) and/or diluents for use in treating ALS or any other diseases, disorders, or conditions. As described in detail, pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Pharmaceutically acceptable salts of provided compounds include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, provided compounds may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing formulations or compositions comprising provided compounds include a step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

Tablets, and other solid dosage forms of pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, one or more provided compounds, or pharmaceutical compositions thereof, is provided to a synucleinopathic subject chronically. Chronic treatments include any form of repeated administration for an extended period of time, such as repeated administrations for one or more months, between a month and a year, one or more years, or longer. In many embodiments, chronic treatment involves administering one or more provided compounds, or pharmaceutical compositions thereof, repeatedly over the life of the subject. Preferred chronic treatments involve regular administrations, for example one or more times a day, one or more times a week, or one or more times a month. In general, a suitable dose such as a daily dose of one or more provided compounds, or pharmaceutical compositions thereof, will be that amount of the one or more provided compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably, the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of one or more provided compounds may be administered as two, three, four, five, six, or more sub-doses administered separately at appropriate intervals throughout the day, optionally, in unit dosage forms.

While it is possible for a provided compound to be administered alone, it is preferable to administer a provided compound as a pharmaceutical formulation (composition) as described above.

Provided compounds may be formulated for administration in any convenient way for use in human or veterinary medicine, by analogy with other pharmaceuticals.

According to the invention, provided compounds for treating neurological conditions or diseases can be formulated or administered using methods that help the compounds cross the blood-brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

In one aspect of the invention, provided compounds that cross the BBB are particularly useful for treating synucleinopathies. In one embodiment, provided compounds that cross the BBB are particularly useful for treating amyotrophic lateral sclerosis (ALS). Therefore it will be appreciated by a person of ordinary skill in the art that some of the compounds of the invention might readily cross the BBB. Alternatively, the compounds of the invention can be modified, for example, by the addition of various substitutents that would make them less hydrophilic and allow them to more readily cross the BBB.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). The method is conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

The permeability of the blood brain barrier can be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, a provided compound can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and a provided compound or analog thereof (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

Administration of agents of the present invention may be for either prophylactic or therapeutic purposes. When provided prophylactically, the agent is provided in advance of disease symptoms. The prophylactic administration of the agent serves to prevent or reduce the rate of onset of symptoms of ALS. When provided therapeutically, the agent is provided at (or shortly after) the onset of the appearance of symptoms of actual disease. In some embodiments, the therapeutic administration of the agent serves to reduce the severity and duration of the disease.

The function and advantage of these and other embodiments of the present invention will be more fully understood from the examples described below. The following examples are intended to illustrate the benefits of the present invention, but do not exemplify the full scope of the invention.

EXAMPLES

Example 1

High Throughput Assays for Protection from Mutant SOD1-induced Cytotoxicity.

Cultured cells are utilized to conduct high throughput assays for compounds that protect against mutant SOD1-induced cytotoxicity. Two assays are used: first, in the cytotoxicity protection assay, compounds are screened for their ability to protect cells from the cytotoxic effects of aggregated mutant SOD1, irrespective of mechanism of drug action. Second, in the protein aggregation assay, compounds are screened for their ability to reduce aggregation of mutant SOD1. The high throughput cytotoxicity protection assay is the primary screen and compounds active in the primary screen (and their analogs) move forward into the secondary screen for protein aggregation.

Assay for Protection Against Mutant SOD1-induced Cytotoxicity.

Figure 1B:
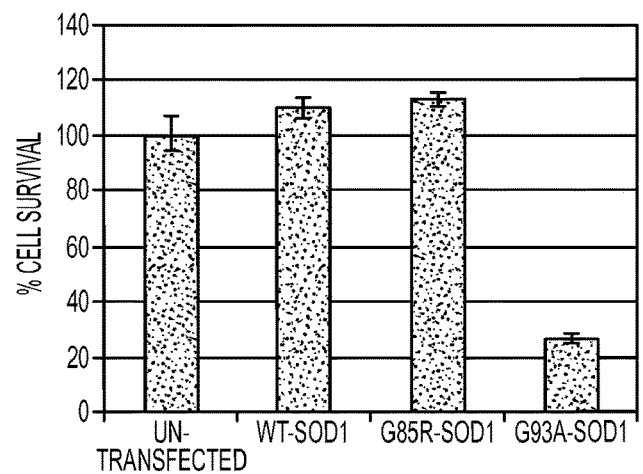
Figure 1C:
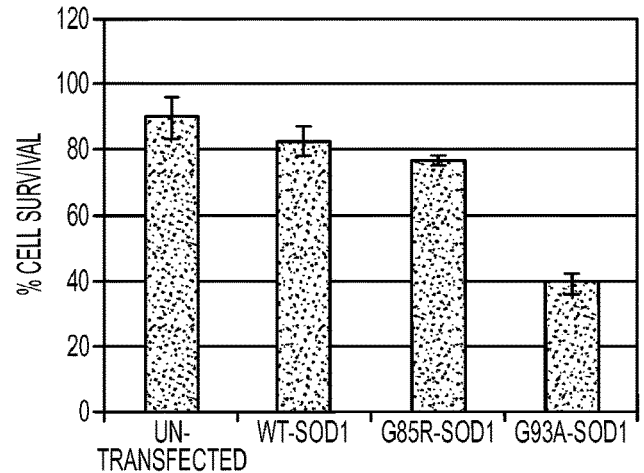

The high throughput cytotoxicity protection assay was carried out in PC12 cells that express mutant G93A SOD1 as a YFP fusion protein from a doxycycline-inducible promoter. Several lines of evidence suggest that cytotoxicity of protein aggregates in ALS is due at least in part to inhibition of the proteasome (Bruijin et al. *Annu. Rev. Neurosci.* 2004, 27, 723-729; Cleveland et al. *Nat. Rev. Neurosci.* 2001, 2(11), 806). This idea was tested by examining the sensitivity of PC12 cells to SOD1 aggregates in the presence and absence of proteasome inhibitor MG132. PC12 cells expressing no SOD1, wild type SOD1, G85R SOD1 or G93A SOD1 were grown with or without MG132 (FIG. 1). Cells expressing no SOD1, wild type SOD1 and G85R SOD1 were relatively insensitive to MG132, with an $IC_{50}$ of approximately 400 nM. In contrast, cells expressing G93A SOD1 were approximately 5-fold more sensitive to MG 132 ($IC_{50}$~75 nM). In these cells, protein aggregation was detected after 24 h and loss of cell viability was detected at approximately 48 h. Qualitatively similar results were obtained with the structurally distinct proteasome inhibitor bortezomib (Velcade®), suggesting that PC12 cells are indeed susceptible to proteasome inhibition and not some other effect of MG 132. The ability of protein aggregates to induce cell death was examined by treating G93A SOD1-expressing cells with MG132 for 24 h, removing the MG132 by washing and assaying cell viability after another 24 h. Because the loss of cell viability was similar following MG132 removal (FIG. 1, part C), it is likely that mutant SOD1 aggregates contribute directly to cytotoxicity in PC12 cells. However, this effect is specific for G93A SOD1 suggesting that this mutant may produce higher levels of a toxic aggregated form of SOD1.

Figure 2:
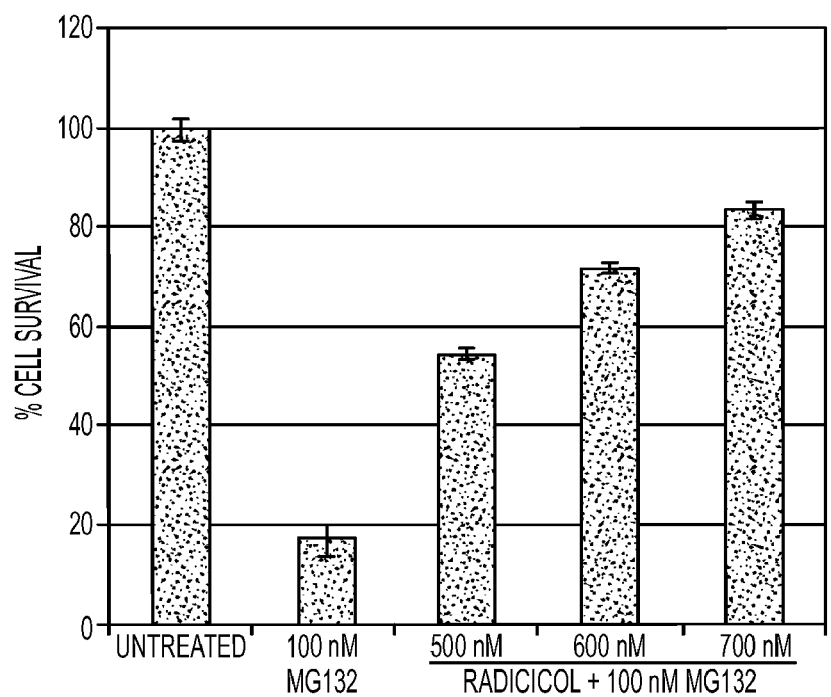
FIG. 2. Radicicol protects PC12 cells expressing mutant G93A SOD1 from the toxic effects of proteasome inhibitor MG132.
Figure 4A:
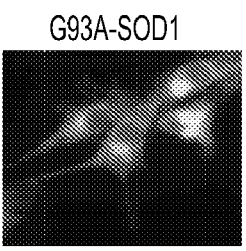
FIGS. 4A-D. Radicicol decreases mutant SOD 1 aggregation induced by proteasome inhibitor MG 132. Fluorescence micrographs of PC 12 cells expressing YFP tagged G93A SOD 1 (left) or G85R SOD 1 (right) proteins. The cells were untreated, treated with 200 nM MG132 to induce protein aggregation (4A and 4C, respectively), or co-treated with MG132 and radicicol for 24 hours (4B and 4D, respectively). Without radicicol treatment, cells show large perinuclear aggregates. The aggregates are reduced in radicicol-treated cells. While the behavior of the two cell lines is generally similar, G85R SOD1 cells show 'brighter' aggregates and more contrast between the aggregates and the cytoplasm.
Figure 4B:
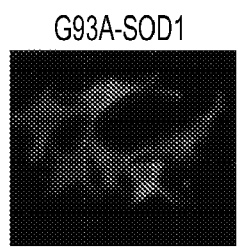
Figure 4C:
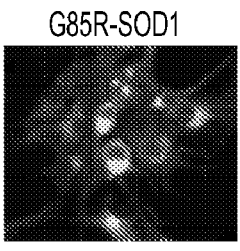
Figure 4D:
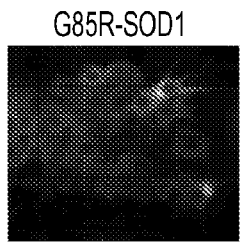

Based on these results, a high throughput screen was developed for compounds that protect against the cytotoxicity of G93A SOD1 protein aggregates using geldanamycin or radicicol as a positive control. PC12 cells expressing G93A SOD1 were treated with 100 nM MG132 with or without co-treatment with geldanamycin or radicicol. The latter compounds inhibit the chaperone HSP90 and induce expression of other chaperones. As anticipated, radicicol reduced formation of protein aggregates and increased cell viability in a dose-dependent manner (FIG. 2). Statistical analysis of the data produced a Z' value of 0.55, which would predict good performance as a positive control in a high throughput screen (Zhang et al., *J. Biomol. Screen* 1999, 4(2), 67-73).

Mutant SOD1 Direct Protein Aggregation Assay.

Compounds that are active in the above assay could theoretically protect against mutant SOD1-induced cytotoxicity through a number of mechanisms, including the following: 1) compounds could nonspecifically block or reverse protein aggregation via chaperone induction, as observed for radicicol and geldanamycin; 2) compounds could block or reverse the aggregation of a specific aggregated protein form; 3) compounds could interfere with an event downstream of protein aggregation that plays a critical role in mutant SOD1-induced cytotoxicity (e.g., proteasome function); and 4) compounds could act directly on SOD1 in a manner that prevents mutant SOD1 aggregation. These possibilities were tested using an assay that directly measures protein aggregation. In addition, unlike the high throughput cytotoxicity protection assay, the protein aggregation assay is based on G85R SOD1; this broadens the scope of the screening strategy, and should eliminate compounds with highly specific activity (i.e., G93A SOD1 limited) against protein aggregation.

In PC12 cells that express wild-type SOD1, SOD1 was diffusely localized throughout the cell (Matsumoto et al., *J. Cell. Biol.* 2005, 171(1), 75-85). In contrast, G85R SOD11 showed heterogeneous patterns of localization; in most cells, G85R was diffusely localized throughout the cell, but in 5% of the cells, G85R SOD was localized in large peri-nuclear aggregates. In cells treated with MG 132, up to 75% of cells expressing G85R SOD1 contain such protein aggregates (FIG. 3), but no aggregation was observed in cells expressing wild-type SOD1. Cells expressing G93A mutant SOD1 showed an intermediate level of protein aggregation: none of the cells developed protein aggregates in the absence of MG132, and ~75% of the cells had protein aggregates following treatment with MG132 (FIG. 3). Similar effects were observed in cells treated with bortezomib (Velcade®). Therefore, these effects are likely to be due to MG132-induced proteasome inhibition, and not due to an off-target effect of MG132.

The sensitivity of this assay was optimized by selecting conditions that maximize the difference between active and inactive samples. The identification of a positive control is a crucial step in assay development. Thus, PC12 cells expressing G85R or G93A mutant SOD1 were treated with MG132 to induce protein aggregation, and then co-treated with candidate chemical suppressors of protein aggregation. Two compounds with similar activity were identified in these experiments: geldanamycin and radicicol. Both compounds induce heat shock transcription factor NSF-1, which in turn induces the heat shock response (FIG. 4). Treatment with radicicol reduced the proportion of cells with aggregates from 75% to 25%, a sufficient difference to allow visual scoring for compounds with efficacy equal to or greater than radicicol.

To allow this assay to be used in a high-throughput manner, a Cellomics Arrayscan® high content microscopy system was used for screening and quantification. Initial experiments indicated that G85R SOD1 aggregates were more readily recognized by the high content microscopy system and its computer algorithm. Because the most robust high content assays measure events on a per cell basis, it was necessary to select a fluorescent stain that marks whole cells to be used with a compatible stain that marks intracellular structures. On the basis of pilot experiments with a number of vital dyes, an Image-iT conjugated wheat germ agglutinin (WGA) dye from Molecular Probes was selected and a computer algorithm for detecting WGA was developed. As shown in FIG. 5, WGA provided an excellent cellular marker that did not interfere with detection of YFP-tagged SOD1.

Initial experiments used geldanamycin and radicicol as positive controls, both of which are reproducibly active, but did not show highly statistically reliable performance when the high content microscopy system was used. Therefore, pyrazolones CMB-3350 and CMB-3319 were tested as alternate positive controls. CMB-3350 and CMB-3319 were selected because of their outstanding activity in the SOD1 cytotoxicity protection assay.

Example 2

Procedures and Protocols for High Throughput Screening

Mutant SOD1-induced Cytotoxicity Protection Assay: Automated High Throughput Screening Protocol.

PC12 cells were maintained in Dulbecco's Modified Eagle's Medium (Invitrogen), supplemented with 10% horse serum, 0.1 µ/ml NGF (Sigma), and 0.1 µ/ml doxycycline (Sigma). Cells were incubated at 37° C. in a humidified atmosphere with 5% $CO_2$. The expression of SOD1 protein was induced by the withdrawal of doxycycline from the media. For screening in microwell format, cells were seeded at 15,000 cells/well in 96-well plates (Falcon-BD) using a Multidrop 384 (Thermo Lab Systems) and incubated 24 h prior to compound addition. Compounds (control and test) were added to wells using a Zymark Sciclone. MG132 was added 24 h later using the Multidrop 384. Cell viability was measured after 48 h using the fluorescent viability probe calcein-AM (Molecular Probes). Fluorescence intensity was measured using a POLARstar fluorescence plate reader (BMG). All experiments included positive control wells treated with radicicol at 700 nM and negative control wells treated with DMSO. Fluorescence data were coupled with compound structural data, then stored and analyzed using the Cambridgesoft Chemoffice Enterprise Ultra software package.

Mutant SOD1 Aggregation Assay: Automated High Content Screening Protocol.

PC12 cells were maintained in Dulbecco's Modified Eagle's Medium (Invitrogen) supplemented with 10% horse serum, plus 0.1 μ/ml NGF (Sigma) and 0.1 μg/ml doxycycline (Sigma). Cells were incubated at 37° C. in a humidified atmosphere with 5% $CO_2$ and are routinely subcultured using 0.05% trypsin-EDTA solution. The expression of SOD1 protein was induced by the withdrawal of doxycycline from the media. For screening in microwell format, cells were seeded at 5,000 cells/well in 96-well plates (Falcon-BD) using a Thermo Labsystems Multidrop 384. Compounds (control and test) were added to wells using a Zymark Sciclone. Test compounds were incubated with the cells for 24 h prior to the addition of MG132. CMB-3350 was used as a positive control at 5 μM, DMSO as a negative control and test compounds were applied at 512M. MG132 was then added at 1 μM final concentration and the cells were grown for an additional 24 hours. To assay protein aggregation, cell culture medium was then removed and the cells were washed once with HBSS then incubated in HBSS containing 5 μg/ml of the Image-iT WGA plasma membrane dye (Molecular Probes) for 15 min at 37° C. Cells were then washed with PBS and imaged using the Cellomics Arrayscan®.

Assay Automation.

Arrayscan images were recorded using a 20× objective and the XF93-TRITC filter set in channel 1 for the Image-iT WGA plasma membrane dye or the XF93-FITC filter set for SOD1-YFP and analyzed using Cellomics spot detector software. Software parameters were set to maximally differentiate cells from background and maximize recognition of SOD1 aggregates without recognizing background cytoplasmic staining as a spot. Data were recorded as spot count (aggregate)/object (cell).

A library was screened using the cytotoxicity protection assay as the primary screen and the protein aggregation assay as the secondary screen. The overall screen produced an average Z' factor of 0.5 and an average Z factor of 0.6. Using 60% viability as the cutoff for activity, 195 primary actives were recovered (0.38% primary hit rate). All primary actives were retested in dose response curves yielding 68 confirmed actives (0.13% confirmed hit rate). These actives were then tested for auto-fluorescence and inhibition of protein synthesis, potential causes of artifactual positives. Confirmed primary actives were assayed in the high content protein aggregation screen and grouped into compounds that were positive or negative in the secondary screen. Cheminformatic analysis of these compounds identified 17 chemotypes of structurally-related active and inactive compounds plus 15 singleton hits. Most active compounds were also active in the secondary high content assay, two of the confirmed primary actives were not. Initial biological analysis focused on the arylsulfanyl pyrazolone lead series. The compound collection includes riluzole, which tested negative indicating that the actives tested here differ from the sole clinically approved drug for ALS.

Counterscreens.

All active compounds were tested for autofluorescence, a potential artifact in any fluorescence assay. This test only identified one compound with significant autofluorescence. This low rate of autofluorescence might be due to the use of calcein-AM to measure cell viability. Calcein-AM is a high quantum yield reagent and thus only highly fluorescent compounds produce a comparable signal. All active compounds were tested for ability to inhibit protein synthesis, as this could artificially reduce protein aggregation. Specific reduction in the cellular concentration of SOD1 was estimated using a modification of the high content assay, in which YFP fluorescence was measured with a plate reader prior to counting the number of cells per well with ArrayScan. This yielded a value for YFP fluorescence per cell, which is equivalent to SOD1 content per cell. No compounds tested active in this assay. Lastly, all active compounds were tested for nonspecific cytotoxicity in untransfected PC12 cells. The vast majority of the active compounds lacked or had extremely low non-specific cytotoxicity. One possible explanation for the low level of cytotoxicity associated with active compounds is that the primary protection screen selected specifically against such compounds.

Discovery and Preliminary SAR of Chemical Lead Series.

Results show that certain provided compounds and analogs thereof were active ($ED_{50} \leq 20$ μM) in the cytotoxicity protection assay. Compounds that were tested in the SOD1 protein aggregation assay are also indicated.

Chemical Identification and Analog Selection.

All active compounds were reordered and re-tested from dry powder to confirm activity. Confirmed active compounds were characterized by an iterative process designed to establish preliminary SAR. This process included reanalyzing the screening files to identify structurally-related but weakly active or inactive compounds and testing structurally-related compounds purchased from commercial suppliers. Over 300 chemical compounds were acquired from an extensive search of over 2 million unique available commercial compounds on the basis of a substructure and Tanimoto similarity analysis carried out using an in-house vendor chemical warehouse database system. All compounds were ≥90% pure (by LC/MS and/or $^1$H NMR).

Biological Assays to Guide SAR Analysis.

The high throughput cytotoxicity protection assay and the high content protein aggregation assay only score compounds as active or inactive. Two quantitative metrics were therefore developed to evaluate compound activity for SAR development: potency ($ED_{50}$), which is the concentration producing half maximal cell viability, and efficacy, which is defined as the maximum viability produced by a compound at its optimum dosage. Cytotoxicity is measured by determining the concentration that reduces PC12 cell viability by 50% and is reported as the cytotoxicity $IC_{50}$ (FIG. 2). Compounds were also tested for nonspecific inhibition of protein synthesis, inhibition of protein aggregation (i.e., SOD1-YFP fusion) and autofluorescence (to ensure the detection method was not detecting false positives).

Summary of Biological Effects.

Most of the active compounds showed 100% efficacy as compared with the positive control, radicicol, which showed only 80% efficacy at the most efficacious dose. The most potent compounds produce $ED_{50}$ values between 100 nM and 2 μM in the cytotoxicity protection assay. Compounds that were active in the cytotoxicity protection assay were active in the protein aggregation assay with comparable potency (Table 2). Thus, it is reasonable to assume that these compounds reduce cytotoxicity by reducing mutant SOD1 aggregation. These compounds are generally not cytotoxic or only very weakly cytotoxic. Structure-activity relationship studies of provided compounds were conducted by comparing the activity of compounds with substitutions at N-2, C-4 and C-5 around the pyrazole ring. Compounds without substitution at N-2 (R1) or N-2 (R1) & C-4 ($R^3$) that contain an arylsulfanyl moiety at C-5 (R2) were most potent, with ED50 values between 0.374 and 5 µM. Alkene substituted compounds at C-4, such as dimethyl amine and various substituted aromatic and heterocyclic groups, with a C-5 arylsulfanyl group are equally potent, with $ED_{50}$ values between 0.6 and 5 µM. All substituted alkenes were tested as mixed isomers (E and Z). Table 3 lists selected compounds in this series with an $ED_{50}$<µM in the cytotoxicity protection assay. The most potent active compounds (CMB-3319 & CMB-3350) are the C-5 substituted pyrazoles containing an arylsulfanyl group. CMB-3299 is similar to CMB-3319, but has a methyl substitution at C2 rather than a chlorine group on the arylsulfanyl ring system.

Mechanistic Studies on Arylsulfanyl Pyrazolones.

Figure 6:
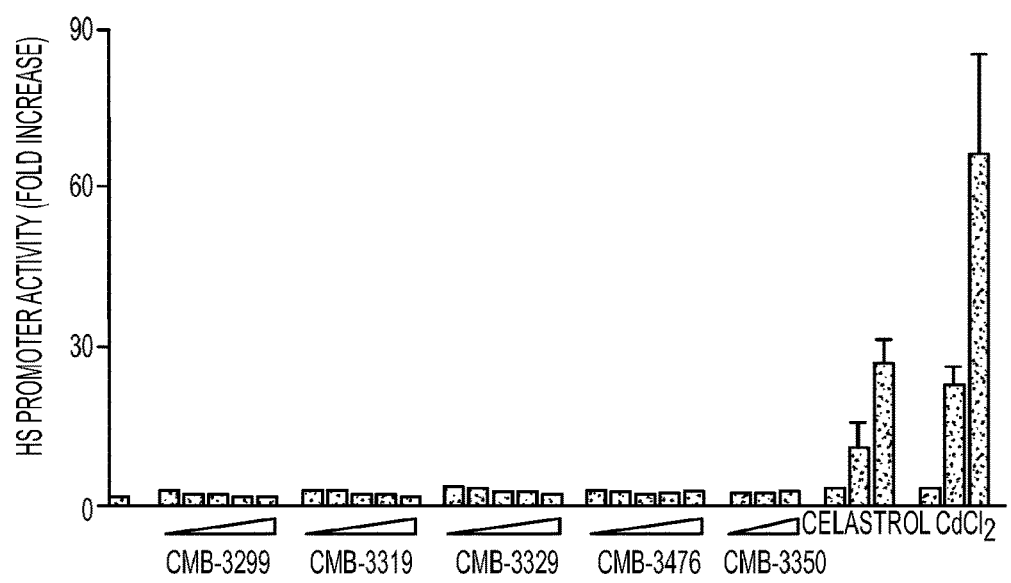
FIG. 6. Arylsulfanyl pyrazolones fail to induce heat shock response in Hsp 70 promotor assays. HeLa hse-luc cells were treated with arylsulfanyl pyrazolones (1 μM-100 μM), celestrol (1 μM-5 μM), or CdC12 (10 μM-10 μM), for 8 h and activation of the heat shock response determined by HSP70 promoter activity.

Mechanism of action studies have been initiated for provided compounds. provided compounds active in the cytotoxicity protection assay were initially assayed for the ability to prevent SOD1 aggregation using manual, low-throughput methods. The results were consistent with the automated screening results, indicating that all provided compounds reduced aggregation of G93A SOD1 in PC12 cells with similar efficacy and potency. The ability of provided compounds to induce expression of molecular chaperones was also tested using stably-transfected HeLa cells (HeLa hse-luc) expressing a luciferase reporter gene under the control of the human HSP70 promoter. This HeLa hse-luc reporter system was used previously to identify small-molecule activators of the heat shock response (Westerheide et al. *J. Biol. Chem.* 2004, 279(53), 56053-56060). The results showed that the five most potent provided compounds, at up to 100 µM, failed to induce luciferase activity in the HeLa hse-luc system, while positive control compounds celastrol and $CdCl_2$ strongly induced luciferase activity (FIG. 6). Provided compounds also failed to induce expression of multiple Hsp70, Hsp40, and Hsp90 genes as determined by RT-PCR. These results suggest that while provided compounds are likely to protect PC12 cells from G93A SOD1 by reducing its aggregation, this effect is not likely to be mediated by increasing the expression of molecular chaperones.

Figure 7:
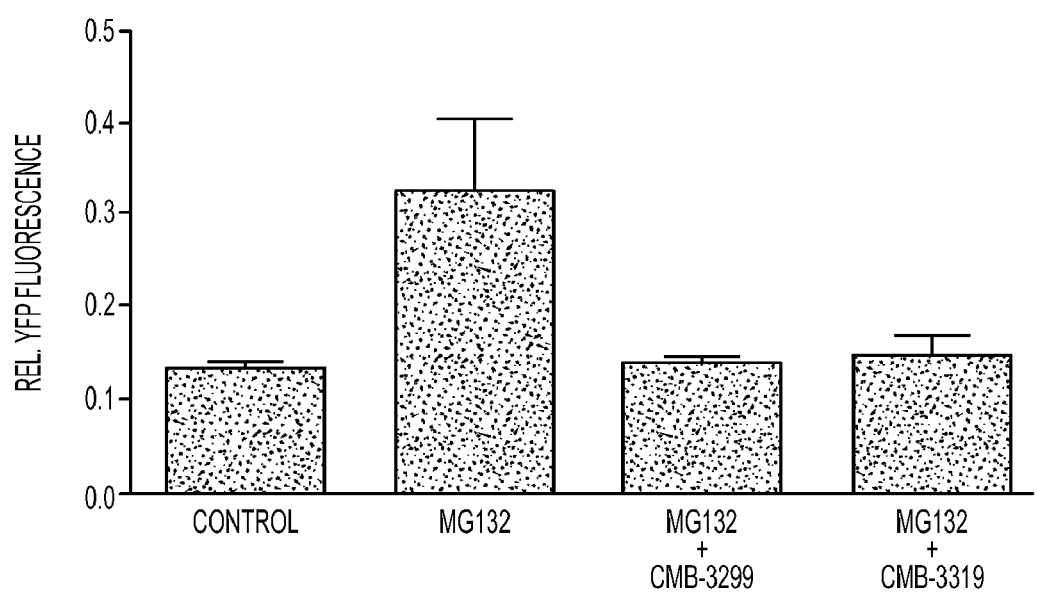
FIG. 7. Arylsulfanyl pyrazolones prevent MG 132-induced accumulation of Ubi-YFP. HeLa cells were co-transfected with Ubi-YFP and. CMV-CFP plasmids, treated with 1 μM MG132 and 25 μM arylsulfanyl pyrazolones and Ubi-YFP fluorescence intensity normalized to CFP.

Since the CMB-003299 cytotoxicity of SOD1 protein aggregates may involve inhibition of proteasome activity, compounds that stimulate proteasome activity could reverse or prevent mutant SOD1-induced cytotoxicity. Thus, active compounds were tested for the ability to stimulate proteasome activity using a cell line expressing ubiquitin-conjugated YFP [Ubi-YFP 74]. In these cells, increased proteasome activity causes increased degradation of Ubi-YFP and decreased YFP fluorescence. Conversely, compounds that inhibit proteasome activity increase accumulation of Ubi-YFP and enhanced YFP fluorescence. As expected, MG132 augments YFP fluorescence intensity ~3-fold compared to untreated controls (FIG. 7). The provided compounds (CMB-3299 or CMB-3319) strongly inhibit MG132-induced Ubi-YFP fluorescence, suggesting that these compounds stimulate proteasome activity. To demonstrate that these compounds are not simply blocking the action of MG132, a group of provided compounds were tested on a *C. elegans* strain which expresses mutant SOD1 in muscle cells. Protein aggregates are present in the absence of MG132 and aggregation is suppressed following treatment with a provided compound. These results suggest that the mechanism by which provided compounds protect cells against mutant SOD1-induced cytotoxicity is by stimulating the proteasome.

Example 3

Procedures and Protocols for Compound Characterization

Activation of Cellular Heat Shock Response.

HeLa cells, stably transfected with a luciferase reporter plasmid under control of the HSP70 promoter, were plated in a 96 well plate at a density of 7500 cells/100 µl. Following a 16 h incubation at 37° C./5% $CO_2$, compounds were added and cells incubated for an additional 8 h. Cells were lysed by the addition of 100 µl BrightGlo reagent (Promega) according to manufacturer's instructions and luciferase activity measured by quantifying luminescence signal. Cells were treated with test compounds at concentrations ranging from 10-100 µM celastrol or $CdCl_2$ serve as positive controls while DMSO is a negative control.

Proteasome Activity Assay.

HeLa cells (20,000/chamber) were plated on 8 chambered Tissue-tek coverglass pretreated with 1 mg/ml poly-D-lysine and allowed to adhere for 18 h at 37° C./5% $CO_2$. Cells were transfected with 0.2 µg each CMV-CFP and Ubi-YFP plasmids using Lipofectamine 2000 according to manufacturer's instructions. Cells were allowed to express CFP and Ubi-YFP for 18 h followed by a 6 h incubation with test compounds (25 µM). MG132 (1 µM) was added for a final 18 h incubation and Ubi-YFP degradation assessed by fluorescence microscopy. Fluorescence intensity of CFP and YFP was calculated on a cell-by-cell basis from captured images using AxioVision software (Zeiss). YFP fluorescence was normalized to CFP fluorescence.

Cytotoxicity Assay.

Nonspecific cytotoxicity was determined using PC12 and other cell lines in conventional dose response assays employing calcein-AM fluorescence as the indicator of cell viability. In addition, compounds could score a false positive by selectively reducing the synthesis of aggregated proteins (i.e., SOD1-YFP fusion). Reduction in SOD1 protein concentration was determined using a modification of the high content assay in which YFP fluorescence is measured on a plate reader prior to determining number of cells per well with the Arrayscan. Specific YFP activity, which is equivalent to SOD1 content per cell, was then calculated.

Expanded Assays for Aggregated Protein Spectrum.

Provided compounds are tested for efficacy in cell lines that express huntingtin protein aggregates instead of SOD1 (Kim et al., *Nat. Cell. Biol.* 2002, 4(10), 826-831; Matsumoto et al., *J. Biol. Chem.* 2005). Other active compound series are tested in these cells as well. If broader characterization is desired, analogous cell lines expressing tau, amyloid Aβ, and prion protein are constructed and similar experiments performed. In addition, a cell line that expresses TDP-43 and produces TDP-43 aggregates is constructed. TDP-43 is an aggregated protein that accumulates in neural cells in patients with sporadic ALS (Neumann et al. *Science,* 2006, 314(5796), 130-133; Arai et al., *Biochem. Biophys. Res. Commun.* 2006, 351(3), 602-611). Active compounds are tested for ability to prevent TDP-43 aggregation and/or reduce its associated cytotoxicity. Compounds that prevent TDP-43-associated cytotoxicity and/or aggregation are expected to have greater potential for efficacy in sporadic ALS patients.

Identification of Chemical Lead(s) Whose Predicted Pharmacological Properties are Suitable for Testing in Mice.

The most common and most rigorous approach to determine the toxicity and pharmacological properties of candidate pharmacological compounds relies on in vivo testing in laboratory animals. Because animal testing is both expensive and time consuming, many drug discovery organizations have turned to in vitro methods to analyze the pharmacological properties of compounds during structural optimization. This approach relies on miniaturized predictive in vitro ADMET assays that are amenable to high- to medium-throughput implementation. These methods have achieved increased popularity, both because animal models are limited in their ability to predict efficacy and toxicity in humans, and because regulatory agencies have begun to require human in vitro testing, such as human liver CYP450 inhibition assays, prior to human clinical trials. The need for methods of this type has also been motivated by the switch from animal disease models to target based in vitro methods for lead discovery (Kerns et al. Curr. Top Med. Chem. 2002, 2(1), 87-98; Di et al., Curr. Opin. Chemn. Biol. 2003, 7(3) 402-408; Kassel et al., Curr. Opin. Chem. Biol. 2004, 8(3), 339-345). The in vitro ADMET approach is based on the use of a suite of chemical tests (compound integrity, compound solubility, compound aggregation, lipophilicity, pKa) and biological assays (Caco-2 and/or PAMPA assays, cytochrome P450 metabolism and inhibition, cardiac risk, and cytotoxicity) that assess the absorption, distribution, metabolism, excretion, and toxic effects of test compounds. The output from ADMET assays is used to identify and select for compounds with low predicted toxicity and desirable predicted pharmacological properties during SAR-based optimization. Compounds optimized by this approach are selected for analysis in the mouse model of ALS. The following suite of assays are performed:

Cytotoxicity: Cytotoxicity is determined in cultured cells.

Compound Purity: Each compound is subjected to chemical analysis to confirm molecular weight and determine purity. Only compounds >95% pure are used for further testing. Compounds <80% pure are re-purified and re-tested.

Compound Aggregation: Aggregation of screening hits is measured using dynamic light scattering.

Solubility: Because compounds are stored in DMSO, it is necessary to determine aqueous solubility of initial hit compounds and their analogs. High solubility in aqueous solution is necessary for high GI absorption, bioavailability, and for chemical formulation. Compounds should be soluble in aqueous solution at >10 µg/ml. Solubility of >50 µg/ml is preferred.

General Permeability: High membrane permeability is required for effective GI absorption and optimal bioavailability. Passive permeability is typically assessed in the PAMPA artificial membrane assay (Kansy et al., J. Med. Chem. 2002, 45(8), 1712-1722). Cell-based permeability determinations using the Caco-2 cell assay are more resource intensive but more predictive of active transport or efflux in vivo (Artursson et al., Adv. Drug. Deliv. Rev. 2001, 46(1-3), 27-43). Caco-2 assays are performed as needed during SAR development.

Blood Brain Barrier: CNS therapeutics must penetrate the blood-brain barrier (BBB) to achieve in vivo efficacy (Basak et al., Pharm Res. 1996, 13(5), 775-778). A QSAR model was developed for predicting in vivo BBB partitioning using the logarithm of the blood-brain concentration ratio as a diagnostic indicator. A 189 compound dataset was constructed from data in the literature (Rose et al., J. Chem. Inf. Comp. Sci. 2002, 42(3), 651-656; Pan et al., J. Chem. Inf. Comp. Sci. 2004, 44(6), 2083-2098) and compounds in the dataset entered as 2D structural drawings with ISIS/Draw and saved as mol files and converted into 3D structures using the Corina software prior to calculating molecular descriptors using Dragon. A Support Vector Machine (SVM) linear regression algorithm was used to generate & validate the model. The prediction accuracy (Q) for the SVM linear regression training model (n=166) and validation set (n=24) was 86.75 and 86.96%, respectively, confirming the validity of the model. Using this BBB predictive model, the potential of active compounds to cross the BBB is appraised early during development. Other BBB predictive models, including a variant of the PAMPA assay developed specifically for this purpose (Di et al., Eur. J. Med. Chem. 2003, 38(3), 223-232), is used as needed. Results of these experiments guide synthesis of compounds with appropriate ADME properties for use as CNS therapeutics.

Lipophilicity and pKa: Lipophilicity is determined via octanol-water partition at pH 7.4 (Hitzel et al., Pharm. Res. 2000, 17(11), 1389-1395) and pKa is determined by capillary electrophoresis and photodiode array detection (Ishihama et al., J. Pharm. Sci. 2002. 91(4), 933-942).

Metabolism (microsome, S9 fraction, CYP450): Liver Cytochrome P450 (CYP450) enzymes are the major route for xenobiotic metabolism and microsomal and hepatocyte stability is the best predictor of pharmacokinetic half-life. Cross-species comparisons of metabolism in liver microsomes can predict potential issues with liver toxicity in humans. Selected active compounds are tested in liver microsomes from efficacy species (mouse), toxicity species (rat, dog, monkey), and humans for metabolic stability.

Drug-drug interaction and cardiac risk potential: Data-mining algorithms and data compiled from the literature, are used to predict whether active compounds are likely to interact with and/or inhibit major Cytochrome P450's (1A2, 2C9. 2 C19, 3A4, 2D6) (Kerns et al., Curr. Top. Med. Chem. 2002, 2(1), 87-98). Synthesized compounds are also tested directly for ability to bind and inhibit human CYP P450. If potential problems are indicated by these approaches, analog synthesis is directed towards developing alternative compounds. This approach allows for the assessment of cardiac safety, since hERG inhibition is assessed simultaneously on the same compounds. The hERG assay is done with the fast-patch methodology, hERG ion channel inhibition is implicated in greater than 90% of reported cases of cardiac toxicity, and is a common cause of after market drug failures and withdrawals. Information on hERG inhibition as well as inhibition of five major human CYP450s (1A2, 2C9. 2 C19, 3A4, 2D6) allows for accurate prediction of potential drug-associated cardiac risk.

Plasma stability: Plasma stability of active compounds is assessed in efficacy species (mouse), toxicity species (rat, dog, monkey), and human cells.

Plasma protein binding: Plasma protein binding is examined in efficacy species (mouse), toxicity species (rat, dog, monkey), and human cells using ultrafiltration methodology.

The compounds identified were evaluated in the transgenic G93A ALS mouse model. ADME data was used to determine optimal route of administration. $LD_{50}$ and maximally-tolerated dose were determined, and that information was used to design and execute pharmacokinetic studies to assess brain bioavailability, and to guide choice of dosing regimen (i.e., frequency, dose, route). Three-dose basic efficacy studies were performed on compounds demonstrating acceptable tolerability and bioavailability. For compounds that demonstrate efficacy, a more complete preclinical study is performed and the efficacies of the test compound and previously characterized neuroprotective agents are compared. This may include further dose optimization, phenotype assessment, comparison with compounds of established efficacy, and analysis of brain tissue in treated animals.

Procedures

Subjects. In the present study, G93A SOD1 mice and littermate controls were bred from existing colonies at the Bedford VA Medical Hospital. The male G93A SOD1 mice were mated with B6SJL females and the offspring were genotyped by PCR using tail DNA. The number of SOD1 transgenes were assessed periodically by PCR to ensure that transgene copy number did not increase or decrease significantly over the course of time. Mice were housed in microisolator cages in complete barrier facilities. A 12 hour light-dark cycle was maintained and animals were given free access to food and water. Control and transgenic mice of the same age (±2 days) and from the same 'f' generation were selected from multiple litters to form experimental cohorts (n=20 per group). Standardized criteria for age and parentage were used for placing individual mice into experimental groups/cohorts. Wild type mice were used for initial toxicity, tolerability, and pharmacokinetic studies and ALS mice were used for one month tolerability studies.

Tolerability, Dosing, and Pharmacokinetics. The tolerable dose range and LD50 for each test compound was determined in wild type mice by increasing the dose b.i.d. one-fold each injection. The route of administration (p.o. by gavage or i.p.) and starting dose was based on solubility and other output from ADME studies. Initial pharmacokinetic (pK) studies were conducted by giving animals a single dose, sacrificing them after 30 min, 1 h, 2 h, 4 h, 6 h, or 12 h, and dissecting brains and spinal cords and determining drug concentration in the target tissue. Drug steady-state levels were determined in animals that have been dosed for 1 week prior to sacrifice. These data are used to optimize the dosing regimen for efficacy studies. Drug doses should achieve a desirable drug concentration in the brain and spinal cord of treated mice. Working doses at least 10-fold lower than the acute tolerability dose are preferable.

Efficacy studies. Efficacy is measured using endpoints that indicate neuroprotective function. These include reversal of degenerative lesions in the brain and neuronal tissues, improved motor function, increased body weight, and prolonged survival. Some mice cohorts are sacrificed at a predetermined time point, while others are sacrificed when they reach criteria for euthanasia.

Survival. Mice were observed three times daily (morning, noon, and late afternoon) throughout the experiment. Mice were euthanized when disease progression is sufficiently severe that they were unable to initiate movement and right themselves after gentle prodding for 30 seconds.

Body weights. Mice are weighed twice a week at the same time each day. Weight loss is a sensitive measure of disease progression in transgenic G93A SOD1 mice and of toxicity in transgenic and wild type mice.

Motor/behavioral. Quantitative methods of testing motor function are used including Rotarod and analysis of open field behavior. Decline of motor function is a sensitive measure of disease onset and progression.

Neuropathology. Selected cohorts (n=10) of treated and untreated G93A SOD1 mice are euthanized at 120 days for isolation and analysis of spinal cord tissue. For this purpose, mice are deeply anesthetized and perfused transcardially with 4% buffered paraformaldehyde at the desired time point. These and other studies are performed in a blinded manner, to avoid bias in interpretation of the results. Brains are weighed, serially sectioned at 50 μm and stained for quantitative morphology (cresyl violet), to assess protein aggregates, and to label ventral neurons. Remaining tissue samples/sections are stored for future use. Stereology is used to quantify ventral horn atrophy, neuronal atrophy, neuronal loss, and protein aggregate load.

Analysis. Data sets are generated and analyzed for each clinical and neuropathological measure. Effects on behavior and neuropathology are compared in treatment and control groups. Dose-dependent effects are assessed in each treatment group using multiple two-sided ANOVA tests. Multiple comparisons in the same subject groups are dealt with post hoc. Kaplan-Meier analysis was used for survival and behavioral function.

Neuronal quantitation. Serial lumbar spinal cord tissue sections (n=20) from L3-L5 spinal cord segments are used for gross spinal cord areas and neuronal analysis. Gross areas of the spinal cord sections are quantified from each experimental cohort using NIH Image. From the same sections, the ventral horn is delineated by a line from the central canal laterally and circumscribing the belly of gray matter. Absolute neuronal counts of Nissl-positive neurons are performed in the ventral horns in the lumbar spinal cord. Only those neurons with nuclei are counted. All counts are performed with the experimenter (JM) blinded to treatment conditions. Counts are performed using Image J (NIH) and manually verified and the data represent the average neuronal number from the sections used.

Interpretation. Compound efficacy is evaluated using behavioral and neuropathological endpoints. Results for the test compound are compared with results from compounds with established efficacy and neuroprotective action in the G93A SOD1 mouse model. These experiments directly test whether the provided compounds provide therapeutic benefit and, if so, the magnitude of the benefit. Along the way, useful information about solubility, administration, and toxicity are also obtained.

Example 4

Synthetic Routes

Synthetic schemes of the selected analogs of the general arylsulfanylpyrazolone scaffold are illustrated below.

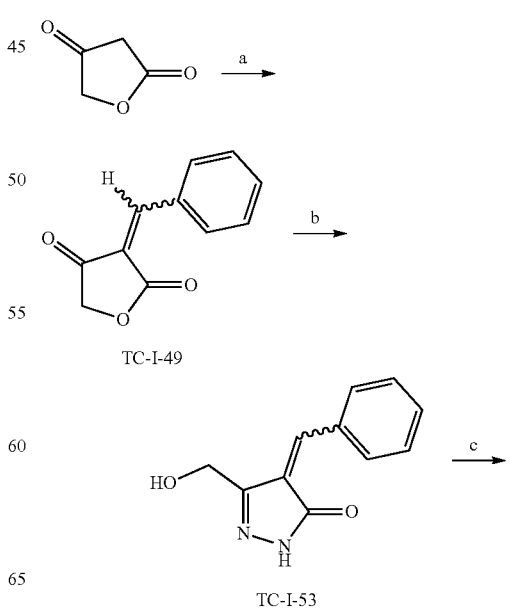

Scheme 1.

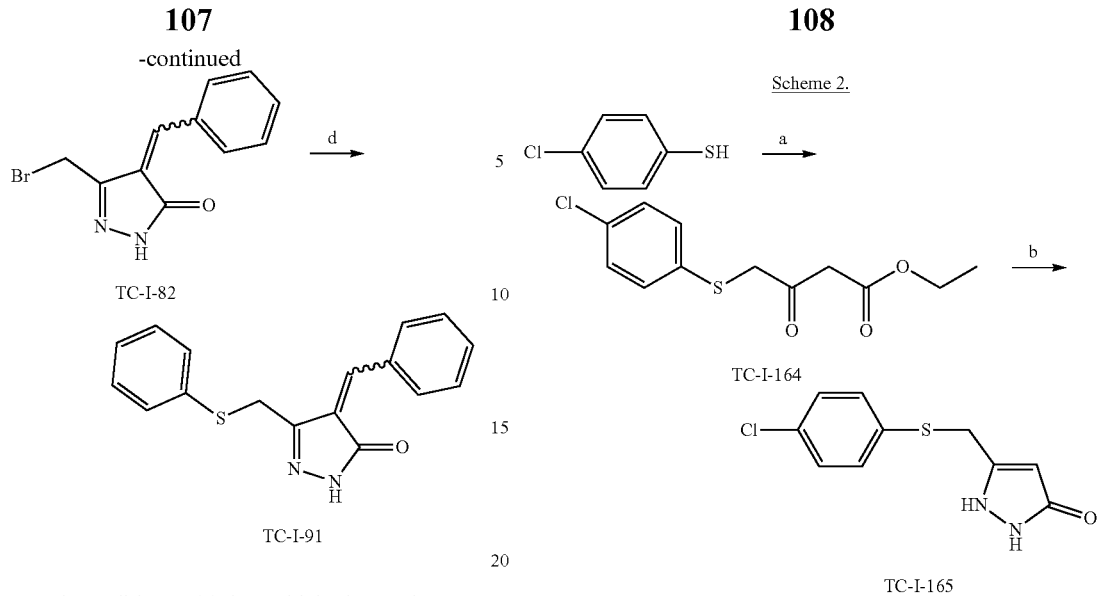

*Reagents and conditions: (a) benzaldehyde, HCl, rt, 5 min; (b) NH₂NH₂, EtOH, reflux, 1 h; (c) PBr₃, THF, rt, 6 h; (d) benzenethiol, K₂CO₃, DMF, 70° C., 18 h.

3-Benzylidenefuran-2,4(3H,5H)-dione (TC-I-49): Tetronic acid (300 mg, 3 mmol) was added to benzaldehyde (1.0 mL, 9 mmol), and the resulting solution was stirred. HCl (37.7%, 0.1 mL) was added drop wise. The reaction mixture was vigorously stirred until it solidified. The solid product was crushed, soaked in hexane and washed with hexane. The crude product was purified by recrystallization (ethyl acetate/hexanes=8/2) to give compound TC-I-49 (0.27 g, 48%) as a yellow solid.

4-Benzylidene-3-(hydroxymethyl)-1H-pyrazol-5(4H)-one (TC-I-53): To a suspension of ethanol (2 mL) and TC-I-49 (367 mg, 2 mmol) was added an ethanolic solution of hydrazine (2 N, 1 mL). The resulting suspension was refluxed for 1 h, during which time all of the TC-I-49 dissolved and a new precipitate formed. The resulting mixture was cooled in an ice-bath for 20 min. The white precipitate was filtered and washed with cold ethanol to give TC-I-53 (77 mg, 28%).

4-Benzylidene-3-(bromomethyl)-1H-pyrazol-5(4H)-one (TC-I-82): PBr₃ (30 μl, 0.38 mmol) was added to a suspension of TC-I-53 (0.23 g, 1.1 mmol) in THF (5 mL) at 0° C. under N₂. The reaction mixture was warmed to room temperature after 5 min. Additional PBr₃ (30 μl, 0.38 mmol) was added after 1 h. The resulting suspension gradually became a solution and was stirred overnight. The reaction mixture was then quenched with brine, and the aqueous layer was extracted with CH₂Cl₂. The combined organic layer was washed with brine, dried over Na₂SO₄, and evaporated to dryness. TC-I-82 (0.125 g, 41%) was obtained by flash column chromatography (ethyl acetate/hexanes=1/4) as a yellow solid.

4-Benzylidene-3-(phenylthiomethyl)-1H-pyrazol-5(4H)-one (TC-I-91): Benzenethiol (61 μL, 0.60 mmol) was added to a suspension of TC-I-82 (0.13 g, 0.50 mmol) and anhydrous potassium carbonate (0.42 g, 3.0 mmol) in DMF (2 ml) at room temperature. The reaction temperature was gently brought to 70° C. After the resulting suspension was stirred for 18 h, the reaction mixture was quenched with HCl (0.25 N), and the aqueous layer was extracted with EtOAc. The combined layer was washed with brine, dried over Na₂SO₄, and evaporated to dryness. TC-I-91 (40 mg, 27%) was obtained by flash column chromatography (ethyl acetate/hexanes=1/2) as a white solid.

*Reagents and conditions: (a) ethyl 4-chloroacetoacetate, Et₃N, 0° C., 30 min; (b) NH₂NH₂, EtOH, reflux, overnight.

Ethyl 4-(4-chlorophenylthio)-3-oxobutanoate (TC-I-164): 4-Chlorothiophenol (1.1 g, 7.61 mmol) was mixed with ethyl 4-chloro-acetoacetate (0.95 mL, 7.00 mmol) in CH₂Cl₂ (100 mL) at 0° C. Triethyl amine (1.5 mL, 10.8 mmol) was then added drop wise. After the resulting suspension was stirred at 0° C. for another 30 min, the reaction mixture was poured into water, and the aqueous layer was extracted with EtOAc. The combined organic layer was washed by saturated NaHCO₃, HCl (0.25 N), brine, concentrated in vacuo, and purified by flash column chromatography (ethyl acetate/hexanes=1/9) to afford TC-I-164 (1.82 g, 96%) as light yellow oil. Exposure to hydrazine in refluxing ethanol, generated TC-II-165.

5-((4-Chlorophenylthio)methyl)-1H-pyrazol-3(2H)-one (TC-I-165): Compound TC-I-164 (0.48 g, 1.76 mmol) was stirred in EtOH (5 mL), and an ethanolic solution of NH₂NH₂ (2 N, 0.88 mL, 1.76 mmol) was added. The resulting solution was refluxed for overnight under Ar, during which a precipitate formed. The reaction mixture was then cooled at room temperature. The precipitate was washed with cold EtOH and dried in vacuo to afford TC-I-165 (0.31 g, 72%) as a white solid.

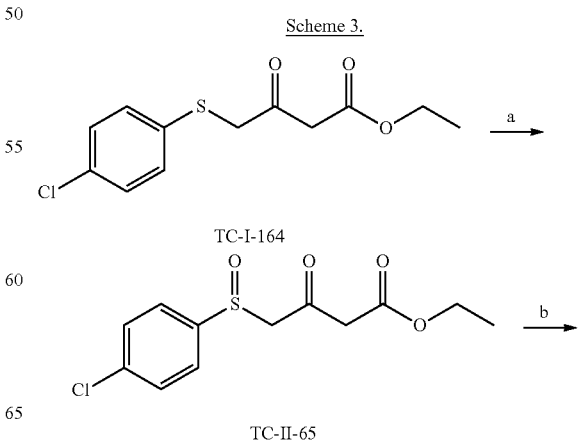

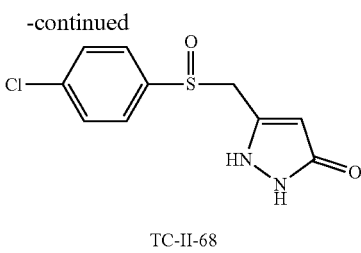

TC-II-68

Reagents and conditions: (a) TBHP, vanadyl acetylacetonate, $CH_2Cl_2$, room temp, overnight; (b) $NH_2NH_2$, EtOH, room temp, overnight.

Ethyl 4-(4-chlorophenylsulfinyl)-3-oxobutanoate (TC-II-65): Compound TC-I-164 (1.27 g, 4.66 mmol) was mixed with t-butyl hydrogen peroxide (70 wt % in water, 1.1 mL, 7.69 mmol) in $CH_2Cl_2$ (50 mL) at room temperature, and vanadyl acetylacetonate (0.1% mol) was added slowly. Extra t-butyl hydrogen peroxide (0.5 mL, 3.50 mmol) was added to the reaction mixture after 2 h. The resulting suspension was stirred overnight at room temperature. The reaction mixture was then concentrated in vacuum and purified by flash column chromatography (ethyl acetate/hexanes=1/4) to afford compound TC-II-65 (0.98 g, 73%) as a light yellow oil. Exposure to hydrazine in refluxing ethanol, generated TC-II-68.

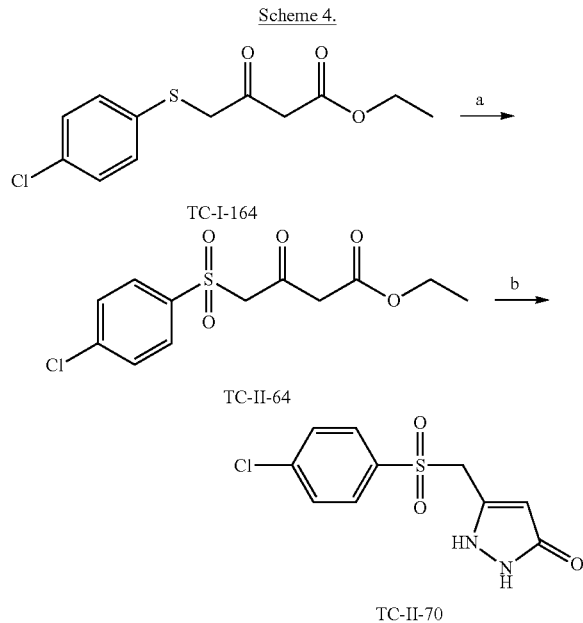

Reagents and conditions: (a) TBHP, vanadyl acetylacetonate, $CH_2Cl_2$, room temp, overnight; (b) $NH_2NH_2$, EtOH, room temp, overnight.

Ethyl 4-(4-chlorophenylsulfonyl)-3-oxobutanoate (TC-II-64): Compound TC-I-164 (3.00 g, 11.0 mmol) was mixed with t-butyl hydrogen peroxide (70 wt % in water, 1.5 mL, 10.50 mmol) in $CH_2Cl_2$ (50 mL) at room temperature, and vanadyl acetylacetonate (0.1% mol) was added slowly. Extra t-butyl hydrogen peroxide (6 mL, 41.94 mmol) was added to the reaction mixture after 2 h. The resulting suspension was stirred overnight at room temperature. The reaction mixture was then concentrated in vacuum and purified by flash column chromatography (ethyl acetate/hexanes=1/4) to afford compound TC-II-64 (1.61 g, 48%) as a light yellow oil. Exposure to hydrazine in refluxing ethanol, generated TC-II-70.

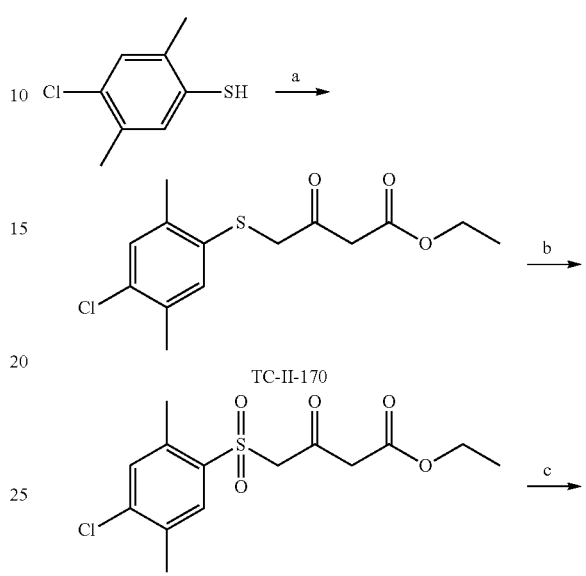

Reagents and conditions: (a) ethyl 4-chloroacetoacetate, $Et_3N$, 0° C., 30 min; (b) $H_2O_2$, AcOH, EtOAc, room temp, overnight; (c) $NH_2NH_2$, EtOH, room temp, overnight.

Ethyl 4-(4-chloro-2,5-dimethylphenylsulfonyl)-3-oxobutanoate (TC-II-171): Compound TC-II-170 (4.68 g, 14.1 mmol) was mixed with AcOH (5 mL) in EtOAc (10 mL), and $H_2O_2$ (30% in water, 10 mL, 84.6 mmol) was added. The resulting solution was left stirring at room temperature for overnight after extra $H_2O_2$ (30% in water, 5 mL, 42.3 mmol) was added. The reaction mixture was then evaporated in vacuo and purified by flash column chromatography (ethyl acetate/hexanes=1/3) to afford TC-II-171 (4.34 g, 85%) as a light yellow oil. Exposure to hydrazine in refluxing ethanol, generated TC-II-172.

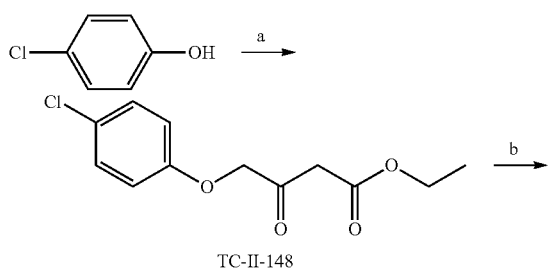

TC-II-148

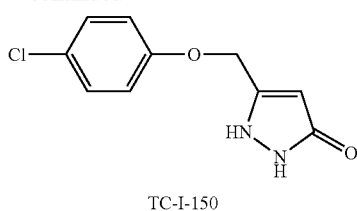

TC-I-150

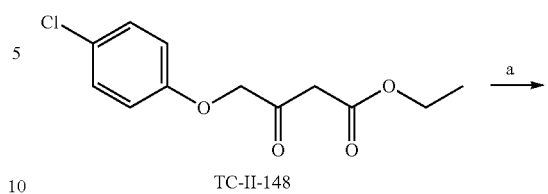

Scheme 8.

TC-II-148

TC-III-87

TC-III-93

Reagents and conditions: (a) ethyl 4-chloroacetoacetate, NaH, dry THF, dry DMF, 70° C., overnight; (b) NH₂NH₂, EtOH, room temp, overnight.

Ethyl 4-(4-chlorophenoxy)-3-oxobutanoate (TC-II-48): A solution of 4-chlorophenol (6.4 g, 50 mmol) in THF (25 mL) was treated with NaH (60% in mineral oil, 2 g, 50 mmol) at 0° C. In another flask, a solution of ethyl 4-chloroacetoacetate (10.21 mL, 75 mmol) in THF (25 mL) was treated NaH (60% in mineral oil, 3.5 g, 75 mmol) at −20° C. The resulting yellowish suspension was slowly added to the solution of sodium 4-chlorophenoxide, which was kept at 0° C. After the addition of DMF (10 mL), the reaction temperature was slowly raised to 70° C. After reaction mixture was stirred at 70° C. for overnight, it was cooled and evaporated to dryness. The residue was purified by flash column chromatography (ethyl acetate/hexanes=1/9) to afford TC-II-148 as a yellowish oil, which still contained some 4-chloroacetoacetate. No further purification was applied for the next step of synthesis. Exposure to hydrazine in refluxing ethanol, generated TC-II-150.

Reagents and conditions: (a) NH₂NH-Me, EtOH, room temp, overnight: (b) Me₂SO₄, CaO, MeOH, room temp, overnight 5-((4-Chlorophenoxy)methyl)-1,2-dimethyl-1H-pyrazol-3(2H)-one (TC-III-93): Compound TC-III-87 (0.145 g, 0.61 mmol) was mixed with CaO (0.20 g, 3.57 mmol) and Me₂SO₄ (0.3 mL, 1.80 mmol) in MeOH (10 mL). The resulting suspension was left stirring at room temperature for overnight. The reaction mixture was then evaporated to dryness. The residue was purified by flash column chromatography (ethyl acetate/hexanes=2/1) to afford TC-III-93 (28.5 mg, 19%) as a white solid.

Scheme 7.

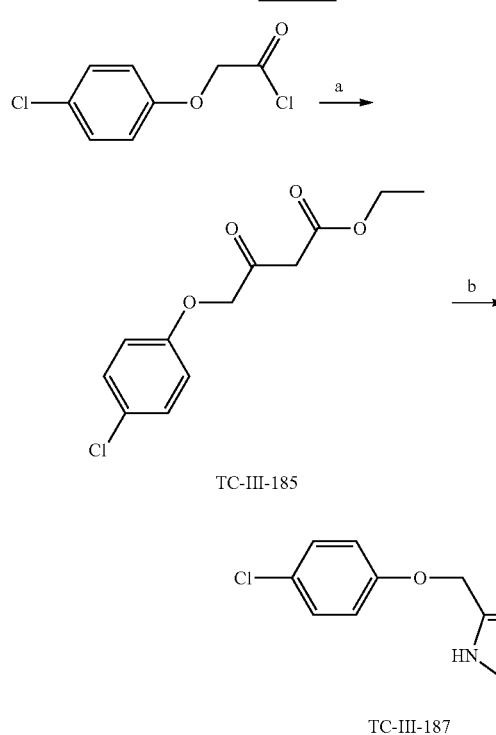

TC-III-185

TC-III-187

Reagents and conditions: (a) EtOAc, LDA. THF, −78° C. to rt, overnight; (b) NH₂NH₂, EtOH, rt, overnight.

Scheme 9.

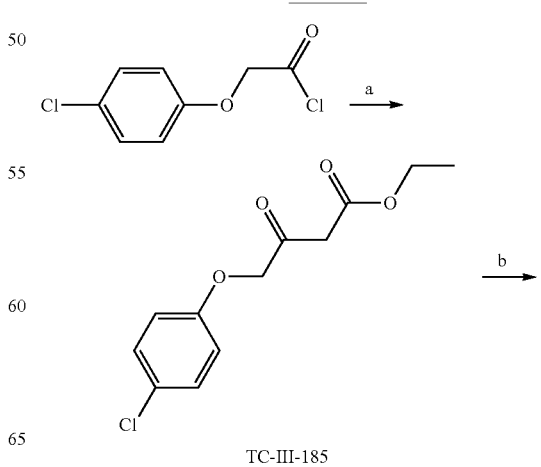

TC-III-185

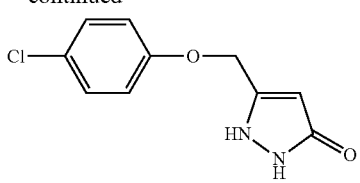

TC-III-187

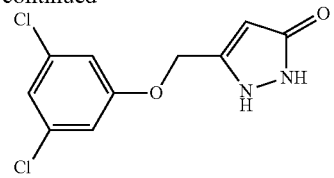

TC-IV-19

Reagents and conditions: (a) EtOAc, LDA, THF, −78° C. to rt, overnight; (b) NH₂NH₂, EtOH, rt, overnight.

4-Chlorophenyl ethyl malonate (TC-III-185): EtOAc (0.63 mL, 6.44 mmol) was added to a solution of n-BuLi (1.6 M in hexanes, 9.2 mL, 14.72 mmol) and diisopropylamine (2.1 mL, 14.85 mmol) at 0° C. After 60 min of stirring, a THF solution of the acetyl chloride (1.31 g, 6.41 mmol) was added at −78° C. The reaction mixture was stirred at −78° C. for 1 h, then at room temperature for overnight. The resulting reaction solution was quenched with diluted HCl (0.25 M), and the aqueous layer was extracted with Et₂O. The combined organic layer was dried over Na₂SO₄ and concentrated in vacuo. The residue was purified by flash column chromatography (ethyl acetate/hexanes=1/9) to give TC-III-85 (0.41 g, 25%) as a yellowish oil.

Scheme 10.

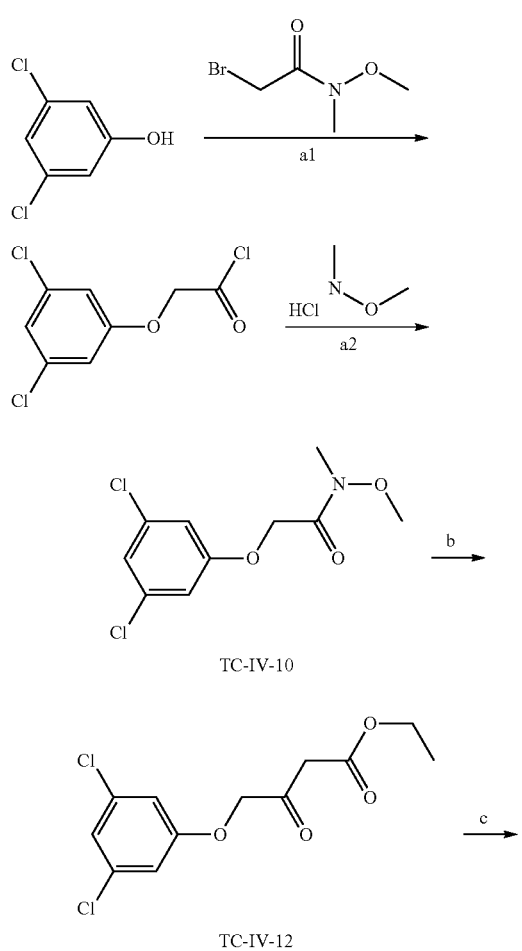

TC-IV-10

TC-IV-12

ᵃReagents and conditions: (a1) NaOEt, EtOH, 70° C., overnight; (a2) DIEA, DCM, rt, 30 min; (b) EtOAc, LiHMDS, THF, −78° C., 8 h; (c) NH₂NH₂, EtOH, rt, overnight.

2-(3,5-Dichlorophenoxy)-N-methoxy-N-methylacetamide (TC-IV-10), method a1: To a solution of phenol (5.27 g, 32.33 mmol) in EtOH (10 mL) was added NaOEt (21 wt % in EtOH, 12.1 mL, 32.41 mmol) at room temperature. The reaction mixture was stirred for 10 min. 2-Bromo-N-methoxy-N-methylacetamide (5.87 g, 32.25 mmol) was then gently added at room temperature. After the resulting solution was stirred at 70° C. for overnight, the reaction mixture was cooled, poured into HCl (0.25 M), and the aqueous layer was extracted with EtOAc. The combined organic layer was concentrated in vacuo and reconstituted in CHCl₃. The precipitate was filtered and washed with CHCl₃. Wienreb amide TC-IV-10 (4.53 g, 53%) was obtained as a white solid.

2-(3,5-Dichlorophenoxy)-N-methoxy-N-methylacetamide (TC-IV-10), method a2: To a solution of N,O-dimethylhydroxylamine HCl salt (5.3 g, 54.33 mmol) in DCM (250 mL) was added DIEA (24 mL, 137.8 mmol) at room temperature. The reaction mixture was stirred for 5 min. Acetyl chloride (13.0 g, 54.28 mmol) was then added in DCM drop by drop at 0° C. The reaction mixture was stirred at room temperature for another 30 min. The resulting reaction solution was washed with HCl (1 N) and concentrated under vacuum. The crude solid product was washed with Et₂O to give Weinreb amide TC-IV-10 (12 g, 84%) as a white solid.

Ethyl 4-(3,5-dichlorophenoxy)-3-oxobutanoate (TC-IV-12): EtOAc (0.9 mL, 9.19 mmol) was added to a solution of LiHMDS (1 N in THF, 21 mL, 21 mmol) at 0° C. and stirred. After 60 min, a THF solution of the Wienreb amide TC-IV-10 (2.4 g, 9.19 mmol) was added at −78° C. After the resulting solution was stirred at −78° C. for 8 h, the reaction mixture was quenched with diluted HCl (0.25 N), and the aqueous layer was extracted with Et₂O. The combined organic layer was dried over Na₂SO₄ and concentrated in vacuo. The residue was purified by flash column chromatography (ethyl acetate/hexanes=1/9) to give TC-IV-12 (1.03 g, 39%) as a white solid.

5-((3,5-Dichlorophenoxy)methyl)-1H-pyrazol-3(2H)-one (TC-IV-19): Ethanolic hydrazine (2 N, 2.5 mL, 5 mmol) was added to a solution of TC-IV-12 (1.5 g, 5.15 mmol) in EtOH (25 mL). The resulting solution was stirred at room temperature for overnight. The reaction mixture was then evaporated in vacuo, purified by flash column chromatography (ethyl acetate/hexanes=1/2) and recrystallized in ethyl acetate/hexanes to give the final product TC-IV-19 (0.368 g, 28%) as a white crystal.

Scheme 11.

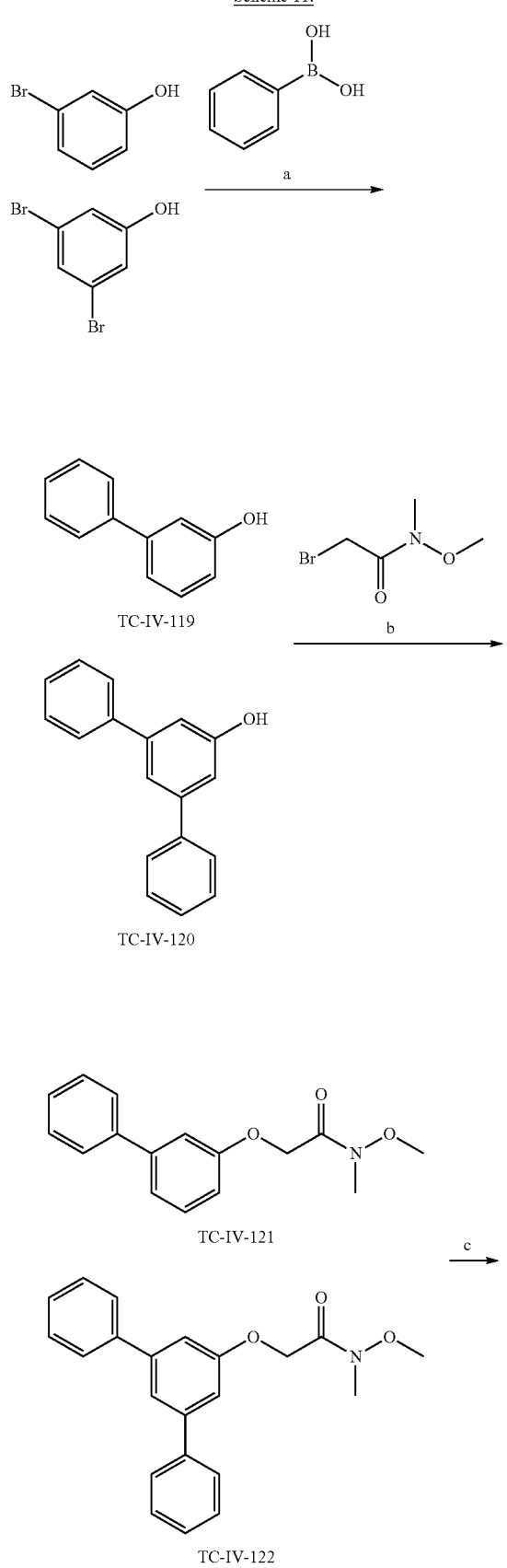

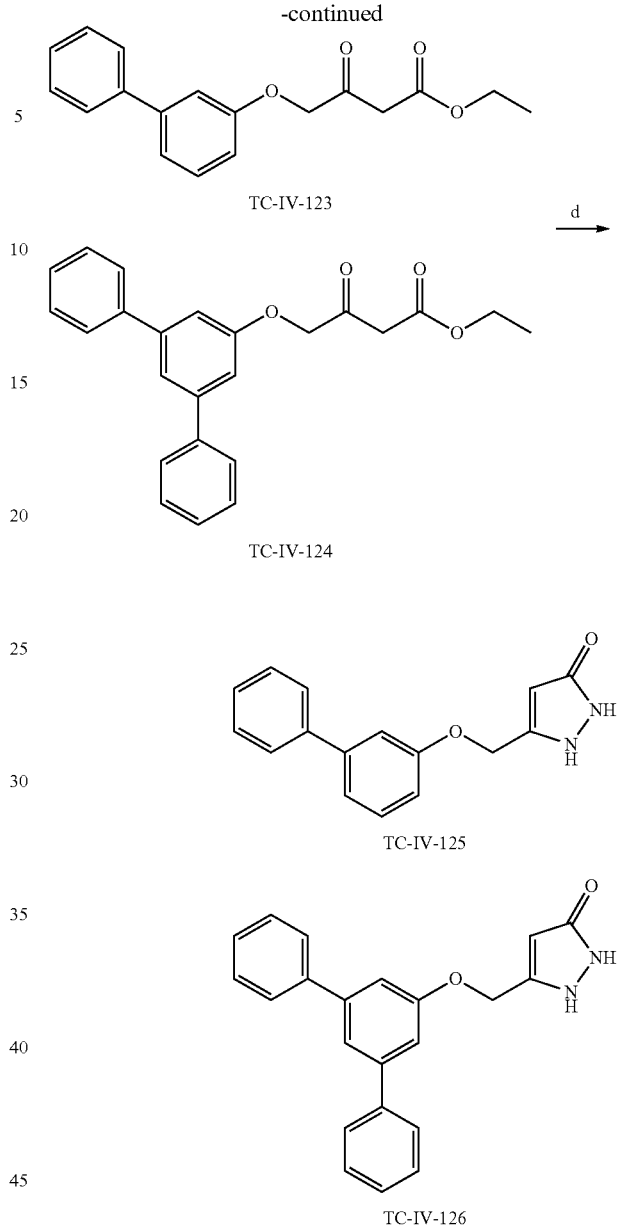

Reagents and conditions: (a) PdCl$_2$(PPh$_3$), K$_2$CO$_3$, dioxane, H$_2$O, 100° C., 16 h; (b) NaOEt, EtOH, 70° C., overnight; (c) EtOAc, LiHMDS, THF −78° C., overnight; (d) NH$_2$NH$_2$, EtOH, rt, overnight.

Biphenyl-3-ol (TC-IV-119): 3-Bromophenol (1.0 g, 5.78 mmol), phenylboronic acid (1.4 g, 11.48 mmol), potassium carbonate (2.0 g, 14.47 mmol), and PdCl$_2$(PPh$_3$) (1/200 eq.) were added to a solution of dioxane/H$_2$O (20 mL/5 mL). The resulting solution was refluxed for 16 h. The reaction mixture was then partitioned between Et$_2$O and water, and the aqueous phase was extracted with Et$_2$O. The combined organic layer was evaporated to dryness and purified by flash column chromatography (ethyl acetate/hexanes=1/9) to give TC-IV-119 (1.02 g, 100%) as a transparent oil.

TC-IV-120: 3,5-Dibromophenol (1.0 g, 3.97 mmol), phenylboronic acid (2 g, 16.4 mmol), potassium carbonate (2.7 g, 19.5 mmol), and PdCl$_2$(PPh$_3$) (1/200 eq.) were added to a solution of dioxane/H$_2$O (20 mL/5 mL). The resulting solution was refluxed for 16 h. The reaction mixture was then partitioned between Et$_2$O and water, and the aqueous phase was extracted with Et$_2$O. The combined organic layer was evaporated to dryness and purified by flash column chromatography (ethyl acetate/hexanes=1/9) to give TC-IV-120 (0.83 g, 83%) as a transparent oil.

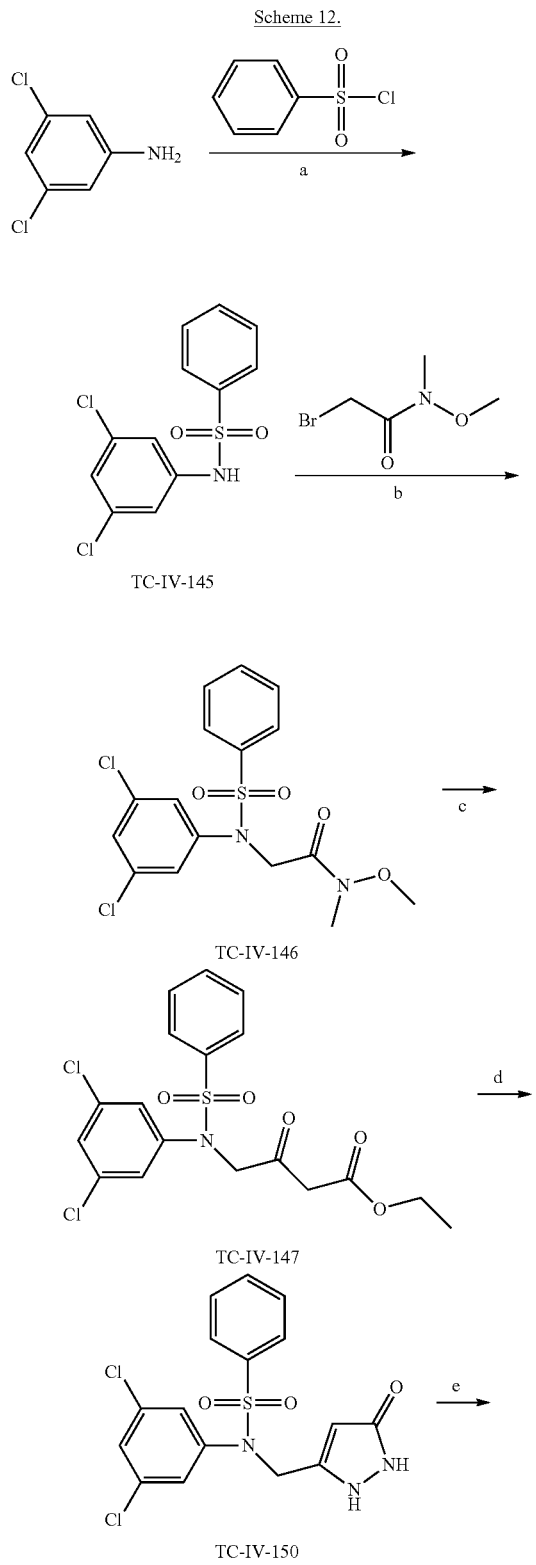

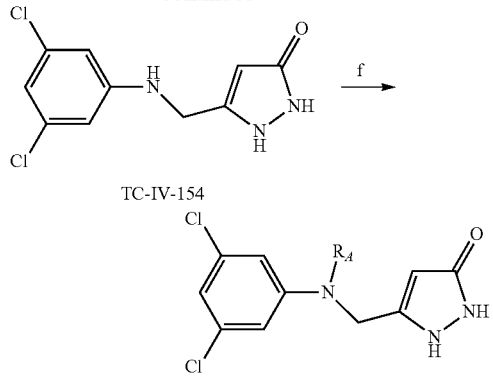

Reagents and conditions: (a) DIEA, DCM, rt, 48 h; (b) K$_2$CO$_3$, acentone, 50° C., overnight; (c) EtOAc, LiHMDS, THF −78° C., 16 h; (d) NH$_2$NH$_2$. EtOH, rt, overnight; (e) HBr, PhOH, H$_2$O, 100° C., 8 h; (f) R$_4$CHO, NaBH(OAc)$_3$, DCM, rt, overnight.

N-(3,5-Dichlorophenyl)benzenesulfonamide (TC-IV-145): Benzenesulfonyl chloride (1.74 mL, 13.57 mmol) and DIEA (0.34 mL, 2.49 mmol) were added to a solution of 3,5-dichloroaniline (2.0 g, 12.34 mmol) in DCM (50 mL). The resulting solution was stirred at room temperature for 48 h, during which a precipitate was formed. The reaction mixture was then evaporated to dryness and purified by flash column chromatography (ethyl acetate/hexanes=1/9) to give TC-IV-145 (1.90 g, 51%) as a yellow solid.

2-(N-(3,5-Dichlorophenyl)phenylsulfonamido)-N-methoxy-N-methylacetamide (TC-IV-146): To a solution of TC-IV-145 (1.90 g, 6.29 mmol) in acetone (30 mL) was added 2-bromo-N-methoxy-N-methylacetamide (1.14 g, 6.26 mmol) and potassium carbonate (0.86 g, 6.22 mmol) at room temperature. After the resulting suspension was stirred at 50° C. for overnight, the reaction mixture was concentrated in vacuo and purified by flash column chromatography (ethyl acetate/hexanes=1/4) to give the Wienreb amide TC-IV-146 (1.15 g, 44%) as a yellow solid.

Ethyl 4-(N-(3,5-dichlorophenyl)phenylsulfonamido)-3-oxobutanoate (TC-IV-147): EtOAc (0.28 mL, 2.86 mmol) was added to a solution of LiHMDS (1 N in THF, 6.3 mL, 6.3 mmol) at −78° C. and stirred. After 60 min, a THF solution of the Weinreb amide TC-IV-146 (1.15 g, 2.86 mmol) was added. After the resulting solution was stirred at −78° C. for overnight, the reaction mixture was quenched with diluted HCl (0.25 N), and the aqueous layer was extracted with Et$_2$O. The combined organic layer was dried over Na$_2$SO$_4$ and concentrated in vacuo. The residue was purified by flash column chromatography (ethyl acetate/hexanes=1/2) to give crude TC-IV-147 (0.60 g, 48%) as a yellow oil.

N-(3,5-Dichlorophenyl)-N-((5-oxo-2,5-dihydro-1H-pyrazol-3-yl)methyl)benzenesulfonamide (TC-IV-150): Ethanolic hydrazine (2 N, 0.69 mL, 1.38 mmol) was added to a solution of TC-IV-147 (0.60 g, 1.39 mmol) in EtOH (10 mL). After the resulting solution was stirred at room temperature for overnight, the reaction mixture was evaporated in vacuo and purified by flash column chromatography (ethyl acetate/hexanes=1/1) to give TC-IV-150 (0.20 g, 32%) as a white solid.

5-((3,5-Dichlorophenylamino)methyl)-1H-pyrazol-3 (2H)-one (TC-IV-154): TC-IV-150 (30 mg, 0.068 mmol) and phenol (60 mg, 0.64 mmol) were added to a solution of HBr in water (48%, 0.75 mL). After the resulting suspension was stirred at 100° C. for 8 h, the reaction mixture was partitioned between water and EtOAc, and the aqueous layer was extracted with EtOAc. The combined organic layer was evaporated to dryness and purified by flash column chromatography (ethyl acetate) to give TC-IV-154 (10 mg, 57%) as a white solid.

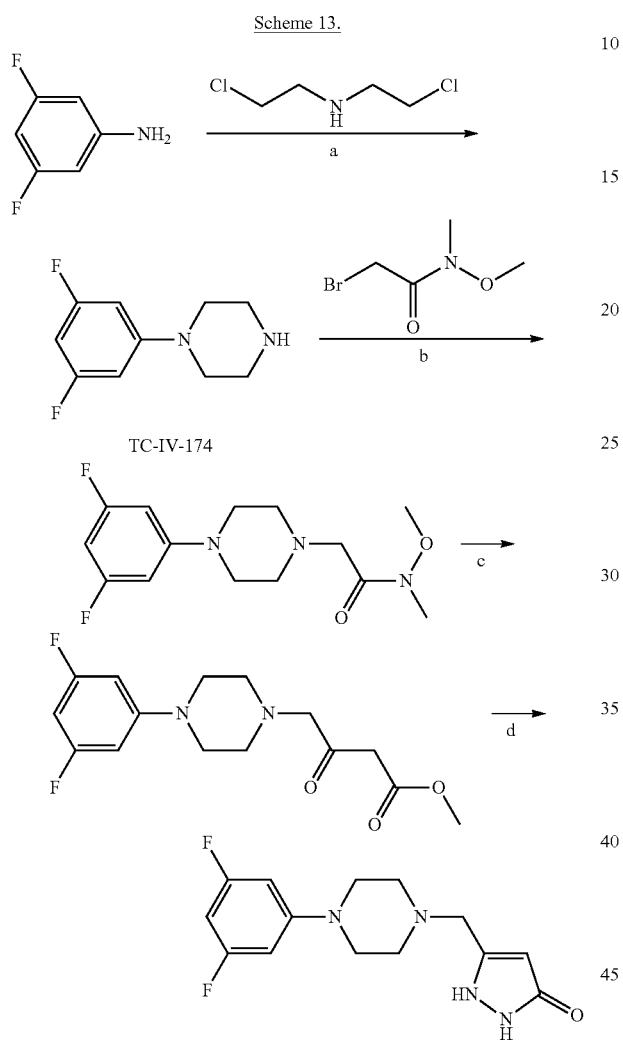

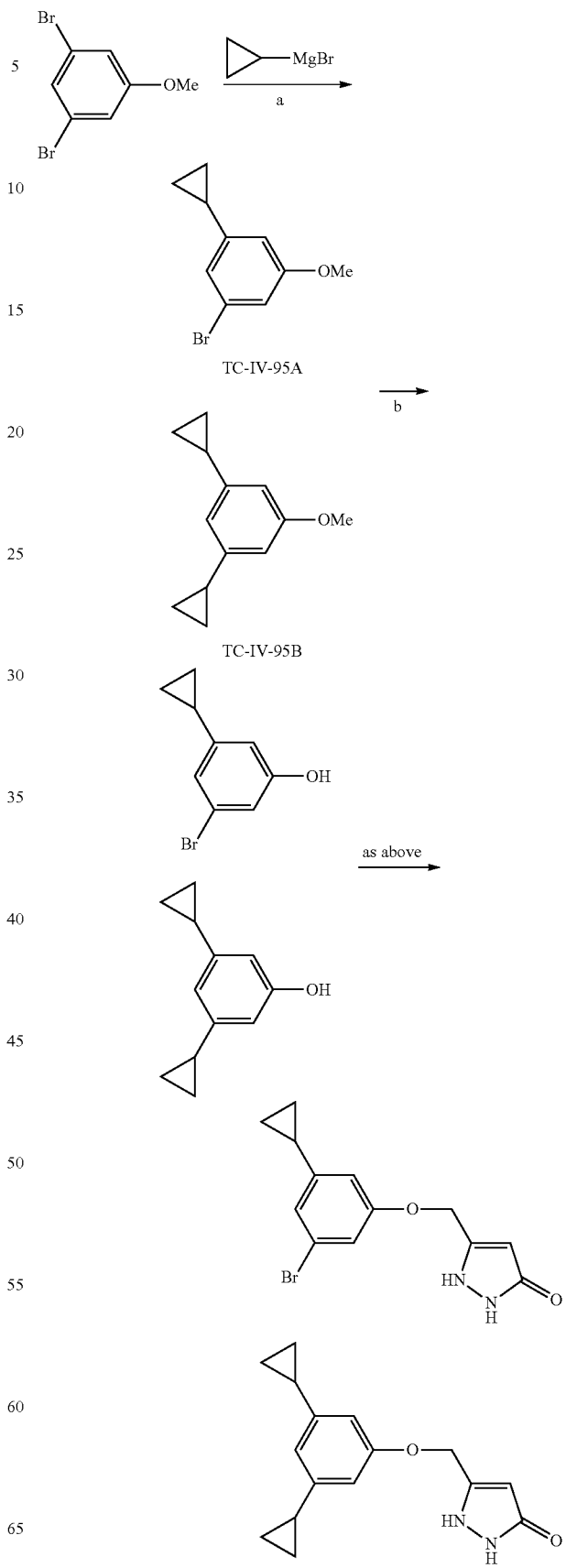

Reagents and conditions: (a) K$_2$CO$_3$, n-BuOH, reflux, 72 h; (b) K$_2$CO$_3$, acentone, 50° C., overnight; (c) EtOAc, LiHMDS, THF −78° C., 16 h; (d) NH$_2$NH$_2$, EtOH, rt, overnight.

1-(3,5-Difluorophenyl)piperazine (TC-IV-174): Bis(2-chloroethyl)amine hydrochloride (2.07 g, 11.60 mmol) was added to a solution of 3,5-difluoroaniline (1.50 g, 11.62 mmol) in n-BuOH (20 mL). After the resulting solution was refluxed for 48 h, anhydrous potassium carbonate (1.61 g, 11.62 mmol) was added. After being refluxed for another 24 h, the reaction mixture was cooled, partitioned between water and CHCl$_3$, and the aqueous layer was extracted with CHCl$_3$. The combined organic layer was washed with water, dried over Na$_2$SO$_4$, and evaporated to dryness. Et$_2$O and 1 N HCl/EtOH were added to the residue, and the precipitate was filtered to give TC-IV-174 (1.17 g, 30%) as a white solid.

Reagents and conditions: (a) NiCl$_2$ (dppp), THF, 60° C., 6 h: (b) (1) BBr$_3$, DCM, −78° C. to rt, 1 h; (2) H$_2$O, −78° C. to rt, 1 h.

Scheme 14 illustrates the use of Kumada couplings to access synthons wherein R$^4$ is cyclic aliphatic.

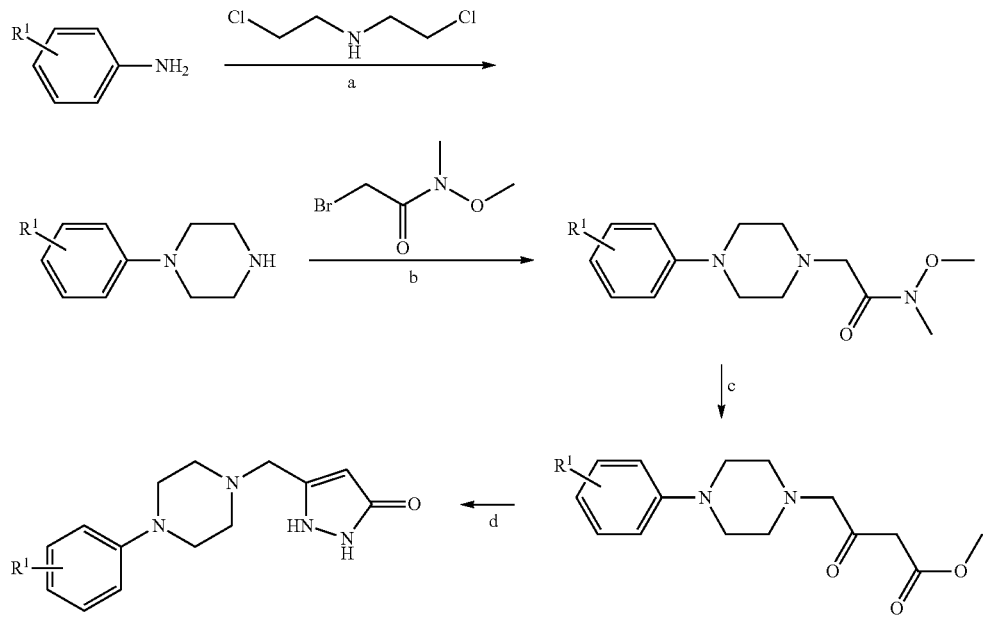

Scheme 15.

Reagents and conditions: (a) K$_2$CO$_3$, n-BuOH, reflux, 48° C.; (b) K$_2$CO$_3$, acetone, 50° C., overnight; (c) EtOAc, LiHMDS, THF, −78° C., 16 h; (d) NH$_2$NH$_2$, EtOH, rt, overnight.

TABLE 2

$^1$H NMR data for selected compounds.

| Structure | $^1$H NMR |
|---|---|
| 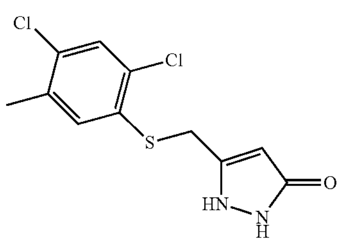 [SMILES: Cc1cc(SCc2cc(=O)[nH][nH]2)c(Cl)cc1Cl] | $^1$H NMR (500 MHz, DMSO-d$_6$, δ): 11.62 (br s, 1H), 9.72 (br s, 1H), 7.57 (s, 1H), 7.46 (s, 1H), 5.39 (s, 1H), 4.15 (s, 2H), 2.30 (s, 3H) |
| 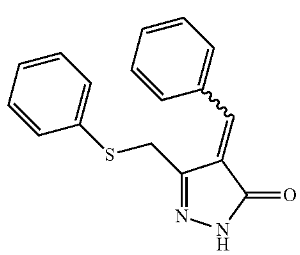 [SMILES: O=C1NN=C(CSc2ccccc2)C1=Cc1ccccc1] | $^1$H NMR (500 MHz, DMSO-d$_6$, δ): 11.29 (s, 1H), 8.03 (s, 1H), 7.68-7.18 (m, 10H), 5.19 (dd, J = 32.0, 16.5 Hz, 2H) |

TABLE 2-continued

¹H NMR data for selected compounds.

| Structure | ¹H NMR |
|---|---|
| | ¹NMR (500 MHz, acetone-d₆, δ): 10.89 (s, 1H), 8.03 (s, 1H), 7.73 (d, J = 6.50, 2H), 7.78-7.22 (m, 7H), 5.22 (dd, J = 16.0, 22.0 Hz) |
| | ¹H NMR (500 MHz, DMSO-d₆, δ): 11.54 (br s, 1H), 9.55 (br s, 1H), 7.34-7.29 (m, 4H), 7.19 (t, J = 7.0 Hz, 1H), 5.31 (s, 1H), 4.07 (s, 2H) |
| | ¹H NMR (500 MHz, DMSO-d₆, δ): 11.22 (br s, 1H), 10.07 (br s, 1H), 7.33-7.26 (m, 4H), 5.34 (s, 1H), 4.04 (s, 2H), 1.25 (s, 9H) |
| | ¹H NMR (500 MHz, DMSO-d₆, δ): 11.64 (br s, 1H), 9.52 (br s, 1H), 8.13 (d, J = 8.5 Hz, 2H), 7.55 (d, J = 8.5 Hz, 2H), 5.41 (s, 1H), 4.26 (s, 2H) |
| | ¹H NMR (500 MHz, DMSO-d₆, δ): 11.55 (br s, 1H), 9.47 (br s, 1H), 7.36 (s, 4H), 5.31 (s, 1H), 4.08 (s, 2H) |
| | ¹H NMR (500 MHz, DMSO-d₆, δ): 11.45 (br s, 1H), 9.79 (br s, 1H), 7.48 (d, J = 8.5 Hz, 2H), 7.28 (d, J = 8.5 Hz, 2H), 5.32 (s, 1H), 4.08 (s, 2H) |

TABLE 2-continued

¹H NMR data for selected compounds.

| Structure | ¹H NMR |
|---|---|
| (3,4-dichlorophenyl-S-CH₂-pyrazolone) | ¹H NMR (400 MHz, DMSO-$d_6$, δ): 10.66 (br s, 1H), 7.59 (s, 1H), 7.52 (d, J = 8.4 Hz, 1H), 7.30 (d, J = 8.0 Hz, 1H), 5.34 (s, 1H), 4.14 (s, 2H) |
| (2,4-dichlorophenyl-S-CH₂-pyrazolone) | ¹H NMR (400 MHz, DMSO-$d_6$, δ): 9.92 (br s, 1H), 7.63 (s, 1H), 7.47-7.39 (m, 2H), 5.38 (s, 1H), 4.15 (s, 2H) |
| (4-dimethylaminophenyl-S-CH₂-pyrazolone) | ¹H NMR (400 MHz, DMSO-$d_6$, δ): 7.20 (d, J = 8.8 Hz, 2H), 6.65 (d, J = 8.8 Hz, 2H), 5.20 (s, 1H), 3.83 (s, 2H), 2.88 (s, 6H) |
| (4-chlorophenyl-S-CH₂-N-phenylpyrazolone) | ¹H NMR (500 MHz, DMSO-$d_6$, δ): 11.67 (br s, 1H), 7.67 (d, J = 8.5 Hz, 2H), 7.45-7.36 (m, 6H), 7.24 (t, J = 7.5 Hz, 1H), 5.46 (s, 1H), 4.11 (s, 2H) |
| (4-fluorophenyl-S-CH₂-pyrazolone) | ¹H NMR (500 MHz, DMSO-$d_6$, δ): 11.52 (br s, 1H), 9.40 (br s, 1H), 7.40-7.37 (m, 2H), 7.17 (t, J = 8.8 Hz, 2H), 5.27 (s, 1H), 4.03 (s, 1H) |

TABLE 2-continued
¹H NMR data for selected compounds.
| Structure | ¹H NMR |
|---|---|
| 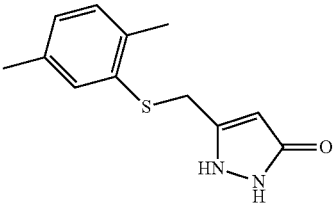 [SMILES: Cc1ccc(C)c(SCc2cc(=O)[nH][nH]2)c1] | ¹H NMR (500 MHz, DMSO-d₆, δ): 11.55 (br s, 1H), 9.38 (br s, 1H), 7.16 (s, 1H), 7.06 (d, J = 7.5 Hz, 1H), 6.90 (d, J = 7.0 Hz, 1H), 5.33 (s, 1H), 4.03 (s, 2H), 2.25 (s, 3H), 2.19 (s, 3H) |
| 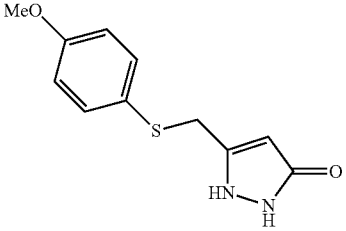 [SMILES: COc1ccc(SCc2cc(=O)[nH][nH]2)cc1] | ¹H NMR (500 MHz, DMSO-d₆, δ): 11.45 (br s, 1H), 9.36 (br s, 1H), 7.29 (d, J = 8.5 Hz, 2H), 6.89 (d, J = 9.0 Hz, 2H), 5.22 (s, 1H), 3.93 (s, 2H), 3.73 (s, 3H) |
| 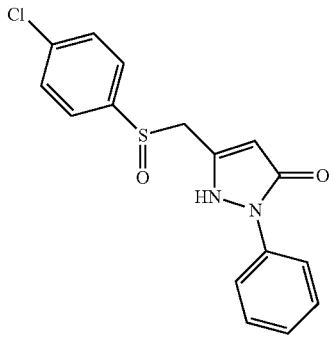 [SMILES: O=c1cc(CS(=O)c2ccc(Cl)cc2)[nH]n1-c1ccccc1] | ¹H NMR (500 MHz, DMSO-d₆, δ): 11.49 (br s, 1H), 9.75 (br s, 1H), 7.62 (d, J = 8.0 Hz, 2H), 7.54 (d, J = 9.0 Hz, 2H), 5.17 (s, 1H), 4.13-3.99 (m, 2H) |
| 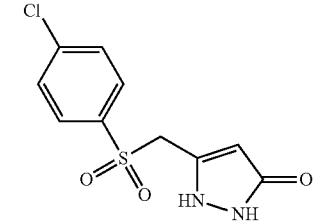 [SMILES: O=c1cc(CS(=O)(=O)c2ccc(Cl)cc2)[nH][nH]1] | ¹H NMR (500 MHz, DMSO-d₆, δ): 11.24 (br s, 1H), 7.75 (d, J = 9.0 Hz, 2H), 7.67 (d, J = 8.5 Hz, 2H), 5.21 (s, 1H), 4.56 (s, 2H) |
| 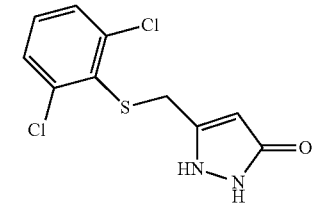 [SMILES: O=c1cc(CSc2c(Cl)cccc2Cl)[nH][nH]1] | ¹H NMR (500 MHz, DMSO-d₆, δ): 11.45 (br s, 1H), 9.35 (br s, 1H), 7.55 (d, J = 8.5 Hz, 2H), 7.38 (t, J = 8.0 Hz, 1H), 5.12 (s, 1H), 4.01 (s, 2H) |
| 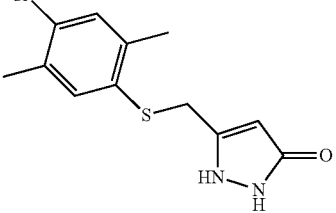 | ¹H NMR (500 MHz, DMSO-d₆, δ): 11.56 (br s, 1H), 9.47 (br s, 1H), 7.32 (s, 1H), 7.26 (s, 1H), 5.33 (s, 1H), 4.05 (s, 2H), 2.27 (s, 3H), 2.19 (s, 3H) |

TABLE 2-continued
$^1$H NMR data for selected compounds.
| Structure | $^1$H NMR |
|---|---|
| 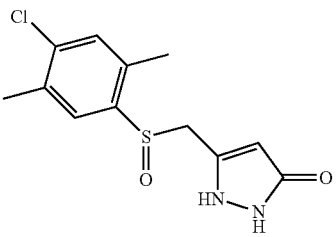 [SMILES: Cc1cc(S(=O)Cc2cc(=O)[nH][nH]2)c(C)cc1Cl] | $^1$H NMR (500 MHz, DMSO-$d_6$, δ): 11.52 (br s, 1H), 9.50 (br s, 1H), 7.58 (s, 1H), 7.37 (s, 1H), 5.22 (s, 1H), 4.03-3.93 (m, 2H), 2.35 (s, 3H), 2.15 (s, 3H) |
| 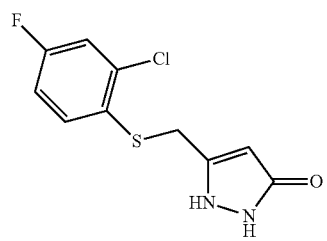 [SMILES: O=c1cc(CSc2ccc(F)cc2Cl)[nH][nH]1] | $^1$H NMR (500 MHz, DMSO-$d_6$, δ): 11.57 (br s, 1H), 9.41 (br s, 1H), 7.50 (m, 2H), 7.25-7.21 (m, 1H), 5.35 (s, 1H), 4.12 (s, 2H) |
| 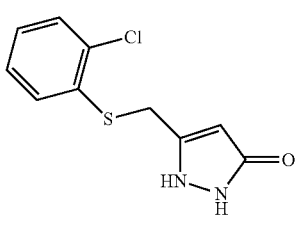 [SMILES: O=c1cc(CSc2ccccc2Cl)[nH][nH]1] | $^1$H NMR (500 MHz, DMSO-$d_6$, δ): 11.60 (br s, 1H), 9.54 (br s, 1H), 7.46-7.17 (m, 4H), 5.39 (s, 1H), 4.14 (s, 2H) |
| 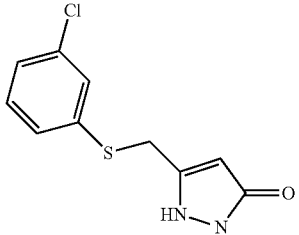 | $^1$H NMR (500 MHz, DMSO-$d_6$, δ): 11.60 (br s, 1H), 9.54 (br s, 1H), 7.40-7.22 (m, 4H), 5.33 (s, 1H), 4.13 (s, 2H) |
| 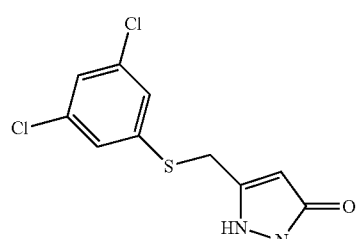 | $^1$H NMR (500 MHz, DMSO-$d_6$, δ): 11.57 (br s, 1H), 9.44 (br s, 1H), 7.39 (s, 3H), 5.34 (s, 1H), 4.18 (s, 2H) |
| 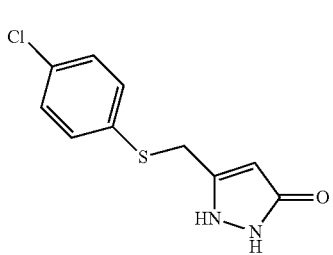 | $^1$H NMR (500 MHz, DMSO-$d_6$, δ): 11.42 (br s, 1H), 9.58 (br s, 1H), 7.35 (dd, J = 28.0, 8.5 Hz, 4H), 5.35 (s, 1H), 3.70 (s, 2H), 3.49 (s, 2H) |

TABLE 2-continued

| Structure | ¹H NMR |
|---|---|
| [structure: 4-chlorophenyl-S-CH2-pyrazolone] | ¹H NMR (500 MHz, DMSO-d₆, δ): 11.48 (br s, 1H), 9.48 (br s, 1H), 7.36 (s, 4H), 5.30 (s, 1H), 4.08 (s, 2H) |
| [structure: 4-chlorophenyl-S-CH2-N-methylpyrazolone] | ¹H NMR (500 MHz, DMSO-d₆, δ): 10.88 (br s, 1H), 7.35 (s, 4H), 5.24 (s, 1H), 3.99 (s, 2H), 3.43 (s, 3H) |
| [structure: pentachlorophenyl-S-CH2-N-methylpyrazolone] | ¹H NMR (500 MHz, CDCl₃, δ): 3.88 (s, 2H), 3.32 (s, 2H) |
| [structure: biphenyl-S-CH2-pyrazolone] | ¹H NMR (500 MHz, DMSO-d₆, δ): 11.39 (br s, 1H), 9.52 (br s, 1H), 7.66-7.34 (m, 9H), 5.36 (s, 1H), 4.12 (s, 2H) |
| [structure: 2-isopropylphenyl-S-CH2-pyrazolone] | ¹H NMR (500 MHz, DMSO-d₆, δ): 11.53 (br s, 1H), 9.37 (br s, 1H), 7.37 (d, J= 8.0 Hz, 1H), 7.27 (d, J = 7.5 Hz, 1H), 7.20-7.14 (m, 2H), 5.29 (s, 1H), 4.02 (s, 2H), 1.15 (d, J = 6.5 Hz, 6H) |
| [structure: phenoxyethyl-S-CH2-pyrazolone] | ¹H NMR (500 MHz, DMSO-d₆, δ): 11.50 (br s, 1H), 9.40 (br s, 1H), 7.28 (t, J = 7.8 Hz, 2H), 6.94-6.90 (m, 3H), 5.39 (s, 1H), 4.08 (t, J = 6.8 Hz, 2H), 3.69 (s, 2H), 2.82 (t, J = 6.5 Hz, 2H) |

TABLE 2-continued

¹H NMR data for selected compounds.

| Structure | ¹H NMR |
|---|---|
| | ¹H NMR (500 MHz, DMSO-d₆, δ): 11.54 (br s, 1H), 9.36 (br s, 1H), 7.36-7.14 (m, 4H), 5.31 (s, 1H), 4.04 (s, 2H), 2.63 (q, J = 7.4 Hz, 2H), 1.12 (t, J = 7.5 Hz, 3H) |
| | ¹H NMR (500 MHz, DMSO-d₆, δ): 11.79 (br s, 1H), 9.56 (br s, 1H), 7.33 (d, J = 9.0 Hz, 2H), 7.02 (d, J = 9.0 Hz, 2H), 5.52 (s, 1H), 4.92 (s, 2H) |
| | ¹H NMR (500 MHz, DMSO-d₆, δ): 11.37 (br s, 1H), 9.72 (br s, 1H), 7.61 (d, J = 8.0 Hz, 2H), 7.46 (d, J = 8.0 Hz, 2H), 4.48 (s, 2H), 3.29 (s, 1H), 2.71 (q, J = 7.5 Hz, 2H), 1.21 (t, J = 7.5 Hz, 3H) |
| | ¹H NMR (500 MHz, DMSO-d₆, δ): 11.56 (br s, 1H), 9.48 (br s, 1H), 7.64 (d, J = 7.5 Hz, 2H), 7.44 (m, 2H), 5.18 (s, 1H), 4.52 (s, 2H), 2.67 (t, J = 7.5 hz, 2H), 1.60-1.54 (m, 2H), 1.33-1.26 (m, 2H), 0.89 (t, J = 7.3 Hz, 3H) |
| | ¹H NMR (500 MHz, DMSO-d₆, δ): 11.62 (br s, 1H), 9.59 (br s, 1H), 7.67 (s, 1H), 7.54 (s, 1H), 5.24 (s, 1H), 4.49 (s, 2H), 2.47 (s, 3H), 2.33 (s, 3H) |

TABLE 2-continued
¹H NMR data for selected compounds.
| Structure | ¹H NMR |
|---|---|
| 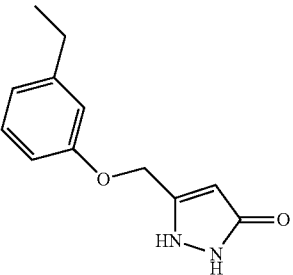 [SMILES: CCc1cccc(OCc2cc(=O)[nH][nH]2)c1] | ¹H NMR (500 MHz, DMSO-d₆, δ): 11.79 (br s, 1H), 9.55 (br s, 1H), 7.18 (t, J = 7.8 Hz, 1H), 6.83-6.79 (m, 3H), 5.52 (s, 1H), 4.89 (s, 2H), 2.56 (q, J = 7.5 Hz, 2H), 1.16 (t, J = 7.5 Hz, 3H) |
| 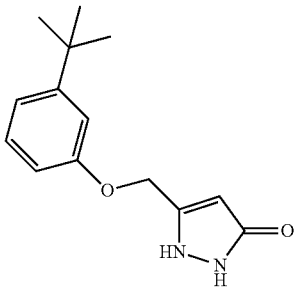 [SMILES: CC(C)(C)c1cccc(OCc2cc(=O)[nH][nH]2)c1] | ¹H NMR (500 MHz, DMSO-d₆, δ): 11.72 (br s, 1H), 9.50 (br s, 1H), 7.20 (t, J = 8.0 Hz, 1H), 6.97-6.80 (m, 3H), 5.52 (s, 1H), 4.91 (s, 2H) |
| 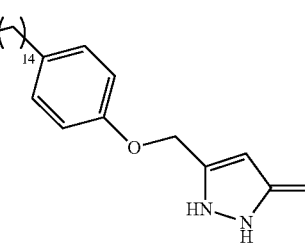 | ¹H NMR (500 MHz, DMSO-d₆, δ): 11.75 (br s, 1H), 9.47 (br s, 1H), 7.17 (t, J = 7.5 Hz, 1H), 6.80-6.75 (m, 3H), 5.54 (s, 1H), 4.90 (s, 2H), 1.54 (m, 2H), 1.26-1.23 (m, 26H), 0.85 (t, J = 5.8 Hz, 3H) |
| 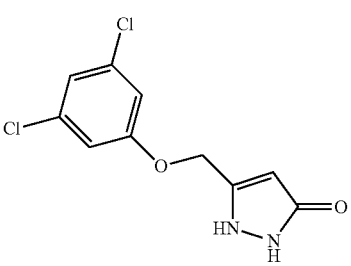 [SMILES: O=c1cc(COc2cc(Cl)cc(Cl)c2)[nH][nH]1] | ¹H NMR (500 MHz, DMSO-d₆, δ): 11.82 (br s, 1H), 9.54 (br s, 1H), 7.16 (s, 1H), 7.12 (d, J = 1.5 Hz, 2H), 5.53 (s, 1H), 4.99 (s, 2H) |
| 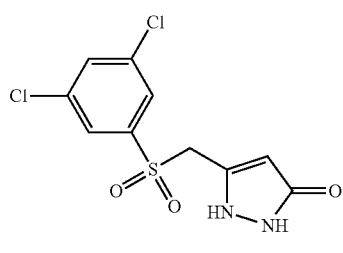 [SMILES: O=c1cc(CS(=O)(=O)c2cc(Cl)cc(Cl)c2)[nH][nH]1] | ¹H NMR (500 MHz, DMSO-d₆, δ): 11.62 (br s, 1H), 9.55 (br s, 1H), 7.77-7.36 (m, 2H), 5.26 (s, 1H), 4.70 (s, 2H) |
| 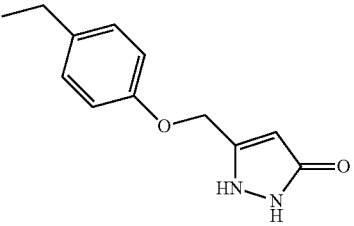 [SMILES: CCc1ccc(OCc2cc(=O)[nH][nH]2)cc1] | ¹H NMR (500 MHz, DMSO-d₆, δ): 11.75 (br s, 1H), 9.50 (br s, 1H), 7.10 (d, J = 8.0 Hz, 2H), 6.89 (d, J = 8.5 Hz, 2H), 5.50 (s, 1H), 4.87 (s, 2H), 2.54-2.51 (m, 2H), 1.13 (t, J = 7.5 Hz, 3H) |

TABLE 2-continued
¹H NMR data for selected compounds.
| Structure | ¹H NMR |
|---|---|
| 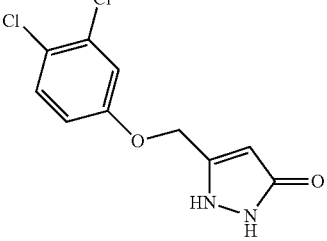 | ¹H NMR (500 MHz, DMSO-d₆, δ): 11.79 (br s, 1H), 9.51 (br s, 1H), 7.52 (d, J = 9.5 Hz, 1H), 7.32 (d, J = 2.5 Hz, 1H), 7.02 (dd, J = 9.0, 2.5 Hz, 1H), 5.56 (s, 1H), 4.98 (s, 2H) |
| 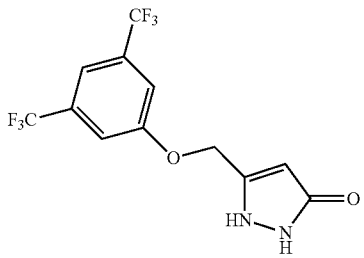 [SMILES: O=c1cc(COc2cc(C(F)(F)F)cc(C(F)(F)F)c2)[nH][nH]1] | ¹H NMR (500 MHz, DMSO-d₆, δ): 11.62 (br s, 1H), 9.50 (br s, 1H), 7.99 (s, 2H), 7.86 (s, 1H), 5.35 (s, 1H), 4.31 (s, 2H) |
| 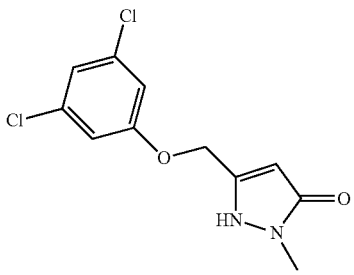 [SMILES: Cn1[nH]c(COc2cc(Cl)cc(Cl)c2)cc1=O] | ¹H NMR (500 MHz, DMSO-d₆, δ): 10.95 (s, 1H), 7.13 (s, 1H), 7.10 (s, 2H), 5.41 (s, 1H), 4.88 (s, 2H), 3.49 (s, 3H) |
| 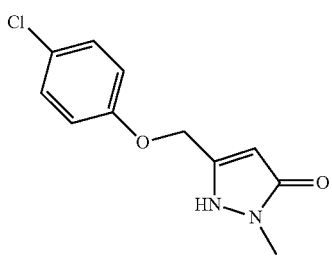 | ¹H NMR (500 MHz, DMSO-d₆, δ): 10.98 (br s, 1H), 7.30 (d, J = 8.5 Hz, 2H), 7.00 (d, J = 8.5 Hz, 2H), 5.40 (s, 1H), 4.82 (s, 2H), 3.48 (s, 3H) |
| 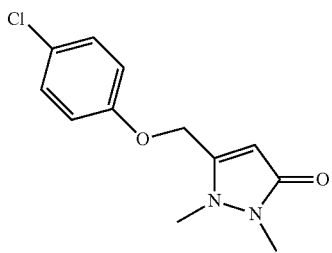 [SMILES: Cn1c(COc2ccc(Cl)cc2)cc(=O)n1C] | ¹H NMR (500 MHz, CDCl₃, δ): 7.22-7.19 (m, 2H), 6.93-6.90 (m, 2H), 5.60 (s, 1H), 4.91 (s, 2H), 3.86 (s, 3H), 3.61 (s, 3H) |

TABLE 2-continued

<sup>1</sup>H NMR data for selected compounds.

| Structure | <sup>1</sup>H NMR |
|---|---|
| (3,5-difluorophenoxymethyl pyrazolone) | <sup>1</sup>H NMR (500 MHz, DMSO-d$_6$, δ): 11.82 (br s, 1H), 9.53 (br s, 1H), 6.80-6.79 (m, 3H), 5.56 (s, 1H), 4.95 (s, 2H) |
| (3,5-dibromophenoxymethyl pyrazolone) | <sup>1</sup>H NMR (500 MHz, DMSO-d$_6$, δ): 11.80 (br s, 1H), 9.52 (br s, 1H), 7.39 (s, 1H), 7.28 (m, 2H), 5.55 (s, 1H), 4.99 (s, 1H) |
| (3-bromophenoxymethyl pyrazolone) | <sup>1</sup>H NMR (500 MHz, DMSO-d$_6$, δ): 11.78 (br s, 1H), 9.50 (br s, 1H), 7.26-7.23 (m, 2H), 7.14-7.13 (m, 1H), 7.02-7.00 (m, 2H), 5.58 (s, 1H), 4.96 (s, 2H) |
| (biphenyl-3-yloxymethyl pyrazolone) | <sup>1</sup>H NMR (500 MHz, DMSO-d$_6$, δ): 11.80 (br s, 1H), 9.50 (br s, 1H), 7.67-6.99 (m, 9H), 5.55 (s, 1H), 5.02 (s, 2H) |
| (m-terphenyl-5-yloxymethyl pyrazolone) | <sup>1</sup>H NMR (500 MHz, DMSO-d$_6$, δ): 11.82 (br s, 1H), 9.50 (br s, 1H), 7.76 (d, J = 8.0 Hz, 4H), 7.50-7.38 (m, 7H), 7.27 (s, 2H), 5.60 (s, 1H), 5.13 (s, 2H) |

TABLE 2-continued

<sup>1</sup>H NMR data for selected compounds.

| Structure | <sup>1</sup>H NMR |
|---|---|
| [Structure: 3,5-dichlorophenyl-N(SO2Ph)-CH2-pyrazolone] | <sup>1</sup>H NMR (500 MHz, DMSO-d$_6$, δ): 11.56 (br s, 1H), 9.39 (br s, 1H), 7.76-7.55 (m, 6H), 7.14 (s, 2H), 5.22 (s, 1H), 4.67 (s, 2H) |
| [Structure: 3,5-dichlorophenyl-NH-CH2-pyrazolone] | <sup>1</sup>H NMR (500 MHz, DMSO-d$_6$, δ): 11.56 (br s, 1H), 9.52 (br s, 1H), 6.64-6.59 (m, 3H), 5.35 (s, 1H), 4.10 (d, J = 5.0 Hz, 2H) |

Example 6

Biological Activity of Synthesized Arylsulfanylpyrazolone Analogs

Compounds synthesized above underwent a mutant SOD1 protein aggregation-induced toxicity protection screen and a direct protein aggregation high content assay. Results differ within a reasonable range from week to week due to bio-variation, however, relative potencies of the analogs were reproducible.

TABLE 3

| Entry | Structure | Best EC50 (μM) | Corresponding 3299 EC50 (μM) | Corresponding % viability | EC50 (μM) after Normalization |
|---|---|---|---|---|---|
| 1 | [Structure: CMB-003299] | 0.4 | | | |
| 2 | [Structure: CMB-053530-1] | >32 | | | |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 3 | CMB-053526-1 | 6.85 | 0.27 | 77 | 10.1 |
| 4 | CMB-053527-1 | 5.38 | 0.93 | 150 | 2.31 |
| 5 | CMB-053528-1 | 5.59 | 0.93 | 136 | 2.4 |
| 6 | CMB-053529-1 | 4.49 | 0.93 | 93 | 1.93 |
| 7 | CMB-053543-1 | 4.24 | 0.93 | 94 | 1.8 |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 8 | CMB-053544-1 | 2.6 | 0.55 | 113 | 1.89 |
| 9 | CMB-053545-1 | 1.58 | 0.55 | 124 | 1.15 |
| 10 | CMB-086476-1 | 1.65 | | 77 | |
| 11 | CMB-086473-1 | 5.11 | 0.59 | 109 | 3.46 |
| 12 | CMB-086478-1 | 4.73 | 0.55 | 104 | 3.44 |

TABLE 3-continued
| Entry | Structure | Best EC50 (μM) | Corresponding 3299 EC50 (μM) | Corresponding % viability | EC50 (μM) after Normalization |
|---|---|---|---|---|---|
| 13 | 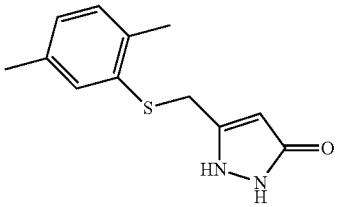 CMB-086479-1 | 0.22 | | | 77 |
| 14 | 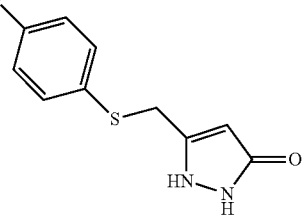 CMB-086477-1 | 4.21 | 0.93 | 102 | 1.81 |
| 15 | 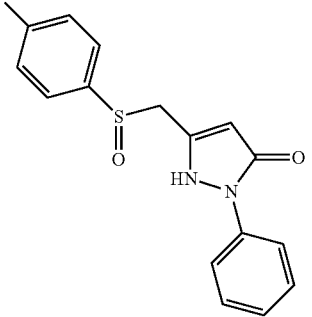 CMB-086474-1 | >32 | | | |
| 16 | 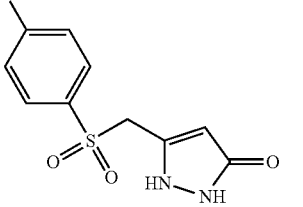 CMB-086475-1 | 6.92 | 0.59 | 110 | 4.7 |
| 17 | 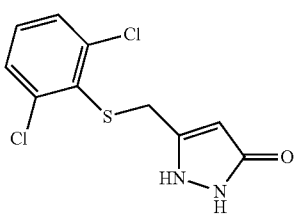 CMB-086480-1 | 0.26 | 0.11 | 142 | 0.95 |

TABLE 3-continued
| Entry | Structure | Best EC50 (μM) | Corresponding 3299 EC50 (μM) | Corresponding % viability | EC50 (μM) after Normalization |
|---|---|---|---|---|---|
| 18 | 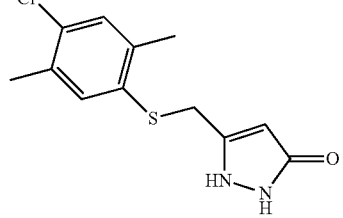<br>CMB-086481-1 | 0.43 | 0.44 | 140 | 0.39 |
| 19 | 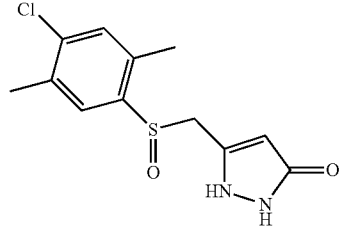<br>CMB-086482-1 | 4.47 | 0.62 | 123 | 2.88 |
| 20 | 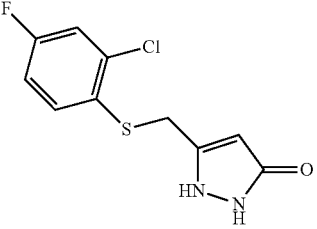<br>CMB-086832-1 | 1.61 | | 68 | |
| 21 | 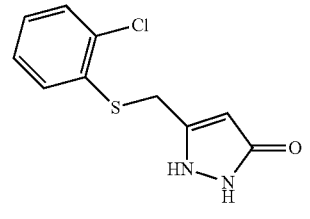<br>CMB-086834-1 | 0.84 | 0.11 | 123 | 3.05 |
| 22 | 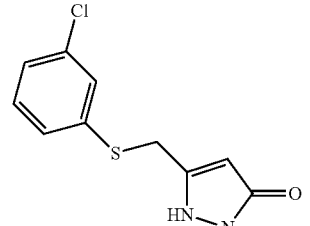<br>CMB-086833-1 | 0.25 | 0.09 | 148 | 1.11 |

TABLE 3-continued

| Entry | Structure | Best EC50 (µM) | Corresponding 3299 EC50 (µM) | Corresponding % viability | EC50 (µM) after Normalization |
|---|---|---|---|---|---|
| 23 | CMB-086835-1 | 0.08 | 0.19 | 134 | 0.17 |
| 24 | CMB-086835-2 | 0.3 | 0.41 | 129 | 0.29 |
| 25 | CMB-086836-1 | 4.14 | | 75 | |
| 26 | CMB-086882-1 | 7.97 | 0.59 | 121 | 5.4 |
| 27 | CMB-086883-1 | 9.44 | 0.93 | 115 | 4.06 |

TABLE 3-continued
| Entry | Structure | Best EC50 (μM) | Corresponding 3299 EC50 (μM) | Corresponding % viability | EC50 (μM) after Normalization |
|---|---|---|---|---|---|
| 28 | 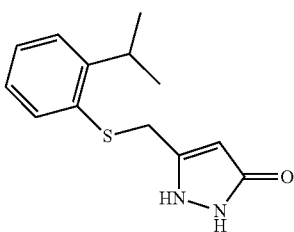<br>CMB-086899-1 | 0.4 | 0.33 | 106 | 0.48 |
| 29 | 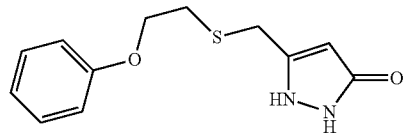<br>CMB-086900-1 | 6.21 | 0.33 | 97 | 7.52 |
| 30 | 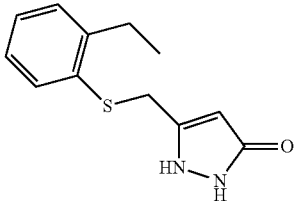<br>CMB-086901-1 | 2.06 | 0.33 | 106 | 2.5 |
| 31 | 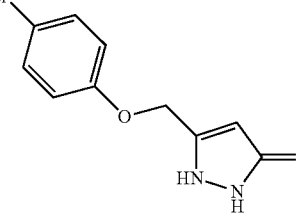<br>CMB-086902-1 | 0.57 | 0.35 | 131 | 0.65 |
| 32 | 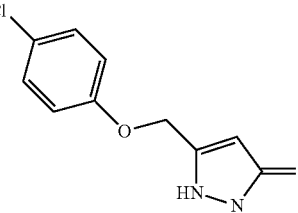<br>CMB-086902-2 | 0.69 | 0.35 | 117 | 0.79 |
| 33 | 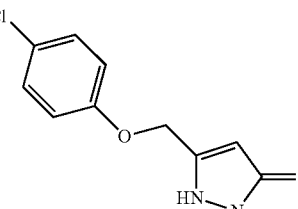<br>CMB-086902-3 | 3.43 | 1.79 | 120 | 0.77 |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 34 | CMB-087210-1 | 0.99 | 0.44 | 101 | 0.9 |
| 35 | CMB-087211-1 | 0.75 | 0.44 | 103 | 0.68 |
| 36 | CMB-087212-1 | 0.99 | 0.44 | 93 | 0.9 |
| 37 | CMB-087213-1 | 2.28 | 0.62 | 116 | 1.47 |
| 38 | CMB-087214-1 | 1.12 | 0.62 | 125 | 0.72 |

TABLE 3-continued
| Entry | Structure | Best EC50 (μM) | Corresponding 3299 EC50 (μM) | Corresponding % viability | EC50 (μM) after Normalization |
|---|---|---|---|---|---|
| 39 | 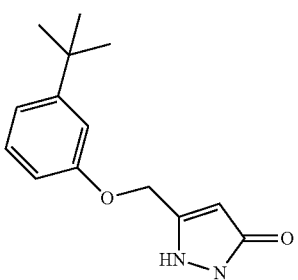<br>CMB-087215-1 | 1.06 | 0.49 | 141 | 0.87 |
| 40 | 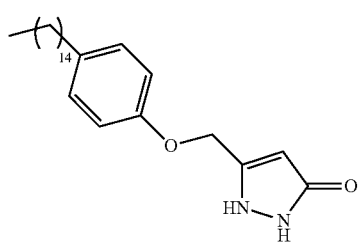<br>CMB-087216-1 | 2.08 | 0.37 | 66 | 2.24 |
| 41 | 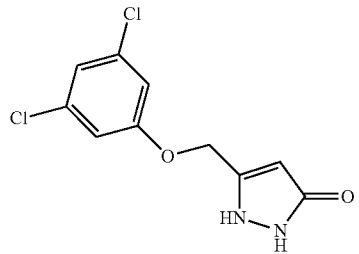<br>CMB-087229-1 | 0.05 | 0.3 | 129 | 0.067 |
| 42 | 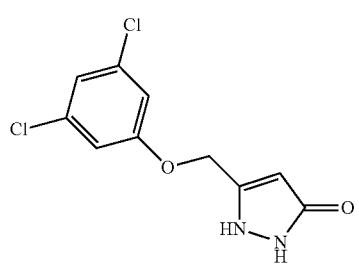<br>CMB-087229-5 | 0.55 | 0.72 | 123 | 0.31 |
| 43 | 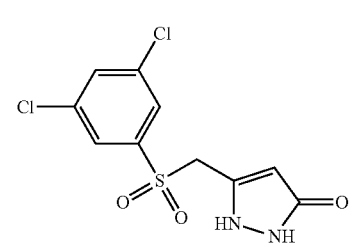<br>CMB-087235-1 | 0.36 | 0.19 | 130 | 0.76 |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 44 | CMB-087235-2 | 0.67 | 0.19 | 132 | 1.41 |
| 45 | CMB-087241-1 | 3.29 | 0.67 | 88 | 1.96 |
| 46 | CMB-087242-1 | 0.13 | 0.09 | 136 | 0.58 |
| 47 | CMB-087260-1 | 0.13 | 0.09 | 120 | 0.58 |
| 48 | CMB-087264-1 | 6.67 | 0.52 | 109 | 5.13 |

TABLE 3-continued
| Entry | Structure | Best EC50 (μM) | Corresponding 3299 EC50 (μM) | Corresponding % viability | EC50 (μM) after Normalization |
|---|---|---|---|---|---|
| 49 | 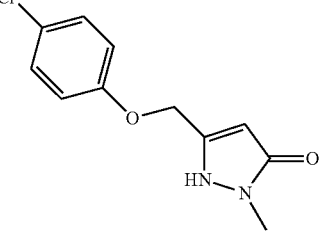<br>CMB-087362-1 | 7.6 | 0.52 | 107 | 5.85 |
| 50 | 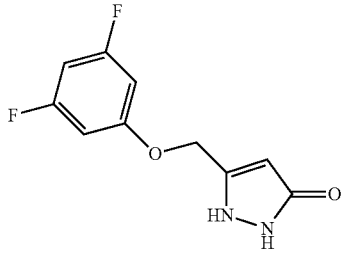 [SMILES: O=c1cc(COc2cc(F)cc(F)c2)[nH][nH]1]<br>CMB-087627-1 | 3.21 | 1.2 | 125 | 1.07 |
| 51 | 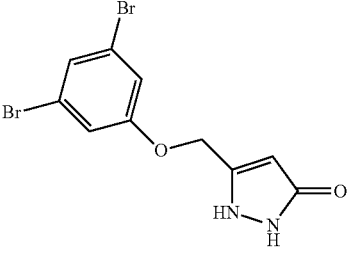<br>CMB-087628-1 | 1.54 | 1.2 | 125 | 0.51 |
| 52 | 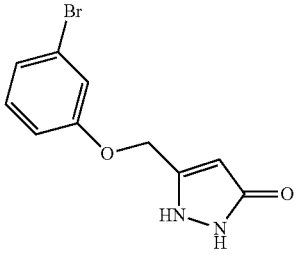 [SMILES: O=c1cc(COc2cccc(Br)c2)[nH][nH]1]<br>CMB-087642-1 | 3.06 | 1.2 | 144 | 1.02 |
| 53 | 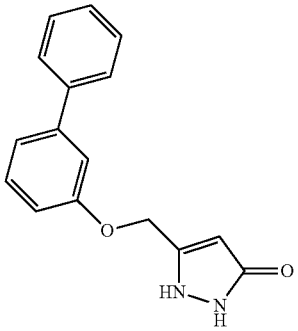 [SMILES: O=c1cc(COc2cccc(-c3ccccc3)c2)[nH][nH]1]<br>CMB-087643-1 | 8.53 | 1.2 | 96 | 2.84 |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 54 | CMB-087644-1 | 11.08 | 1.2 | 68 | 3.7 |
| 55 | CMB-087645-1 | 9.04 | 2.52 | 111 | 1.43 |
| 56 | CMB-087650-1 | 2.11 | 2.52 | 128 | 0.33 |
| 57 | TC-II-140 | 6.2 | | | |
| 58 | TC-II-123 | 4.2 | | | |

TABLE 3-continued

| Entry | Structure | Best EC50 (μM) | Corresponding 3299 EC50 (μM) | Corresponding % viability | EC50 (μM) after Normalization |
|---|---|---|---|---|---|
| 59 | 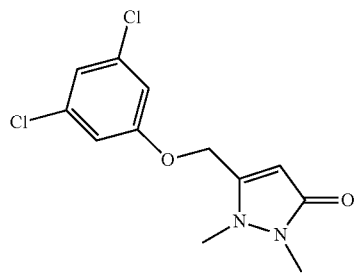 CMB-087363-1 | >32 | | | |

In vitro ADME study of CMB-003319. CMB-003319 was evaluated for its in vitro ADME properties. The study showed that CMB-003319 has a medium metabolic potential, medium CaCO-2 permeability, poor plasma stability, and medium aqueous-solubility.

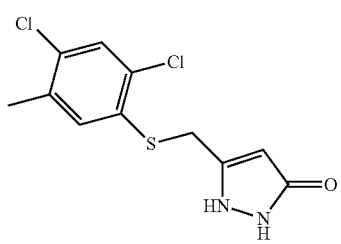

CMB-003319

Figure 11:
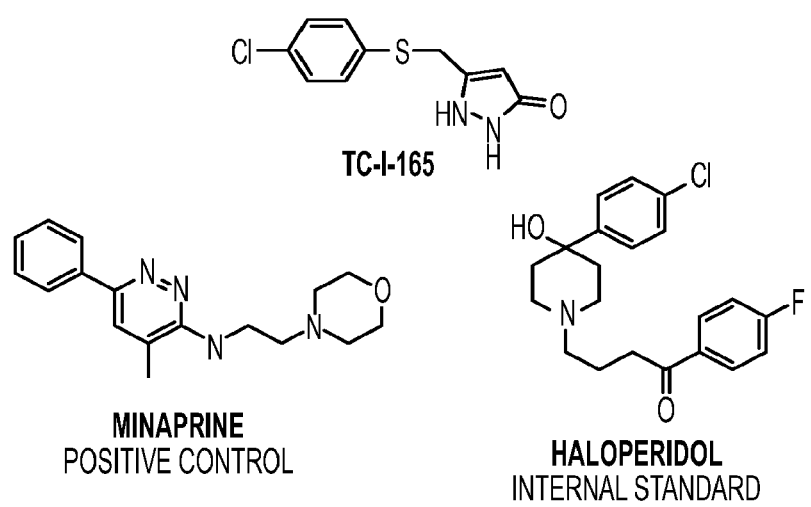
FIG. 11. Structures of compounds used in the rat liver microsomal stability study of TC-I-16.
Figure 12:
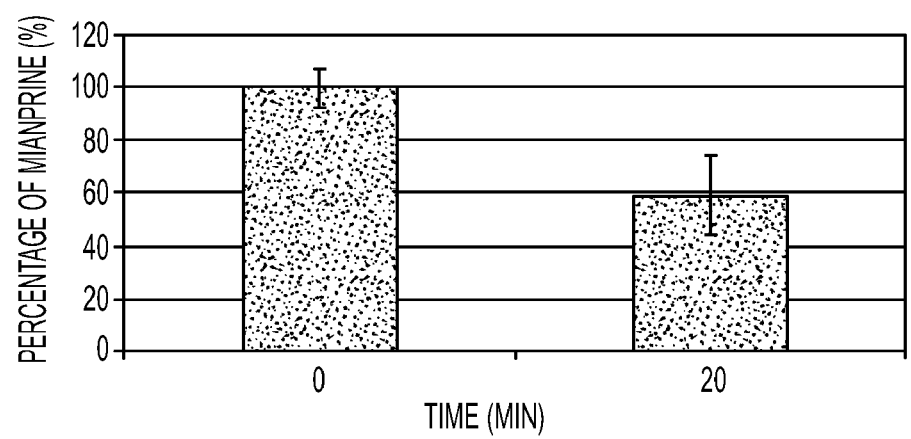
FIG. 12. Minaprine 0-20 minutes HADPH dependent rat liver microsomal stability.
Figure 13:
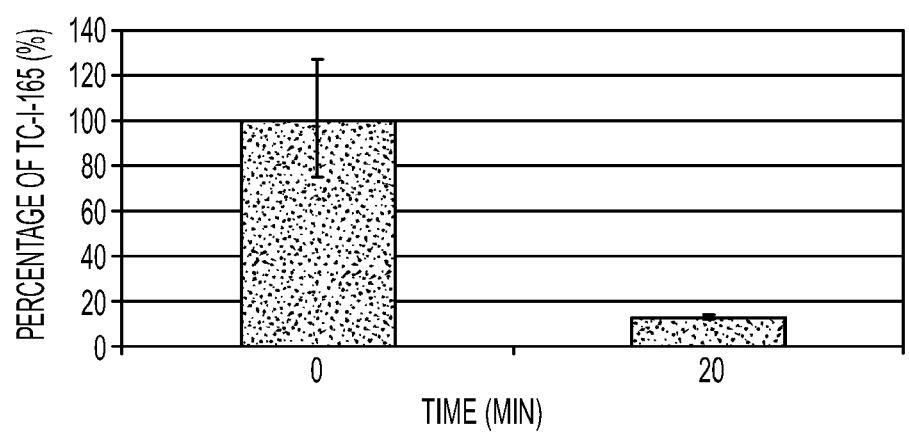
FIG. 13. TC-I-165 0-20 minutes HADPH dependent rat liver microsomal stability.

Rat liver microsomal stability study of TC-I-165. TC-I-165 was applied for an NADPH dependent rat liver microsomal stability study by HPLC. Preliminary results showed that TC-I-165 has poor microsomal stability like CMB-003319. The test (TC-I-165), positive control (minaprine), and internal standard (haloperidol) are shown in FIG. 11.

Microsomal metabolite study of TC-I-165. TC-I-165 was used in a NADPH dependent rat liver microsomal metabolite study by HPLC. TC-II-68 and TC-II-70 were proposed as possible metabolites and prepared before the study. Results showed that only TC-II-68 was a direct metabolite.

Microsomal metabolite study of TC-I-165. TC-II-125 was prepared as a double $^{15}N$ isotope labeled TC-I-165. TC-I-165, TC-II-125, and TC-II-68 were sent for NADPH dependent rat liver microsomal metabolite determination. The results showed that during the first hour the only direct metabolite from TC-I-165 was TC-II-68, with no nitrogen loss on the pyrazolone ring.

Rat liver microsomal stability of TC-II-70. TC-II-70 was applied for an NADPH dependent rat liver microsomal stability test by HPLC. The results showed that TC-II-70 is much more stable compared with TC-I-165 for the first hour of microsomal metabolism.

In vitro ADME properties of analogs. Compounds were sent for in vitro ADME tests to evaluate their ADME properties. By substituting the thioether linkage with an ether linkage or a sulfone linkage in the arylsulfanylpyrazolone scaffold, the microsomal stability and aqueous-solubility were largely improved.

In vitro ADME study of CMB-087229. CMB-087229 was sent for an evaluation of its in vitro ADME properties. The study showed that CMB-087229 has a potency ($ED_{50}$) of 74 nM, medium human metabolic potential ($T_{1/2}$=93 minutes), medium mouse metabolic potential ($T_{1/2}$=36 minutes), high predicted CaCO-2 permeability (A-B=37×10$^{-6}$ cm/s), medium plasma stability ($T_{1/2}$=17 minutes), and aqueous solubility of 250 μM. CMB-087229 has a metabolic half-life in rats of approximately 2 hours.

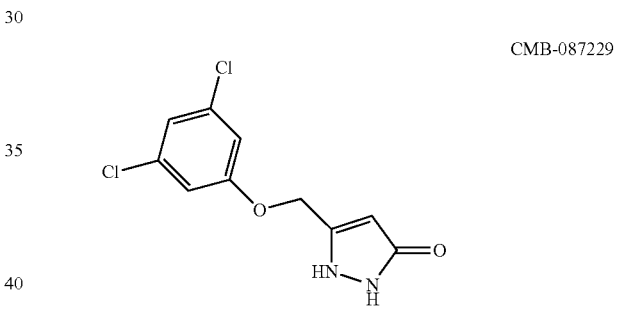

CMB-087229

UV Spectra and Chromatography

Using a UV/VIS spectrometer (Perkin Elmer, Lamda 10), samples were scanned from 200-500 nm to determine the maximum UV absorbance. A wavelength of 260 nm was found to be optimal for HPLC monitoring. Samples were analyzed with a Beckman HPLC using a 166 UV detector coupled to a reverse phase C18 analytical column (Phenomenex, Luna 5μ C18 (2), 250*4.60 mm). After separation of the samples on the C18 column using an acetonitrile-water HPLC program, peaks were analyzed by 32 Karat™ software, version 5.1.

Microsomal Stability Study

Test agents (15 μM) were incubated in Eppendorf tubes with mouse microsomes (pooled male rat liver microsomes (Sprague Dawley), BD Science) at 37° C. Each reaction mixture was carried out in PBS (pH 7.4), which contained 1 mg/mL microsomal protein with 1.3 mM NADP$^+$, 3.3 mM glucose-6-phosphate, 0.4 U/mL glucose-6-phosphate dehydrogenase, and 3.3 mM magnesium chloride. A control using minaprine was run to test the activity of the microsomal activity. After 0 and 20 minutes incubation, 40 μL of acetonitrile was added to quench the reactions. The reaction mixture was vortexed and incubated in an ice bath for 2 h. Haloperidol (100 μL, 100 μM) was added to every test tube as an internal standard. The samples were diluted in water and centrifuged to remove the precipitated protein. The supernatant solutions were loaded for solid phase extraction. Extraction fractions were evaporated and reconstituted for HPLC analysis.

Excel was used for data processing. The Response Ratio (RR) was calculated by dividing the peak area of the analyte by the peak area of the internal standard. Data suggest that TC-I-165 has low NADPH dependent rat liver microsomal stability.

TABLE 4

Microsomal stability data processing

| Sample Name | RR Mean | % Mean ± S.E. |
|---|---|---|
| Mina 0 min | 22.88 | 100 ± 7.11 |
| Mina 20 min | 13.54 | 59.2 ± 14.9 |
| TC-I-165 0 min | 2.529 | 100 ± 26.4 |
| TC-I-165 20 min | 0.314 | 12.4 ± 0.89 |

NADPH Rat Liver Microsomal Metabolites Study for TC-I-165

Test Methods

Figure 14:
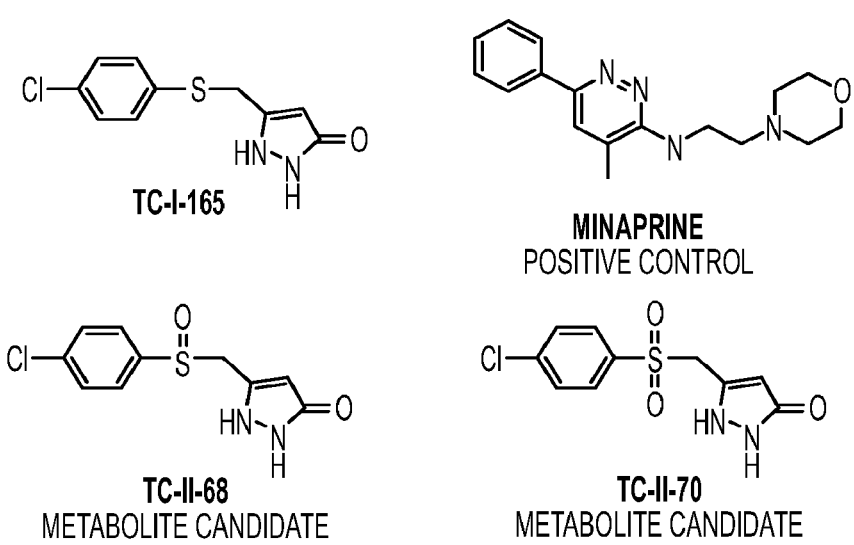
FIG. 14. Structures of TC-I-165 metabolite candidates (sulfoxide metabolite candidate TC-II-68 and sulfone metabolite candidate TC-II-70).
Figure 15:
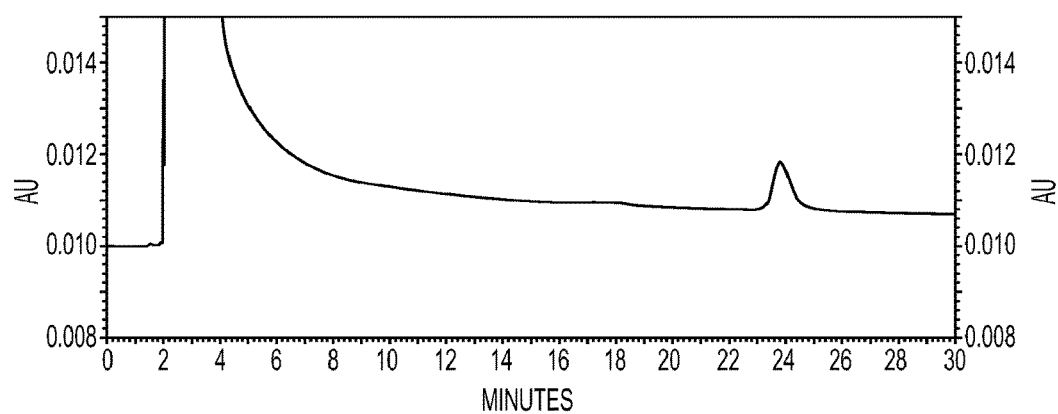
FIG. 15. HPLC trace of TC-I-165 [0 min NADPH (tube 1)].
Figure 16:
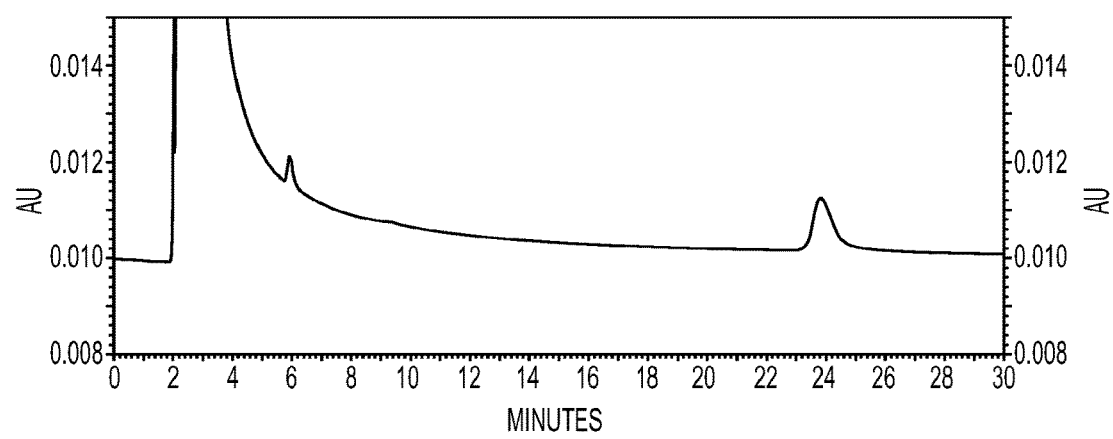
FIG. 16. HPLC trace of TC-I-165 [5 min NADPH (tube 2)] and a new peak with a retention time of 5.900 minutes.
Figure 17:
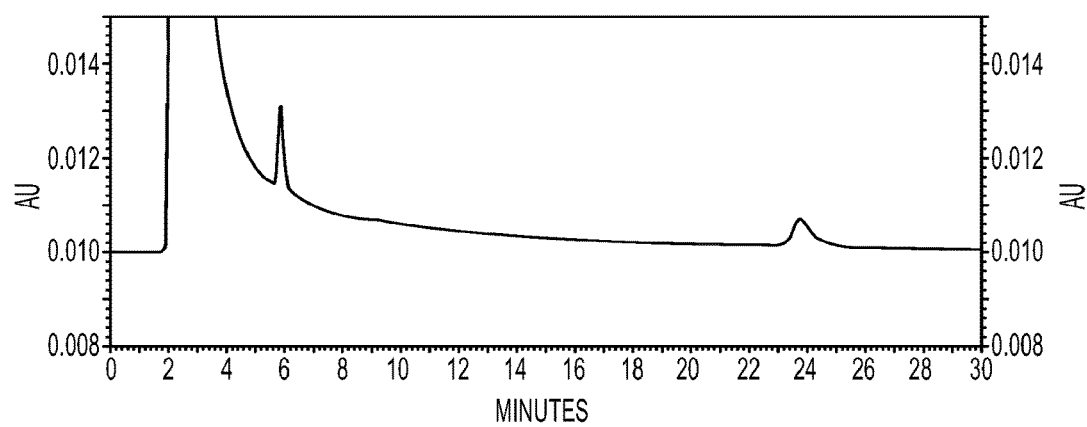
FIG. 17. HPLC trace of TC-I-165 [60 min NADPH (tube 1)] and a new peak with a retention time of 5.917 minutes.
Figure 18:
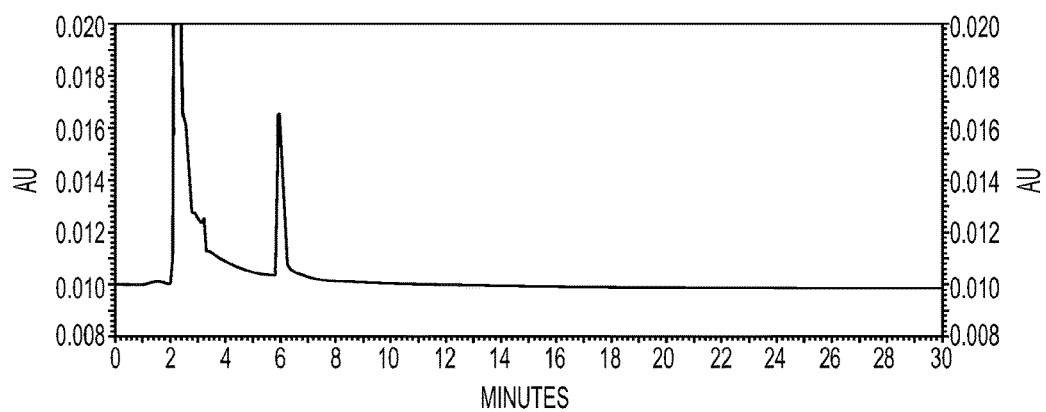
FIG. 18. HPLC trace of TC-II-68 [10 μM standard solution (tube 1)] and a new peak with a retention time of 5.933 minutes.
Figure 19:
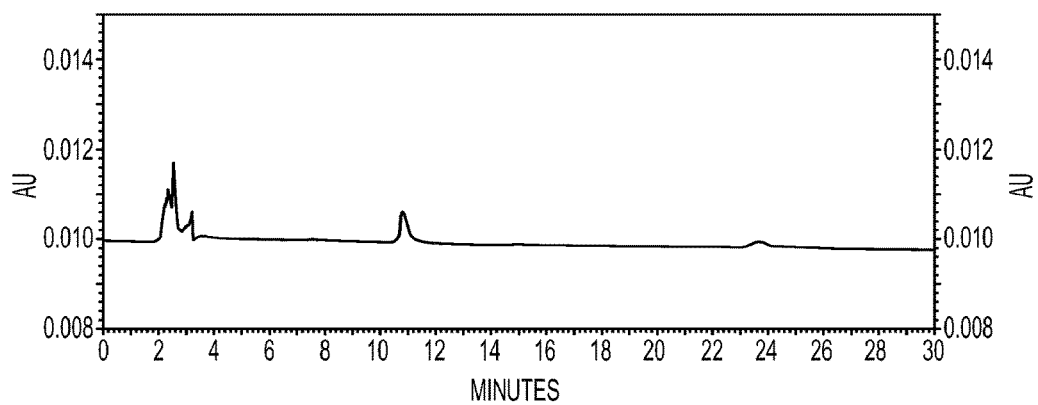
FIG. 19. HPLC trace of TC-11-70 [10 μM standard solution (tube 2)] and a new peak with a retention time of 11.000 minutes.
Figure 20:
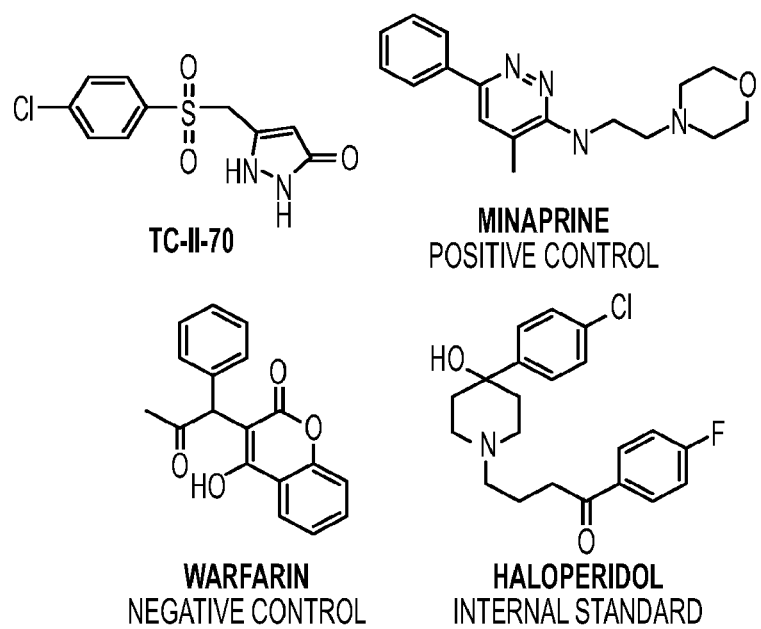
FIG. 20. Structures of compounds used in the rat liver microsomal stability study of TC-II-70.

TC-I-165 was used for a NADPH dependent rat liver microsomal metabolites study, and the corresponding sulfoxide, TC-II-68, and sulfone, TC-II-70, also were prepared (FIG. 14).

Experiments were generally carried out according to the general procedure from the microsomal stability study of TC-I-165. After 0, 5, 10, 20, 40, and 60 minutes incubation with rat liver microsome, 50 µL acetonitrile was added to quench reactions. The reaction mixture was vortexed and incubated in an ice bath for 2 h. The samples were centrifuged to remove the precipitated protein. The supernatant solutions were loaded directly for HPLC analysis.

Data and Results

TC-II-68 was a metabolite from TC-I-165 after 60 minutes of NADPH dependent rat liver microsome incubation. TC-II-70 is not a metabolite. Only one new peak was observed from the microsomal residue of TC-I-165. Using the same HPLC program (25% acetonitrile, isocratic, 30 minutes), the retention time of the new peak was approximately identical to the one from TC-II-68. The retention time of TC-II-70 was well separated from that of the new peak (see FIGS. 15-20).

Rat Liver Microsomal Stability Studies of TC-II-70

Test Methods

Figure 21:
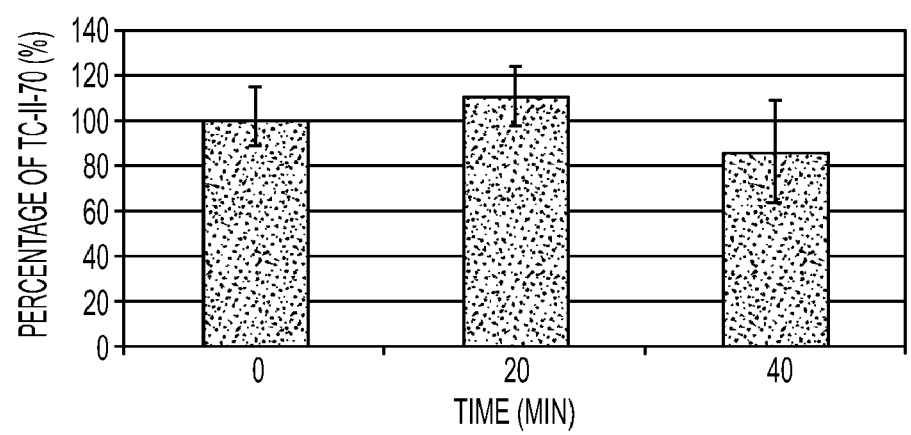
FIG. 21. NADPH dependent rat liver microsomal stability study of TC-II-70.
Figure 22:
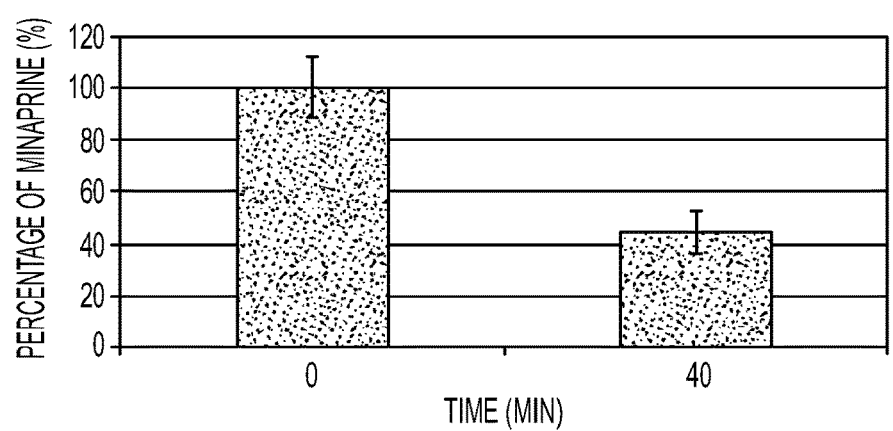
FIG. 22. NADPH dependent rat liver microsomal stability study of minaprine.
Figure 23:
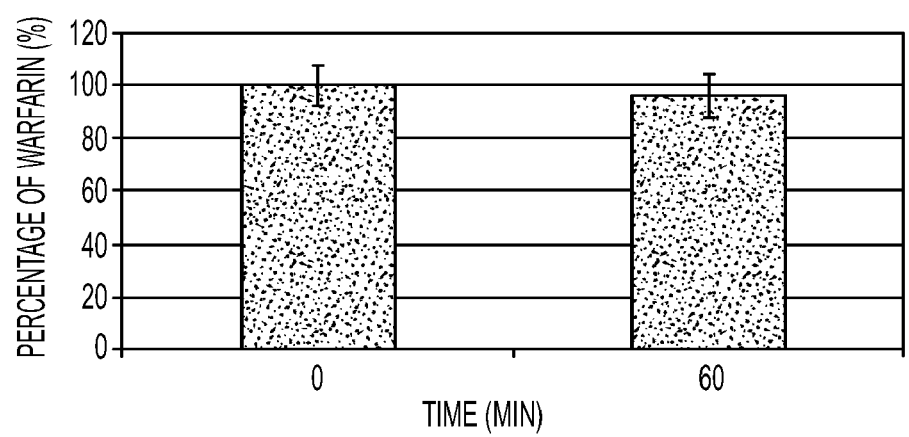
FIG. 23. NADPH dependent rat liver microsomal stability study of warfarin.
Figure 26:
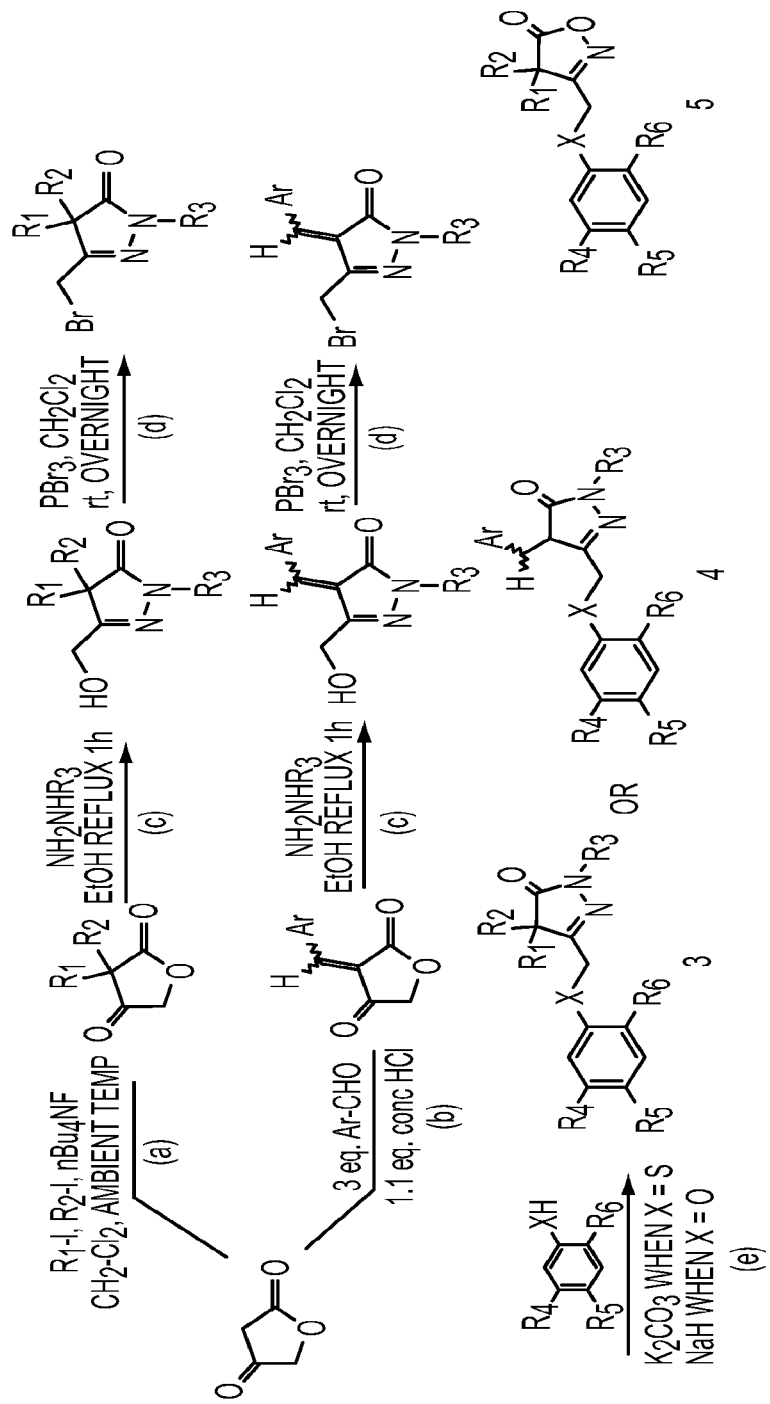
FIG. 26. Synthesis of arylsulfanylpyrazolones (Scheme 1).
Figure 27:
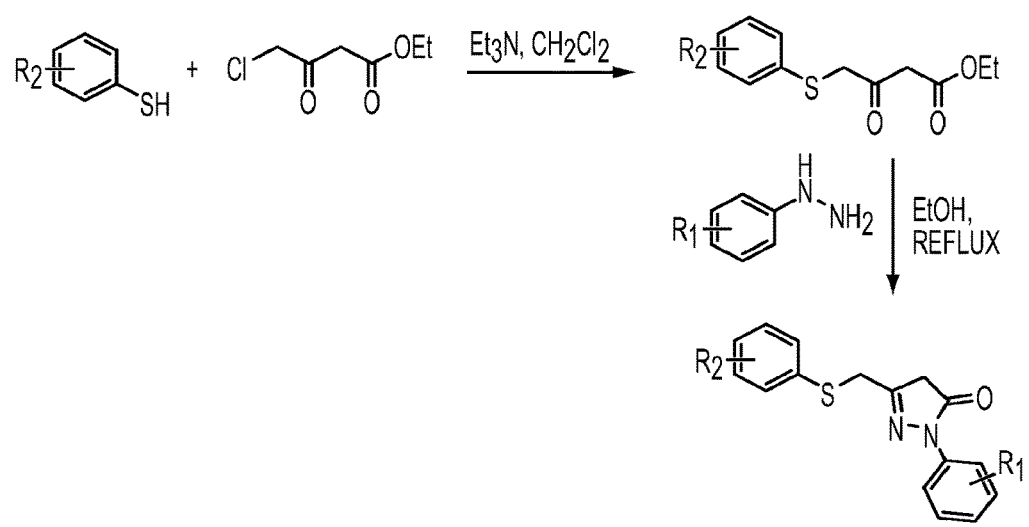
FIG. 27. Synthesis of arylsulfanylpyrazolones (Scheme 2).
Figure 28:
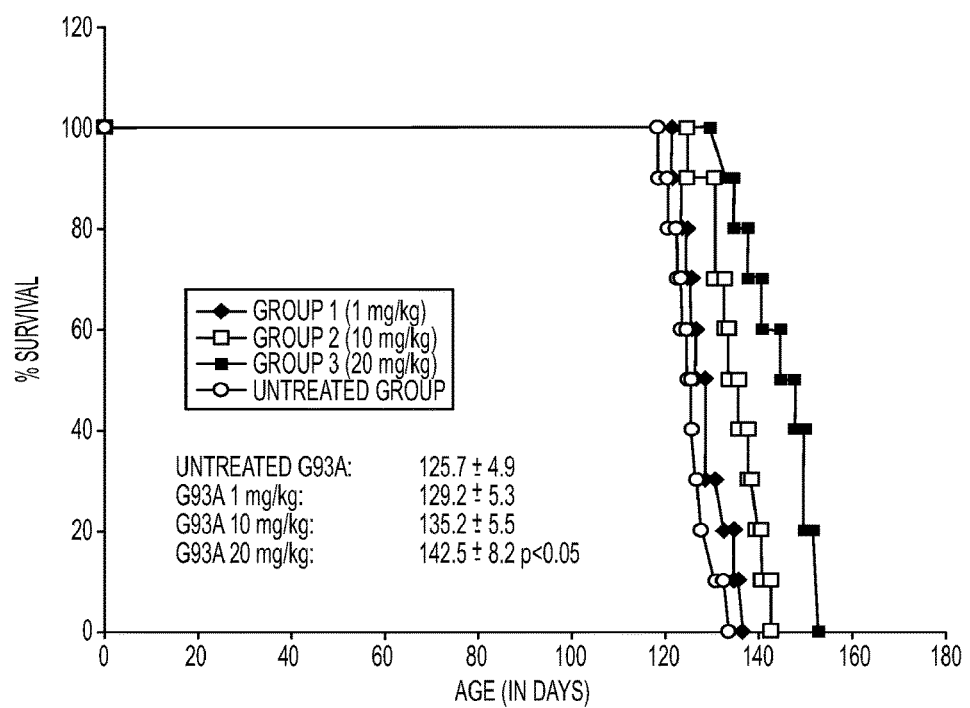
FIGS. 28-36.

TC-II-70 was used in a NADPH dependent rat liver microsomal stability study. The test (TC-II-70), positive control (minaprine), negative control (warfarin), and internal standard (haloperidol) compounds in this experiment are listed in FIG. 21. The experiment was carried out mostly according to the general procedure from the microsomal stability study of TC-I-165. After 0, 20, and 40 minutes incubation, 100 µL acetonitrile was added to quench reactions. The reaction mixture was vortexed and incubated in an ice bath for 2 h. Haloperidol (50 µL, 100 µM) was added to every test tube as an internal standard. The samples were centrifuged to remove the precipitated protein. The supernatant solutions were loaded directly for HPLC analysis.

Results

TC-II-70 is more stable in a NADPH dependent rat liver microsomal stability study compare with its sulfide, TC-I-165 (FIGS. 22-25). Table 5 shows results of microsomal stability data processing.

TABLE 5

| Sample Name | RR Mean | % Mean ± S.E. |
|---|---|---|
| Mina 5 µM 0 min | 0.711 | 100 ± 11.5 |
| Mina 5 µM 40 min | 0.321 | 45.2 ± 8.1 |
| TC-II-70 15 µM 0 min | 0.237 | 100 ± 12.6 |
| TC-II-70 15 µM 20 min | 0.261 | 109 ± 13.3 |
| TC-II-70 15 µM 40 min | 0.201 | 84.8 ± 21.8 |
| War 15 µM 0 min | 0.488 | 100 ± 7.75 |
| War 15 µM 60 min | 0.470 | 96.1 ± 7.66 |

Blood Brain Barrier Studies

Preliminary Blood Brain Barrier (BBB) Penetration Experiment. An in vivo BBB penetration experiment was carried out for CMB-087229. CMB-003319 was used as the internal standard due to its structural similarity to CMB-003299. CMB-087229 was formulated in 100 µL DMSO in 2 mL phosphate buffered saline. Blood concentration of CMB-087229 (MTD of 75 mg/kd IP) 1 hour following a single 1 mg IP dose was approximately 10 nM. Brain concentration of CMB-087229 1 hour following a single 1 mg IP dose was approximately 120 nM. After four hours, concentration in the brain was 194 µM. At 3 hours, plasma concentration measured 342 µM. At 6 hours, plasma concentration measured 347 µM. At 12 hours, plasma concentration measured 248 µM. At 24 hours, plasma concentration measured 1.68 µM. CMB-087229 reaches approximately 55% of the blood level in the brain.

Brain Uptake Procedure

CMB-087229 Mice Brain and Plasma Data CMB-087229 (1 mg/kg) was administrated to mice (Tg6799 colony with B6/SJL background) by intraperitoneal injection in a 60% PBS and 40% dimethyl sulfoxide solution. At 10 minutes after compound administration the mice were sacrificed. Blood was harvested and plasma was transferred to flash freeze in liquid nitrogen after centrifugation. Mice were perfused. The brain was homogenized in 100% acetonitrile. CMB-003319 (0.5 µg, 1.73 nmol) was added as an internal standard. The homogenates were centrifuged at 12000×g for 12 min, and the supernatant was evaporated. The residue was reconstituted in 33.3% acetonitrile. Solid phase extraction followed by LCMS (API 300 liquid chromatography-tandem mass spectrometry system, Applied Biosystems, Foster City, Calif.; Agilent 1100 series HPLC system, Agilent Technologies, Wilmington, Del.) was used to quantify the amount of CMB-087229 in mouse brain. Solid-phase extraction cartridges (Sep-Pak CI 8, Water Associates, Milford, Mass.) were washed with 1 mL acetonitrile and equilibrated with 1 mL of water. The reconstituted supernatant was then loaded, washed with 1 mL×2 of 33.3% acetonitrile. CMB-087229 was then dried and submitted for LCMS.

Results

Figure 8:
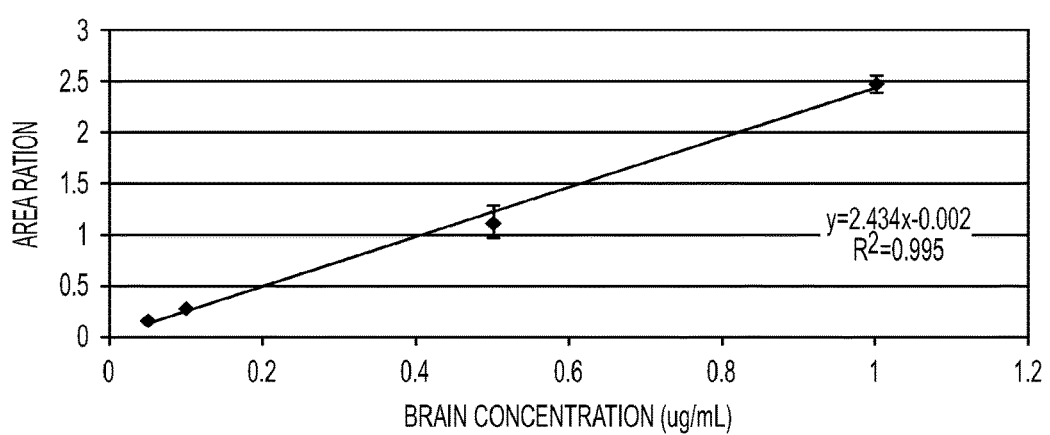
FIG. 8. Brain standard curve for CMB-087229.
Figure 9:
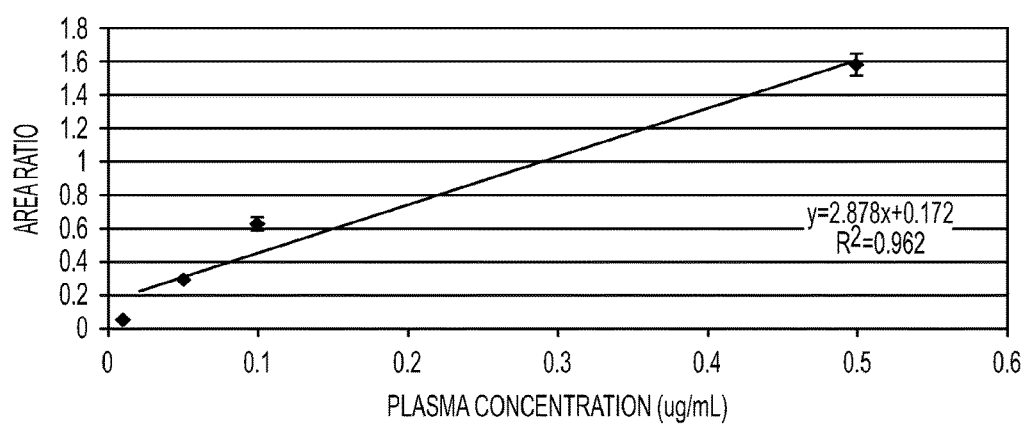
FIG. 9. Plasma standard curve for CMB-087229.
Figure 10:
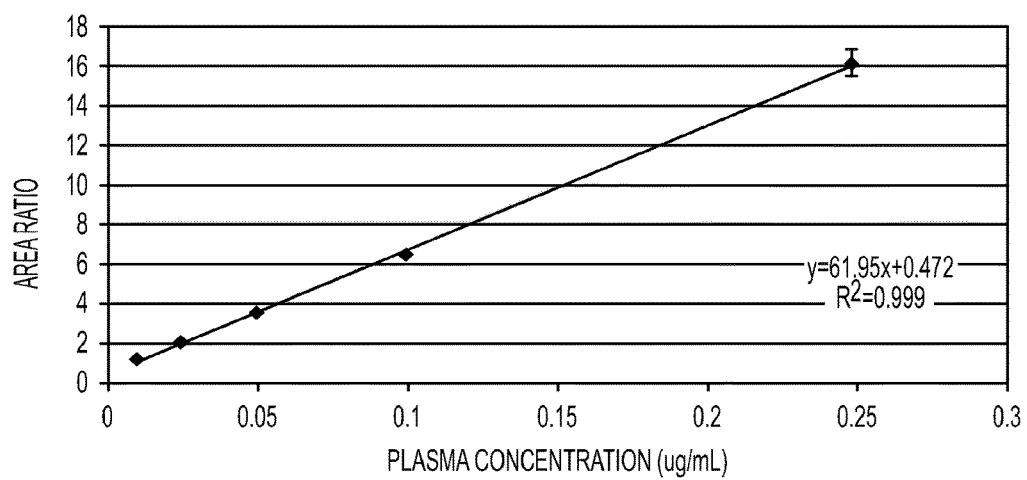
FIG. 10. Plasma standard curve for CMS-087229.

It should be noted that data obtained in March were not identical to data obtained in July. However, the brain standard curve and mice brain samples maintain fair standard deviations and linearity, and thus, the results from the brain studies can still be quantified. In light of this data, it appears that some amount of CMB-003329 does penetrate the BBB (FIG. 8-10).

TABLE 6

CMB-087229 Brain Standard Curve

| Brain Extract Concentration (µg/mL) | Brian Area Ratio (Mean ± S.E.) |
|---|---|
| 0.05 | 0.148 ± 0.0007 |
| 0.10 | 0.268 ± 0.0087 |
| 0.50 | 1.11 ± 0.155 |
| 1.00 | 2.48 ± 0.084 |

TABLE 7

CMB-087229 Plasma Standard Curve

| Plasma Concentration (µg/mL) | Plasma Area Ratio (Mean ± S.E.) |
|---|---|
| 0.01 | 0.068 ± 0.00042 |
| 0.05 | 0.304 ± 0.00436 |
| 0.10 | 0.637 ± 0.0337 |
| 0.50 | 1.58 ± 0.0604 |

TABLE 8

CMB-087229 Plasma Standard Curve

| Plasma Concentration (µg/mL) | Plasma Area Ratio (Mean ± S.E.) |
|---|---|
| 0.01 | 1.210 ± 0.0374 |
| 0.025 | 2.068 ± 0.0316 |
| 0.05 | 3.554 ± 0.0775 |
| 0.10 | 6.429 ± 0.109 |
| 0.25 | 16.05 ± 0.684 |
| 0.50 | 30.22 ± 1.351 |
| 1.0 | 59.67 ± 3.379 |
| 2.5 | 149.2 ± 1.744 |
| 5.0 | 297.8 ± 7.539 |
| 10 | 591.9 ± 0.758 |

TABLE 9

| | Brain Area Ratio | Brain Extract concentration (µg/ml) | Brain weight (g) | Brain concentration (µg/g) | Plasma concentration (µg/ml) July | Brain/plasma Ratio July |
|---|---|---|---|---|---|---|
| #2 | 0.292 | 0.121 | 0.470 | 0.257 | 0.0904 | 2.84 |
| #3 | 0.384 | 0.159 | 0.432 | 0.366 | 0.0892 | 4.10 |
| #4 | 0.453 | 0.187 | 0.399 | 0.467 | 0.149 | 3.13 |
| #5 | 0 | 0 | 0.415 | 0 | 0 | 0 |

TABLE 10

CMB-087229 Mice Brain and Plasma Data

| | Brain concentration (Mean ± S.E.) (µg/g) | Plasma concentration (Mean ± S.E.) (µg/ml) | Brain/Plasma Ratio (Mean ± S.E.) |
|---|---|---|---|
| 10 min July | 0.363 ± 0.105 | 0.110 ± 0.0342 | 3.36 ± 0.660 |

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

As discussed above, although the mechanistic basis of ALS, as well as the cause of motor neuron death, remain controversial, a cohort of susceptibility genes producing ALS have been identified from familial ALS patients, such as fused in sarcoma, senataxin, TAR DNA binding protein (TDP-43), and UBQLN2. The discovery of the toxicity of mutant Cu/Zn superoxide dismutase 1 (SOD1) provides the first insight into potential causes for ALS and contributes the most to our understanding of ALS pathology, which includes calcium mediated excitotoxicity, oxidative stress, mitochondrial dysfunction, and aberrant RNA processing. (See, e.g., Rosen, D. R.; Siddique, T.; Patterson, D.; Figlewicz, D. A.; Sapp, P.; et al. Mutations in Cu/Zn superoxide dismutase gene are associated with familial amyotrophic lateral sclerosis. *Nature*, 1993, 362, 59-62; Turner, B. J.; Talbot, K. Transgenics, toxicity and therapeutics in rodent models of mutant SOD1-mediated familial ALS. *Prog. Neurobiol.* 2008, 85, 94-134.) Recent observations that mutant SOD1-expressing astrocytes are toxic to motor neurons in both familial and sporadic ALS, together with the fact that SOD1 mediated protein misfolding and aggregation have proven to be associated with ALS pathogenesis, suggest a possible therapeutic treatment involving protection against mutant SOD1-induced cytotoxicity. (See, e.g., Nagai, M.; Re, D. B.; Nagata, T.; Chalazonitis, A.; Jessell, T. M.; Wichterle, H.; Przedborski, S. Astrocytes expressing ALS-linked mutated SOD1 release factors selectively toxic to motor neurons. *Nat. Neurosci*, 2007, 10, 615-622; Haidet-Phillips, A. M.; Hester, M. E.; Miranda, C. J.; Meyer, K.; Braun, Ashley Frakes, L.; Song, S. W.; Likhite, S.; Murtha, M. J.; Foust, K. D.; Rao, M.; Eagle, A.; Kammesheidt, A.; Christensen, A.;

Mendell, J. R.; Burghes, A. H. M.; Kaspar, B. K. Astrocytes from familial and sporadic ALS patients are toxic to motor neurons. *Nature Biotech.* 2011, 29, 824-830; Gruzman, A.; Wood, W. L.; Alpert, E.; Prasad, M. D.; Miller, R. G.; Rothstein, J. D.; Bowser, R.; Hamilton, R.; Wood, T. D.; Cleveland, D. W.; Lingappa, V. R.; Liu, J. Common molecular signature in SOD1 for both sporadic and familial amyotrophic lateral sclerosis. *Proc. Natl. Acad. Sci. USA* 2007, 104, 12524-12529.)

With reference to the preceding, such observations led to a high-throughput screen to identify compounds that protected these cells from protein aggregation and toxicity. While arylsulfanylpyrazolones (ASP) were initially identified and exhibited good in vitro potency, but were rapidly metabolized. The metabolic hot spot was identified as the sulfur atom, which was readily oxidized. Conversion to the corresponding ether led to much more stable compounds, and one analogue extended the life of G93A ALS mice by 13.3% at 20 mg/kg. However, further evaluation of some of these compounds indicated weak pharmacokinetic properties and a relatively low maximum tolerated dose. Accordingly, there remains an on-going search in the art for more potent and metabolically stable compounds, which also would allow diverse substitutions to carry out target identification studies.

In light of the foregoing, it is an object of the present invention to provide a class of arylpyrazolone compounds and/or methodologies for their use, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to enhance metabolic stability of arylpyrazolone compounds.

It can be another aspect of the present invention to provide a molecular scaffold with potential for greater structural diversity, as compared to the sulfanyl- and ether-linked compounds.

It can also be an object of the present invention, alone or in conjunction with one or more of the preceding objectives, to provide a basic methodology for the treatment of ALS and/or cellular dysfunction typical of the progression of ALS pathogenesis. Accordingly, it can also be an object of this invention to provide one or more arylazanylpyrazolone compounds for the inhibition and/or modulation of mutant SOD1 dependent protein aggregation and/or cytotoxicity.

Other objects, features, benefits and advantages of the present invention will be apparent from this summary and the following descriptions of certain embodiments, and will be readily apparent to those skilled in the art having knowledge of synthetic techniques useful in their preparation. Such objects, features, benefits and advantages will be apparent from the above, as taken into conjunction with the accompanying examples, data, figures and all reasonable inferences to be drawn therefrom, alone or with consideration of the reference(s) incorporated herein.

In part, the present invention can be directed to a compound selected from compounds of a formula

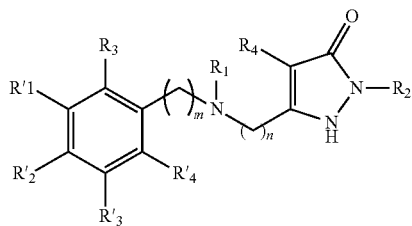

wherein each of $R_1$-$R_4$ can be independently selected from moieties including but not limited to H, sulfonyl, carbonyl and optionally substituted alkyl, cycloalkyl, arylalkyl, alkenylalkyl and alkynylalkyl moieties, and moieties where $R_3$ and $R_1$ together and $R_1$ and $R_4$ together form optionally substituted alkylene moieties; each of $R'_1$-$R'_4$ can be selected from moieties including but not limited to H, alkyl, alkoxy, cyano, and halo moieties and moieties where $R'_1$ and $R'_2$ together and $R'_3$ and $R'_4$ together form optionally substituted alkylene or alkenylene moieties; and each of m and n can be an integer independently selected from 0-3. Such a compound can be a salt, a tautomer or a combination of a salt and a tautomer.

Without limitation, $R_1$ can be an alkyl moiety. In certain embodiments, each of $R'_1$ and $R'_3$ can be chloro. In certain such embodiments, m can be 0, and n can be 1-2. Without limitation, $R_1$ can be selected from methyl and ethyl moieties. In certain such embodiments, each of $R'_1$ and $R'_3$ can be chloro, and each of $R_3$, $R'_2$ and $R'_4$ can be H.

It will be understood by those skilled in the art that compounds of this invention can comprise an acid salt, hydrate and/or solvate of any such compound. Without limitation, certain embodiments can be partially or fully protonated, comprising a secondary, tertiary and/or quaternary amine, whereby the counter ion(s) can be a conjugate base of a protic acid. Regardless, any such compound(s) can be provided as part of a pharmaceutical composition comprising a pharmaceutically-acceptable carrier component for use in conjunction with a method or medicament of this invention.

In part, the present invention can also be directed to a compound selected from compounds of a formula

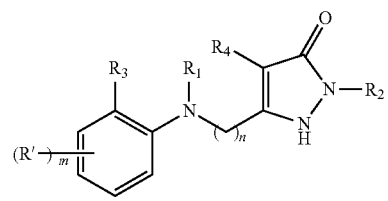

wherein each of $R_1$-$R_4$ can be independently selected from H, alkyl, cycloalkyl, arylalkyl, alkenylalkyl and alkynylalkyl moieties, providing $R_1$ is not H or arylalkyl, and moieties where $R_3$ and $R_1$ together and $R_1$ and $R_4$ together form alkylene moieties; $R^1$ can be a halo moiety and m can be an integer selected from 1-4; and n can be an integer selected from 1-2. Such a compound can be a salt and/or tautomer thereof.

Without limitation, $R_1$ can be alkyl. In certain embodiments, $R^1$ can be chloro and m can be 2. In certain such embodiments, $R_1$ can be selected from methyl and ethyl moieties, and each of $R_2$-$R_4$ can be H and n can be 1-2.

In part, the present invention can also be directed to a compound selected from compounds of a formula

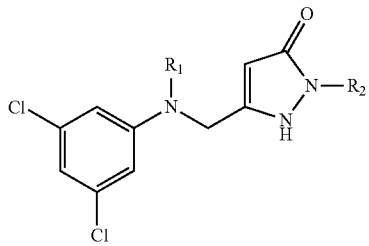

wherein $R_1$ and $R_2$ can be independently selected from H, alkyl and arylalkyl moieties, providing $R_1$ is not H or arylalkyl. Such a compound can be a salt and/or tautomer thereof. In certain embodiments, without limitation, $R_1$ can be alkyl, and $R_2$ can be selected from H, methyl and benzyl moieties. In certain such embodiments, $R_1$ can be selected from methyl and ethyl moieties.

More generally, the present invention can be directed to compounds schematically illustrated as follows:

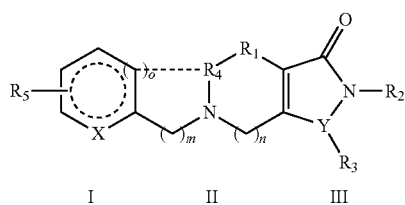

such compounds as can be considered in the context of substructures I, II and III. Without limitation, substructure I can comprise a substituted aromatic ring where X can be selected from CH, N, O and S, and o can be zero or 1; $R_5$ can be but is not limited to various mono-, di- and tri-substituted groups, such as halogen, $OCH_3$, $CH_3$, $NO_2$ and CN or combinations thereof. Without limitation, substructure III can comprise a 5-member ring where Y can be N or CH. Without limitation, substructure II can comprise a linear or cyclic linker between substructures I and III, where each of m and n can independently be 0, 1, or 2, provided at least one of m and n is 1. Further, $R_2$ and $R_3$ can be independently selected from H, alkyl, aryl or substituted alkyl and aryl (e.g., including, but not limited to aminoalkyl or hydroxyalkyl) moieties. $R_1$ and $R_4$ can be independently selected from H, alkyl and aryl moieties and alkylene moieties to provide a carbon ring structure between substructures I and II or between substructures II and III (e.g., including, but not limited to $R_1$ or $R_4$ as $CH_2$).

Alternatively, such compounds can incorporate an N-aryl substituted pyrrolidinyl linker moiety, with a pendant pyrazolinyl moiety at the 2- or 3-position thereof. Various other embodiments can comprise substructures I and II together providing an indolinyl moiety with a pendant pyrazolinyl moiety at the 1, 2 or 3-position thereof. Certain such compounds have one or more chiral centers, and such compounds are without stereochemical limitation. Such compounds and/or their intermediates can be available as racemic mixtures from which isomers can be resolved or are diastereomers, from which cis- and/or trans-isomers can be separated. Accordingly, any stereocenter can be (S) or (R) with respect to any other stereocenter(s). Further, it will be understood by those skilled in the art that certain such compounds of this invention can comprise an acid salt, hydrate and/or solvate of any such compound. Certain such embodiments can be partially protonated, comprising a secondary, tertiary and/or quaternary amine, whereby the counter ion(s) can be a conjugate base of a protic acid.

In part, the present invention can also be directed to a method of modulating the activity of a superoxide dismutase. Such a method can comprise providing a compound of the sort described herein; and contacting such a compound with a cellular medium expressing a mutant superoxide dismutase 1, such a compound as can be present in an amount at least partially sufficient to affect protein aggregation within such a cellular medium. Without limitation, in certain embodiments, such a compound can be provided in a fluid medium. In certain such embodiments, such a compound can be present as a tautomer thereof. Regardless, such a methodology can be utilized in the treatment of ALS.

In part, the present invention can also be directed to a method of treating, inhibiting, protecting against, affecting and/or otherwise modulating mutant SOD1-induced cytotoxicity. Such a method can comprise providing a compound of the sort described above, such as and without limitation, of a formula of

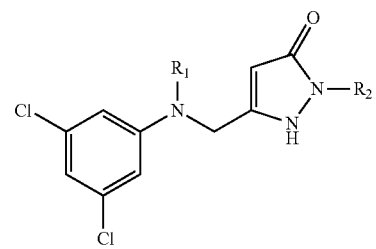

and contacting a cellular medium, expressing or capable of expressing an mutant SOD1, with a therapeutically-effective amount of such a compound. Functionally, such a method can be considered in the context of inhibition and/or modulation of or protection from mutant SOD1 dependent protein aggregation and/or related toxicity. Regardless, the effect of such a compound against SOD1-induced cytotoxicity can be determined, as understood by those skilled in the art, through an assay of the sort described herein. Accordingly, compounds of this invention can be used in vivo against protein aggregation and cytotoxicity and/or in the treatment of or evaluation for ALS.

Without limitation, the chemistry and activity of several embodiments of this invention can be considered in conjunction with the following and with reference to examples 1-41 and Tables 1-3, below. Two synthetic strategies were utilized to synthesize β-ketoesters, the critical intermediate for the construction of the pyrazolone ring. As shown in Scheme 1, the upper route started from the reaction of alkyl anilines or sulfonyl amides with ethyl bromoalkanoate. The ester intermediates reacted with the enolate of ethyl acetate, providing the anilino substituted β-ketoesters in moderate to high yields. The lower single-step route was carried out using an optimized methodology based on the reaction of the aniline with ethyl 4-chloroacetoacetate, resulting in a series of anilino substituted β-ketoester intermediates with varied R and R' substituents. (Zhang, Y.; Silverman, R. Direct amination of γ-halo-β-ketoesters with anilines. *J. Org. Chem.* 2012, 77, 3462-3467.) All of the β-ketoester intermediates were transformed to pyrazolones in high yields with hydrazine.

Scheme 1. Synthetic routes for arylazanyl pyrazolones

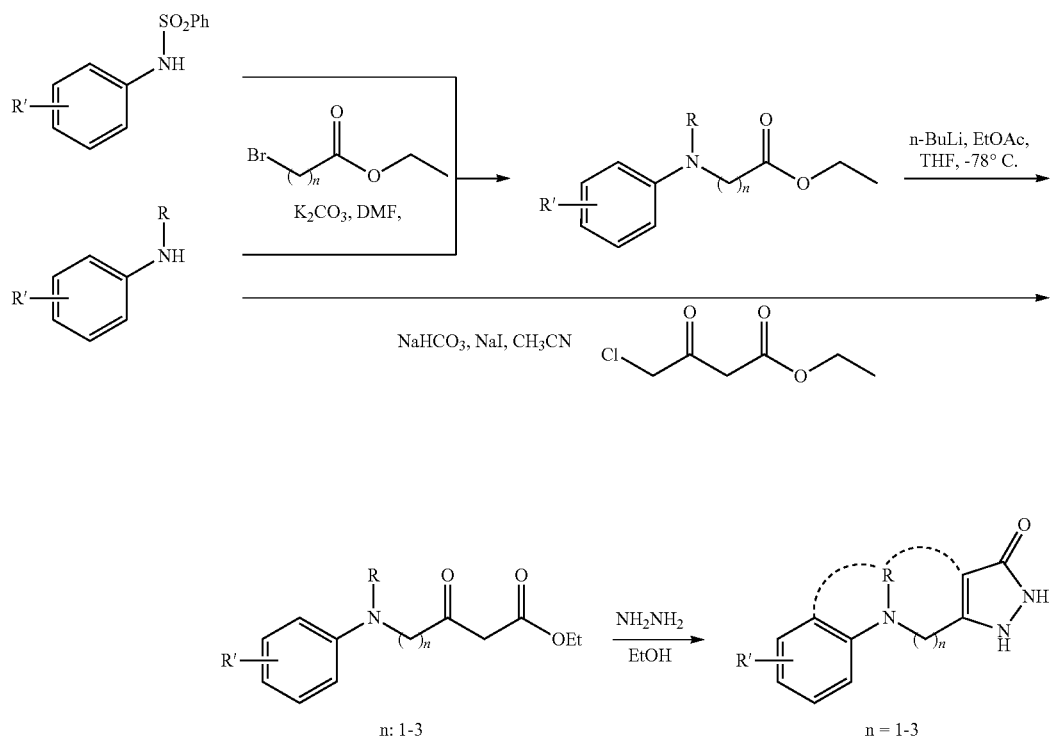

n: 1-3    n = 1-3

An alternative synthetic route (Scheme 2) was designed for bulky R groups, such as t-butyl, phenyl, and benzyl, which gave low yields of anilino esters in the reaction above. By employing ethyl diazoacetate, an NH insertion occurred to achieve the anilino esters in good yields, which were used to generate the β-ketoester intermediates by attack of the enolate of ethyl acetate.

Scheme 2. Synthesis of β-ketoester intermediates with bulky R groups

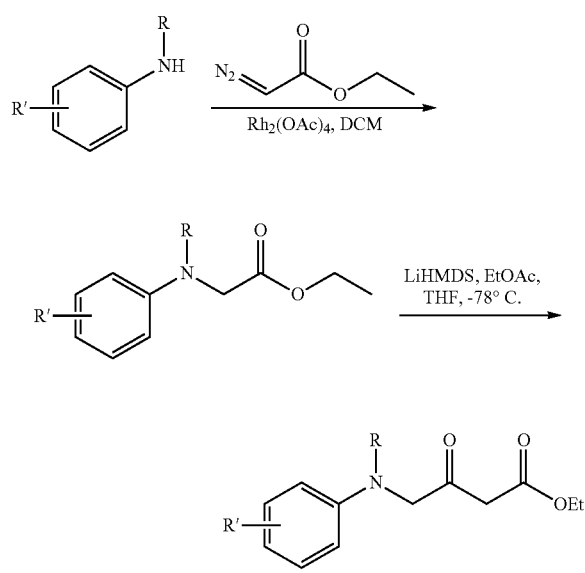

The $N^1$-methyl pyrazolone analogue (30) was easily obtained by replacing hydrazine with methyl hydrazine in the heterocycle formation (Scheme 3). The $N^1$-methyl pyrazolones can be further modified to dimethyl- and trimethyl-substituted pyrazolone analogues (32-34). Although it has been reported that the condensation between methyl hydrazine and a β-ketoester produces a mixture of $N^1$-alkyl and $N^2$-alkyl isomers, no $N^1$-alkyl product was observed with this particular substrate. With the help of a method developed by Janin and coworkers, attempts to synthesize the $N^2$-alkyl product (31) were successful, as shown in Scheme 3. (Zimmermann, D.; Krogsgaard-Larsen, P.; Ehrhard, J.-D.; Madsen, U.; Janin, Y. L. Unambiguous synthesis of 1-methyl-3-hydroxypyrazoles. *Tetrahedron*, 1998, 54, 9393-9400.) The β-ketoester intermediate was initially converted to $N^1$-2-hydroxylethyl-$N^2$-tosyl pyrazolone derivative 35 in an 85% yield, which was then treated with sodium hydride to give key intermediate 36 containing a 2,3-dihydropyrazolo[3,2-b]oxazole ring. Alkylation with MeOTf, dihydrooxazole ring-opening with sodium iodide, followed by elimination of hydrogen iodide, led to $N^1$-vinyl-$N^2$-methyl pyrazolone 37 in a 55% yield. Acid hydrolysis gave the desired $N^1$-methyl pyrazolone analogue (31).

Scheme 3. Synthesis of analogues substituted on the pyrazolone moiety

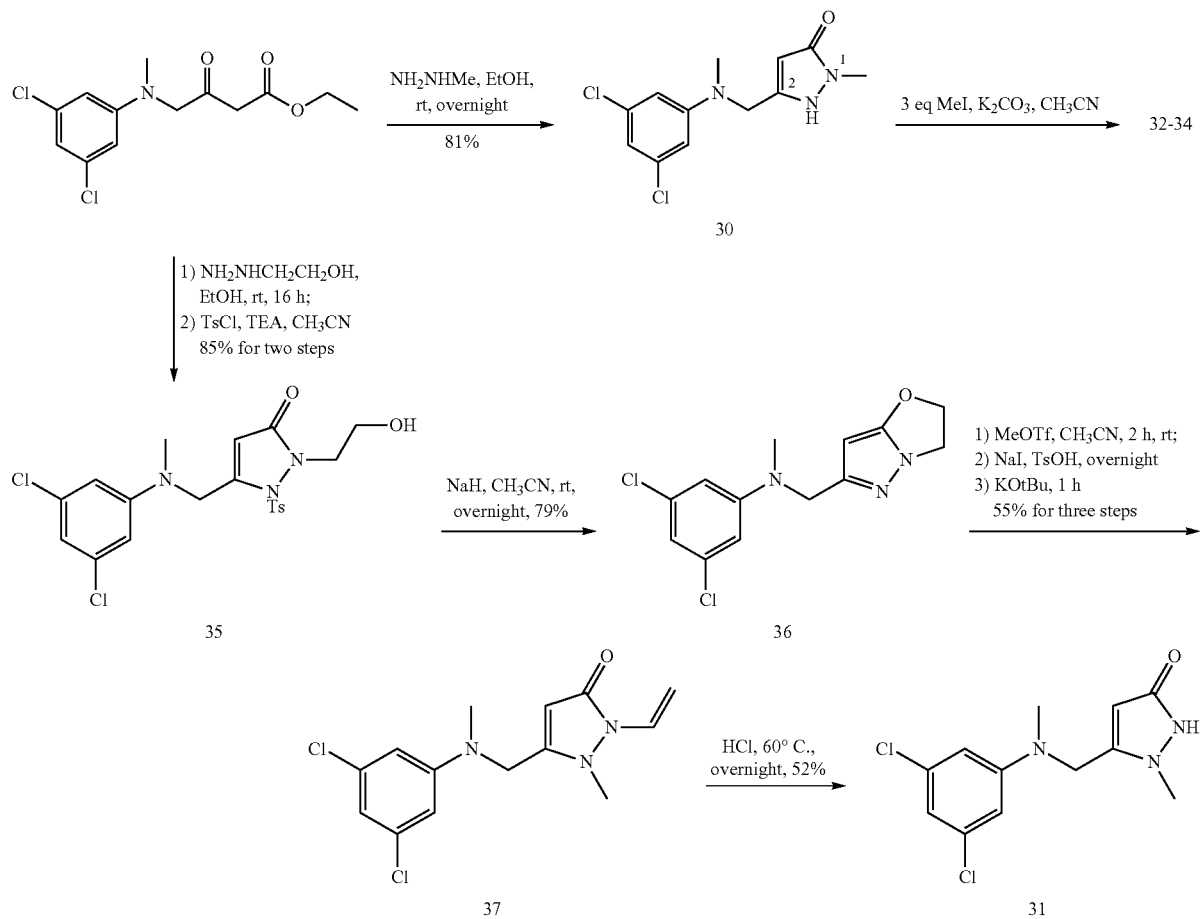

Compound 1 has an oral bioavailability of 27%, PK half-life of 3.6 hours, and maximum tolerated dose of 75 mg/kg, which meet the standard minimal criteria for preclinical advancement. (Kerns, E. H.; Di, L. *Drug-like Properties: Concepts, Structure, Design, and Methods*; Academic Press: Amsterdam, 2008; pp. 65.) However, some pharmacokinetic properties of 1 suggest areas for improvement. For example, as indicated by the oral bioavailability, the AUC/dose of 1 showed a distinct difference between i.v. (184 ng*h/mL/dose) and p.o. (50 ng*h/mL/dose) administration. Given good aqueous solubility and cell permeability, one of the most likely causes for the difference between these two routes of administration may be the first-pass clearance from hepatic and gut metabolism. To increase metabolic stability and to allow further structure diversification, the ether oxygen was replaced by the amine functional group. Without limitation, reference is made to the schematic illustration of FIG. 29.

Two possible amines, secondary and tertiary AAP analogues, were initially screened in the protection assay (FIG. 30) and for in vitro microsomal stability (Table 1) and Caco-2 permeability (Table 2). Introduction of the nitrogen led to a potency decrease in the cell-based protection assay; however, the tertiary arylazanyl analogue had a slightly better activity over the secondary arylazanyl analogue. The solubilities of 2 and 3 were good in aqueous media (≥150 μM), and no precipitation occurred at the highest concentration. The in vitro plasma half-life for both compounds was >60 min. Tertiary amine 3 exhibited a remarkable stability enhancement in human liver microsomes compared with the moderate half-life and clearance rates of the ether and secondary amine analogues. Whereas 2 and 3 exhibited less than optimal Caco-2 permeability and both had high efflux potential (although 3 was superior to 2), tertiary amine analogue (3) showed improved human microsome stability, and provided a basis for the present tertiary amine analogues.

TABLE 1

In vitro microsomal stability of 1-3[a]

| | Cmpd | NADPH-dependent | | NADPH-absent | |
| | | $CL_{int}$[b] (mL in$^{-1}$ kg$^{-1}$) | $T_{1/2}$[c] (min) | $CL_{int}$[b] (mL min$^{-1}$ kg$^{-1}$) | $T_{1/2}$[c] (min) |
|---|---|---|---|---|---|
| Human | 1 | 25 | 93 | 13 | 173 |
| | 2 | 24 | 95 | 0 | >180 |
| | 3 | 0 | >180 | 0 | >180 |
| Mouse | 1 | 64 | 36 | 21 | 111 |
| | 2 | 78 | 30 | 23 | 100 |
| | 3 | 93 | 25 | 0 | >180 |

[a]Data were obtained from Apredica.
[b]Microsomal intrinsic clearance.
[c]Half-life.

TABLE 2

In vitro Caco-2 permeability of 1-3.[a]

| Cmpd | $P_{app}$ (A→B)[b] ($10^{-6}$ cm/s) | $P_{app}$ (B→A)[b] ($10^{-6}$ cm/s) | Efflux ratio (B→A)/(A→B) |
|---|---|---|---|
| 1 | 36.7 | 14.1 | 0.4 |
| 2 | 0.6 | 28.1 | 47.1 |
| 3 | 2.2 | 7.6 | 3.5 |

[a]Data were obtained from Apredica.
[b]Apparent permeability.

Figure 29:
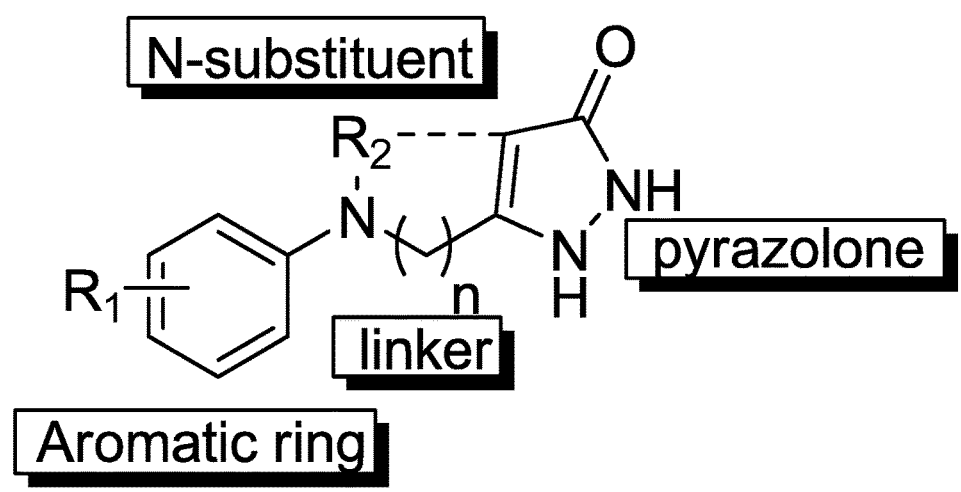
Figure 31:
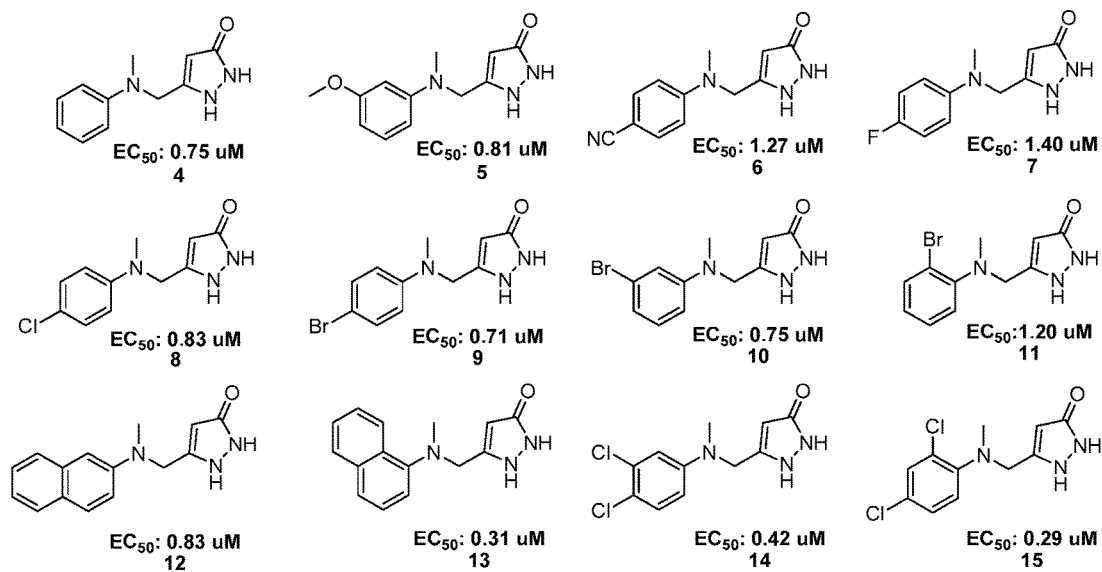

Compound activity was determined using the previously described cytotoxicity protection assay (Table 1). The variability of the $EC_{50}$ values is about a factor of 2. As shown in FIG. 29, the tertiary amine AAP scaffold contains four sub-structural moieties: aromatic ring, N-substituent, linker, and the pyrazolone. Structural modifications were conducted on each moiety. A variety of substituents in the aryl moiety was investigated using a synthetic approach for amination of anilines and γ-halogen-β-ketoesters (FIG. 31). In general, the potencies of these AAPs were slightly poorer than the ether counterparts (compound 1 vs 3). Previous reports on arylsulfanyl- and aryloxanylpyrazolones (AXP), showed that the 3,5-dichloro substitution pattern in the aromatic ring gave greater potency over the other substitution patterns (about 5-10 fold enhancement). Here, neither the electronic properties (compounds 4-6) nor the positions of substitution (compounds 9-11) in the aromatic ring exhibited a large activity change, but the size of the substituents affected the activity in the following order: F<CN<OMe<Cl~Br<di-Cl~naphthalene. 2,4-Dichloro- and α-naphthyl substitution in the aromatic ring moiety were the most effective.

Figure 32:
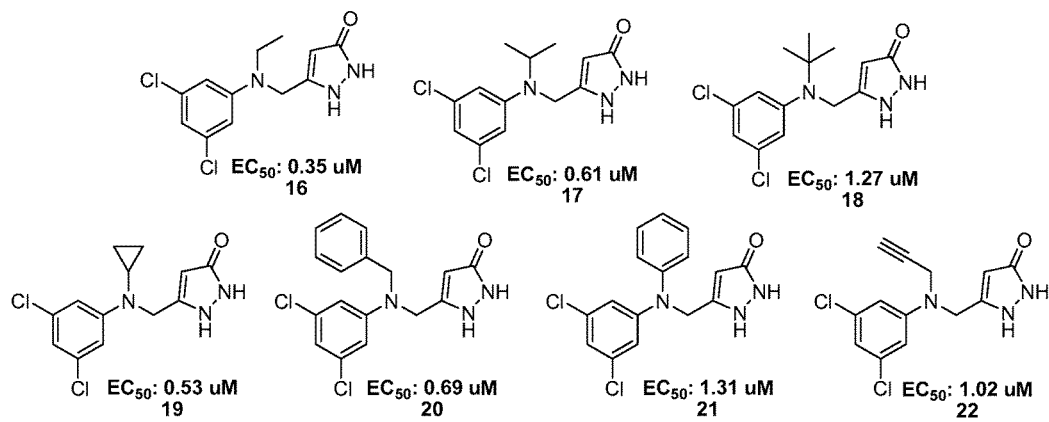

With the aromatic ring substituents, linker, and pyrazolone held constant, a series of N-substituted AAPs was synthesized (FIG. 32; these compounds were being synthesized prior to the measurements in FIG. 31, so 3,5-dichloro was selected for aryl substitution). Although the range of potency changed by less than four-fold, the ethyl analogue was the most potent and the potency decreased with an increase of the size of substituents in the following order: Et>c-Pr>i-Pr~Bn>propargyl>t-Bu~Ph; however, the smaller methyl analogue was comparable in potency to the cyclopropyl analogue. The propargyl analogue can be beneficial with respect to target identification studies, providing a terminal triple bond for reporter group attachment via click chemistry.

Figure 33:
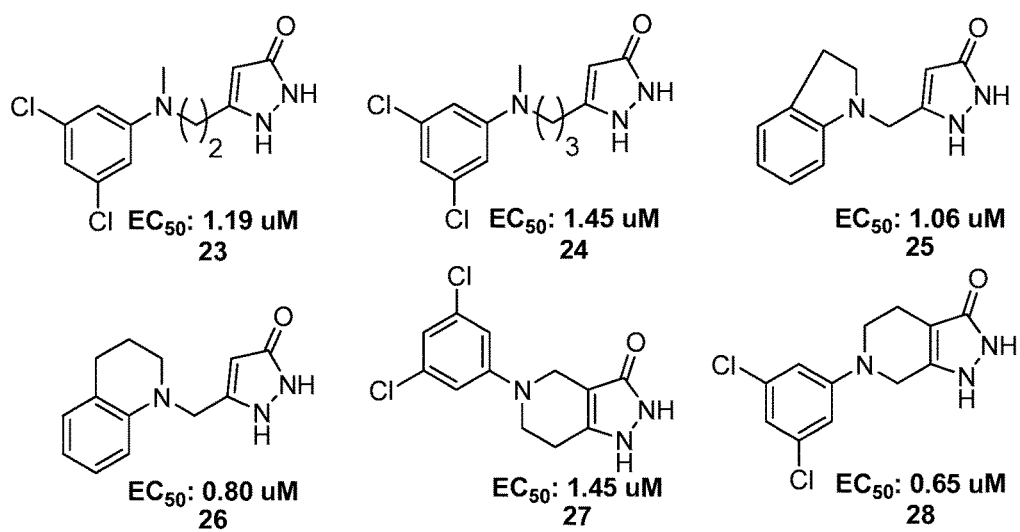

An investigation of the linker between the aryl moiety and the pyrazolone also was carried out to determine the influence of length and shape. As shown in FIG. 33, one carbon is the optimal length between the nitrogen and the pyrazolone moiety; longer linkers reduce the activity. One useful modification to enhance the pharmacokinetic properties is a ring-chain transformation. Four ring linkers were introduced to the AAP scaffold (25-28). The connection between the aryl group and the N-substituent (25 and 26) favored 26; the linker between the N-substituent and the pyrazolone ring (27 and 28) has a preference for that described by 28. The latter two compounds reveal that substitution at the 5-position of the pyrazolone does not affect potency.

Selected compounds were tested with cortical neurons—a useful preliminary step prior to the expensive and time-consuming ALS mouse model studies. Although long linker compound 24 and cyclic linker compound 27 are active in the PC12 assay, they are not active with cortical neurons. Compound 3 gave better results than the ether counterpart (1), recovering 100% neuronal activity at 10 µM concentration.

Figure 30:
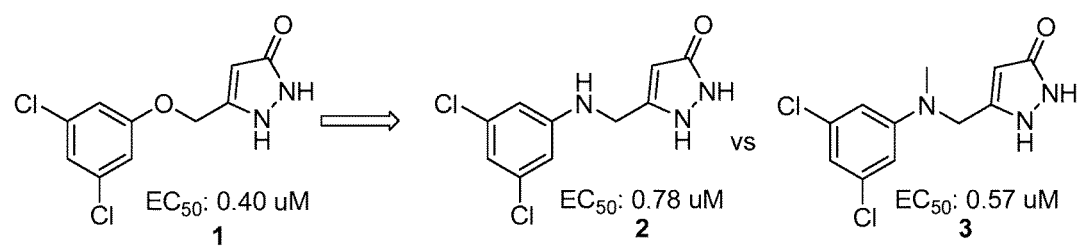

The pyrazolone ring has been related to activity in all of the AXP scaffolds. The compounds without a pyrazolone or with N,N'-dimethyl substituted pyrazolone in aryloxanyl series had no activity. Given that there are three potential H-bonding donors/acceptors in the pyrazolone ring, a determination of their pharmacophoric nature can be useful. A putative explanation for the pyrazolone activity is the availability of the $N^2$-hydrogen (3a-type) for hydrogen bonding. For that purpose, single $N^2$-nitrogen substituted pyrazolone analogue 31 and other $N^2$-substituted analogues were synthesized (Scheme 3). As shown in FIG. 6, 29 and 30 were comparable in activity to parent compound 3, while compounds 31-34, all of which do not have a $N^2$—H, were devoid of activity, demonstrating the significance of the $N^2$—H for activity in this series as well.

Figure 34:
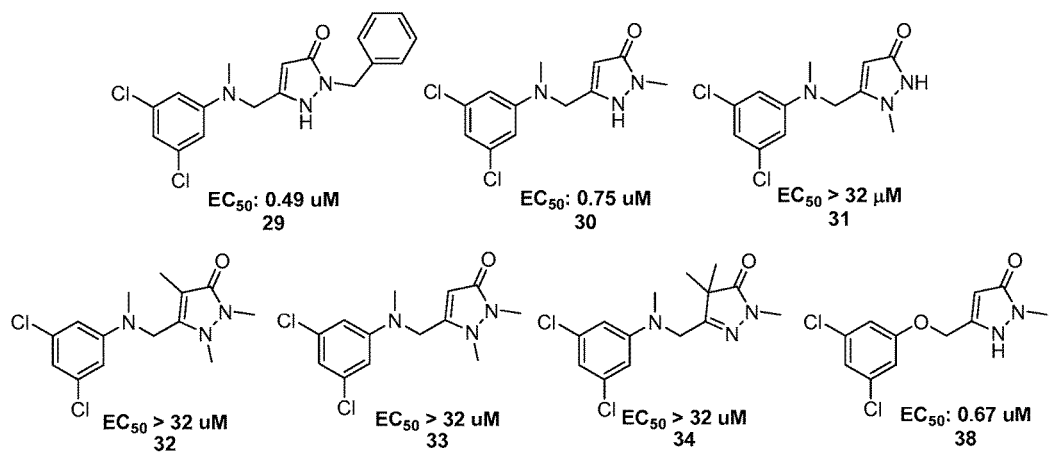
Figure 35:
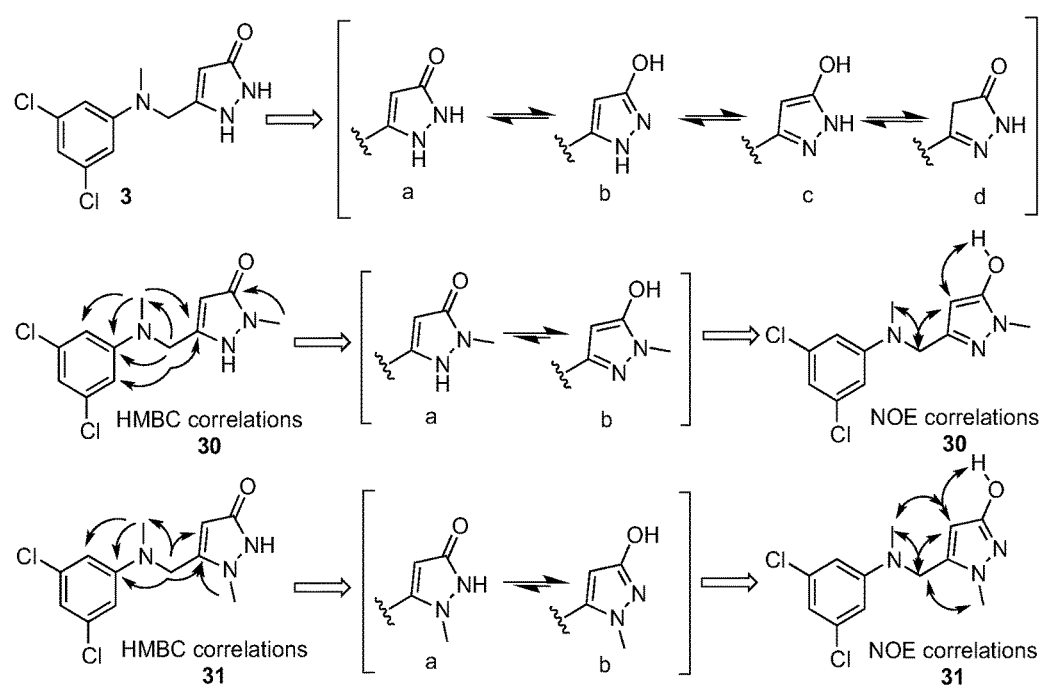

Several spectrometric analyses were carried out to determine if the pyrazolone structure shown in FIG. 34 is most prevalent. Because of a rapid equilibrium among the pyrazolone tautomers, the $^{13}$C-NMR spectrum of 3 gave a carbon signal with obscure bumps in the region of the pyrazolone and methylene group. However, clear $^{13}$C-NMR spectra of those carbons in 30 and 31 suggested the presence of a tautomer. HSQC, HMBC, and NOE spectra of 30 and 31 were then collected. The HSQC spectrum permitted the assignment of all of the protons with their bonding carbons. Analysis of the HMBC spectrum enabled the connectivity of the phenyl, the linker, and the pyrazolone moieties. The cross peaks between the phenol hydrogen and the 4-hydrogen of the pyrazolone in the NOE spectrum determined the spatial approach of these two neighboring hydrogens, which supported a tautomer present in 30 and 31 as the phenol form (30b and 31b, FIG. 35).

In an attempt to rationalize these observations, comprehensive theoretical calculations were performed on the four possible tautomers of 3 using density-functional theory (DFT); the predicted energy order was d<b<c<a in the gas phase (Table 3). The largest energy difference among all of the forms is 22.6 kJ/mol, which is an insufficient energy barrier to detect a preferred tautomeric form. Since the tautomerization of pyrazolone was first discovered by Knorr in 1895, several reported calculations have predicted a similar prediction for the stability of the pyrazolone tautomers, and calculations of similar structures predicted that the phenol forms are favored for 1- or 2-substituted pyrazolones in aprotic solvents, as observed here.

TABLE 3

Calculated energies of the tautomers of 3

| Tautomers | Energy (a.u.) | ΔE (kJ/mol) |
|---|---|---|
| 3a | −1585.125802 | 22.60 |
| 3b | −1585.129852 | 11.97 |
| 3c | −1585.128450 | 15.64 |
| 3d | −1585.134409 | 0 |

To further characterize a tautomeric form of the pyrazolone heterocycles in 30 and 31, quantum chemical calculations were performed. A pertinent conformation can be identified by comparing the experimental IR spectra with the predicted IR spectra of the different tautomers. All of the predicted spectra of keto tautomers have a similar high frequency at ~1730 cm$^{-1}$, while the spectra of phenol-type tautomers have no absorption band in the same region. Hence, the frequency at ~1730 cm$^{-1}$, the stretching vibration of the C═O bond, is an important band to differentiate these two tautomers. The experimental IR spectra do not contain a band at 1730 cm$^{-1}$. Furthermore, the most highly predictive bands for phenol forms are in good agreement with the experimental data. All of these results indicate that phenol forms of 30 and 31 are the more stable tautomers. Similar NOE and IR spectral observations for ether analogue 38 suggest that the active pyrazolone tautomer in the AOP series also is the phenol form spectral (spectra not shown).

On the basis of the above results, a pyrazolone phenol-type tautomer appears present in solution and in solid phase, but, given that the target(s) is unknown, it cannot be concluded definitively whether this tautomer is the pharmacophoric core responsible for the activity of any or all AAP analogues. However, without restriction to any one theory or mode of operation, if such a tautomer is an active species, then biological activity may suggest the following two criteria: 1) $N^2$ has unsubstituted $sp^2$ hybridization rather than $sp^3$ hybridization; and 2) there is a phenol hydrogen, presumably as a H-bonding donor. The loss of activity by di- and trimethyl substituted derivatives also supports this hypothesis regarding activity.

As demonstrated, AAP analogues provide superior properties relative to the corresponding ether derivative in potential structural diversity and in preliminary metabolic studies. Observations from the SAR study include: (1) the size of the aryl moiety, rather than the electronic properties, can affect potency; (2) potency can decrease when the size of the N-substituents increases; as a potential chemical reporter, the alkynyl group is well tolerated; (3) while one carbon is an optimal length for the linker; the linker can be linear or cyclic; and (4) the pyrazolone pharmacophore of this structure can provide a phenol-type tautomer in solution and solid phase.

As would be understood by those skilled in the art, the present invention can also be extended to or include methods using or in conjunction with a pharmaceutical composition comprising a compound of the sort described herein and a physiologically or otherwise suitable formulation. In a some embodiments, the present invention includes one or more such compounds, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a human cellular medium, astrocyte and/or a mutant SOD1 expressed or otherwise present therein. Whether or not in conjunction with a pharmaceutical composition, "contacting" means that such a cellular medium and one or more compounds of this invention are brought together for purpose of inhibiting or otherwise affecting enzyme activity or a result of enzyme activity. Amounts of a compound effective to modulate or protect against enzyme activity may be determined empirically, and making such determinations is within the skill in the art.

It is understood by those skilled in the art that dosage amount will vary with the activity of a particular compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing a compound of this invention into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more arylazanylpyrazolone compounds of this invention for the manufacture of a medicament for therapeutic use in the treatment of ALS.

The following non-limiting examples and data illustrate various aspects and features relating to the compounds and/or methods of the present invention, including the preparation and use of various arylazanylpyrazolone compounds, as are available through the synthetic methodologies described herein. In comparison with the prior art, the present invention provides results and data which are surprising, unexpected and contrary thereto. While the utility of this invention is illustrated through the use of several compounds, moieties thereof and/or substituents thereon, it will be understood by those skilled in the art that comparable results are obtainable with various other compounds, moieties and substituents, as are commensurate with the scope of this invention.

General experimental methods. All reactions were carried out with magnetically stirring and were monitored by thin-layer chromatography on precoated silica gel 60 F254 plates. Column chromatography was performed with silica gel 60 (230-400 mesh). Proton and carbon NMR spectra were recorded in deuterated solvents on a Bruker Ag500 (500 MHz) spectrometer. The chemical shifts were reported in $\delta$ (ppm) ($^1$H NMR: CDCl$_3$, $\delta$ 7.26 ppm; DMSO-d$_6$, $\delta$ 2.50 ppm; $^{13}$C NMR: $\delta$ 77.23 ppm; DMSO-d$_6$, $\delta$ 39.52 ppm). The following abbreviations were used to define the multiplicities: s=singlet, d=doublet, t=triplet, q=quartet, p=pentet, m=multiplet. Electrospray mass spectra (ESIMS) were obtained using an Agilent 1100 MSD with methanol as the solvent in the positive ion mode. IR was recorded on a Bruker tensor FT-IR spectrometer. Elemental microanalysis was performed by Atlantic Microlab Inc. (Norcross, Ga.). The C, H, and N analyses were performed by combustion using automatic analyzers, and all of the compounds analyzed showed >95% purity. All reagents purchased from Aldrich, Alfa Aesar, and TCI were used without further purification unless stated otherwise.

Abbreviations. AAP, arylazanyl pyrazolone; ADME, absorption, distribution, metabolism, excretion; ALS, amyotrophic lateral sclerosis; ASP, arylsulfanyl pyrazolone; AXP, aryl heteroatom pyrazolone; CNS, central nervous system; DFT, density functional theory; FALS, familial ALS; IR, infrared spectroscopy; NOE, nuclear overhauser effect spectroscopy; PBS, phosphate buffered saline; PK, pharmacokinetics; SALS, sporadic ALS; SOD1, Cu/Zn superoxide dismutase Example 1

General procedure A for nucleophilic amination of anilines and bromoacetates. To a solution of K$_2$CO$_3$ (200 mol %) and the aniline (1.0 equiv) in DMF (2 mL/mmol) was added ethyl bromoacetate (150 mol %). The reaction mixture was stirred at room temperature or 80° C. for 16 h. The reaction solution was diluted with ethyl acetate, washed twice with water to remove the reaction solvent, and washed with brine. The collected organic layers were combined, dried over $Na_2SO_4$, filtered, and concentrated. The crude product was purified on a silica gel column, eluting with a mixture of ethyl acetate and hexane (5% to 20% ethyl acetate) to afford the product as a colorless to pale yellow oil in a yield of 30%-80%.

Example 2

General procedure b for carbene insertion of anilines. To a solution of the aniline (1.0 equiv) and $Rh_2(OAc)_4$ (2 mol %) in anhydrous dichloromethane (1 mL/mmol) was added ethyl diazoacetate dropwise. Caution: much $N_2$ is released! The reaction mixture was stirred at room temperature for 1 h. After evaporating the volatiles, the reaction residue was purified on a silica gel column, eluting with a mixture of ethyl acetate and hexane (5% to 20% ethyl acetate) to afford the product as a colorless to pale yellow oil in a yield of 50%-95%.

Example 3

General procedure C for the synthesis of β-ketoesters from aminoacetates. Ethyl acetate (110 mol %) was added to a THF (5 mL/mmol) solution of LiHMDS (1 N in THF, 120 mol %) at −78° C. and stirred for 60 min. A THF (1 mL/mmol) solution of β-aminoacetate (1.0 equiv) was added dropwise to the reaction mixture at −78° C. After the resulting solution was stirred at −78° C. for another 2 h, the reaction mixture was quenched with saturated $NH_4Cl$. The aqueous layer was extracted with ethyl acetate, washed twice with water and brine. The collected organic layers were combined, dried over $Na_2SO_4$, filtered, and concentrated. The crude product was purified on a silica gel column, eluting with a mixture of ethyl acetate and hexane (10% to 30% ethyl acetate) to afford the product as a colorless to pale yellow oil in a yield of 40%-80%.

Example 4

General procedure D for direct amination of γ-Halo-β-ketoesters with anilines. To a solution of $NaHCO_3$ (200 mol %), NaI (200 mol %), and the aniline (1 equiv) in acetonitrile (1 mL/mol) was added ethyl α-chloracetoacetate (200 mol %). The resulting reaction mixture was stirred at room temperature or at 80° C. for 1-16 h. After the mixture was cooled to room temperature, saturated $Na_2S_2O_3$ solution (1 mL/mol) was added. The resulting solution was extracted with ethyl acetate, and the organic layer was collected, which was then washed with water and brine. The collected organic layers were combined, dried over $Na_2SO_4$, filtered, and concentrated. The residue was subjected to column chromatography eluting with a mixture of hexane and ethyl acetate (10% to 30% ethyl acetate) to afford the product as a pale yellow oil in a yield, as specified in the literature. (Trippier, P. C.; Benmohammed, R.; Kirsch, D. R.; Silverman, R. B. Substituted pyrazolones require $N^2$ hydrogen bond donating ability to protect against cytotoxicity from protein aggregation of mutant superoxide dismutase 1. *Bioorg. Med. Chem. Lett.* 2012, 22, 6647-6650.)

Example 5

General procedure E for the synthesis of pyrazolones from β-ketoesters. To a solution of β-ketoesters (1 equiv) in EtOH (5 mL/mmol) was added anhydrous hydrazine (200 mol %). The resulting solution was stirred at room temperature overnight. After evaporating the volatiles, the reaction residue was purified on a silica gel column, eluting with a mixture of MeOH and dichloromethane (2% to 10% MeOH) to afford the product as a colorless to pale pink solid. The solid was then recrystallized in dichloromethane/hexane to give the pure product as a white solid in a yield of 60%-75%.

Example 6

5-((3,5-Dichlorophenylamino)methyl)-1H-pyrazol-3 (2H)-one (2). Following general procedures A, C, and E provided the phenylsulfonyl protected N-(3,5-dichloro phenyl)-N-((5-oxo-2,5-dihydro-1H-pyrazol-3-yl)methyl) benzenesulfonamide. $^1$H NMR (DMSO-$d_6$, 500 MHz): δ=11.56 (br s, 1H), 9.45 (br s, 1H), 7.78-7.74 (m, 1H), 7.64-7.63 (m, 4H), 7.56 (s, 1H), 7.14 (d, J=1.5 Hz, 2H), 5.21 (s, 1H), 4.67 (s, 2H); $^{13}$C NMR (DMSO-$d_6$, 125 MHz): δ=140.8, 136.6, 133.8×2, 133.7×2, 129.6×2, 127.6×2, 127.5, 127.0 ppm; MS (ESI): m/z 398.0 $[M+H]^+$.

N-(3,5-dichlorophenyl)-N-((5-oxo-2,5-dihydro-1H-pyrazol-3-yl)methyl) benzenesulfonamide (398 mg, 1 mmol) and 4-hydroxybenzoic acid (800 mg, 5.8 mmol, 200% weight) were added to a solution of HBr (48% in $H_2O$, 4 mL) and AcOH (4 mL). After the resulting suspension was stirred at 100° C. for 2 h, the reaction mixture was partitioned between 1N HCl (10 mL) and ethyl acetate (30 mL×2). The collected organic layers were combined, dried over $Na_2SO_4$, filtered, and concentrated. The residue was subjected to column chromatography eluting with a mixture of MeOH and dichloromethane (5% MeOH) to afford 2 (142 mg, 55% yield) as a white solid. $^1$H NMR (DMSO-$d_6$, 500 MHz): δ=6.65 (t, J=5.5 Hz, 1H), 6.61 (s, 1H), 6.59, (s, 2H), 5.35 (s, 1H), 4.10 (d, J=5.0 Hz, 2H); $^{13}$C NMR (DMSO-$d_6$, 125 MHz): δ=150.7, 134.3×2, 114.6, 110.4×2 ppm; MS (ESI): m/z 280.0 $[M+Na]^+$; CHN calculated for $C_{10}H_9Cl_2N_3O$: C, 46.53; H, 3.51; N, 16.28; found: C, 46.44; H, 3.61; N, 16.36.

Example 7

5-(((3,5-Dichlorophenyl)(methyl)amino)methyl-1H-pyrazol-3(2H)-one (3). The title compound was prepared according to general procedures D and E. $^1$H NMR (DMSO-$d_6$, 500 MHz): δ=9.93 (br s, 1H), 6.72 (m, 3H), 5.24 (s, 1H), 4.40 (s, 2H), 2.96 (s, 3H); $^{13}$C NMR (DMSO-4, 125 MHz): δ=150.8, 134.6×2, 114.8, 110.7×2, 88.1, 47.9, 38.6 ppm; MS (ESI): m/z 272.0 $[M+H]^+$; CHN calculated for $C_{11}H_{11}Cl_2N_3O$: C, 48.55; H, 4.07; N, 15.44; found: C, 48.80; H, 4.13; N, 15.35.

Example 8

5-((Methyl(phenyl)amino)methyl)-1H-pyrazol-3(2H)-one (4). The title compound was prepared according to general procedures D and E. $^1$H NMR (DMSO-$d_6$, 500 MHz): δ=7.15 (dt, J=2.0, 7.5 Hz, 2H), 6.76 (d, J=8.0 Hz, 2H), 6.63 (t, J=7.5 Hz, 1H), 5.21 (s, 1H), 4.36 (s, 2H), 2.90 (s, 3H); $^{13}$C NMR (DMSO-$d_6$, 125 MHz): δ=149.0, 128.9×2, 116.3, 112.7, 88.4, 47.7, 38.3 ppm; MS (ESI): m/z 204.0 $[M+H]^+$; CHN calculated for $C_{11}H_{13}N_3O$: C, 65.01; H, 6.45; N, 20.68; found: C, 64.98; H, 6.34; N, 20.68.

Example 9

5-(((3-Methoxyphenyl)(methyl)amino)methyl)-1H-pyrazol-3(2H)-one (5). The title compound was prepared according to general procedures D and E. $^1$H NMR (DMSO-d$_6$, 500 MHz): δ=11.47 (br s, 1H), 9.36 (br s, 1H), 7.04 (t, J=8.0 Hz, 1H), 6.35 (dd, J=2.0, 7.5 Hz, 1H), 6.26-6.21 (m, 2H), 5.21 (s, 1H), 4.33 (s, 2H), 3.68 (s, 3H), 2.89 (s, 3H); $^{13}$C NMR (DMSO-d$_6$, 125 MHz): δ=160.2, 150.3, 129.6, 105.7, 101.6, 99.0, 88.8, 54.8, 38.4 ppm; MS (ESI): m/z 234.1 [M+H]$^+$; CHN calculated for C$_{12}$H$_{15}$N$_3$O$_2$: C, 61.79; H, 6.48; N, 18.01; found: C, 61.77; H, 6.47; N, 18.09.

Example 10

4-(Methyl((5-oxo-2,5-dihydro-1H-pyrazol-3-yl)methyl) amino)benzonitrile (6). The title compound was prepared according to general procedures D and E. $^1$H NMR (DMSO-d$_6$, 500 MHz): δ=7.53 (d, J=8.0 Hz, 2H), 6.82 (d, J=8.0 Hz, 2H), 5.25 (s, 1H), 4.47 (s, 2H), 3.04 (s, 3H); $^{13}$C NMR (DMSO-d$_6$, 125 MHz): δ=151.6, 133.2×2, 120.4, 112.2×2, 38.4 ppm; MS (ESI): m/z 251.1 [M+Na]$^+$; CHN calculated for C$_{12}$H$_{12}$N$_4$O: C, 63.15; H, 5.30; N, 24.55; found: C, 62.87; H, 5.35; N, 24.34.

Example 11

5-(((4-Fluorophenyl)(methyl)amino)methyl)-1H-pyrazol-3(2H)-one (7). The title compound was prepared according to general procedures D and E. $^1$H NMR (DMSO-d$_6$, 500 MHz): δ=11.47 (br s, 1H), 9.34 (br s, 1H), 7.00 (t, J=4.0 Hz, 2H), 6.75 (ddd, J=2.5, 4.5, 11.0 Hz, 2H), 5.21 (s, 1H), 4.32 (s, 2H), 2.86 (s, 3H); $^{13}$C NMR (DMSO-d$_6$, 125 MHz): δ=160.3, 156.6, 153.8, 145.9, 141.5, 115.3, 115.1, 114.1, 114.0, 88.2, 48.5, 38.7 ppm; MS (ESI): m/z 222.1 [M+H]$^+$; CHN calculated for C$_{11}$H$_{12}$FN$_3$O: C, 59.72; H, 5.47; N, 18.99; found: C, 59.53; H, 5.56; N, 18.96.

Example 12

5-(((4-Chlorophenyl)methyl)amino)methyl)-1H-pyrazol-3(2H)-one (8). The title compound was prepared according to general procedures D and E. $^1$H NMR (DMSO-d$_6$, 500 MHz): δ=7.16 (t, J=8.5 Hz, 2H), 6.75 (d, J=8.5 Hz, 2H), 5.20 (s, 1H), 4.36 (s, 2H), 2.90 (s, 3H); $^{13}$C NMR (DMSO-d$_6$, 125 MHz): δ=147.8, 128.5×2, 119.9, 114.1×2, 88.3, 47.9, 38.5 ppm; MS (ESI): m/z 238.1 [M+H]$^+$; CHN calculated for C$_{11}$H$_{12}$ClN$_3$O: C, 55.59; H, 5.09; N, 17.68; found: C, 55.55; H, 5.17; N, 17.58.

Example 13

5-(((4-Bromophenyl)methyl)amino)methyl)-1H-pyrazol-3(2H)-one (9). The title compound was prepared according to general procedures D and E. $^1$H NMR (DMSO-d$_6$, 500 MHz): δ=7.27 (d, J=7.5 Hz, 2H), 6.70 (d, J=7.5 Hz, 2H), 5.21 (s, 1H), 4.36 (s, 2H), 2.90 (s, 3H); $^{13}$C NMR (DMSO-d$_6$, 125 MHz): δ=148.1, 131.3×2, 114.7×2, 107.4, 88.1, 47.9, 38.4 ppm; MS (ESI): m/z 282.0 [M+H]$^+$; CHN calculated for C$_{11}$H$_{12}$BrN$_3$O: C, 46.83; H, 4.29; N, 14.89; found: C, 46.93; H, 4.30; N, 14.87.

Example 14

5-(((3-Bromophenyl)methyl)amino)methyl)-1H-pyrazol-3(2H)-one (10). The title compound was prepared according to general procedures D and E. $^1$H NMR (DMSO-4, 500 MHz): δ=11.50 (br s, 1H), 9.45 (br s, 1H), 7.08 (t, J=8.0 Hz, 1H), 6.86 (s, 1H), 6.75 (dt, J=2.5, 8.0 Hz, 2H), 5.22 (s, 1H), 4.37 (s, 2H), 2.92 (s, 3H); $^{13}$C NMR (DMSO-d$_6$, 125 MHz): δ=150.3, 130.6, 122.6, 118.5, 114.6, 111.5, 38.4 ppm; MS (ESI): m/z 282.0 [M+H]$^+$; CHN calculated for C$_{11}$H$_{12}$BrN$_3$O: C, 46.83; H, 4.29; N, 14.89; found: C, 46.92; H, 4.36; N, 14.87.

Example 15

5-(((3-Bromophenyl)(methyl)amino)methyl)-1H-pyrazol-3(2H)-one (11). The title compound was prepared according to general procedures D and E. $^1$H NMR (DMSO-d$_6$, 500 MHz): δ=7.58 (dd, J=1.0, 8.0 Hz, 1H), 7.30 (dt, J=1.0, 8.0 Hz, 1H), 7.13 (dd, J=1.0, 8.0 Hz, 1H), 6.97 (dt, J=1.0, 8.0 Hz, 1H), 5.24 (s, 1H), 4.02 (s, 2H), 2.62 (s, 3H); $^{13}$C NMR (DMSO-d$_6$, 125 MHz): δ=150.0, 133.5, 128.4, 124.6, 122.6, 119.2, 39.0 ppm; MS (ESI): m/z 282.0 [M+H]$^+$; CHN calculated for C$_{11}$H$_{12}$BrN$_3$O: C, 46.83; H, 4.29; N, 14.89; found: C, 46.86; H, 4.31; N, 14.88.

Example 16

5-((Methyl(naphthalen-2-yl)amino)methyl)-1H-pyrazol-3(2H)-one (12). The title compound was prepared according to general procedures D and E. $^1$H NMR (DMSO-d$_6$, 500 MHz): δ=7.70 (t, J=9.0 Hz, 2H), 7.64 (d, J=8.5 Hz, 1H), 7.34-7.28 (m, 2H), 7.16 (dt, J=1.0, 8.0 Hz, 1H), 6.97 (d, J=2.0 Hz, 1H), 5.21 (s, 1H), 4.49 (s, 2H), 3.00 (s, 3H); $^{13}$C NMR (DMSO-d$_6$, 125 MHz): δ=147.0, 134.6, 128.4, 127.2, 126.4, 126.1, 126.0, 121.9, 116.7, 38.5 ppm; MS (ESI): m/z 254.1 [M+H]$^+$; CHN calculated for C$_{15}$H$_{15}$N$_3$O: C, 71.13; H, 5.97; N, 16.59; found: C, 70.94; H, 6.02; N, 16.54.

Example 17

5-((Methyl(naphthalen-1-yl)amino)methyl)-1H-pyrazol-3(2H)-one (13). The title compound was prepared according to general procedures D and E. $^1$H NMR (DMSO-d$_6$, 500 MHz): δ=8.27 (d, J=8.0 Hz, 1H), 7.90 (dt, J=1.5, 7.5 Hz, 1H), 7.59 (d, J=8.0 Hz, 1H), 7.53-7.49 (m, 2H), 7.41 (t, J=8.0 Hz, 1H), 7.14 (d, J=7.0 Hz, 1H), 5.31 (s, 1H), 4.08 (s, 2H), 2.73 (s, 3H); $^{13}$C NMR (DMSO-d$_6$, 125 MHz): δ=149.0, 134.4, 128.5, 128.3, 125.9, 125.8, 125.4, 123.6, 123.1, 115.7, 39.0 ppm; MS (ESI): m/z 254.1 [M+H]$^+$; CHN calculated for C$_{15}$H$_{15}$N$_3$O: C, 71.13; H, 5.97; N, 16.59; found: C, 71.29; H, 6.01; N, 16.51.

Example 18

5-(((3,4-Dichlorophenol)(methyl)amino)methyl)-1H-pyrazol-3(2H)-one (14). The title compound was prepared according to general procedures D and E. $^1$H NMR (DMSO-d$_6$, 500 MHz): δ=7.32 (d, J=9.0 Hz, 1H), 6.91 (d, J=3.0 Hz, 1H), 6.74 (dd, J=3.0, 9.0 Hz, 1H), 5.22 (s, 1H), 4.39 (s, 2H), 2.94 (s, 3H); $^{13}$C NMR (DMSO-d$_6$, 125 MHz): δ=148.8, 131.3, 130.3, 117.3, 113.5, 112.9, 38.5 ppm; MS (ESI): m/z 272.0 [M+H]$^+$; CHN calculated for C$_{11}$H$_{11}$Cl$_2$N$_3$O: C, 48.55; H, 4.07; N, 15.44; found: C, 48.55; H, 4.04; N, 15.46.

Example 19

5-(((2,4-Dichlorophenyl)methyl)amino)methyl)-1H-pyrazol-3(2H)-one (15). The title compound was prepared according to general procedures D and E. $^1$H NMR (DMSO-d$_6$, 500 MHz): δ=7.53 (d, J=2.0 Hz, 1H), 7.31 (dd, J=2.0, 8.5 Hz, 1H), 7.09 (d, J=8.5 Hz, 1H), 5.20 (s, 1H), 4.05 (s, 2H), 2.64 (s, 3H); $^{13}$C NMR (DMSO-d$_6$, 125 MHz): δ=147.6, 129.7, 128.5, 127.6, 126.7, 123.3, 39.0 ppm; MS (ESI): m/z 272.0 [M+H]⁺; CHN calculated for $C_{11}H_{11}Cl_2N_3O$: C, 48.55; H, 4.07; N, 15.44; found: C, 48.33; H, 4.18; N, 15.21.

Example 20

5-(((3,5-Dichlorophenyl)(ethyl)amino)methyl)-1H-pyrazol-3(2H)-one (16). The title compound was prepared according to general procedures D and E. ¹H NMR (DMSO-d₆, 500 MHz): δ=6.67 (m, 3H), 5.26 (s, 1H), 4.34 (s, 2H), 3.42 (d, J=7.0 Hz, 2H), 1.06 (t, J=7.0 Hz, 3H); ¹³C NMR (DMSO-d₆, 125 MHz): δ=149.6, 134.6×2, 114.3, 110.2×2, 44.8, 11.8 ppm; MS (ESI): m/z 286.0 [M+H]⁺; CHN calculated for $C_{12}H_{13}Cl_2N_3O$: C, 50.37; H, 4.58; N, 14.68; found: C, 50.54; H, 4.58; N, 14.68.

Example 21

5-(((3,5-Dichlorophenyl)(isopropyl)amino)methyl-1H-pyrazol-3(2H)-one (17). The title compound was prepared according to general procedures B, C, and E. ¹H NMR (DMSO-d₆, 500 MHz): δ=7.25-7.21 (m, 3H), 5.11 (s, 1H), 4.17 (s, 2H), 1.12 (m, 9H); ¹³C NMR (DMSO-d₆, 125 MHz): δ=150.5, 134.5×2, 114.6, 110.9×2, 48.1, 19.5×2 ppm; MS (ESI): m/z 300.1 [M+H]⁺; CHN calculated for $C_{13}H_{15}Cl_2N_3O$: C, 52.01; H, 5.04; N, 14.00; found: C, 52.10; H, 5.19; N, 13.87.

Example 22

5-((tert-Butyl(3,5-dichlorophenyl)amino)methyl)-1H-pyrazol-3(2H)-one (18). The title compound was prepared according to general procedures B, C, and E. ¹H NMR (DMSO-d₆, 500 MHz): δ=6.68-6.67 (m, 3H), 5.22 (s, 1H), 4.25 (s, 2H), 4.17-4.15 (m, 1H), 1.13 (d, J=7.0 Hz, 6H); ¹³C NMR (DMSO-d₆, 125 MHz): δ=151.4, 133.0×2, 127.4, 123.9, 55.7, 17.8×3 ppm; MS (ESI): m/z 314.1 [M+H]⁺; CHN calculated for $C_{14}H_{17}Cl_2N_3O$: C, 53.52; H, 5.45; N, 13.37; found: C, 53.45; H, 5.45; N, 13.40.

Example 23

5-(((Cyclopropyl(3,5-dichlorophenyl)amino)methyl-1H-pyrazol-3(2H)-one (19). The title compound was prepared according to general procedures B, C, and E. ¹H NMR (DMSO-d₆, 500 MHz): δ=9.42 (br s, 1H), 6.86 (s, 2H), 6.74 (s, 1H), 5.10 (s, 1H), 4.37 (s, 2H), 2.43 (s, 1H), 0.83-0.82 (m, 2H), 0.55 (s, 2H); ¹³C NMR (DMSO-d₆, 125 MHz): δ=151.3, 134.2×2, 116.1, 112.3×2, 88.4, 46.7, 32.2, 9.1×2 ppm; MS (ESI): m/z 298.0 [M+H]⁺; CHN calculated for $C_{13}H_{13}Cl_2N_3O$: C, 52.37; H, 4.39; N, 14.09; found: C, 52.33; H, 4.37; N, 14.89.

Example 24

5-((Benzyl(3,5-dichlorophenyl)amino)methyl)-1H-pyrazol-3(2H)-one (20). The title compound was prepared according to general procedures B, C, and E. ¹H NMR (DMSO-d₄, 500 MHz): δ=7.34 (t, J=7.5 Hz, 2H), 7.25 (t, J=7.5 Hz, 1H), 7.21 (d, J=7.5 Hz, 2H), 6.70 (s, 1H), 6.68 (s, 2H), 5.32 (s, 1H), 4.66 (s, 2H), 4.52 (s, 2H); ¹³C NMR (DMSO-d₆, 125 MHz): δ=150.0, 137.8, 134.4×2, 128.6×2, 127.0, 126.4×2, 115.0, 110.8×2, 53.8 ppm; MS (ESI): m/z 298.0 [M+H]⁺; CHN calculated for $C_{17}H_{15}Cl_2N_3O$: C, 58.63; H, 4.34; N, 12.07; found: C, 59.01; H, 4.63; N, 11.83.

Example 25

5-(((3,5-Dichlorophenyl)(phenyl)amino)methyl)-1H-pyrazol-3(2H)-one (21). The title compound was prepared according to general procedures B, C, and E. ¹H NMR (DMSO-d₆, 500 MHz): δ=11.59 (br s, 1H), 9.65 (br s, 1H), 7.43 (t, J=7.0 Hz, 2H), 7.28-7.22 (m, 3H), 6.88 (s, 1H), 6.72 (s, 2H), 5.24 (s, 1H), 4.77 (s, 2H); ¹³C NMR (DMSO-d₆, 125 MHz): δ=150.0, 145.6, 134.4×2, 130.0×2, 125.8×2, 125.6, 117.2, 113.8×2 ppm; MS (ESI): m/z 334.0 [M+H]⁺; CHN calculated for $C_{16}H_{13}Cl_2N_3O$: C, 57.50; H, 3.92; N, 12.57; found: C, 57.70; H, 4.27; N, 12.94.

Example 26

5-(((3,5-Dichlorophenyl)(prop-2-ynyl)amino)methyl-1H-pyrazol-3(2H)-one (22). The title compound was prepared according to general procedures B, C, and E. ¹H NMR (DMSO-d₆, 500 MHz): δ=6.82 (s, 3H), 5.35 (s, 1H), 4.41 (s, 2H), 4.21 (d, J=2.0 Hz, 2H), 3.26 (d, J=2.0 Hz, 1H); ¹³C NMR (DMSO-d₆, 125 MHz): δ=149.4, 134.4×2, 116.1, 111.8×2, 89.1, 79.6, 75.2 ppm; MS (ESI): m/z 296.1 [M+H]⁺; CHN calculated for $C_{13}H_{11}Cl_2N_3O$: C, 52.72; H, 3.74; N, 14.19; found: C, 52.63; H, 3.91; N, 13.92.

Example 27

5-(2-((3,5-Dichlorophenyl)(methyl)amino)ethyl)-1H-pyrazol-3(2H)-one (23). The title compound was prepared according to general procedures A, C, and E. ¹H NMR (DMSO-d₆, 500 MHz): δ=11.35 (br s, 1H), 9.41 (br s, 1H), 6.69 (d, J=1.5 Hz, 1H), 6.66 (d, J=2.0 Hz, 2H), 5.33 (s, 1H), 3.54 (t, J=7.5 Hz, 2H), 2.85 (s, 3H), 2.64 (t, J=7.5 Hz, 2H); ¹³C NMR (DMSO-d₆, 125 MHz): δ=150.4, 134.7×2, 114.3, 110.0×2, 88.7, 51.1, 37.9 ppm; MS (ESI): m/z 286.0 [M+H]⁺; CHN calculated for $C_{12}H_{13}Cl_2N_3O$: C, 50.37; H, 4.58; N, 14.68; found: C, 50.66; H, 4.80; N, 14.58.

Example 28

5-(3-((3,5-Dichlorophenyl)(methyl)amino)propyl)-1H-pyrazol-3(2H)-one (24). The title compound was prepared according to general procedures B, C, and E. ¹H NMR (DMSO-d₆, 500 MHz): δ=11.27 (br s, 1H), 9.30 (br s, 1H), 6.66 (d, J=1.5 Hz, 1H), 6.61 (d, J=1.5 Hz, 2H), 5.26 (s, 1H), 3.32 (t, J=7.5 Hz, 2H), 2.88 (s, 3H), 2.45 (t, J=7.5 Hz, 2H), 1.76-1.73 (m, 2H); ¹³C NMR (DMSO-d₆, 125 MHz): δ=150.7, 134.7×2, 114.0, 109.8×2, 50.9, 38.0, 25.4 ppm; MS (ESI): m/z 300.1 [M+H]⁺; CHN calculated for $C_{13}H_{15}Cl_2N_3O$: C, 52.01; H, 5.04; N, 14.00; found: C, 52.23; H, 5.14; N, 14.94.

Example 29

5-(Indolin-1-ylmethyl)-1H-pyrazol-3(2H)-one (25). The title compound was prepared according to general procedures D and E. ¹H NMR (DMSO-d₆, 500 MHz): δ=7.02 (d, J=7.0 Hz, 1H), 6.98 (t, J=7.5 Hz, 1H), 6.62 (d, J=7.5 Hz, 1H), 6.58 (t, J=7.5 Hz, 1H), 5.31 (s, 1H), 4.12 (s, 2H), 3.24 (t, J=8.0 Hz, 2H), 2.85 (t, J=8.0 Hz, 2H); ¹³C NMR (DMSO-d₆, 125 MHz): δ=151.7, 129.8, 127.0, 124.3, 117.5, 107.5, 89.0, 52.6, 44.0, 27.9 ppm; MS (ESI): m/z 216.1 [M+H]⁺; CHN calculated for $C_{12}H_{13}N_3O$: C, 66.96; H, 6.09; N, 19.52; found: C, 66.85; H, 6.11; N, 19.44.

Example 30

5-((3,4-Dihydroquinolin-1(2H)-yl)methyl)-1H-pyrazol-3(2H)-one (26). The title compound was prepared according to general procedures D and E. ¹H NMR (DMSO-d₆, 500 MHz): δ=6.91 (t, J=7.0 Hz, 1H), 6.86 (d, J=7.0 Hz, 1H), 6.64

(d, J=8.5 Hz, 1H), 6.47 (t, J=7.5 Hz, 1H), 5.26 (s, 1H), 4.28 (s, 2H), 3.28 (t, J=5.5 Hz, 2H), 2.66 (t, J=5.5 Hz, 2H), 1.87 (p, J=6.0 Hz, 2H); $^{13}$C NMR (DMSO-d$_6$, 125 MHz): δ=144.9, 128.8, 126.7, 122.2, 115.8, 111.2, 88.4, 49.1, 46.5, 39.0, 27.5, 21.8 ppm; MS (ESI): m/z 216.1 [M+H]$^+$; CHN calculated for C$_{13}$H$_{15}$N$_3$O: C, 68.10; H, 6.59; N, 18.33; found: C, 68.02; H, 6.60; N, 18.29.

Example 31

5-(3,5-Dichlorophenyl)-4,5,6,7-tetrahydro-1H-pyrazolo [4,3-c]pyridin-3(2H)-one (27). The title compound was prepared according to the literature procedure and general procedure E. $^1$H NMR (DMSO-d$_6$, 500 MHz): δ=6.95 (s, 2H), 6.82 (d, J=1.5 Hz, 1H), 4.06 (s, 2H), 3.59 (t, J=6.0 Hz, 1H), 2.63-2.62 (m, 2H); $^{13}$C NMR (DMSO-d$_6$, 125 MHz): δ=152.1, 134.7×2, 116.4, 112.9×2, 45.0, 43.0 ppm; MS (ESI): m/z 284.0 [M+H]$^+$; CHN calculated for C$_{12}$H$_{11}$Cl$_2$N$_3$O: C, 50.72; H, 3.90; N, 14.79; found: C, 50.53; H, 4.03; N, 14.83.

Example 32

6-(3,5-Dichlorophenyl)-4,5,6,7-tetrahydro-1H-pyrazolo [3,4-c]pyridin-3(2H)-one (28). The title compound was prepared according to the literature procedure and general procedure E. $^1$H NMR (DMSO-d$_6$, 500 MHz): δ=6.96 (d, J=1.5 Hz, 2H), 6.83 (d, J=1.5 Hz, 1H), 4.26 (s, 2H), 3.55 (t, J=6.0 Hz, 2H), 3.16 (d, J=5.0 Hz, 1H), 2.41-2.39 (m, 2H); $^{13}$C NMR (DMSO-d$_6$, 125 MHz): δ=152.0, 134.7×2, 116.6, 113.1×2, 46.2, 29.5, 18.6 ppm; MS (ESI): m/z 284.0 [M+H]$^+$; CHN calculated for C$_{12}$H$_{11}$Cl$_2$N$_3$O: C, 50.72; H, 3.90; N, 14.79; found: C, 50.51; H, 3.78; N, 14.57.

Example 33

2-Benzyl-5-(((3,5-dichlorophenyl)(methylamino) methyl)-1H-pyrazol-3(2H)-one (29). To a solution of ethyl 4-((3,5-dichlorophenyl)(methyl)amino)-3-oxobutanoate (304 mg, 1.0 mmol) and benzyl hydrazine chloride (388 mg, 2.0 mmol) in EtOH (5 mL) was added anhydrous triethylamine (570 uL, 4.0 mmol). The resulting solution was stirred at room temperature overnight. After evaporating the volatiles, the residue was purified on a silica gel column, eluting with a mixture of MeOH and dichloromethane (1% to 2% MeOH) to afford the product as a pale yellow solid (320 mg, 88%). The solid was then recrystallized in dichloromethane/ hexane to give the product as a white solid. $^1$H NMR (DMSO-d$_6$, 500 MHz): δ=11.00 (br s, 1H), 7.28 (t, J=7.0 Hz, 2H), 7.23 (d, J=7.0 Hz, 1H), 7.11 (d, J=7.0 Hz, 2H), 6.74 (d, J=1.5 Hz, 2H), 6.69 (s, 1H), 5.12 (s, 1H), 5.01 (s, 2H), 4.33 (s, 2H), 2.98 (s, 2H); $^{13}$C NMR (DMSO-d$_6$, 125 MHz): δ=152.7, 151.0, 146.8, 138.0, 134.4×2, 128.4×2, 127.1, 127.0×2, 114.4, 110.6×2, 84.6, 50.3, 49.2, 38.9 ppm; MS (ESI): m/z 284.0 [M+H]$^+$; CHN calculated for C$_{18}$H$_{17}$Cl$_2$N$_3$O: C, 59.68; H, 4.73; N, 11.60; found: C, 59.79; H, 4.68; N, 11.48.

Example 34

5-(((3,5-Dichlorophenyl)(methyl)amino)methyl)-2-methyl-1H-pyrazol-3(2H)-one (30). To a solution of ethyl 4-((3,5-dichlorophenyl)(methyl)amino)-3-oxobutanoate (304 mg, 1.0 mmol) in EtOH (5 mL) was added anhydrous methyl hydrazine (105 uL, 2.0 mmol). The resulting solution was stirred at room temperature overnight. After evaporating the volatiles, the residue was purified on a silica gel column, eluting with a mixture of MeOH and dichloromethane (2% to 10% MeOH) to afford the product as a pale yellow solid (231 mg, 81%). The solid was then recrystallized in dichloromethane/hexane to give the product as a white solid. $^1$H NMR (DMSO-d$_6$, 500 MHz): δ=6.72 (d, J=1.5 Hz, 2H), 6.68 (t, J=1.5 Hz, 1H), 5.13 (s, 1H), 4.29 (s, 2H), 3.43 (s, 3H), 2.95 (s, 3H); $^{13}$C NMR (DMSO-d$_6$, 125 MHz): δ=152.5, 151.0, 146.0, 134.4×2, 114.3, 110.4×2, 84.5, 49.9, 38.5, 33.0 ppm; MS (ESI): m/z 286.1 [M+H]$^+$; CHN calculated for C$_{12}$H$_{13}$Cl$_2$N$_3$O: C, 50.37; H, 4.58; N, 14.68; found: C, 50.60; H, 4.65; N, 14.62; FTIR (solid), v 1591, 1552, 1495, 1445, 1309, 1272, 1094, 1012, 980, 950, 813, 756, 662 cm$^{-1}$; (DMSO), v 1591, 1552, 1436, 1309, 1042 (bw), 950, 806, 756, 697, 663 cm$^{-1}$.

Example 35

3,5-Dichloro-N-((2,3-dihydropyrazolo[5,1-b]oxazol-6-yl)methyl)-N-methylaniline (36). To a solution of ethyl 4-((3,5-dichlorophenyl)(methyl)amino)-3-oxobutanoate (304 mg, 1.0 mmol) in EtOH (5 mL), 2-hydroxyethylhydrazine (85 uL, 1.1 mmol) was added and stirred for 3 h. After evaporating the volatiles, the residues were dissolved with dry acetonitrile (10 mL) and triethylamine (156 uL, 1.1 mmol) followed by the addition of tosyl chloride (190 mg, 1.0 mmol). The solution was stirred for 20 min, diluted in ethyl acetate (20 mL), washed with water (10 mL), dried over Na$_2$SO$_4$, and concentrated. The residue was purified on a silica gel column, eluting with a mixture of MeOH and dichloromethane (2% MeOH) to afford the product as a pale yellow liquid 35 (400 mg, 85%).

Under an inert atmosphere, 35 was dissolved in anhydride acetonitrile (8.5 mL) followed by the addition of sodium hydride (40 mg, 1.0 mmol). The mixture was stirred overnight at room temperature and evaporated to give the residue, which was purified on a silica gel column, eluting with a mixture of MeOH and dichloromethane (1% MeOH) to afford the product as a pale yellow solid 36 (200 mg, 79%). $^1$H NMR (CDCl$_3$, 500 MHz): δ=6.66 (d, J=1.5 Hz, 1H), 6.63 (d, J=1.5 Hz, 2H), 5.19 (s, 1H), 5.00 (dd, J=7.5, 9.0 Hz, 2H), 4.36 (s, 2H), 4.25 (t, J=7.5 Hz, 2H), 2.99 (s, 3H); $^{13}$C NMR (CDCl$_3$, 125 MHz): δ=159.7, 155.0, 151.0, 135.6×2, 116.4, 111.0×2, 79.5, 75.3, 51.6, 45.4, 38.8 ppm; MS (ESI): m/z 298.0 [M+H]$^+$.

5-(((3,5-Dichlorophenyl)(methyl)amino)methyl)-1-methyl-2-vinyl-1H-pyrazol-3(2H)-one (37). To a solution of compound 36 (200 mg, 0.67 mmol) in anhydrous acetonitrile (6 mL), methyl trifluoromethanesulfonate (85 uL, 0.75 mmol) was added, and the solution was stirred for 2 h before the addition of sodium iodide (195 mg, 1.3 mmol) and TsOH (127 mg, 0.67 mmol). After conversion to the iodinated intermediate by overnight stirring, KOtBu (188 mg, 1.7 mmol) was added to the mixture, which was further stirred for 1 h. After evaporating the volatiles, the residue was purified on a silica gel column, eluting with a mixture of MeOH and dichloromethane (4% MeOH) to afford the product as a yellow liquid (115 mg, 55%). $^1$H NMR (CDCl$_3$, 500 MHz): δ=6.85 (dd, J=9.0, 16.0 Hz, 1H), 6.77 (t, J=1.5 Hz, 2H), 6.56 (d, J=1.5 Hz, 2H), 5.37 (s, 1H), 4.88-4.80 (m, 2H), 4.31 (s, 2H), 3.17 (s, 3H), 2.99 (s, 3H); $^{13}$C NMR (CDCl$_3$, 125 MHz): δ=165.4, 159.2, 150.3, 136.0×2, 126.3, 118.0, 111.3×2, 101.1, 99.5, 49.6, 39.0, 37.3 ppm.

5-(((3,5-Dichlorophenyl)methyl)amino)methyl)-1-methyl-1H-pyrazol-3(2H)-one (31). Compound 37 (115 mg, 0.37 mmol) was suspended in 2 N HCl (7 mL) and stirred at 60° C. overnight. Ethyl acetate was added to the mixture, and the organic layer was separated, washed with water and brine, dried over Na$_2$SO$_4$, and concentrated. The residue was purified on a silica gel column, eluting with a mixture of MeOH and dichloromethane (4% MeOH) to afford the product as a white solid (55 mg, 52%). $^1$H NMR (DMSO-d$_6$, 500 MHz): δ=9.42 (s, 1H), 6.75 (m, 3H), 5.08 (s, 1H), 4.54 (s, 2H), 3.52 (s, 3H), 2.94 (s, 3H); $^{13}$C NMR (DMSO-d$_6$, 125 MHz): δ=159.5, 150.8, 139.4, 134.6×2, 115.0, 110.7×2, 89.7, 46.9, 38.2, 35.7 ppm; MS (ESI): m/z 286.1 [M+H]$^+$; CHN calculated for C$_{12}$H$_{13}$Cl$_2$N$_3$O: C, 50.37; H, 4.58; N, 14.68; found: C, 50.57; H, 4.73; N, 14.74; FTIR (solid), v 1587, 1552, 1493, 1447, 1345, 1125, 1098, 1018, 959, 813, 801, 774, 663 cm$^{-1}$; (DMSO), v 1587, 1552, 1493, 1435, 1282, 1043 (bw), 952, 800, 697, 664 cm$^{-1}$.

Example 36

5-(((3,5-Dichlorophenyl)(methyl)amino)methyl)-1,2,4-trimethyl-1H-pyrazol-3(2H)-one (32). The solution of compound 30 (200 mg, 0.7 mmol), MeI (132 uL, 2.1 mmol), and K$_2$CO$_3$ (290 mg, 2.1 mmol) in acetonitrile (3.5 mL) was stirred at 50° C. for 24 h. After evaporating the volatiles, the residue was purified on a silica gel column, eluting with a mixture of MeOH and dichloromethane (1%-5% MeOH) to afford the product (compounds 32-34) as a pale yellow solid or liquid. $^1$H NMR (CDCl$_3$, 500 MHz): δ=6.78 (t, J=1.5 Hz, 1H), 6.65 (d, J=1.5 Hz, 2H), 4.23 (s, 2H), 3.32 (s, 3H), 3.08 (s, 3H), 2.82 (s, 3H), 1.86 (s, 3H); $^{13}$C NMR (CDCl$_3$, 125 MHz): δ=166.5, 151.1, 147.3, 136.0×2, 118.2, 111.9×2, 108.7, 46.7, 37.6, 35.0, 29.1, 7.27 ppm; MS (ESI): m/z 314.1 [M+H]$^+$.

Example 37

5-(((3,5-Dichlorophenyl)(methyl)amino)methyl)-1,2-dimethyl-1H-pyrazol-3(2H)-one (33). $^1$H NMR (CDCl$_3$, 500 MHz): δ=6.76 (t, J=1.5 Hz, 1H), 6.57 (d, J=2.0 Hz, 2H), 5.28 (s, 1H), 4.27 (s, 2H), 3.38 (s, 3H), 3.25 (s, 3H), 2.96 (s, 3H); $^{13}$C NMR (CDCl$_3$, 125 MHz): δ=166.0, 151.4, 150.4, 135.9×2, 118.0, 111.4×2, 98.1, 49.0, 38.7, 34.2, 28.8 ppm; MS (ESI): m/z 300.1 [M+H]$^+$.

Example 38

3-(((3,5-Dichlorophenyl)(methyl)amino)methyl)-1,4,4-trimethyl-1H-pyrazol-5(4H)-one (34). $^1$H NMR (CDCl$_3$, 500 MHz): δ=6.72 (t, J=1.5 Hz, 1H), 6.58 (d, J=1.5 Hz, 2H), 4.17 (s, 2H), 3.30 (s, 3H), 3.00 (s, 3H), 1.23 (s, 6H); $^{13}$C NMR (CDCl$_3$, 125 MHz): δ=178.4, 162.6, 150.6, 135.8×2, 117.2, 110.9×2, 50.6, 48.0, 39.3, 31.5, 21.3 ppm; MS (ESI): m/z 314.1 [M+H].

Example 39

Mutant SOD1-Induced Cytotoxicity Protection Assay. Viability and EC50 values were determined for 1a, 1b, 2a, and 2b according to the previously reported assay procedure. (See, Benmohamed, R.; Arvanites, A. C.; Silverman, R. B.; Morimoto, R. I.; Ferrante, R. J.; Kirsch, D. R. Identification of compounds protective against G93A SOD1 toxicity for the treatment of amyotrophic lateral sclerosis. *Amyotrophic Lateral Scler. Other Mot. Neuron Disord.* 2011, 12, 87-96.) PC12 cells were seeded at 15000 cells/well in 96-well plates and incubated 24 h prior to compound addition. Compounds were assayed in 12-point dose-response experiments to determine potency and efficacy. The highest compound concentration tested was 32 µM, which was decreased by one-half with each subsequent dose. After a 24 h incubation with the compounds, MG132 was added at a final concentration of 100 nM. MG132 is a well-characterized proteasome inhibitor, which would be expected to enhance the appearance of protein aggregation by blocking the proteosomal clearance of aggregated proteins. Cell viability was measured 48 h later using the fluorescent viability probe, Calcein-AM (Molecular Probes). Briefly, cells were washed twice with PBS, Calcein-AM was added at a final concentration of 1 µM for 20 min at room temperature, and fluorescence intensity was read in a POLARstar fluorescence plate reader (BMG). Fluorescence data were coupled with compound structural data, then stored, and analyzed using the CambridgeSoft Chemoffice Enterprise Ultra software package.

Example 40

In vitro ADME assays. In vitro microsomal stability, aqueous solubility, and Caco-2 permeability were determined for 1b and 2b at Apredica Inc. (Watertown, Mass.).

Example 41

Computational Methods. Possible initial tautomer structures were constructed with molecular modeling software Sybyl-X 1.2 (Tripos International, St. Louis, Mo.). After primary optimization by use of MM2 molecular mechanical module encoded in the program CS Chem3D, these two structures were subjected to full optimization within the density-functional theory (DFT). The Lee-Yang-Parr correlation functional approximation (B3LYP) method was used in a 6-31+G(d,p) basis set. (Becke, A. D. Density-functional thermochemistry. III. The role of exact exchange. *J. Chem. Phys.* 1993, 98, 5648-5652; Lee, C.; Yang, W.; Parr, R. G. Development of the Colle-Salvetti conelation energy formula into a functional of the electron density. *Phys. Rev. B* 1988, 37, 785-789.) On the basis of the optimized geometries, energy or frequency calculations were carried out at the same levels of B3LYP so as to verify the reasonability of the optimized structures. A frequency scaling factor of 0.964 was used in the comparison of the calculated results with the experimental spectra. (Merrick, J. P.; Moran, D.; Radom, L. An Evaluation of Harmonic Vibrational Frequency Scale Factors. *J. Phys. Chem. A* 2007, 111, 11683-11700) All of the Quantum Chemical calculations were carried out with the Gamess (2012R1) program. (Schmidt, M. S.; Baldridge, K. K.; Boatz, J. A.; Elbert, S. T.; Gordon, M. S.; Jensen, J. H.; Koseki, S.; Matsunaga, N.; Nguyen, K. A.; Su, S.; Windus, T. L.; Dupuis, M.; Montgomery, J. A. General atomic and molecular electronic structure system. *J. Comput. Chem.* 1993, 14, 1347-1363.)

Figure 36:
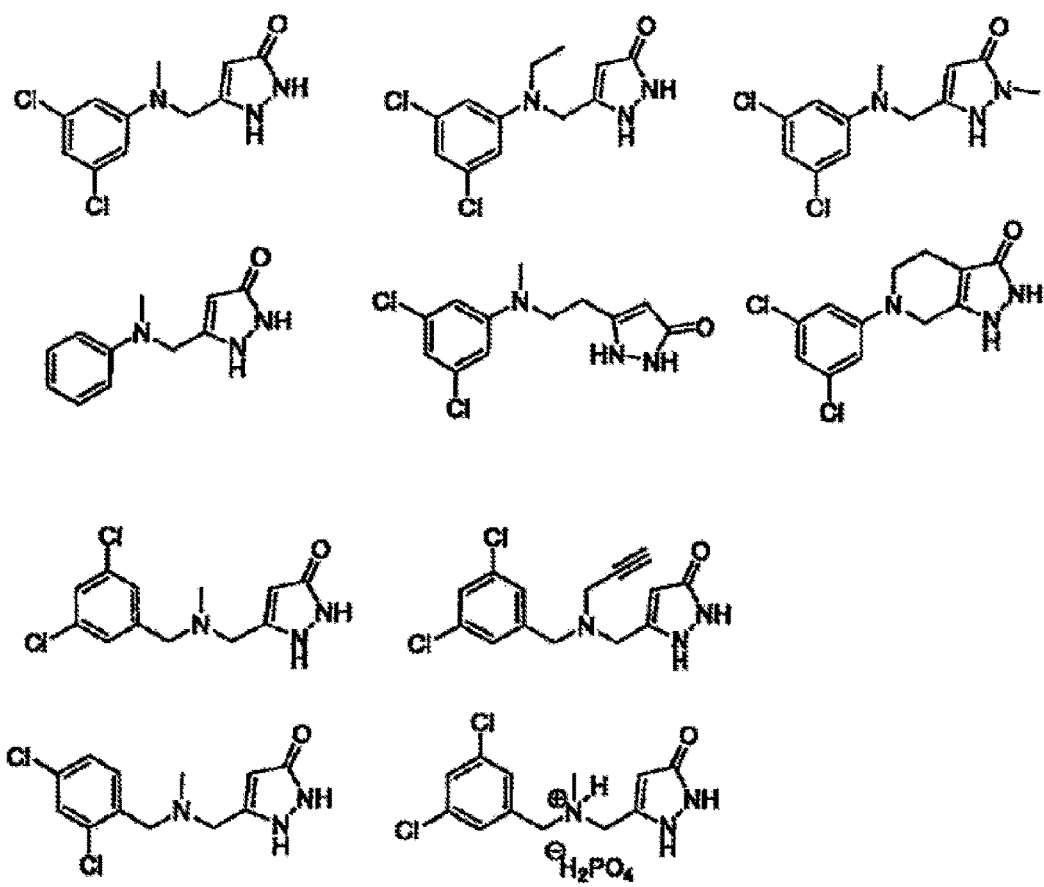

While the present invention can be illustrated in the context of non-limiting compounds of the sort described above (e.g. see also, FIG. 36), it will be understood by those skilled in the art that this invention can further comprise other compounds and related pharmaceutically-acceptable compositions, such compounds and related compositions as can be considered with reference to the substructural moieties illustrated in FIG. 29. Without limitation, the aromatic ring substructure of FIG. 29 can be varied as described in co-pending application Ser. No. 13/129,854 in conjunction with ring A and substituent(s) thereon, in particular as described in paragraphs 104 and 164-186 and Tables 2-3 thereof, such paragraphs and tables which are incorporated herein by reference in their entirety. The N-substituted moiety of the linker substructure of FIG. 29 can be varied as described in the aforementioned incorporated application, in particular such substituents as described in paragraphs 104, 142 and 153-160 also incorporated herein by reference in their entirety. Likewise the pyrazolone substructure of FIG. 29 can be varied as described in the aforementioned co-pending application, in conjunction with the pyrazolone moiety and substituent(s) thereon, in particular as described in paragraphs 104-136, also incorporated herein by reference in their entirety. Such varied compounds can be prepared using synthetic techniques of the sort illustrated above or in the incorporated reference, or in straight-forward modifications of such synthetic techniques—such modifications as would also be understood by those skilled in the art and made aware of this invention—and are limited only by commercial or synthetic availability of suitable starting materials and/or reagents.

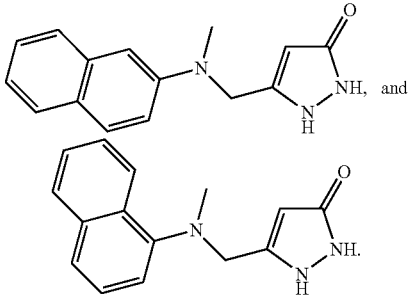

We claim:

1. A compound having a formula as follows or a pharmaceutical salt thereof:

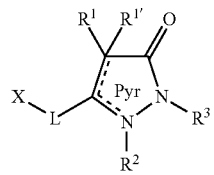

wherein:
the Pyr ring comprises one double bond and the compound is a substituted 1H-pyrazol-3(2H)-one or a substituted 1H-pyrazol-5(4H)-one;
$R^1$ is selected from H, alkyl, cycloalkyl, alkylsulfonyl, alkylcarbonyl, aryl, arylalkyl, alkenylalkyl and alkynylalkyl moieties;
$R^{1'}$ is absent or present, and when present $R^{1'}$ is selected from H, alkyl, cycloalkyl, alkylsulfonyl, alkylcarbonyl, aryl, arylalkyl, alkenylalkyl and alkynylalkyl moieties;
$R^2$ is absent or present, and when present $R^2$ is selected from H, alkyl, cycloalkyl, alkylsulfonyl, alkylcarbonyl, aryl, arylalkyl, alkenylalkyl and alkynylalkyl moieties;
$R^3$ is selected from H, alkyl, cycloalkyl, alkylsulfonyl, alkylcarbonyl, arylalkyl, alkenylalkyl and alkynylalkyl moieties;
L is —(CH$_2$)$_n$— where n is 1 or 2;
X is

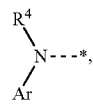

wherein
$R^4$ is selected from H or alkyl moieties; and
Ar is phenyl optionally substituted at one or more positions with alkyl, amino, alkylamino, alkylsulfonyl, alkylcarbonyl, alkoxy, alkoxycarbonyl, cyano, or halo moieties.

2. The compound of claim 1, wherein the compound is a substituted 1H-pyrazol-3(2H)-one having a formula:

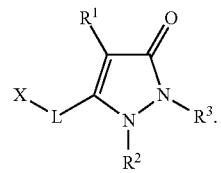

3. The compound of claim 1, wherein the compound is a substituted 1H-pyrazol-5(4H)-one having a formula:

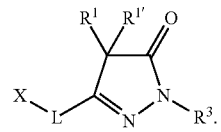

4. The compound of claim 1, wherein $R^1$ is selected from H and alkyl moieties.
5. The compound of claim 1, wherein $R^{1'}$ is selected from H and alkyl moieties.
6. The compound of claim 1, wherein $R^2$ is selected from H and alkyl moieties.
7. The compound of claim 1, wherein $R^3$ is selected from H and alkyl moieties.
8. The compound of claim 1 having a formula selected from:

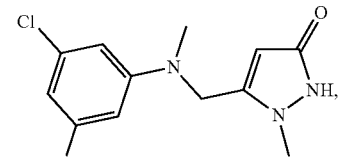

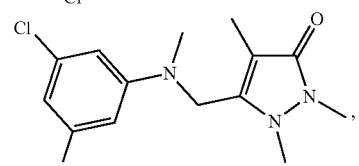

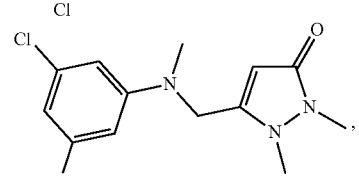

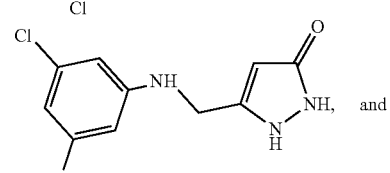

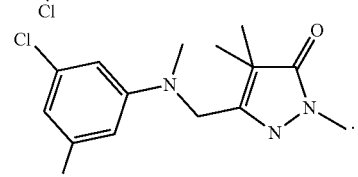

9. A pharmaceutical composition comprising the compound of claim 1 and a carrier component.

10. A method of treating amyotrophic lateral sclerosis (ALS) in a subject in need thereof, the method comprising administering the pharmaceutical composition of claim 9 to the subject.

11. A compound having a formula:

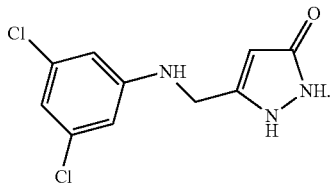 [SMILES: O=c1cc(CNc2cc(Cl)cc(Cl)c2)[nH][nH]1]

12. A pharmaceutical composition comprising the compound of claim 11 and a carrier component.

13. A compound having a formula as follows or a pharmaceutical salt thereof:

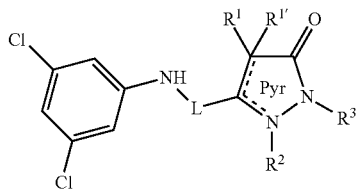

wherein:
the Pyr ring comprises one double bond and the compound is a substituted 1H-pyrazol-3(2H)-one or a substituted 1H-pyrazol-5(4H)-one;

$R^1$ is selected from H, alkyl, cycloalkyl, alkylsulfonyl, alkylcarbonyl, aryl, arylalkyl, alkenylalkyl and alkynylalkyl moieties;

$R^{1'}$ is absent or present, and when present $R^{1'}$ is selected from H, alkyl, cycloalkyl, alkylsulfonyl, alkylcarbonyl, aryl, arylalkyl, alkenylalkyl and alkynylalkyl moieties;

$R^2$ is absent or present, and when present $R^2$ is selected from H, alkyl, cycloalkyl, alkylsulfonyl, alkylcarbonyl, aryl, arylalkyl, alkenylalkyl and alkynylalkyl moieties;

$R^3$ is selected from H, alkyl, cycloalkyl, alkylsulfonyl, alkylcarbonyl, aryl, arylalkyl, alkenylalkyl and alkynylalkyl moieties;

L is $-(CH_2)_n-$ where n is 1-2.

14. The compound of claim 13, wherein the compound is a substituted 1H-pyrazol-3(2H)-one having a formula:

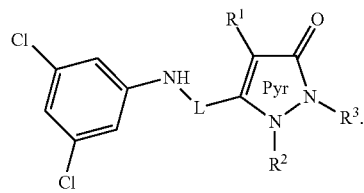

15. The compound of claim 13, wherein the compound is a substituted 1H-pyrazol-5(4H)-one having a formula:

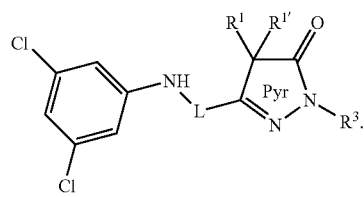

16. The compound of claim 13, wherein $R^1$ is selected from H and alkyl moieties.

17. The compound of claim 13, wherein $R^{1'}$ is selected from H and alkyl moieties.

18. The compound of claim 13, wherein $R^2$ is selected from H and alkyl moieties.

19. The compound of claim 13, wherein $R^3$ is selected from H and alkyl moieties.

20. A pharmaceutical composition comprising the compound of claim 13 and a carrier component.

21. A method of treating amyotrophic lateral sclerosis (ALS) in a subject in need thereof, the method comprising administering the pharmaceutical composition of claim 20 to the subject.

22. A compound having a formula selected from: